US012667586B2

(12) United States Patent
Scranton et al.

(10) Patent No.: US 12,667,586 B2
(45) Date of Patent: Jun. 30, 2026

(54) TREATMENTS FOR OCULAR SURFACE DISORDERS

(71) Applicant: Glaukos Corporation, Aliso Viejo, CA (US)

(72) Inventors: Shawn A. Scranton, Carlsbad, CA (US); Colin Richard Green, Auckland (NZ); Brian Levy, Tampa, FL (US)

(73) Assignee: Glaukos Corporation, Aliso Viejo, CA (US)

( * ) Notice: Subject to any disclaimer, the term of this patent is extended or adjusted under 35 U.S.C. 154(b) by 0 days.

(21) Appl. No.: 18/224,017

(22) Filed: Jul. 19, 2023

(65) Prior Publication Data

US 2024/0299440 A1 Sep. 12, 2024

Related U.S. Application Data

(60) Provisional application No. 63/521,298, filed on Jun. 15, 2023, provisional application No. 63/450,597, filed on Mar. 7, 2023.

(51) Int. Cl.

| | |
|---|---|
| ***A61K 31/7125*** | (2006.01) |
| ***A61K 9/00*** | (2006.01) |
| ***A61K 47/10*** | (2017.01) |
| ***A61P 27/02*** | (2006.01) |
| ***C12N 15/11*** | (2006.01) |
| ***C12N 15/113*** | (2010.01) |

(52) U.S. Cl.

CPC ........ *A61K 31/7125* (2013.01); *A61K 9/0051* (2013.01); *A61K 47/10* (2013.01); *A61P 27/02* (2018.01); *C12N 15/111* (2013.01); *C12N 15/113* (2013.01)

(58) Field of Classification Search

CPC . C12N 2310/11; C12N 15/113; C12N 15/111; A61P 27/02; A61K 9/0048; A61K 31/713; A61K 31/7088; A61K 48/005

See application file for complete search history.

(56) References Cited

U.S. PATENT DOCUMENTS

| | | | | |
|---|---|---|---|---|
| 3,687,808 | A | 8/1972 | Merigan et al. | |
| 3,773,919 | A | 11/1973 | Boswell et al. | |
| 4,485,045 | A | 11/1984 | Regen | |
| 4,544,545 | A | 10/1985 | Ryan et al. | |
| 4,861,757 | A | 8/1989 | Antoniades et al. | |
| 5,034,506 | A | 7/1991 | Summerton et al. | |
| 5,044,810 | A | 9/1991 | Matsuoka et al. | |
| 5,166,195 | A | 11/1992 | Ecker | |
| 5,234,809 | A | 8/1993 | Boom et al. | |
| 5,503,828 | A * | 4/1996 | Testa .................... | C07K 14/56 424/85.4 |
| 5,948,811 | A | 9/1999 | Chan et al. | |
| 5,998,148 | A | 12/1999 | Bennett et al. | |
| 6,319,907 | B1 | 11/2001 | Ferguson | |
| 6,331,298 | B1 | 12/2001 | Ferguson | |
| 6,334,856 | B1 | 1/2002 | Allen et al. | |
| 6,387,364 | B1 | 5/2002 | Ferguson | |
| 6,455,569 | B1 | 9/2002 | Ferguson | |
| 6,458,590 | B1 | 10/2002 | Mukherjee et al. | |
| 6,506,559 | B1 | 1/2003 | Fire et al. | |
| 6,566,339 | B1 | 5/2003 | Ferguson et al. | |
| 6,611,707 | B1 | 8/2003 | Prausnitz et al. | |
| 6,685,971 | B2 | 2/2004 | Xu et al. | |
| 6,696,433 | B2 | 2/2004 | Ferguson et al. | |
| 6,743,211 | B1 | 6/2004 | Prausnitz et al. | |
| 6,752,987 | B1 | 6/2004 | Hammond et al. | |
| 6,855,505 | B2 | 2/2005 | Ferguson et al. | |
| 6,900,181 | B2 | 5/2005 | Ferguson et al. | |
| 6,903,078 | B1 | 6/2005 | Williams | |
| 6,991,813 | B2 | 1/2006 | Xu et al. | |
| 7,052,684 | B2 | 5/2006 | Ferguson | |
| 7,097,776 | B2 | 8/2006 | Raju | |
| 7,098,190 | B1 | 8/2006 | Becker et al. | |
| 7,153,822 | B2 | 12/2006 | Jensen et al. | |
| 7,250,397 | B2 | 7/2007 | Larsen et al. | |
| 7,470,787 | B2 | 12/2008 | Delong et al. | |
| 7,521,191 | B2 | 4/2009 | Khvorova et al. | |
| 7,627,938 | B2 | 12/2009 | Kim et al. | |
| 7,671,205 | B2 | 3/2010 | Delong et al. | |
| 7,786,074 | B2 | 8/2010 | Gourdie et al. | |
| 7,888,319 | B2 | 2/2011 | Gourdie et al. | |
| 7,918,814 | B2 | 4/2011 | Prausnitz et al. | |
| 8,034,789 | B2 | 10/2011 | Laux | |
| 8,034,943 | B2 | 10/2011 | Delong et al. | |

(Continued)

FOREIGN PATENT DOCUMENTS

| | | | |
|---|---|---|---|
| AU | 2009290861 | B2 | 8/2015 |
| DE | 3218121 | | 11/1983 |

(Continued)

OTHER PUBLICATIONS

ClinicalTrials.gov Id NCT04081103, "Nexagon for the treatment of corneal persistent epithelial defects following severe ocular chemical and/or thermal injuries (EXPEDE)", last update posted Aug. 30, 2022. (Year: 2022).*

Donnenfeld et al., A multicenter randomized controlled fellow eye trial of pulse-dosed difluprednate 0.05% versus prednisolone acetate 1% in cataract surgery, American Journal of Ophthalmology, vol. 152, pp. 609-617. (Year: 2011).*

"A Chinese procedure involving stem cell transplants is providing some very interesting results." Oct. 24, 2003. Canadian Paraplegic Association. Sep. 27, 2006 http://www.canparapleQic.oro/national/level12.to1?var1=storv&var2=20031024154627.

Abdullah et al. "Cell-to-Cell Communication and Expression of Gap Junctional Proteins in Human Diabetic and Nondiabetic Skin Fibroblasts." Endocrine, 1999, 10(1):35-41, Humana Press Inc.

(Continued)

*Primary Examiner* — Dana H Shin

(74) *Attorney, Agent, or Firm* — Wilson Sonsini Goodrich & Rosati

(57) ABSTRACT

The inventions relate to compounds and compositions comprising connexin modulators and their use in dose regimens for the treatment of non-healing or persistent ocular surface or corneal defects and disorders.

20 Claims, 1 Drawing Sheet

Specification includes a Sequence Listing.

(56) References Cited

U.S. PATENT DOCUMENTS

| | | | |
|---|---|---|---|
| 8,063,023 | B2 | 11/2011 | Becker et al. |
| 8,197,435 | B2 | 6/2012 | Prausnitz et al. |
| 8,247,384 | B2 | 8/2012 | Green et al. |
| 8,357,699 | B2 | 1/2013 | Delong et al. |
| 8,450,344 | B2 | 5/2013 | Delong et al. |
| 8,455,513 | B2 | 6/2013 | Delong et al. |
| 8,455,514 | B2 | 6/2013 | Delong et al. |
| 8,455,647 | B2 | 6/2013 | Delong et al. |
| 8,636,713 | B2 | 1/2014 | Prausnitz et al. |
| 8,716,310 | B2 | 5/2014 | Delong et al. |
| 8,808,225 | B2 | 8/2014 | Prausnitz et al. |
| 8,809,326 | B2 | 8/2014 | Bosanac et al. |
| 8,815,556 | B2 | 8/2014 | Gourdie et al. |
| 8,815,819 | B2 | 8/2014 | Laux |
| 8,921,392 | B2 | 12/2014 | Delong et al. |
| 8,975,237 | B2 | 3/2015 | Becker |
| 9,096,569 | B2 | 8/2015 | Delong et al. |
| 9,248,141 | B2 | 2/2016 | Becker |
| 9,302,903 | B2 | 4/2016 | Park et al. |
| 9,415,043 | B2 | 8/2016 | Kopczynski et al. |
| 9,457,044 | B2 | 10/2016 | Green |
| 9,738,892 | B2 | 8/2017 | Becker |
| 10,465,188 | B2 | 11/2019 | Green |
| 10,472,632 | B2 | 11/2019 | Laux et al. |
| 10,787,667 | B2 | 9/2020 | Laux et al. |
| 11,401,516 | B2 | 8/2022 | Green |
| 11,466,069 | B2 | 10/2022 | Green |
| 2003/0105165 | A1 | 6/2003 | Griffith |
| 2003/0108886 | A1 | 6/2003 | Finn et al. |
| 2003/0148968 | A1 | 8/2003 | Hammond |
| 2003/0215424 | A1 | 11/2003 | Seul et al. |
| 2004/0092429 | A1 | 5/2004 | Jensen et al. |
| 2004/0259768 | A1 | 12/2004 | Lauermann |
| 2005/0026836 | A1 | 2/2005 | Dack et al. |
| 2005/0053918 | A1 | 3/2005 | Barnea et al. |
| 2005/0075280 | A1 | 4/2005 | Larsen et al. |
| 2005/0119211 | A1 | 6/2005 | Chowrira et al. |
| 2005/0137525 | A1 | 6/2005 | Wang et al. |
| 2006/0105013 | A1 | 5/2006 | Ashkar et al. |
| 2006/0122117 | A1 | 6/2006 | Smith |
| 2007/0021704 | A1 | 1/2007 | Hariri et al. |
| 2007/0042964 | A1 | 2/2007 | Jensen |
| 2007/0232526 | A1 | 10/2007 | Kvistgaard et al. |
| 2007/0244062 | A1 | 10/2007 | Laux et al. |
| 2007/0254828 | A1 | 11/2007 | Dubreucq et al. |
| 2008/0095819 | A1 | 4/2008 | Gourdie et al. |
| 2008/0159979 | A1 | 7/2008 | Moore et al. |
| 2008/0261867 | A1 | 10/2008 | Klagsbrun et al. |
| 2009/0142295 | A1 | 6/2009 | Becker |
| 2009/0209627 | A1 | 8/2009 | Chatterton et al. |
| 2009/0215665 | A1 | 8/2009 | Gourdie et al. |
| 2010/0150877 | A1 | 6/2010 | O'Brien et al. |
| 2010/0279921 | A1 | 11/2010 | Duft |
| 2011/0038920 | A1 | 2/2011 | Mori et al. |
| 2011/0092449 | A1 | 4/2011 | Duft |
| 2011/0130345 | A1 | 6/2011 | Rohrer et al. |
| 2011/0130710 | A1 | 6/2011 | Becker et al. |
| 2011/0217313 | A1 | 9/2011 | Becker et al. |
| 2011/0243964 | A1 | 10/2011 | Duft |
| 2011/0245184 | A1 | 10/2011 | Duft |
| 2011/0300130 | A1 | 12/2011 | Becker et al. |
| 2011/0319482 | A1 | 12/2011 | Blower et al. |
| 2012/0093768 | A1 | 4/2012 | Laux et al. |
| 2012/0289579 | A1 | 11/2012 | Becker |
| 2012/0309822 | A1 | 12/2012 | Blower |
| 2013/0143952 | A1 | 6/2013 | Becker |
| 2013/0281524 | A1 | 10/2013 | Blower et al. |
| 2014/0018305 | A1 | 1/2014 | Rohrer |
| 2014/0371297 | A1 | 12/2014 | Laux |
| 2016/0331805 | A1 | 11/2016 | Green |
| 2017/0296571 | A1 | 10/2017 | Green |
| 2019/0290719 | A1 | 9/2019 | Becker |
| 2020/0063160 | A1* | 2/2020 | Ando .................. A61K 48/005 |
| 2021/0115445 | A1 | 4/2021 | Green |

FOREIGN PATENT DOCUMENTS

| | | | |
|---|---|---|---|
| EP | 0036676 | | 9/1981 |
| EP | 0052322 | | 5/1982 |
| EP | 0058481 | | 8/1982 |
| EP | 0088046 | | 9/1983 |
| EP | 0102324 | | 3/1984 |
| EP | 0142641 | | 5/1985 |
| EP | 0143949 | | 6/1985 |
| EP | 1 514 929 | A1 | 3/2005 |
| EP | 1100529 | B1 | 6/2005 |
| EP | 2238250 | | 10/2010 |
| EP | 2242844 | A2 | 10/2010 |
| EP | 2252690 | | 11/2010 |
| EP | 2510939 | | 10/2012 |
| JP | H11-502853 | | 3/1999 |
| JP | 2002-529421 | | 9/2002 |
| JP | 2002-535377 | A | 10/2002 |
| JP | 2003-238441 | A | 8/2003 |
| JP | 2003-529567 | | 10/2003 |
| JP | 2005-509621 | | 4/2005 |
| WO | WO 1994/012633 | | 6/1994 |
| WO | WO-1995034545 | A1 | 12/1995 |
| WO | WO 1996/19194 | A1 | 6/1996 |
| WO | WO 1998/024797 | | 6/1998 |
| WO | WO-2000000484 | A1 | 1/2000 |
| WO | WO 2000/044409 | A1 | 8/2000 |
| WO | WO 2000/069896 | | 11/2000 |
| WO | WO 2002/094981 | | 11/2000 |
| WO | WO 2002/042422 | | 5/2002 |
| WO | WO 2002/056910 | | 7/2002 |
| WO | WO 2003/014303 | | 2/2003 |
| WO | WO 2003/032964 | A2 | 4/2003 |
| WO | WO 2003032964 | | 4/2003 |
| WO | WO 2003/063891 | A1 | 8/2003 |
| WO | WO 2005/053600 | A2 | 6/2005 |
| WO | WO 2005/119211 | | 12/2005 |
| WO | WO 2006/032847 | A1 | 3/2006 |
| WO | WO 2006/069181 | A2 | 6/2006 |
| WO | WO 2006069181 | | 6/2006 |
| WO | WO 2006/134494 | | 12/2006 |
| WO | WO 2006134494 | A2 | 12/2006 |
| WO | WO-2007136769 | A2 | 11/2007 |
| WO | WO 2008/060622 | A2 | 5/2008 |
| WO | WO 2008/073479 | | 6/2008 |
| WO | WO-2008100636 | A2 | 8/2008 |
| WO | WO 2008/151022 | A2 | 12/2008 |
| WO | WO 2008/157840 | A2 | 12/2008 |
| WO | WO 2009/075881 | A2 | 6/2009 |
| WO | WO 2009/075881 | A3 | 6/2009 |
| WO | WO 2009/075882 | A2 | 6/2009 |
| WO | WO 2009/075882 | A3 | 6/2009 |
| WO | WO 2009/082039 | A1 | 7/2009 |
| WO | WO 2009/085268 | A2 | 7/2009 |
| WO | WO 2009/085269 | A2 | 7/2009 |
| WO | WO 2009/085270 | A2 | 7/2009 |
| WO | WO 2009/085271 | A2 | 7/2009 |
| WO | WO 2009/085272 | A2 | 7/2009 |
| WO | WO 2009/085273 | A2 | 7/2009 |
| WO | WO 2009/085274 | A2 | 7/2009 |
| WO | WO 2009/085275 | A2 | 7/2009 |
| WO | WO 2009/085277 | A2 | 7/2009 |
| WO | WO 2009/085268 | A3 | 8/2009 |
| WO | WO 2009/085269 | A3 | 8/2009 |
| WO | WO 2009/085270 | A3 | 8/2009 |
| WO | WO 2009/085271 | A3 | 8/2009 |
| WO | WO 2009/085273 | A3 | 8/2009 |
| WO | WO 2009/085274 | A3 | 8/2009 |
| WO | WO 2009/085275 | A3 | 8/2009 |
| WO | WO 2009/097077 | A2 | 8/2009 |
| WO | WO 2009/085277 | A3 | 10/2009 |
| WO | WO 2009/147442 | A1 | 12/2009 |
| WO | WO 2009/148613 | A1 | 12/2009 |
| WO | WO 2009155209 | | 12/2009 |
| WO | WO 2009/085272 | A3 | 6/2010 |
| WO | WO 2011/067608 | A1 | 6/2011 |
| WO | WO 2011072091 | A1 | 6/2011 |
| WO | WO 2013012758 | | 1/2013 |
| WO | WO 2013148736 | | 10/2013 |

(56) References Cited

FOREIGN PATENT DOCUMENTS

| | | | |
|---|---|---|---|
| WO | WO 2013163423 A1 | 10/2013 | |
| WO | WO 2014006407 | 1/2014 | |
| WO | WO-2014140510 A1 | 9/2014 | |
| WO | WO-2014144188 A1 * | 9/2014 | ............ A61L 27/54 |
| WO | WO-2015097461 A1 | 7/2015 | |
| WO | WO-2024187046 A1 | 9/2024 | |

OTHER PUBLICATIONS

Abramova, Tatyana. "Frontiers and approaches to chemical synthesis of oligodeoxyribonucleotides." Molecules 18.1 (2013): 1063-1075.

Abstracts, Society for Neuroscience, vol. 25, Part 1, 29th Annual Meeting, Miami Beach, FL, Oct. 23-28, 1999.

Addicks, et al., "Histologic characteristics of filtering blebs in glaucomatous eyes", Arch. Opthalmol., 1983, 101:795-798.

Adwan, et al. "Downregulation of osteopontin and bone sialoprotein II is related to reduced colony formation and metastasis formation of MDA-MB-231 human breast cancer cells." Cancer Gene Therapy (2004) 11: p. 109-120: Nature Publishing Group.

Agrawal, ed., "Antisense Oligonucleotides, towards clinical trials." Protocols for Oligonucleotides and Analogs, Synthesis and Properties Human Press Inc., "Antisense Oligonucleotides, towards clinical trials." New Jersey, 1996.

Aguayo, A.J., et al. J. Exp. Biol. 95:231-240 (1981).

Ahmadi, et al. Int. Ophthalmol. Clinics, 42(3):13-22 (2002).

Aitken, et. al. "Adenoviral Down-Regulation of Osteopontin Inhibits Human Osteoclast Differentiation In Vitro." Journal of Cellular Biochemistry (2004) 93: p. 896-903. Wiley-Liss, Inc.

Akopian, A., et al., "Gap Junction-Mediated Death of Retinal Neurons is Connexin and Insult Specific: A Potential Target for Neuroprotection," The Journal of Neuroscience, Aug. 6, 2014, 34(32):10582-10591.

Altschul, S.F. et al., "Basic Local Alignment Search Tool", J. Mol. Biol., 1990, 215:403-410.

Altschul, S.F., "A Protein Alignment Scoring System Sensitive at All Evolutionary Distances," J Mol Evol (1993) 36:290-300.

Anonymous: "EP13153125 Align Seq ID No. 6, 7, 31, 45, 50, 55, 60", Dec. 1, 2015, XP55232734, Retrieved from the Internet: URL:http://ibis.internal.epo.org/exam/jobResult?id=359213 [retrieved on Dec. 1, 2015].

Anwar, Saeed, Farin Mir, and Toshifumi Yokota. "Enhancing the Effectiveness of Oligonucleotide Therapeutics Using Cell-Penetrating Peptide Conjugation, Chemical Modification, and Carrier-Based Delivery Strategies." Pharmaceutics 15.4 (2023): 1130, 40 pages.

Antisense Research and Applications (1993), CRC Press, Chps. 2, 19, 28, 32.

Arnold, et. al., Seminars in Ophthalmology 17:39-46 (2002).

Ashcroft, et al. Nat Cell Biol. 1:260-6 (1999).

Baker, D.W. et al., "ACC/AHA Guidelines for the Evaluation and Management of Chronic Heart Failure in the Adult." 2001 American Colleae of Cardioloav and the American Heart Association.

Baldwin, Heather C., et. al., "Growth factors in corneal wound healing following refractive surgery: A Review" ACTA Ophthalmologica Scandinavica 80(3):238-247.

Barany and Merrifield, "The Peptides," eds. E. Gross and F. Meienhofer, vol. 2 (Academic Press, 1980) DD, 3-285.

Barker, and Gourdie, R.G. (Jan. 10, 2002). Connexin Interacting Proteins. In: Heart Cell Coupling and Impulse Propagation in Health and Disease. Eds., De Mello W.C. and Janse M.J., Kluwer, Boston, pp. 25-50.

Bashyam, Hema. "Scar-Free Healing." (Jan. 7, 2008) JEM 205(1): p. 2-3.

BBC News "Gels heal wounds more quickly"; http://news.bbc.co.uk/1/hi/health/3243633.stm. (2003).

Beaucage et al., eds., Current Protocols in Nucleic Acid Chemistry John Wiley & Sons, Inc., New York, 2000.

Becker DL, Green CR (2001) Gap junction-mediated interactions between cells. Chapter 3 in Cell-Cell Interactions—A Practical Approach TP Fleming, ed., Oxford University Press, pp. 47-70.

Becker, D., "Wound-healing technology shortlisted for award," University College London News, Oct. 2003, www.ucl.ac.uk/news-archive/2003/october-2003/latest/newsitem.shtml?0309 . . . , captured Sep. 29, 2006.

Becker, D.L. and Davies, C.S. (1995) The role of gap junctions in the development of the preimplantation mouse embryo. In Microscopy of Intercellular Communicating Junctions. Ed. R. Gourdie. Microsc. Res. Tech. 31, 364-374.

Becker, D.L. and Mobbs, P. (1999) Connexin alphal and cell proliferation in the developing chick retina. Experimental. Neurol. 156(2): 326-332.

Becker, D.L., Bonness, V., and Mobbs, P. (1998) Cell coupling in the retina: Patterns and purpose. Cell Biol. Int. 22 781-792.

Becker, D.L., Bonness, V., Catsicas, M. and Mobbs, P. (2002) Changing patterns of ganglion cell coupling and connexin expression during chick retinal development. J. Neurobiol. 52, 280-293.

Becker, D.L., Ciantar, D., Catslcas, M., Pearson, R. and Mobbs, P. (2001) Use of pIRES vectors to express EGFP and connexin constructs in studies of the role of gap junctional communication in the early development of the chick retina and brain. Cell Commun. Adhes. 8. 355-359.

Becker, D.L., Cook, J.E., Davies, C.S., Evans, W.H. and Gourdie, R. (1998) Expression of major gap junction connexin types in the working myocardium of eight chordates. Cell Biol. Int. 22, 527-543.

Becker, D.L., David-Leclerc, C. and Warner A.E. (1992) The relationship of gap junctions and compaction in the preimplantation mouse embryo. Development Suppl., 113-118.

Becker, D.L., et al. "Abnormal Connexin Expression is Associated with Delayed Would Healing in Diabetic Skin", Diabetes, vol. 56, Nov. 2007.

Becker, D.L., Evans, W.H., Green C.R. and Warner, A.E. (1995) Functional analysis of amino acid sequences in connexin 43 involved in intercellular communication through gap junctions. J. Cell Sci. 108, 1455-1467.

Becker, D.L., Evans, W.H., Green C.R. and Warner, A.E. (1995) Functional block of gap junctional communication using antipeptide antibodies: Molecular localization of the putative binding sites. Intercellular communication through gap junctions: Ed. Y. Kanno. Progress in Cell Research, 4; 427-430.

Becker, D.L., Lin, J.S. and Green G.R. (1999) Pluronic gel as a means of antisense delivery. In Antisense techniques in the CNS. A practical approach. Eds. R. Leslie, A.J. Hunter and H.A. Robertson. pp. 149-157.

Becker, D.L., McGonnell, I., Makarenkova, H., Patel, K., Tickle, C., Lorimer, J., and Green, C.R. (1999) Roles for alphal connexin in morphogenesis of chick embryos using a novel antisense approach. Dev. Genetics. 24, 33-42.

Becker, David L., et al. "Translating connexin biology into therapeutics." Seminars in Cell & Developmental Biology. vol. 50. Academic Press, 2016, p. 49-58.

Beeley N., Trends Biotechnol. Jun;12(6): 213-6 (1994).

Behrend, et. al. "Reduced Malignancy of ras-transformed NIH 3T3 Cells Expressing Antisense Osteopontin RNA." Cancer Research (Feb. 1, 1994) 54: p. 832-837.

Bennett, Zukin RS. Electrical coupling and neuronal synchronization in the Mammalian brain. Neuron. Feb. 19, 2004; 41(4):495-511.

Berge, et al., J. of Pharma Sci. 66, 1-19 (1977).

Berkovitz, B.K.B. and Becker, D.L. (2003) The detailed morphology and distribution of gap junction protein associated with cells from the intra-articular disc of the rat temporomandibular joint. Conn. Tiss. Res. 44, 12-18.

Bernstein, et. al. Invest Ophthalmol Vis Sci 44:4153-4162 (2003).

Berthoud, et al, "Peptide inhibitors of intercellular communication", Am. J. Physiol. Lung Cell Mol. Physiol., 2000, 279:L619-L622.

Bindlish et al., "Efficacy and safety of mitomycin-C in primary trabeculectomy: five-year follow-up", Ophthalmology, 2002, 109:1336-1341 & discussion 1341-1332.

Bioconjugate Techniques (Greg T. Hermanson, ed., Academic Press, 1996), Chapter 2 and 17.

(56) References Cited

OTHER PUBLICATIONS

Bittman, K., et al. (2002) Connexin expression in homotypic and heterotypic cell coupling in the developing cerebral cortex. J. Compo Neural 443, 201-212.
Blackburn JP, Connat JL, Severs NJ, Green CR. "Connexin43 gap junction levels during development of the thoracic aorta are temporally correlated with elastic laminae deposition and increased blood pressure." Cell Biol Int. Feb. 1997;21(2):87-97. PMID: 9080656 [PubMed—indexed for Medline.
Blackburn JP, Peters NS, Yeh HI, Rothery S, Green CR, Severs NJ. "Upregulation of connexin43 gap junctions during early stages of human coronary atherosclerosis." Arterioscler Thromb Vase Biol. Aug. 1995;15(8):1219-28. PMID: 7627716 [PubMed—indexed for Medline].
Bobbie et al., "Reduced connexin 43 expression and its effect on the development of vascular lesions in retinas of diabetic mice", Invest. Ophthalmol. Vis. Sci., 2010, 51(7):3758-63.
Boitano, et al., "Connexin mimetic peptides reversibly inhibit Ca2+ signaling through gap junctions in airway cells", Am. J. Physiol Lung Cell Mol. Physiol., 2000, 279:L623-L630.
Bork et al. Go hunting in sequence databases but watch out for the traps. Trends in Genetics. 12(10): 425-427, 1996.
Bork, A. "Powers and pitfalls in sequence analysis: the 70% hurdle." Genome Res 1O: 398-400, 2000.
Boto, Alicia, et al. "Site-selective modification of peptide backbones." Organic Chemistry Frontiers 8.23 (2021): 6720-6759.
Braasch, D.A. and Corey, D.R., Biochemistry 41, 4503-451 O (2002).
Braet, K., et al., "Pharmacological senstivity of aTP release triggered by photoliberation of inositol-1,4,5-triphosphate and zero extracellular calcium in brain endothelial cells," Journal of Cellular Physiology, 197(2):205-213 (2003).
Branch, A.D. Hepatology 24, 1517-1529 (1996).
Branch, et. al. "A good antisense molecule is hard to find." TIBS (Feb. 1998) 23: p. 45-50. Elsevier Science Ltd.
Brandner, et. al., "Connexins 26, 30, and 43: Differences Among Spontaneous, Chronic, and Accelerated Human Wound Healing." J. Invest Dermatol. 122:1310-20 (2004).
Bregman, B.S., Experimental Neurology 149, 13-27 (1998).
Brenner, S.E. Errors in genome function. Trends in Genetics 15(4): 132-133, 1999.
Brummelkamp T., et al., Science 296:550-553 (2002).
Brunton. Chapter 38. In: Goodman & Gilman's The Pharmacological Basis of Therapeutics, 9th Ed., (1996).
Brysch, W. "Antisense Technology in the Ventral Nervous System", ed. H.A. Robertson; Oxford University Press. pp. 21-41 (1999).
Buono, et. al. Survey of Ophthalmology 50:15-26 (2005).
Buur, et al. J. Control Rel. 14:43-51 (1990).
Cairns, et al. Nat. Biotech 17:480-486 (1999).
Calabrese, A., "Connesin 36 Controls Snychronization of Ca2+ Oscillations and Insulin Secretion in MIN6 Cells," Diabetes, vol. 52, Feb., 2003.
Camelliti P, Devlin GP, Matthews KG, Kohl P, Green CR. Spatially and temporally distinct expression of fibroblast connexins after sheep ventricular infarction. Cardiovasc Res. May 1, 2004 ;62(2):415-25. PMID: 15094361 [PubMed—indexed for Medline].
Camelliti P, Green CR, Kohl P. Structural and functional coupling of cardiac myocytes and fibroblasts. Adv Cardiol. 2006;42:132-49. Review. PMID: 16646588 [PubMed—indexed for Medline].
Caplen N. et al., Proc Natl Acad Sci 98:9742-9747 (2001).
Caufriez, Anne, et al. "Peptide-based targeting of connexins and pannexins for therapeutic purposes." Expert Opinion on Drug Discovery 15.10 (2020): 1213-1222.
Cech, Biotechnology 13:323-326 (1995) Group I Introns: New Molecular Mechanisms for MRNA repair.
Celetti, et. al. "Overexpression of the Cytokine Osteopontin Identifies Aggressive Laryngeal Squamous Cell Carcinomas and Enhances Carcinoma Cell Proliferation and Invasiveness." (2005) Clinical Cancer Res 11(22): p. 8019-8027. AACR Journals.
Chakraborti, S. and Banerjee, A.C., Mol. Thar. 7, 817-826 (2003).
Chang CY, et al "Comparison of stem cell properties in cell populations isolated from human central and limbal corneal epithelium." Cornea. Oct. 2011;30(10):1155-1162.
Chauhan, Dhruv, Lieselotte Vande Walle, and Mohamed Lamkanfi. "Therapeutic modulation of inflammasome pathways." Immunological Reviews 297.1 (2020): 123-138.
Chen et al. Cytotoxicity and vitreous stability of chemically modified connexin43 mimetic peptides for the treatment of optic neuropathy. Journal of Pharmaceutical Science. 2013;102:2322-2331.
Chen et al. Intravitreal injection of lipoamino acid modified Connexin43 mimetic peptide enhances neuroprotection after retinal ischemia. Drug Deliv Transl Res. 2015; 5:480-488.
Chen et al. Sustained intravitreal delivery of connexin43 mimetic peptide by poly(D,L-lactide-co-glycolide) acid micro- and nanoparticles—Closing the gap in retinal ischaemia. European Journal of Pharmaceutics and Biopharmaceutics. 2015. 95(Pt B):378-386.
Chen YS, et al "Neuroprotection in the treatment of glaucoma—A focus on connexin43 gap junction channel blockers" Eur J Pharm Biopharm. Sep. 2015;95(Pt B):182-193.
Chen, et al, "In vitro release characteristics and cellular uptake of poly(D, L-lactic-co-glycolic acid) nanoparticles for topical delivery of antisense oligonucelotides", Drug Delivery, 2011, 18:493-50.
Chen, et al., "Cytotoxicity and vitreous stability of chemically modified connexin-43 mimetic peptides for the treatment of optic neuropathy", J. Pharm. Sci., 2013, 102:2322-2331.
Chen, Qing, et al. "Carcinoma-astrocyte gap junctions promote brain metastasis by cGAMP transfer." Nature 533.7604 (2016): 493-498.
Cheng et al. "Spinal Cord Repair in Adult Paraplegic Rats: Partial Restoration of Hind Limb Function" Science, Jul. 26, 1996, 273:510-513.
Cheng et al., J. Biol. Chem. 263:15110-15117 No. 29, (Oct. 15, 1998).
Cheng, et al., TrkB Gene Transfer Protects Retinal Ganglion Cells from Axotomy-Induced Death in Vivo., J. Neurosci., 2002, 22:3977-3896.
Chew SS, et al "Response of retinal Connexin43 to optic nerve injury." Invest Ophthalmol Vis Sci. Jun. 1, 2011;52(6):3620-3629.
Chonn, et al., Current Op. Biotech. 6, 698-708 (1995).
Chou et al. "Quantitative Analysis of Dose-Effect Relationships: The Combined Effects of Multiple Drugs or Enzyme Inhibitors", Ad. Enzyme Reg., 1984, 22:27-55.
Chou, C., Current Protocols in Nucleic Acid Chemistry (2000) 10.1.1-10.1.25.
Coffey KL, Krushinsky A, Green CR, Donaldson PJ. "Molecular profiling and cellular localization of connexin isoforms in the rat ciliary epithelium." Exp Eye Res. Jul. 2002;75(1):9-21. PMID: 12123633 [PubMed • indexed for Medline].
Collaborative Neuroscience the Spinal Cord Injury Project. Care Cure Community Postings for "Gel is helping wounds heal in half the time'/nexagon." Sep. 29, 2006 http://sci.rutgers.edu/forum/showthread.php?t=6653.
Collaborative Normal-Tension Glaucoma Study Group, Comparison of glaucomatous progression between untreated patients with normal-tension glaucoma and patients with therapeutically reduced intraocular pressures, Am. J. Ophthalmol., 1998, 126:487-497.
Collignon et al., Ophthalmology 111 :1663-1672 (2004).
Common, J.E.A, Becker, D.L., Di, W.L., Leigh, I.M., O'Toole, E.A. and Kelsell, D.P. (2002) "Functional studies of human skin disease- and deafness-associated Connexin 30 mutations." Biochem. Biophys. Res. Commun. 298, 651-656.
Concise Encyclopedia of Polymer Science and Engineering, pp. 858-859 (1990).
Contreras, et al., "Functioning of Cx43 Hemichannels Demonstrated by Single Channel Properties, Cell Communication and Adhesion", 2003, 10(4-6):245-249.
Cook, J.E. and Becker, D.L. (1995) Gap Junctions in the vertebrate retina. In Microscopy of Intercellular Communicatina Junctions. Ed. R. Gourdie. Microsc. Res. Tech. 31, 408-419.
Cooper, et.al. "Wound healing and inflammation genes revealed by array analysis of macrophageless PU.I null mice." Genome Biology (2004) 6(I): Article 5.

(56) References Cited

OTHER PUBLICATIONS

Corredor and Goldberg, "Retinal Ganglion Cell Life and Death—Mechanisms and Implications for Ophthamology," European Ophthalmology Review Touch Briefings, p. 109-112 (2009).
Cotrina, et al. "Astrocytic gap junctions remain open during eschemic conditions." J. Neurosci., 18:2520-2537.
Cotter et al. Curr Opin Cardiol 16: 159-163, 2001.
Courtman, et al. J Biomed Mater Res 28:655-666 (1994).
Coutinho, et al. "Dynamic Changes in connexin expression correlate with key events in the wound healing process." Cell Biology International 27 (2003) 525-541.
Coutinho, P., Frank, S., Qiu, C., Wang, C.M., Brown, T., Green, C.R. and Becker D.L. (2005) Limiting wound extension by transient inhibition of connexin43 expression at the site of injury. Brit. J. Plast. Surg. 58, 658-667.
Cronin M, Anderson PN, Green CR, Becker DL. "Antisense delivery and protein knockdown within the intact central nervous system" Front Biosci 11 (2006): 2967-2975.
Crooke et al., J. Pharmacol. Exp. Ther., 1996, vol. 277, 923-937.
Crowe, M. et al., "Delayed Wound Healing in Immunodeficient TGF-β1 Knockout Mice", *J. Invest. Dermatol.*, 2000, 115:3-11.
Cupps, et al., "Corticosteroid-mediated immunoregulation in man", Immunol. Rev., 1982, 65:133-155.
Current Protocols in Immunology (J.E. Coligan et al., eds., 1991) vol. I, Ch. 1.
Current Protocols in Molecular Biology (F.M. Ausubel et al., 1987, including supplements through 2001).
Cutroneo, K., "How Is Type I Procollagen Synthesis Regulated at the Gene Level During Tissue Fibrosis", *J. Cell. Biochem.*, 2003, 90:1-5.
Dagle et al., Nucleic Acids Research 19:1805 (1991).
Dahl, et al., "Attempts to Define Functional Domains of Gap Junction Proteins with Synthetic Peptides", Biophys. J., 1994, 67:1816-1822.
Danesh-Meyer et al. Connexin43 in retinal injury and disease. Prog Retinal Eye Res 51: 41-68, 2016.
Danesh-Meyer et al. Connexin43 mimetic peptide reduces vascular leak and retinal ganglion cell death following retinal ischaemia. Brain 135: 506-520, 2012.
Dang, et. al. "The carboxy-tail of connexin-43 localizes to the nucleus and inhibits cell growth." Molecular and Cellular Biochemistry (2003) 242: p. 35-38. Kluwer Academic Publishers. Netherlands.
Dao-Yi et al. Pathogenesis and intervention stratedies in diabetic retinopathy. Clin Exp Ophthalmol 29: 164-166, 2001.
Darrow, B.J., "Expression of Multiple Connexins in Cultured Neonatal Rat Ventricular Myocytes," Circulation Research, 1995; 76:381-387.
Das, et al., "Protection of retinal cells from ischemia by a novel gap junction inhibitor", Biochem. Biophys. Res. Commun., 2008, 373:504-508.
Database EMBL, Jul. 9, 2006, "Rattus norvegicus piRNA piR-152346, complete sequence." Retrieved from EBI accession No. EMBL: DQ737024.
Database Geneseq, Dec. 28, 2007, "Viral regulatory miRNA Seq ID No. 263327" Retrieved from EBI accession No. GSN: AJK11008.
Database Geneseq, Dec. 28, 2007, "Viral regulatory miRNA Seq ID No. 286128" Retrieved from EBI accession No. GSN AJK33809.
Davidson JO, et al "Battle of the hemichannels—Connexins and Pannexins in ischemic brain injury." Int J Dev Neurosci. Oct. 2015;45:66-74.
Davidson JO, et al "Connexin hemichannel blockade is neuroprotective after asphyxia in preterm fetal sheep" PLoS One. May 27, 2014;9(5):e96558.
Davidson JO, et al "Deleterious effects of high dose connexin 43 mimetic peptide infusion after cerebral ischaemia in near-term fetal sheep." Int J Mol Sci. 2012;13(5):6303-6319.
Davidson JO, et al "Non-additive effects of delayed connexin hemichannel blockade and hypothermia after cerebral ischemia in near-term fetal sheep." J Cereb Blood Flow Metab. Dec. 2015;35(12):2052-2061.
Davidson JO, et al. "A key role for connexin hemichannels in spreading ischemic brain injury." Curr Drug Targets. Jan. 1, 2013;14(1):36-46.
Davidson JO, et al. "Connexin hemichannel blockade improves outcomes in a model of fetal ischemia" Ann Neurol. Jan. 2012;71(1):121-132.
Davidson, J.O. et al., Connexin Hemichannel Blockade is Neuroprotective After, But Not During, Global Cerebral Ischemia in Near-Term Fetal Sheep, Experimental Neurology, 2013, 248:301-308.
Davidson. "Animal Models for Wound Repair." Arch Dermatol. Res., 1998, 290:S1-S11, Springer-Verlag.
Davis, et al. "Modulation of Connexin43 Expression: Effects on Cellular Coupling" Journal of Cardiovascular Electroohvsioloav, Futura Publishina Co., 6(2):103-114 (1995).
Dean, Nicholas M., et al. "The use of antisense oligonucleotides to inhibit expression of isozymes of protein kinase C." Applied Antisense Oligonulceotide Technology, Stein,C. and Krieg,A. (eds), (1998) Chapter 10, pp. 193-205.
De Carvalho, A.C.C., "Conduction Defects and Arrhythmias in Chagas' Disease: Possible Role of Gap Junctions and Humoral Mechanisms," J Cardiovasc Electrophysiol, vol. 5, pp. 686-698, Aug. 1994.
Degruyter, Justine N., Lara R. Malins, and Phil S. Baran. "Residue-specific peptide modification: a chemist's guide." Biochemistry 56.30 (2017): 3863-3873.
De Jong, "Age-related macular degeneration", N. Engl. J. Med., 2006, 355:1474-1485.
Delmar, M, Laird, DW, et al. Connexins and Disease, Cold Spring Harb Perspect Biol 10.9:a029348 (2018), 20 pages.
De Vries and Schwartz, "Hemi-gap-junction channels in solitary horizontal cells of the catfish retina" Journal of Physiology, 445:201-230 (1992).
De Vriese, An S., Johan Van de Voorde, and Norbert H. Lameire. "Effects of connexin-mimetic peptides on nitric oxide synthase-and cyclooxygenase-independent renal vasodilation." Kidney International 61.1 (2002): 177-185.
Decrock E, et al "Connexin and pannexin signaling pathways, an architectural blueprint for CNS physiology and pathology?" Cell Mol Life Sci. Aug. 2015;72(15):2823-2851.
Deitz, et al. Ophthalmology 93:1284 (1986).
Deva, Narmadai C., et al. "Connexin43 modulation inhibits scarring in a rabbit eye glaucoma trabeculectomy model." Inflammation 35 (2012): 1276-1286.
Devereux, J. et al., "A comprehensive set of sequence analysis programs for the VAX", Nucleic Acids Research, 1984, 12(1):387-395.
Devlin, G., et al. J. "An ovine model of chronic stable heart failure" J. Card. Fail. 6:140-143 (2000).
Dhein, et al., "A new synthetic antiarrhythmic peptide reduces dispersion of epicardial activation recovery interval and diminishes alterations of epicardial activation patterns induced by regional ischemia. A mapping study", Naunyn-Schmiedeberg's Arch. Pharm., 1994, 350:174-184.
Dhein, et al.,"Effects of the New Antiarrhythmic Peptide ZP123 on Epicardial Activation and Repolarization Pattern," Cell Commun. Adhes., 2003, 10:371-378.
Dhokchawle, B, et al., Promoieties Used in Prodrug Design: A Review. Indian Journal of Pharmaceutical Education 48(2):35-40 (2014).
Di, W.-L., Lachelin, G.C.L., McGarrigle, H.H.G., Thomas, N.S.B. and Becker, D.L. (2001) Oestriol and oestradiol increase cell to cell communication and connexin 43 protein expression in cultured human mvometrial cells. Mol. Human Reorod. 7, 671-679.
Dias, N. and Stein, C.A. Mol. Cancer Thor. 1347-355 (2002).
Diaz-Valle, David, et al. "Comparison of the efficacy of topical insulin with autologous serum eye drops in persistent epithelial defects of the cornea." Acta Ophthalmologica 100.4 (2022): e912-e919.

(56) References Cited

OTHER PUBLICATIONS

Diegelmann, et. al. "Wound Healing: An Overview of Acute, Fibrotic and Delayed Healing." (Jan. 1, 2004) Frontiers in Bioscience 9: p. 283-289. Irvine, CA.
Dixon et al., VEGF Trap-Eye for the treatment of Neovascular age-related macular degeneration, Expert Opinion on Investigational Drugs, 18:1573-1580 (2009).
Doerks et al. Protein annotation: detective work for function prediction. Trends in Genetics 14(6): 248-250, 1998.
Dovi, J.V., et al. J Leukoc Biol 73:448-55 (2003).
Dublin, et. al. "Satellite glial cells in sensory ganglia: Their possible contribution to inflammatory pain." (2007) Brain, Behaviior, and Immunity 21: p. 592-598. Elsevier Inc.
Duffy, H.S., Ashton, AW., O'Donnell, P., Coombs, W., Taffet, S.M., Delmar, M., and Spray, D.C. (Feb. 6, 2004). Regulation of connexin43 protein complexes by intracellular acidification. Circ. Res. 94, 215-222.
Eckstein, F., ed. Oligonucleotides and Analogues, A Practical Approach, IRL Press at Oxford University Press (1991).
Edgington, Biotechnology 10:256 (1992).
Einarson, M.B. et al., "Identification of Protein-Protein Interactions with Glutathione S-Transferase Fusion Proteins," In Protein-Protein Interactions: A Molecular Cloning Manual, Cold Springs Harbor Laboratory Press DD., Chapt. 4, pp. 37-57 (2002).
Elbashir S., et al., "Duplexes of 21-nucleotide RNAs mediate RNA interference in cultured mammalian cells." Nature 411 :494-498 (2001).
El-Fouly, et al., "Scrape-Loading and dye transfer: A rapid and simple technique to study gap junctional intercellular communication", Experimental Cell Research, 1987, 168(2):422-430.
El-Hariri, et al. J. Pharm. Pharmacol. 44:651-654 (1992).
Englisch et al., Angewandte Chemie, International Edition, 30, 613-722 (1991).
Evans and Boitano, "Connexin mimetic peptides: specific inhibitors of gap-junctional intercelluar communication", Biochem. Soc. Trans., 2001, 29(Pt. 4):606-612.
Evans et al., J. Med. Chem. 30:1229 (1987).
Evans, W.H., et al. "Connexin mimetic peptides: specific inhibitors of gap-junctional intercellular communication." Biochem. Soc. Trans., 2001, 29:606-612.
Fairless, R. et al., "N-cadherin differentially determines Schwann cell and olfactory ensheathing cell adhesion and migration responses upon contact with astrocytes", Mol. Cell. Neurosci., 2005, 28(2):253-263.
Fauchere, J. Adv. Drug Res. 15:29 (1986).
Fearon, K.L., Current Protocols in Nucleic Acid Chemistry (2000) 4.7.1-4.7-40.
Feng, Jiajun, et al. "Connexin 43 upregulation in burns promotes burn conversion through spread of apoptotic death signals." Burns 46.6 (2020): 1389-1397.
Ferrin, Lance J. and Camerini-Otero, R. Daniel. "Selective Cleavage of Human DNA: RecA-Assisted Restriction Endonuclease (RARE) Cleavage." Science, Dec. 6, 1991, 254:1494-1497.
Finger, et al., "Opthalmic plaque radiotherapy for age-related macular degeneration associated with subretinal neovascularization", Am. J. Opthalmol., 1999, 127:170-177.
Fingl, et al., In: The Pharmacological Basis of Therapeutics, Ch.1, p. 1, 1975.
Flower NE, and Green CR. A new type of gap junction in the phylum Brachiopoda. Cell Tissue Res. 1982;227(1 ):231-4.
Fonseca CG, Green CR, Nicholson LF. Upregulation in astrocytic connexin 43 gap junction levels may exacerbate generalized seizures in mesial temporal lobe epilepsy. Brain Res. Mar. 1, 2002; 929(1): 105-16. PMID: 11852037 [PubMed—indexed for Medline].
Foote et al. "The Pattern of Disulfide Linkages in the Extracellular Leep Regions of Connexin 32 Suggests a Model for the Docking Interface of Gap Junctions." Journal of Cell Biology, 1998, 140(5):1187-1197.
Ford et al., "Expression and role of VEGF-A in the ciliary body", Invest. Ophthalmol. Vis. Sci., 2012, 53:7520-7527.
Forge, "The inner ear contains heteromeric channels composed of cx26 and cx30 and deafness-related mutations in cx26 have a dominant negative effect on cx30", Cell Commun. Adhes., 2003, 10(4-6):341-346.
Forge, A, Becker, D.L., Casalotti, S., Edwards, J., Evans, W.H., Lench, N. and Souter, M. (1999) Gap junctions and connexin expression in the inner ear. In gap junction-mediated intercellular signalling in health and disease. Novartis Foundation Symposium 219. 134-156. Wiley.
Forge, A., Becker, D.L., Casalotti, S., Edwards, J., Marziano, N. and Nevill, G. (2003) Gap Junctions in the Inner Ear: Comparison of Distribution Patterns in Different Vertebrates and Assessment of Connexin Composition in Mammals, J. Comp. Neurol. 467, 207-231.
Forge, A., Becker, D.L., Casalotti, S., Edwards, J., Marziano, N. and Nickel, R. (2002) Connexins and gap junctions in the inner ear. Audiol. Neuro. Otol. 7 141-145.
Fortes, P. et al., Proc. Natl. Acad. Sci. USA 100, 8264-8269 (2003).
Foulkes MR, et al., Stroke 19:547-54 (1988).
Frantseva, M., et al. "Ischemia-Induced Brain Damage Depends on Specific Gap-Junctional Coupling." Journal of Cerebral Blood Flow and Metabolism, 22:453-462 (2002).
Fraser SE, Green CR, Bode HR, Gilula NB. Selective disruption of gap junctional communication interferes with a patterning process in hydra. Science. Jul. 3, 1987;237(4810):49-55. PMID: 3037697 [PubMed—indexed for Medline].
Friedman et al., "Prevalence of age-related macular degneration in the United States", Arch. Ophthalomol., 2004, 122:564-572.
Galasso, et. al. Seminars in Ophthalmology 19:75-77 (2004).
Garcia-Dorada et al. "Gap Junction Uncoupler Heptanol Prevents Cell-to-Cell Progression of Hypercontracture and Limits Necrosis During Myocardial Reperfusion", Circulation, Nov. 18, 1997, 96(10):3579-3586.
Gaudana, Ripal, et al. "Ocular drug delivery." The AAPS Journal 12 (2010): 348-360.
Gee et al., in Huber and Carr, 1994, "Molecular and Immunologic Approaches," Futura Publishing co, Mt. Kisco NY.
Gerrits, et al., Pediatr Res 57(3):342-6 (2005).
Ghatnekar et al. Regrn Med. 4(2):205-223, 2009.
Giaume, C., et al. "Control of gap-junctional communication in astrocytic networks." TINS, 19:319-325.
Giepmans BN. Gap junctions and Connexin-interacting proteins. Cardiovasc Res. May 1 ;62(2):233-45 (May 1, 2004).
Giepmans et al. "Interaction of c-Src with gap junction protein connexin-43. Role in the regulation of cell-cell communication." J Biol. Chem., 2001, 276(11):8544-8549.
Gil, J., Esteban M., "Induction of apoptosis by the dsRNA-dependent protein kinase (PKR): Mechanisms of action." Apoptosis 2000, 5:107-114.
Gil-Parrado, S., et al. (Mar. 2003). Calpastatin exon 1 B-derived peptide, a selective inhibitor of calpain:enhancing cell permeability by conjugation with penetratin. Biol Chem 3 84, 395-402.
Goadsby, Peter J. "Bench to bedside advances in the 21st century for primary headache disorders: migraine treatments for migraine patients." (2016): Brain, 139(10), 2571-2577.
Goldberg, Gary S., Virginijus Valiunas, and Peter R. Brink. "Selective permeability of gap junction channels." Biochimica et Biophysica Acta (BBA)-Biomembranes 1662.1-2 (2004): 96-101.
Goliger et al. "Wounding Alters Epidermal Connexin Expression and Gap Junction-mediated Intercellular Communication." Molecular Biology of the Cell, 1995, 6:1491-1501.
Gonzalez-Mariscal, L. et al. (Jan. 2003). Tight junction proteins, Prog Biophys Mol Biol 81, 1-44.
Goodenough, "Topological distribution of two connexin32 antigenic sites in intact and split rodent hepatocyte gap junctions", J. Cell Biol., 1988, 107:1817-1824.
Goodenough et al. (Apr. 2003). Beyond the gap: functions of unpaired connexon channels. Nat Rev Mol Cell Biol 4, 285-294.
Görbe, A., Becker, DL., Dux, L., Stelkovics, E., Krenacs, L., Bagdi, E., and Krenacs, T. (2005) Transient upregulatlon of connexin 43 gap junction coupling in myoblasts may synchronize cell cycle control preceding syncytial fusion during skeletal muscle differentiation. Histochem. Cell Biol. 123; 573-583.

(56) References Cited

OTHER PUBLICATIONS

Gorbe, Aniko, et al. "In differentiating prefusion myoblasts connexin43 gap junction coupling is upregulated before myoblast alignment then reduced in post-mitotic cells." Histochemistry and cell biology 125 (2006): 705-716.
Gourdie RG, Green CR, Severs NJ, Anderson RH, Thompson RP. Evidence for a distinct gap-junctional phenotype in ventricular conduction tissues of the developing and mature avian heart. Circ Res. Feb. 1993;72(2):278-89. PMID: 8380357 [PubMed—indexed for Medline].
Gourdie RG, Green CR, Severs NJ. Gap junction distribution in adult mammalian myocardium revealed by an anti-peptide antibody and laser scanning confocal microscopy. J Cell Sci. May 1991;99 (Pt 1):41-55. PMID: 1661743 [PubMed—indexed for Medline].
Gourdie RG, Harfst E, Severs NJ, Green CR. Cardiac gap junctions in rat ventricle: localization using site-directed antibodies and laser scanning confocal microscopy. Cardioscience. Mar. 1990;1(1 ):75-82 PMID: 1966373 [PubMed—indexed for Medline].
Gourdie, et al. "Immunolabeling patterns of gap junction connexins in the developing and mature rat heart." Anat Embrvol 185:363-378 (1992).
Gourdie, et al. "The spatial distribution and relative abundance of gap-junctional connexin40 and connexin43 correlate to functional properties of components of the cardiac atrioventricular conduction system." Journal of Cell Science 105, 985-991 (1993).
Gourdie, et. al. "The Unstoppable Connexin43 Carboxyl-Terminus" (2006) Ann. N.Y. Acad. Sci. 1080: p. 49-62. New York Academy of Sciences.
Grazul-Bilska, et al. Abstract, Biology Reproduction, 58(1):78 (1998).
Green and Severs. "Distribution and role of gap junctions in normal myocardium and human ischaemic heart disease." Histochemistry, 1993, 99: 105-120.
Green C.R, Law, L.Y., Lin, U.S. and Becker, D.L. (2001) "Spatiotemporal depletion of connexins using antisense oligonucleotides. Techniques in the study of gap junctions." Connexin methods and protocols 154 175-185. Eds R. Bruzzone and C. Giuame.
Green CR, Bowles L, Crawley A, Tickle C. Expression of the connexin43 gap junctional protein in tissues at the tip of the chick limb bud is related to the epithelial-mesenchymal interactions that mediate morohoaenesis. Dev Biol. Jan. 1994;161(1):12-21. PMID: 8293868 [PubMed—indexed for Medline].
Green CR, Harfst E, Gourdie RG, Severs NJ. Analysis of the rat liver gap junction protein: clarification of anomalies in its molecular size. Proc R Soc Lond B Biol Sci. Mar. 22, 1988;233(1271):165-74. PMID: 2898146 (PubMed—Indexed for Medline).
Green CR, Peters NS, Gourdie RG, Rothery S, Severs NJ. "Validation of immunohistochemical quantification in confocal scanning laser microscopy: a comparative assessment of gap junction size with confocal and ultrastructural techniques." J Histochem Cytochem. Sep. 1993;41 (9):1339-49. PMID: 8354875 [PubMed—indexed for Medline].
Green CR, Severs NJ. Connexon rearrangement in cardiac gap junctions: evidence for cytoskeletal control? Cell Tissue Res. 1984;237(1):185-6. PMID: 6090023 [PubMed—indexed for Medline].
Green CR, Severs NJ. Gap junction connexon configuration in rapidly frozen myocardium and isolated intercalated disks. J Cell Biol. Aug. 1984.99(2):453-63.
Green CR. Evidence mounts for the role of gap junctions during development. Bioessays. Jan. 1988;8(1):7-10. Review. No abstract available. PMID: 2835035 [PubMed—indexed for Medline].
Greene CA, "Cells from the adult corneal stroma can be reprogrammed to a neuron-like cell using exogenous growth factors." Exp Cell Res. Mar. 10, 2014;322(1):122-132.
Greenfield et al., "Late-onset bleb leaks after glaucoma filtering surgery", Arch.Opthalmol., 1998, 116:443-447.
Grose, R. et al.., "Wound-Healing Studies in Transgenic and Knockout Mice", *Molecular Biotechnology*, 2004, 28:147-166.
Grupcheva CN, et al "Improved corneal wound healing through modulation of gap junction communication using connexin43-specific antisense oligodeoxynucleotides." Invest Ophthalmol Vis Sci. Mar. 2, 2012;53(3):1130-1138.
Guadana, et al., "Ocular Drug Delivery", The AAPS Journal, 2010, 12(3):348-360.
Guan, et al., Neuroscience, vol. 95, No. 3, pp. 831-839 (2000).
Gunn, et al., J Clin Invest 99(2):248-256 (1997).
Gunn, et al., Pediatr Res 46(3):274-280 (1999).
Guo CX, et al.. "Gap junction proteins in the light-damaged albino rat." Mol Vis. May 27, 2014;20:670-682.
Guo et al. Connexin43 mimetic peptide improves retinal function and reduces inflammation in a light damaged albino rat model. *Investigative Ophthalmology and Visual Science*, 2016; 57: 3961-3973.
Hall, Celia. "Gel is helping wounds heal in half the time." Telegraph UK. Oct. 20, 2003. http://www.telegraph.co.uk/news/main.i htm il?xml=/news/2003/10/20/nQe 120.xml&sSheet == . . . .
Han Chunmao, et al. "Optimal time for the administration of rhGH in severely burned patients-analysis of the dynamic changes in IGF axis and blood sugar," Aug. 31, 2003, Chin J. Burns, vol. 19, No. 4 pp. 213-215.
Hao, Min, Jianjun Qiao, and Hao Qi. "Current and emerging methods for the synthesis of single-stranded DNA." Genes 11.2 (2020): 116, 15 pages.
Haopeng, L., Abstract: "Experimental study on spinal cord injury treated with the combination of fetal spinal cord transplantation and methylprednisolone," j Xi'an Med Uni (2001) vol. 13, No. 2, pp. 138-141.
Hardman, et al. McGraw-Hill, New York, N.Y., 934-935 (1996).
Hardy, K., Spanos, S. and Becker, D.L. (2003) Cell death (Apoptosis) in human blastocysts. Chpt. 9 p. 185-202 an Atlas of Human Blastocysts. Eds. L.L. Veeck and N. Zaninovic. CRC Press.
Hardy, K., Warner, A.E., Winston, R.M.L. and Becker, D.L. (1996) Expression of intercellular junctions durino the preimolantation develooment of the human embrvo. Molec. Human Reprod. 2, 621-632.
Harfst E, Severs NJ, Green CR. Cardiac myocyte gap junctions: evidence for a major connexon protein with an apparent relative molecular mass of 70,000. J Cell Sci. Aug. 1990;S6 (Pt 4):591-604.
Harlow and Lane (1988) Antibodies, A Laboratory Manual, Cold Spring Harbor Publications, New York, 5 Pages.
Harlow and Lane (1999) Using Antibodies: A Laboratory Manual Cold Spring Harbor Laboratory Press, Cold Spring Harbor, NY, pp. 189-242, 511-531.
Haseloff and Gerlach, Nature Aug. 18;334(6183):585-91 (1988).
Hauge et al, Effects of tonabersat on migraine with aura: a randomised, double-blind, placebo-controlled crossover study, The Lancet Neurology, 2009, 8:718.
Hawat et al., "Connexin 43 mimetic peptide Gap26 confers protection to intact heart against myocardial ischemia injury," Pflugers Arch.—Eur. J. Physiol. 460(3):583-592 (Jun. 1, 2010).
Heart, The Pathologic Basis of Disease, 2nd Edition, 1979, Chapter 15, pp. 643-710.
Heasman, J., Dev. Biol., 243, 209-214 (2002).
Heijl et al., Reduction of intraocular pressure and glaucoma progression: results from the Early Manifest Glaucoma Trial, Arch. Opthalmol., 2002, 120:1268-1279.
Henikoff and Henikoff. "Amino acid substitution matrices from protein blocks." Proc. Natl. Acad. Sci. USA, 1992, 89:10915-10919.
Hennemann et al. "Molecular cloning. of mouse connexins26 and -32: similar genomic organization but distinct promoter sequences of two gap junction genes" European Journal of Cell Biology, 1992, 58(1):81-89.
Herbertt, et. al. "Protein Kinase C a Expression is required for heparin inhibition of rat smotth muscle cell proliferation in vitro and in vivo." (Oct. 18, 1996) J Biol Chem. 271(42):259 p. 28-35. The American Society for Biochemistry and Molecular Biology, Inc. U.S.A.
Herve et al. Diversity in protein-protein interactions of connexins: emerging roles. Biochim Biophys Acta 1662: 22-41, 2004.
Higginbotham et al., "Bleb-related endophthalmitis after trabeculectomy with mitomycin C", Opthalmology, 1996, 103:650-656.
Ho et. al. "Ischemic Optic Neuropathy Following Spine Surgery." Journal of Neurosurgical Anesthesiology, Jan. 2005, 17(1):38-44.

(56) References Cited

OTHER PUBLICATIONS

Hodgins, M. "Connecting Wounds with Connexins" J. Invest. Dermatol. 122:(5):ix-x commentary (2004).
Honjo, Megumi, et al. "Effects of rho-associated protein kinase inhibitor Y-27632 on intraocular pressure and outflow facility." Investigative Ophthalmology & Visual Science 42.1 (2001): 137-144.
Huang, et al. J Cell Biol 143:1725-34 (1998).
Hunter, et. al. "Zonula occludens-1 alters connexin43 gap junction size and organization by influencing channel accretion." (Dec. 2005) Molecular Biology of the Cell 16: p. 5686-5698. The American Society for Cell Biology.
Hutnik et al., "The Protective Effect of Functional Connexin43 Channels on a Human Epithelial Cell Line Exposed to Oxidative Stress", Investigative Opthalmology & Visual Science, 2008, 49:800.
Iivesaro et al. Connexin-mimetic peptide Gap 27 decreases osteoclastic activity. BMC Musculoskel Dis 2:10, 2001 (6 pages total).
Inoue et al., "Rho-Associated Kinase Inhibitors: A Novel Glaucoma Therapy," Prog. Retin Eye Res., 2013, 37:1-12.
International Search Report/Written Opinion issued Jan. 20, 2016 in counterpart PCT Application No. PCT/US2015/46425.
Jackowski et al. Brit J Neurosurg 9: 303-317, 1995.
Jacobs, Deborah S., et al. "BCLA CLEAR-Medical use of contact lenses." Contact Lens and Anterior Eye 44.2 (2021): 289-329.
Janes, Andrew. "Speed healing." Dec. 1, 2004. Issue 67. Unlimited. Sep. 29, 2006 http://unlimited.co.nz/unlimited.nsf/ulfuture/250EA628CE599A70CC256F6B00046325.
Jen et al. "Suppression of Gene Expression by Targeted Disruption of Messenger RNA: Available Options and Current Strategies." Stem Cells, 2000, 18:307-319.
Jester, et al., Cornea 11:191 (1992).
Jiang-Depeng et al. "The expression of secretory leukocyte protease inhibitor in dermal pluripotent stem cells," May 31, 2006, Chin J. Crit. Care Med. vol. 26, No. 5 pp. 345-348.
Jin, Y., et al., Abstract: "Combination of fetal tissue transplantation and gene therapy to promote spinal cord regeneration," 2003 Neuroscience Meeting Planner, New Orleans, LA; Society for Neuroscience, 2003, Online.
Johnson et al. Am J Opthalmol 147: 11-21, 2009.
Johnsson et al. Transplant Int 12: 235-243, 1999.
Jyung, et al., "Increased wound-breaking strength induced by insulin-like growth factor I in combination with insulin-like growth factor binding protein-1", *Surgery*, 1994,115:233-239.
Kaal et al. Curr Opin Oncol 16: 593-600, 2004.
Kabanov et al., FEBS Lett. 259,327 330 (1990).
Kajstura J, et al. Bone marrow cells differentiate in cardiac cell lineages after infarction independently of cell fusion. Circ Res. Jan 7;96(1 ):127-37 (Jan. 2005; published online Nov. 29, 2004).
Kandel ER, Schwartz JH, Jessell TM. Principles of Neural Science, 4th ed., pp. 178-180. McGraw-Hill, New York (2000).
Kandyba, et al. "A murine living skin equivalent amenable to live cell imaging: analysis of the roles of connexins in the epidermis." (Apr. 2008) The Society for Investigative Dermatology, 1039-1049.
Kanter, H. Lee, et al., Molecular Cloning of Two Human Cardiac Gap Junction Proteins, Connexin40 and Connexin45, Nov. 18, 1993, 861-864, vol. 26, J Mol Cell Cardiol, Academic Press Limited.
Karlin and Atschul, "Applications and statistics for multiple high-scoring segments in molecular sequences", Proc. Natl. Acad. Sci. ,1993, 90:5873-5787.
Katzman, Lee R., and Bennie H. Jeng. "Management strategies for persistent epithelial defects of the cornea." Saudi Journal of Ophthalmology 28.3 (2014): 168-172.
Kaur, C., et al. "Cellular and Molecular Mechanisms of Retinal Ganglion Cell Death in Hypoxic-Ischemic Injuries." J Neurol Exp Neurosci 1.1 (2015): 10-19.
Keirstead, H.S., et al. Exp. Neural. 159:225-236 (1999).
Kerr NM, et al "Gap junction protein connexin43 (GJA1) in the human glaucomatous optic nerve head and retina." J Clin Neurosci. Jan. 2011;18(1):102-108.
Kerr NM, et al "High pressure-induced retinal ischaemia reperfusion causes upregulation of gap junction protein connexin43 prior to retinal ganglion cell loss" Exp Neurol. Mar. 2012;234(1):144-152.
Kerr NM, et al "Immunolocalization of gap junction protein connexin43 (GJA1) in the human retina and optic nerve." Invest Ophthalmol Vis Sci. Aug. 2010;51(8):4028-4034.
Khosla, et. al., Journal of Postgraduate Medicine 50:219-221 (2004).
Kieber-Emmons T, et al., Curr Opin Biotechnol. Aug;8(4):435-41 (1997).
Kim et al., "Intrastromal Delivery of Bevacizumab Using Microneedles to Treat Corneal Neovascularization", Invest. Ophthalmol. Vis. Sci., 2014, 55(11):7376-7386.
Kim, Y et al., Role of Hemichannels in CNS Inflammation and the Inflammasome Pathway Adv. Protein Chem. Struct. Biol. 2016; 1-4:1-37.
Kim Yeri et al: "Tonabersat Prevents Inflammatory Damage in the Central Nervous System by Blocking Connexin43 Hemichannels", Neurotherapeutics, Elsevier Inc, US, vol. 14, No. 4, May 30, 2017 (May 30, 2017), pp. 1148-1165.
Kim, et al. Characterizing the mode of action of extracellular Connexin43 channel blocking mimetic peptides in an in vitro ischemia injury model. Biochim Biophys Acta. 2017; 1861 :68-78.
King, D. Ryan, et al. "Mechanisms of connexin regulating peptides." International Journal of Molecular Sciences 22.19 (2021): 10186, 22 pages.
Kurpakus-Wheater, et al. Biotech. Histochem. 74:146-59 (1999).
Laird and Lampe, Therapeutic strategies targeting connexins, Nat Rev Drug Discov. 17(12): 905-921 (Dec. 2018).
Laird, Dale W., and Paul D. Lampe. "Cellular mechanisms of connexin-based inherited diseases." Trends in Cell Biology 32.1 (2022): 58-69.
Lampe, Paul D., and Dale W. Laird. "Recent advances in connexin gap junction biology." Faculty Reviews 11 (2022), 7 pages.
Lampugnani, M.G., "Cell Migration into a wounded area in vitro" Adhesion protein protocols (1999): 177-182.
Landau et al. Am Heart J 129(5): 924-931, 1995.
Laux-Fenton, W.T., et al., "Connexin Expression Patterns in the Rat Cornea," Cornea 22(5): 457-464, 2003.
Law, et. al. "In vitro optimization of antisense ologodeoxynucleotide design: an example using the connexin gene family." Journal of Biomolecular techniques. (Sep. 2006) 17(4): p. 270-282.
Law, L.-Y., Lin, J.S, Becker, D.L. and Green, C.R. (2002) Knockdown of Connexin 43 mediated regulation of ZPA activity in the developing chick limb bud leads to digit truncation. Dev. Growth Differ. 44, 537-547.
Laxat, "Nice blurb on biologics on cbsnews.com," Sep. 9, 2006 http://www.laxat.com/Nice-blurb-on- biolooics-on-cbsnews-com-1219610.html.
Le Gurun, S., "Connexin-36 Contributes to Control Function of Insulin-producing Cells," J of Biological Chemistry, vol. 278, No. 82, Sep. 26, 2003, pp. 37690-37697.
Lee, V.H.L., Mucosal Penetration Enhancers for Facilitation of Peptide and Protein Drug Absorption, Critical Reviews in Therapeutic Drug Carrier Systems 8:91-192 (1991).
Leithe, Edward, Marc Mesnil, and Trond Aasen. "The connexin 43 C-terminus: A tail of many tales." Biochimica et Biophysica Acta (BBA)-Biomembranes 1860.1 (2018): 48-64.
Lemanske et al. J Allergy Clin Immunol 111 :S502-19, 2003.
Lepisto, J. et al., "Platelet-Derived Growth Factor Isoforms PDGF-AA, -AB and- BB Exert Specific Effects on Collagen Gene Expression and Mitotic Activity of Cultured Human Wound Fibroblasts", *Biochem. Biophys. Res. Comm.*, 1995, 209(2):393-399.
Letsinger et al., Proc. Natl. Acad. Sci. USA 86, 6553-6556 (1989).
Leung, Benjamin, and Drew Lowery. "The patent landscape of inflammasome modulators." Nature Reviews Drug Discovery 19.3 (2020): p. 158.
Leybeart et. al., Cell Commun Adhes 10:251-257 (2003).
Li, C.H., "Hormonal Proteins and Peptides," Academic Press, Inc., New York, NY, 1973, vol. II, pp. 46-267.
Li, H., et al., "Properties and regulation of gap junctional hemichannels in the plasma membranes of cultured cells," Journal of Cell Biology 134(4):1019-1030 (1996).
Li, W.E.I., et al. Dev. 129:2031-42 (2002).

(56) References Cited

OTHER PUBLICATIONS

Li, X., et al. Neuronal connexin36 association with zonula occludens-1 protein (Z0-1) in mouse brain and interaction with the first PDZ domain of Z0-1. (Apr. 2004). Eur J Neurosci. 19,2132-46.
Liaw, et. al. "Altered wound healing in mice lacking a functional osteopontin gene (spp1)" (Apr. 1998) The Journal of Clinical Investigation 101(7): p. 1468-1478.
Lichter et al., "Interim clinical outcomes in the Collaborative Initial Glaucoma Treatment Study comparing initial treatment randomized to medications or surgery," Ophthalmology, 2001. 180:1943-1953.
Lim, Li, and Elizabeth Wen Ling Lim. "Therapeutic contact lenses in the treatment of corneal and ocular surface diseases—A review." The Asia-Pacific Journal of Ophthalmology 9.6 (2020): 524-532.
Lin, et. al. "v-Src phosphorylation of connexin 43 on Tyr247 and Tyr265 disrupts gap junctional communication." (Aug. 20, 2001) Journal of Cell Biology. 154: p. 815-827. The Rockefeller University Press.
Lin, J.H. et al.,"Gap-Junction-mediated propagation and amplification of cell injury." Nature Neurosci. 1:431-432 (1998).
Liu KC, et al "Synergistic effect of chemical penetration enhancer and iontophoresis on transappendageal transport of oligodeoxynucleotides." Int J Pharm. Jan. 30, 2013;441(1-2):687-692.
Liu, et. al. "The Inhibition of in vivo tumorigenesis of osteosarcoma (OS)-732 Cells by antisense human osteopontin RNA." (2008) 13: p. 11-19. University of Wroclaw, Poland.
Loirand et al., "Rho Kinases in Cardiovascular Physiology and Pathophysiology", Circ. Res., 2006, 98:322-334.
Louie et al. Connexin43 hemichannel block inhibits NLRP3 inflammasome activation in a human retinal explant model of diabetic retinopathy Experimental Eye Research (2021) 202:108384, 10 pages.
Lyon, H. et al., Tonabersat Inhibits Connexin43 Hemichannel Opening and Inflammasome Activation in an In Vitro Retinal Epithelial Cell Model of Diabetic Retinopathy Int. J. Mol. Sci. Jan. 2021; 22(1): 298, 12 pages.
Lyttle, M.H., "3'-Modified Oligonucleotides and their Conjugates," Current Protocols in Nucleic Acid Chemistry (2000), 4.6.1-4.6.8.
Makarenkova, H., Becker, D.L., Tickle, C. and Warner, A.E. (1997) Fibroblast growth factor 4 directs gap iunction expression in the mesenchvme of the vertebrate limb bud. J. Cell Biol. 138 1-13.
Mallard C, "Astrocytes and microglia in acute cerebral injury underlying cerebral palsy associated with preterm birth" Pediatr Res. Jan. 2014;75(1-2):234-240.
Malone et al. "Detergent-extracted small-diameter vascular prostheses." J Vasc Surg, 1984, 1:181-191.
Manoharan et al. Nucleosides & Nucleotides 14, (3-5) 969-973 (1995).
Manoharan et al., Bioorg (1992). Med. Chem. Let. 3(12), 2765-2770 (1993).
Manoharan et al., Bioorg. Med. Chem. Lett. 4, 1053-1060 (1994).
Manoharan et al., Tetrahedron Lett. 36(21). 3651-3654 (1995).
Marmarou, A. Neurosurg Focus 22(5): E1-10, 2007.
Martin et al. "Wound Healing-Aiming for Perfect Skin Regeneration." Science, 1997, 276:75-81, Downloaded from www.sciencemag.org on Mar. 12, 2010.
Martin et al., "Ranibizumab and Bevacizumab for Treatment of Neovascular Age-Related Macular Degeneration: 2-Year Results: Comparison of Age-related Macular Degeneratiob Treatments Trials (CATT) Research Group," Ophthalmology, 2012, 119(7):1388-98.
Martin et al., Helv. Chim. Acta 1995, 78, 486-504.
Martin, P. et al., "Inflammatory cells during wound repair: the good, the bad and the ugly", *Trends in Cell Biology*, Nov. 2005, 15(11):599-607.
Martin, P., et al. Curr Biol 13:1122-8 (2003).
Martin, Patricia E., et al. "Connexins: sensors of epidermal integrity that are therapeutic targets." FEBS Letters 588.8 (2014): 1304-1314.
Marx, Jean. "Interfering with Gene Expression." Science 288:1370-1372 (2000).
Marziano et al., "Mutations in the gene for connexin 26 (GJB2) that cause hearing loss have a dominant negative effect on connexin 30", Hum. Mol. Genet., 2003, 12:805-812.
Masseyeff, R.F., "Methods of Immunological Analysis," VCH Publishers, New York, 1993, vol. 1., pp. 1-319.
Masseyeff, R.F., "Methods of Immunological Analysis-Cell Fractionation and Purification," VCH Publishers, New York, 1993, vol. 3., pp. 1-201.
Mat Nor, MN et al., Connexin Hemichannel Block Using Orally Delivered Tonabersat Improves Outcomes in Animal Models of Retinal Disease Neurotherapeutics Jan. 2020; 17(1): 371-387.
Matsushita M, et al. Photo-acceleration of protein release from endosome in the protein transduction system. FEBS Lett. 13;572(1-3}:221-6.J2004} Jul. 26, 2004.
Mattu et al. Emerg Med Clin N Am 23: 1105-1125, 2005.
Mcdonald, et al. Scientific American. 55-63 (Sep. 1999).
Mcdonnell, P.J., "Early Changes in Refractive Error Following Radial Keratotomy," Arch Opthalmol—vol. 106, Feb. 1988.
McDouall, Alice, et al. "Connexins, Pannexins and Gap Junctions in Perinatal Brain Injury." Biomedicines 10.6 (2022): 1445, 21 pages.
Mcgonnell, I., Green, C.R., Tickle, C. and Becker, D.L. (2001) Communication through connexin 43 gap junction channels contributes to the normal development of the embryonic face. Dev. Dynam. 222, 420-438.
Medical Futures—Innovation Awards. May 26, 2006 http://www.medicalfutures.co.uk/runner.php?bctWin=1.
Meienhofer in "Hormonal Proteins and Peptides," ed.; C.H. Li, vol. 2 (Academic Press, 1973) pp. 48-267.
Melton, D.A. Antisense RNA and DNA, Ed., Cold Spring Harbor Laboratory, Cold Spring Harbor, NY (1988).
Merrifield, J. Am. Chem. Soc. 85 2149 (1963).
Messmer et al., "In vivo confocal microscopy of filtering blebs after trabeculectomy," Arch. Opthalmol., 2006, 124:1095-1103.
Methods of Immunological Analysis (R. Masseyeff, W.H. Albert, and NA Staines, eds., Weinheim: VCH Verlaos oesellschaft mbH 1993) vol. I Ch. 1. 2 3. 4 vol. III, Ch. 4.
Meyer et al., "Inhibition of Gap Junction and Adherens Junction Assembly by Connexin and A-CAM Antibodies", J. Cell Biol., 1992, 119(1):179-189.
Middleton, "Synthesis biodegradable polymers as orthopedic devices", Biomaterials, 2000, 21(23):2335-2346.
Miller et al., "Wound healing in an animal model of glaucoma fistulizing surgery in the rabbit", Ophthalmic Surg., 1989, 20:350-357.
Miller et al., "Trabeculectomy combined with beta irradiation for congenital glaucoma", Br. J. Ophthalmol., 1991, 75:584-590.
Miller, J.H., et al., Gene Transfer Vectors for Mammalian Cells, Introduction: Development and Uses of Gene Transfer Vectors, 1987 Cold Spring Harbor Laboratory, pp. 1-3.
Mishra et al., Biochim. Biophys. Acta 1264, 229-237 (1995).
Miyazaki, et. al. "Corneal Wound Healing in an Osteopontin-Deficient Mouse." (Apr. 2008) Investigative Ophthalmology & Visual Science 49(4): p. 1367-1375. Association for Research in Vision and Ophthalmology.
Molecular cloning: A Laboratory Manual, 3rd Edition Chapter 10 (Sambrook and Russel, 2001), 52 pages.
Montgomery, Jade, et al. "Connexin 43-based therapeutics for dermal wound healing." International Journal of Molecular Sciences 19.6 (2018): 1778, 11 pages.
Moore et al. "Selective block of gap junction channel expression with connexin-specific antisense oligodeoxynucleotides." American Journal of Physiology, Nov. 1994, 265(1):C1371-C1388.
Moore, Clinical Techniques in Small Animal Practice, 18(3):168-177, 2003.
Mora et al.,"Trabeculectomy with intraoperative sponge 5-fluorouracil", Ophthalmology, 1996, 103:963-970.
Mori, et al. Supplemental Materials and Methods. Online Supplemental Material. (2008) http://www.jem.org/cgi/content/full/jem.20071412/DC1 JEM The Rockefeller University Press.
Mori, et al., "Acute downregulation of connexin43 at wound sites leads to a reduced inflammatory response, enhanced keratinocyte

(56) References Cited

OTHER PUBLICATIONS proliferation and wound fibroblast migration." Journal of Cell Science. 119(24): p. 5193-5203 (Dec. 2006). The Company of Biologists 2006.
Mori, et. al. "Molecular mechanisms linking wound inflammation and fibrosis: knock down of osteopontin leads to rapid repair and reduced scarring." Department of Physiology and Biochemistry, School of Medical Sciences, University of Bristol, Bristol BS8 1TD, United Kingdom. (Jan. 7, 2008); p. 43-55.
Mori, R., et al. "Impairment of skin wound healing in beta-1,4-galactosyltransferase-deficient mice with reduced leukocyte recruitment." Am J. Pathol., 2004, 164:1303-14.
Morrissey, et al. J. Neuroscience 11 :2433-2442 (1991).
Mugisho, et al. The inflammasome pathway is amplified and perpetuated in an autocrine manner through connexin43 hemichannel mediated ATP release. Biochim Biophys Acta. 2017.
Mugisho et al. Targeting connexin hemichannels to control the inflammasome: the correlation between connexin43 and NLRP3 expression in chronic eye disease Expert Opinion on Therapeutic Targets vol. 23, 2019, pp. 855-863.
Mugisho, OO et al., Connexin43 hemichannel block protects against the development of diabetic retinopathy signs in a mouse model of the disease J. Mol. Med. (Berl) Feb. 2019;97(2):215-229.
Muramatsu, et. al. "Inhibition of osteopontin expression and function in oral cancer cell lines by antisense oligonucleotides." (2005) Cancer Letters 217:87-95. Elsevier.
Muranishi. Critical Reviews in Therapeutic Drug Carrier Systems. 7:1-33 (1990).
Mustoe, T.A., et al. Science 237, 1333-6 (1987).
Nadarajah, B., Makarenkova, H., Becker, D.L., Evans, W.H. and Pamavelas, J.G. (1998) Basic FGF increases communication between cells of the developing a neocortex. J. Neurosci. 18, 7881-7890.
Nakano, et al. "Connexin43 Knockdown Accelerates Wound Healing but Inhibits Mesenchymal Transition after Corneal Endothelial Injury In Vivo" Investigative Ophthalmology & Visual Science, Jan. 2008, vol. 49, No. 1.
Nakano, et. al. "Changes in the expression of the gap junction protein connexin43 during wound healing of the rat corneal endothelium." (Dec. 2004) Bioimages 12(2-4). Bioimaging Society.
Neckers, et al. "Anti-sense technology: biological utility and practical considerations." Am. J. Physiol., Lung Cell Mol Physiol., 265(1) 1993, L1-L12.
Neckers, L., et al., "Nonantisense Effects of Antisense Oligonucleotides," Applied Antisense Oligonulceotide Technology, Stein,C. and Krieg,A. (eds), (1998) Chapters 7, 10 & 22, pp. 147-159; 193-205, 397-405.
New bio-active gel cuts wound healing time in half. Oct. 20, 2003. UCL Media Relations. University College London. Sep. 29, 2006 http://www.ucl.ac.uk/media/library/nexaoon0.
Ngo et al. Computational complexity, protein structure prediction, and the Levinthal paradox. The Protein Folding Problem and Tertiary Structure Prediction, pp. 492-495, 1994.
Nickel, R., Becker, D.L. and Forge, A. Molecular and functional characterization of gap junctions in the avian inner ear. J. Neurosci. Jun. 7, 2006:26(23):6190-9.
Nielsen et al., Science 254:1497 (1991).
Niessen et al., "Selective permeability of different connexin channels to the second messenger inositol 1,4,5-trisphosphate", J. Cell, Sci., 2000, 113(8):1365-1372.
Nowak, J.Z. Age-related macular degeneration (AMO): pathogenesis and therapy. Pharmacol Reports 58: 353-363, 2006.
Oberhauser et al., Nucl. Acids Res. 20, 533-538 (1992).
O'Boyle et al., "Synthesis and Evaluation of Azetidinone Analogues of Combretastatin A-4 as Tubulin Targeting Agents", Journal of Medicinal Chemistry, 2010, 53(24):8569-8584.
O'Carroll et al., "Connexin 43 mimetic peptides reduce swelling, astrogliosis, and neuronal cell death afterspinal cord injury", Cell Communication & Adhesion, 2008, 15(1):27-42.
O'Carroll et al., "Connexin43 mimetic peptide is neuroprotective and improves function following spinal cord injury", Neurosci. Research, Mar. 2013, 75(3):256-26.
O'Carroll SJ, et al "The use of connexin-based therapeutic approaches to target inflammatory diseases." Methods Mol Biol. 2013;1037:519-546.
Office Action in Australian counterpart application No. 2021282410, dated Feb. 20, 2023, in 11 pages;.
Okada, et. al. "Osteopontin expressed by renal tubular epithelium mediates interstitial monocyte infiltration in rats." Am Physiol Renal Physiol. (2000) 278:F110-F121. The American Physiological Society.
Oligonucleotide Synthesis Chapter 1 (M.J. Gait, ed., 1984.
O'Quinn, Michael P., et al. "A peptide mimetic of the connexin43 carboxyl terminus reduces gap junction remodeling and induced arrhythmia following ventricular injury." Circulation Research 108.6 (2011): 704-715.
Ormonde S, et al "Regulation of connexin43 gap junction protein triggers vascular recovery and healing in human ocular persistent epithelial defect wounds." J Membr Biol. Jul. 2012;245(7):381-388.
Oviedo-Orta E., et. al. "Gap Junctions and Connexin-Mediated Communication in the Immune System." Biochimica et Biophysica Acta. Biomembranes, Amsterdam, NL vol. 1662, No. 1-2, 23, Mar. 2004, pp. 102-112.
Oviedo-Orta et al. Gap junctions and connexins: potential contributors to the immunological synpase. J Leuk Biol 72: 636-642, 2002.
Oviedo-Orta, E. et al., "Intercellular communication in the immune system: differential expression of connexin40 and 43, and perturbation of gap junction channel functionsin peripheral blood and tonsil human lymphocyte subpopulations", *Immunology*, 2000, 99:578-590.
Oviedo-Orta, E., "Immunoglobulin and cytokine expression in mixed lymphocyte cultures is reduced by disruption of gap junction intercellular communication," The FASEB Journal vol. 15, No. 3, pp. 768-774, May 2017.
Paddison, P., Caudy A., Bernstein, E., Hannon, G., Conklin, D., "Short hairpin RNAs (shRNAs) induce sequence-specific silencinQ in mammalian cells." Genes & Dev 16:948-958 (2002).
Paddison, P., Caudy A., Hannon G., "Stable suppression of gene expression by RNAi in mammalian cells." Proc Natl Acad Sci USA 99:1443-1448 (2002).
Papangelou et al. Curr Treatment Options in Neurol 11 :64-73, 2009.
Parker, J.D., et al. Nucleic Acids Res 19:3055-60 (1991).
Parsons et al., "Tonabersat (SB-220453) a novel benzopyran with anticonvulsant properties attenuates trigeminal nerve-induced neurovascular reflexes", British Journal of Pharmacology, 2001, 132(7):1549-1557.
PCR: The Polymerase Chain Reaction Chapter 1-19 (Mullis et al., eds., 1994).
Pearson, R., Uineborg N., Becker D.L. and Mobbs P. (2005) Gap junctions modulate interkinetic nuclear miQration in retinal oroaenitor cells. J. Neurosci. 25, 10803-10814.
Penn, et. al., Autoimmunity Reviews 2:199-203 (2003).
Pepose, J.S., et al. "The cornea; Adler's Physiology of the eye: Clinical application," 9th Ed. St. Louis: Mosby Year Book, 1992, 29-47.
Peters NS, Green CR, Poole-Wilson PA, Severs NJ. Cardiac arrhythmogenesis and the gap junction. J Mol Cell Cardiol. Jan. 1995;27(1):37-44. Review. No abstract available. PMID: 7760358 [PubMed—indexed for Medline].
Peters NS, Green CR, Poole-Wilson PA, Severs NJ. Reduced content of connexin43 gap junctions in ventricular myocardium from hypertrophied and ischemic human hearts. Circulation. Sep. 1993;88(3):864-75. PMID: 8394786 [PubMed—indexed for Medline].
Peters NS, Rowland E, Bennett JG, Green CR, Anderson RH, Severs NJ. The Wolff-Parkinson-White syndrome: the cellular substrate for conduction in the accessory atrioventricular pathway. Eur Heart J. Jul. 1994;15(7):981-7. PMID: 7925521 [PubMed—indexed for Medline].
Peters NS, Severs NJ, Rothery SM, Lincoln C, Yacoub MH, Green CR. Spatiotemporal relation between gap junctions and fascia adherens junctions during postnatal development of human ven-

(56) References Cited

OTHER PUBLICATIONS tricular mvocardium. Circulation. Aug. 1994;90(2):713-25. PMID: 8044940 [PubMed—indexed for Medline].
Peters, T., et al. EMBO J. 24:3400-10 (2005).
Pich, A, et al. Prognostic relevance of cell proliferation in head and neck tumors Annals of Oncology 200415(9): 1319-1329. Sep. 2004.
Polo, L.M., et al., “Analysis of Oligonucleotides by Electrospray Ionization Mass Spectrometry,” Current Protocols in Nucleic Acid Chemistry (2000) 10.2.1-10.2.20.
Pon, R.T., “Solid-Phase Supports for Oligonucleotide Synthesis,” Current Protocols in Nucleic Acid Chemistry (2000) 3.1.1-3.1.28.
Postlethwaite, A.E., et al. “Stimulation of the chemotactic migration of human fibroblasts by transforming growth factor beta.” The Journal of Experimental Medicine 165.1 (1987): 251-256.
Qin et al, “Lysosomal and Proteasomal Degradation Play Distinct Roles in the Life Cycle of Cx43 in Gap Junctional Intercellular Communication-deficient and-competent Breast Tumor Cells, The Journal of Biological Chemistry”, 2003, 278:30005-30014.
Qiu, et al., “Targeting connexin43 expression accelerates the rate of wound repair.” Current Biology 13:1967-1703 (2003).
Qiu, et al; “Supplemental Data: Targeting Connexin43 Expression Accelerates the Rate of Wound Repair”; (2003) S1.
Rabbani, Leroy, E., et al., “Antisense Therapy to Inhibit Angioplasty Restenosis,” Applied Antisense Oligonulceotide Technology, Stein,C. and Krieg,A. (eds), (1998) Chapter 22, pp. 397-405.
Rabinstein, A. Neurologist 12: 59-73, 2006.
Ramdas et al., J. Biol. Chem. 264:17395 (1989).
Ramer, et al. Spinal Cord. 38:449-472 (2000).
Ramezani A., et al., Frontiers in Bioscience 7:a,29-36 (2002).
Ramkumar, Hema L., et al. “Reduced Ganglion Cell Volume on Optical Coherence Tomography in Patients with Geographic Atrophy.” Retina 38.11 (2018): 2159-2167.
Rando, J., “CoDa Therapeutics Achieves Positive Phase 2 Efficacy of Nexagon® in Chronic Venous Leg Ulcers,” http://www.codatherapeutics.com/news-nexagon.html, San Diego, CA, May 25, 2010.
Rapoport, Antimigraine Drugs: new Frontiers, Neurol sci 30(Suppl 1): S49-S54 (2009).
Ratkay-Traub, I., Hopp, B., Bor, Zs., Dux, L., Becker, D.L. and Krenacs, T. (2001) Regeneration of rabbit cornea following excimer laser photorefractive keratectomy: a study on gap junctions, epithelial junctions and epidermal growth factor receptor expression in correlation with cell proliferation. Exp. Eye Res. 73, 291-302.
Reddy, K., et al., Pediatric Research 43(5):674-682 (1998).
Rennick RE, Connat JL, Bumstock G, Rothery S, Severs NJ, Green CR. Expression of connexin43 gap junctions between cultured vascular smooth muscle cells is dependent upon phenotype. Cell Tissue Res. Feb. 1993;271’2):323-32. PMID: 8384084 [PubMed—indexed for Medline].
Reynolds, et al. Nat. Med. 11 :167-74 (2005).
Rhett, et. al. “Novel therapies for scar reduction and regenerative healing of skin wounds.” (Mar. 4, 2008). Trends in Biotechnology. 26(4): 173-180. Cell Press.
Rigas et al., Proc. Natl. Acad. Sci U.S.A. 83:9591 (1986).
Rininsland et al., Proc. Natl. Acad. Sci. USA 94:5854 (1997).
Robbins, S. and Cotran, R. 1979 Pathologic basis of disease. 2nd edition. Chapters 1-3 WB Saunders Co. Philadelphia.
Roberts et al. “Follicle-stimulating hormone affects metaphase I chromosome alignment and increases aneuploidy in mouse oocytes matured in vitro.” Biology of Reproduction, 2005, 72: 107-118, Published online before print Sep. 15, 2004.
Roberts, A.B., et al., “Transforming growth factor type Beta: Rapid induction of fibrosis and angiogenesis in vivo an stimulation of collagen formation in vitro,” Proc. Natl. Acad. Sci. USA, vol. 83, pp. 4167-4171, Jun. 1986.
Roelfsema, et .al., J Cereb Blood Flow Metab 24(8):877-886 (2004).
Rosendaal M, Green CR, Rahman A, Morgan D. Up-regulation of the connexin43+ gap junction network in haemopoietic tissue before the growth of stem cells. J Cell Sci. Jan. 1994; 107 (Pt 1 ):29-37.
Rossi, D., et al., “The Biology of Chemokines and Their Receptors,” Annu. Rev. Immunol. 2000, 18:217-242.
Rozenthal, et al. “Stable Transfection With Connexin43 Inhibits Neuronal Differentiation of PC12 Cells” Society for Neuroscience Abstracts, Society for Neuroscience 23(1-3), Oct. 25, 1997, p. 22.
Ruch et al. “Inhibition of Gap Junctional Intercellular Communication and Enhancement of Growth in BALBk 3T3 Cells Treated With Connexin43 Antisense Oligonucleotides.” Molecular Carcinogenesis, 1995, 14:269-274.
Rupenthal ID, et al “Ion-activated in situ gelling systems for antisense oligodeoxynucleotide delivery to the ocular surface.” Mol Pharm. Dec. 5, 2011;8(6):2282-2290.
Rutherford, R.B., Vascular Surgery, 3rd Ed. (W.B. Saunders Co. 1989).
Sabiston, D., The Textbook of Surgery, 14th Ed. Chapter 56 (W .B. Saunders Co. 1991).
Saez et al. Physiol Rev 83:1359-1400, 2003.
Saison-Behmoaras et al. EMBO J. 10, 1111-11118 (1991).
Saitongdee, P., Becker, D.L., Milner, P., Knight, G.E., and Bumstock, G. (2004) Levels of gap junction proteins in coronary arterioles and aorta of hamsters exposed to cold and during hibernation and arousal. J. Histochem Cvtochem 52). 603-615.
Saitongdee, P., Milner, P., Becker, D.L., Knight, G.E., and Bumstock, G. (2000) Increased connexin43 gap unction protein in hamster cardiomyocytes during cold acclimatization and hibernation. Cardiovascular Res. 47, 108-115.
Salameh et al., Pharmacology of Gap Junctions. New pharmacological targets for treatment of arrhythmia, seizure and cancer?, Biochim. Biophys. Acta, 2005, 1719:36-58.
Sambrook, J., et al., “Molecular Cloning A Laboratory Manual,” $2^{nd}$ Ed., 1989, Chapters 11 and 12, 105 pages.
Sanghvi, Y.S., Antisense Research and Applications, Chapter 15, 1993 by CRC Press, Inc., pp. 273-288.
Santoro, S.W. and Joyce, G.F. “A General Purpose RNA-Cleaving DNA Enzyme.” Proc. Natl. Acad. Sci. USA 94, 4262-4266 ( 1997).
Santoro, S.W. and Joyce, G.F. Biochem. 37:13330-13342 (1998).
Scatchard et al., “The Attractions of Proteins for Small Molecules and Ions”, Ann. N.Y. Acad., Sci., 1994, 51(4):660-672.
Scatchard, G., “The Attractions of Proteins for Small Molecules and Ions,” Anals of the New York Academy of Sciences, vol. 51, Art. 4, pp. 575-852, May 31, 1949.
Scherer, L. J. and Rossi, J.J. Nature Biotechnol. 21(12):1457-1465 (2003).
Schmidt, C.E., et al. Ann. Rev. Biomed. Eng. 5:293-347 (2003).
Schubert, S. et al., Nucleic Acids Res. 31, 5982-5992 (2003).
Schuck, P., “Reliable determination of binding affinity and kinetics using surface plasmon resonance biosensor,” Current Opinion in Biotechnology, 8(4):498-502 (1997).
Schulz et al. Connexin 43 is an emerging therapeutic target in ischemia/reperfusion injury, cardioprotection and neuroprotection. Pharmacol Therapeut 153: 90-106, 2015.
Schumacher et al. Circulation 97: 645-650, 1998.
Segretain, D., et al. (2004). Regulation of connexin biosynthesis, assembly, gap junction formation, and removal. Bioch. Bioph. Acta 1662, 3-21. (Mar. 23, 2004).
Serena et al., “Acceleration of Venous Ulcer Healing Using a Topical Eonnexin43 Antisense Compound; Phase 2 Results.” Symposium on Advanced Wound Care, Apr. 14-17, 2011 (Abstract Supp. at BRG.23).
Severs NJ, Gourdie RG, Harfst E, Peters NS, Green CR. Intercellular junctions and the application of microscopical techniques: the cardiac gap junction as a case model. J Microsc. Mar. 1993;169 (Pt 3):299-328. Review. PMID: 8478912 [PubMed—indexed for Medline].
Severs NJ, Shovel KS, Slade AM, Powell T, Twist VW, Green CR. Fate of gap junctions in isolated adult mammalian cardiomyocytes. Circ Res. Jul. 1989;65( 1 ):22-42. PMID: 2736737 [Pub Med—indexed for Medline].
Severs NJ, Slade AM, Powell T, Twist VW, Green CR. Integrity of the dissociated adult cardiac myocyte gap junction tearing and the

(56) References Cited

OTHER PUBLICATIONS mechanism of plasma membrane resealing. J Muscle Res Cell Motil. Apr. 1990;11C2):154-66. PMID: 2351753 [PubMed—indexed for Medline].
Severs, N.J., et al. Remodelling of gap junctions and connexin expression in hemt disease. Biochim Biophys Acta. 1662, 138-48 (Mar. 23, 2004).
Shah, M. et al., "Role of Elevated Plasma Transforming Growth Factor-β1 Levels in Wound Healing", *Am. J. Pathol.*, 1999, 154(4):1115-1124.
Shea et al., Nucl. Acids Res. 18, 3777-3783 (1990).
Sheehan et al. "Percentage Change in Wound Area of Diabetic Foot Ulcers Over a 4-Week Period Is a Robust Predictor of Complete Healing in a 12-week Prospective Trial." Diabetes Care, Jun. 2003, 26(6): 1879-1882.
Shelley et al., "Cone degeration in aging and age-related macular degenerations", Arch. Opththalmol., 2009, 127(4):483-492.
Shen, Xiulong, and David R. Corey. "Chemistry, mechanism and clinical status of antisense oligonucleotides and duplex RNAs." Nucleic Acids Research 46.4 (2018): 1584-1600.
Sherwood et al., "Long-term morphologic effects of antiglaucoma drugs on the conjunctiva ad Tenon's capsule in glaucomatous patients", Ophthalmology., 1989, 96:327-335.
Shevde, et. al "Osteopontin knockdown suppresses tumorigenicity of human metastatic breast carcinoma, MDA-MB-435." Clin Exp Metastasis (2006) 23: p. 123-133. Springer Science + Business Media B.V.
Shibayama et al., "Effect of Change Substitutions at Residue His-142 on Voltage Gating of Connexin43 Channels", Biophys. J., 2006, 91(11):4054-4063.
Sibbald et al. "Venous leg ulcers, in Chronic Wound Care: A Clinical Source Book for Healthcare Professionals." HMP Communications, Krasner DL, Rodeheaver GT, Sibbald RG, Eds., 4th ed. 2007, 429-442.
Sica, D. Heart Failure Clin 4: 511-518, 2008.
Sidoti et al., "Trabeculectomy with intraoperative 5-fluorouracil", Opthalmic Surg. Lasers, 1998, 29:552-561.
Silverman et al., "The Pannexin I Channel Activagtes the Inflammasome in Neurons and Astrocytes", J. Biological Chem.,Jul. 3, 2009, 284(27):18143-1815.
Simo et al. Angiogenic and Antiangiogenic factors in proliferative diabetic retinopathy. Current Diabetes Rev 2: 71-98, 2006.
Simons, et. al. "Anti-sense c-myb oligonucleotides inhibit intimal arterial smooth muscle cell accumulation in vivo." (Sep. 3, 1992): Nature, 359: p. 67-70. Nature Publishing Group.
Singh et al., "Intravenous transferring, RGD peptide and dual-targeted nanoparticles enhance anti-VEGF intraceptor gene delivery to laser-induced CNV", Gene Therapy, 2009, 16:645-659.
Singh, et. al. "Inhibition of connexin 43 synthesis by antisense RNA in rat glioma cells." (1997) Cytobios 91: p. 103-123. The Faculty Press. Great Britain.
Skolnick et al. From genes to protein structure and function: novel applications of computational approaches in the genomic era. Trends in Biotech 18(1 ): 34-39, 2000.
Smith et al. The challenges of genome sequence annotation or "The devil is in the details". Nature Biotech 15: 1222-1223, 1997.
Smith JH, Green CR, Peters NS, Rothery S, Severs NJ. Altered patterns of gap junction distribution in ischemic heart disease. An immunohistochemical study of human myocardium using laser scanning confocal microscopy. Am J Pathol. Oct. 1991;139(4):801-21. PMID: 1656760 [PubMed—indexed for Medline].
Söhl et al., "Gap junctions and the connexin protein family", Cardiovasc. Res.,2004, 62(2):228-232.
Söhl, G., et al., "The murine gap junction gene connexin36 is highly expressed in mouse retina and regulated during brain development," FEB Setters 428 (1998) 27-31.
Sotozono, C. et al., "Keratinocyte Growth Factor Accelerates Corneal Epithelial Wound Healing In Vivo", *Investigative Opthalmology &Visual Science*, 1995, 36(8):1524-1529.
Spanos, S., Rice, S., Karagiannis, P., Taylor, 0., Becker, O.L., Winston, R.M.L. and Hardy, K. (2002) Caspase activity and expression of cell death genes during human preimplantation embryo development. J. Reprod. 124, 353-363.
Spencer, W.H., "The cornea: Ophthalmic Patholgy: an atlas and textbook" 4th Ed. Philadelphia: W.B. Saunders Co. 1996. 157-165.
Stein C.A. and Krieg A.M. (eds), Chapters 7, 10, 22. Applied Antisense Oligonucleotide Technology, 1998 (Wilev-Uss).
Stewart, et al., "Solid Phase Peptide Synthesis," Chapter 2 Part B, Chapter 3. W .H. Freeman Co., San Francisco (1969).
Stilinovic A., Green, C.R., Klette R., Franke S., Klette G and Becker D.L. (2004) Texture analysis of collagen fibers in scar tissue. In Proc. Image Vision Computing New Zealand Nov. 21, 00185-190.
Strobel et al., Science 254:1639 (1991).
Sui, et al., Proc Natl Acad Sci 99(8):5515-5520 (2002).
Summary of Safety and Effectiveness Data for Apligraf, May 8, 2000; available at http://www.accessdata.fda.gov/cdrh docs/pdf/P950032S016b.pdf.
Sundstrom, Drug Discovery Today 10:993-1000 (2005).
Suzuki, et. al. Protective effects of recombinant osteopontin on early brain injury after subarachnoid hemorrhage in rats. (2010) Crit Care Med 38(2): p. 612-618.
Svinarchuk et al., Biochimie 75, 49-54 (1993).
Takahashi, et al. J. Pharm. Pharmacol. 40:252-257 (1998).
Tan, et al., Ann Neural 32(5):677-682 (1992).
Tanaka, T., et al. Jpn. J. Ophthalinol. 43:348-54 (1999).
Tarnow, et al. Scand J. Plast Reconstr Hand Surg. 28:255-259 (1994).
The Chemistry of Reactive Groups, Bioconjugate Techniques, 1st Edition, Greg T Hermanson, 1996, Chapter 2, pp. 137-166, Academic Press, Published by Elsevier.
Thompson AM, et al "A Study Investigating a Possible Link Between Lens Protein in the Vitreous Fluid of Eyes After Uncomplicated Cataract Surgery and Chronic Cystoid Macular Edema." Asia Pac J Ophthalmol (Phila). May-Jun. 2014;3(3):194-197.
Tian et al., "Effects of Topical H-7 on Outflow Facility, Intraocular Pressure, and Corneal Thickness in Monkeys", Arch. Ophthalmol., 2004, 122(8):1171-1178.
Tokuriki et al. Stability effects of mutations and protein evolvability. Curr Opinion Structural Biol 19: 596-604, 2009.
Tonkin RS, et al. "Gap junction proteins and their role in spinal cord injury." Front Mol Neurosci. Jan. 6, 2015;7:102, 9 pages.
Topol, E.J. (ed.) The Textbook of Interventional Cardiology, 2nd Ed. (W.B. Saunders Co. 1994).
Uhlmann, et al., Chem. Reviews 90:543-584 (1990).
Unger et al., "Electron cryo-crystallography of recombinant cardiac gap junction channel, Novartis Found Symp. & Discussion", 1999, 219:22-30, 31-43.
Upton et al., "Profile of SB-204269, a mechanistically novel anticonvulsant drug, in rat models of focal and generalized epileptic seizures", British Journal of Pharmacology, 1997, 121:1679-1686.
Van Campenhout, Raf, et al. "Mechanisms underlying connexin hemichannel activation in disease." International Journal of Molecular Sciences 22.7 (2021): 3503, 14 pages.
Veber and Freidinger, TINS, 392 (1985).
Vig, Balvinder S., et al. "Amino acids as promoieties in prodrug design and development." Advanced Drug Delivery Reviews 65.10 (2013): 1370-1385.
Vikis, H.G. and Guan, K.L. Glutathione-S-Transferase-Fusion Based Assays for Studying Protein-Protein Interactions in Protein-Protein Interactions, Methods and Applications, Methods in Molecular Biology, 261, Fu. H.Ed. Humana Press Totowa N.J. pp. 175-186 (2004).
Vis JC, Nicholson LF, Faull RL, Evans WH, Severs NJ, Green CR. Connexin expression in Huntington's diseased human brain. Cell Biol Int. Nov. 1998;22(11-12):837-47. PMID: 10873295 [PubMed—indexed for Medline].
Wadia JS, et al. Transducible TAT-HA fusogenic peptide enhances escape of TAT-fusion proteins after lipid raft macropinocytosis. Nat Med. 10(3):310-5. (Feb. 8, 2004).
Waggett A.O., et al. Connexin 32 and 43 gap junctions differentially modulate tenocyte esonse to cyclic mechanical load. Eur. J. Cell. Biol. 085:1145-1154 (2006).

(56) References Cited

OTHER PUBLICATIONS

Wagner, R.W., et al. "Gene inhibition using anti-sense oligodeoxynucleotides." Nature 372:333-335 (1994).
Wai, et. al. "Osteopontin silencing by small interfering RNA suppresses in vitro and in vivo CT26 murine colon adenocarcinoma metastasis." (2005) Carcinogenesis 26(4): p. 741-751. Oxford University Press.
Walker, et al. Dev biol .284:479-98 (2005).
Wan CK, et al "Comparison of bidirectional and bicistronic inducible systems for coexpression of connexin genes and fluorescent reporters." Anal Biochem. Dec. 15, 2012;431(2):90-95.
Wan CK, et al "Spatiotemporal changes in Cx30 and Cx43 expression during neuronal differentiation of P19 EC and NT2/D1 cells." Cell Biol Int Rep (2010). Dec. 2013;20(2):13-23.
Wang et al., "Abnormal Connexin Expression Underlies Delayed Wound Healing in Diabetic Skin," Diabetes, Nov. 2007, 56:2809-2817.
Wang, Zhao, et al. "Novel contact lenses embedded with drug-loaded Zwitterionic nanogels for extended ophthalmic drug delivery." Nanomaterials 11.9 (2021): 2328, 18 pages.
Wang Xianyuan, et al. "The studies on thymosin beta-4 and the prospect thereof," Dec. 31, 2002, Foreign Medical Sciences (Section of Biologics for Prophylaxis, Diagnosis and Therapy) vol. 25, No. 3 pp. 126-129.
Waring, et al., Amer. J. Ophthalmol. 111 :133 (1991).
Wei, et al., "Connexins and Cell Signaling in Development and Disease," Annu. Rev. Cell Dev. Biol., 2004, 20:811-38.
Weir, O.M. & C.C. Blackwell, eds. Handbook of Experimental Immunology, 1986.
Welcome to the lab of David Becker and Jeremy Cook. Becker/Cook Lab. May 26, 2006 http://www.anat.ucl.ac.uk/research/becker/oeoole.htm.
Wells. J.A. Additivity of mutational effects in proteins. Biochemistry 29 (37): 8509-8517, 1990.
Wheater, M.K., "Review Corneal Cell Proteins and Ocular Surface Pathology," Biotechnic & Histochemistry, 1999, vol. 74, No. 3, pp. 146-159.
Wild, The Immunoassay Handbook (D. Wild, ed., Stockton Press NY 1994).
Wilgus TA, et al. Reduction of scar formation in full-thickness wounds with topical celecoxib treatment. Wound Rep Reg Jan.-Feb. 2003; 11 :25-34.
Willebrords J, et al "Connexins and their channels in inflammation" Crit Rev Biochem Mol Biol. Nov./Dec. 2016;51(6):413-439.
Willecke et al., "Structural and functional diversity of connexin genes in the mouse and human genome", Biol. Chem., 2002, 383:725-737.
Willecke, et. al. "Mouse connexin37: Cloning and functional expression of a gap function gene highly expressed in lung." (Sep. 1991) The Journal of Cell Biology 114(5): p. 1049-1057. The Rockefeller University Press.
Wilson, et al. "Accellular Matrix" Trans Am Soc Artif Intern 36:340-343 (1990).
Wood, W.G., "Luminescent Labels," Principles of Immunoassays, 1993, pp. 320-715.
Wound-healing technology shortlisted for award. UCL News. University College London. Sep. 27, 2006 http://www.ucl.ac.uk/news-archive/archive/2003/october-2003/latest/newsitem.shtml?0309 . . . .
Wright et al., "Cell motility in models of wounded human skin is improved by Gap27 despite raised glucose, insulin and IGFBP-5," Experimental Cell Research, 2013, 319:390-401.
Wright, C.S., Becker, D.L., Lin, S.J., Warner, A.E. and Hardy, K. (2001) Stage-specific and differential expression of gap junctions in the mouse ovary: connexin-specific roles in follicular regulation. J. Reprod. Fert. 121, 77-88.
Wright, et. al. "Connexin mimetic peptides improve cell migration rates of human epidermal keratinocytes and dermal fibroblasts in vitro." (2009) Wound Rep Reg 17: p. 240-249. The Wound Healing Society.
Wu A, et al "Role of gap junctions in chronic pain." J Neurosci Res. Feb. 2012;90(2):337-345.
Wyngaarden J.B., et al. (eds.), The Cecil Textbook of Medicine, 19th Ed. (W.B. Saunders, 1992).
Xu, X.M., et al. J. Comp. Neurol. 351:145-160 (1995).
Xu, X.M., et al. J. Neuroscience. 11 :1723-1740 (1999).
Yamashita, et al. J. Phann. Pharmacol. 39:621-626 (1987).
Yang et al., "Synthesis and biological activities of potent peptidomimetics selective for somatostatin receptor subtype 2", Proc. Natl. Acad. Sci. U.S.A., 1998, 95:10836-10841.
Yeager, "Structure of cardiac gap junction intercellular channels", J. Struct. Biol., 1998, 121:231-245.
Yick, L.W., et al. Exp. Neurol. 159:131-138 (1999).
Yoon JJ, et al "Dose-dependent protective effect of connexin43 mimetic peptide against neurodegeneration in an ex vivo model of epileptiform lesion." Epilepsy Res. Dec. 2010;92(2-3):153-162.
Yuan, Xiaoyong, et al. "Expression pattern of connexins in the corneal and limbal epithelium of a primate." Cornea 28.2 (2009): 194-199.
Yuan, Xiaoyong et al, "Ocular Drug Delivery Nanowafer with Enhanced Therapeutic Efficacy", ACS Nano, 2015, 9(2):1749-1758.
Zarbin, "Current Concepts in the Pathogenesis of Age-Related Macular Degeneration," Arch. Ophthalmol. 122(4):598-614 (Apr. 2004).
Zhai, Jiajie, Q. I. N. Wang, and Liang Tao. "Connexin expression patterns in diseased human corneas." Experimental and Therapeutic Medicine 7.4 (2014): 791-798.
Zhang et al., "Anti-inflammatory therapy for diabetic retinopathy", Immunotherapy, 2011, 3(5):609-28.
Zhang et al., "The Gap Junction-independent Tumor-suppressing Effect of Connexin 43," J. Biol. Chem. 278(45):44852-44856 (Nov. 2003).
Zhang J, et al. "Connexin hemichannel induced vascular leak suggests a new paradigm for cancer therapy." FEBS Lett. Apr. 17, 2014;588(8):1365-1371.
Zhang, X., Oglesbee, M., "Use of surface plasmon resonance for the measurement of low affinity binding interactions between HSP72 and measles virus nucleocapsid protein." Biological Procedures Onlin 5(1):170-181 (2003).
Zhou, et. al. "Blockade of Osteopontin Inhibits Glomerular Fibrosis in a Model of Anti-Glomerular Basement Membrane Glomerulonephritis." (Aug. 19, 2010) Am J Nephrol 32: p. 324-331. Karger AG, Basel. (Published Online.).
Ziaei, Mohammed, Carol Greene, and Colin R. Green. "Wound healing in the eye: Therapeutic prospects." Advanced Drug Delivery Reviews 126 (2018): 162-176.
Zimmer DB, Green CR, Evans WH, Gilula NB. Topological analysis of the major protein in isolated intact rat liver gap junctions and gap junction-derived single membrane structures. J Biol Chem. Jun. 5, 1987:262(16):7751-63. PMID: 3034905 [PubMed—indexed for Medline].
Zlotnik, A., et al. Annu rev Immunol 18:217-42 (2000).
Zon, G., Ann. N.Y. Acad. Sci., 616, 161-172 (1990).
International Search Report and Written Opinion in International Patent Application No. PCT/US2024/018964, dated Jun. 28, 2024, in 11 pages.
Leung, Benjamin, and Drew Lowery. The patent landscape of inflammasome modulators. Nature reviews Drug discovery 19(3):158 (2020).

* cited by examiner

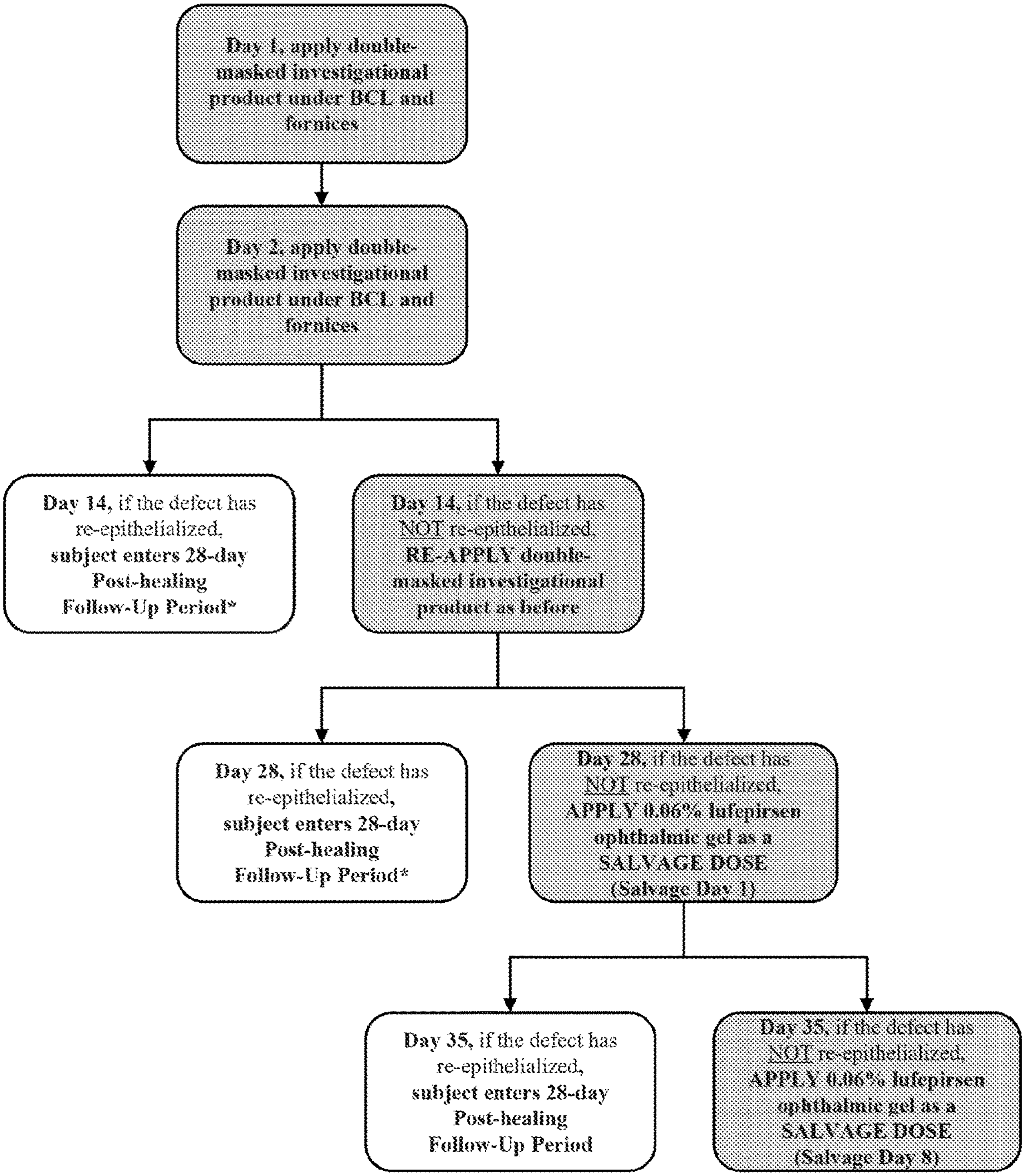
Day 1, apply double-masked investigational product under BCL and fornices
Day 2, apply double-masked investigational product under BCL and fornices
Day 14, if the defect has re-epithelialized, subject enters 28-day Post-healing Follow-Up Period*
Day 14, if the defect has NOT re-epithelialized, RE-APPLY double-masked investigational product as before
Day 28, if the defect has re-epithelialized, subject enters 28-day Post-healing Follow-Up Period*
Day 28, if the defect has NOT re-epithelialized, APPLY 0.06% lufepirsen ophthalmic gel as a SALVAGE DOSE (Salvage Day 1)
Day 35, if the defect has re-epithelialized, subject enters 28-day Post-healing Follow-Up Period
Day 35, if the defect has NOT re-epithelialized, APPLY 0.06% lufepirsen ophthalmic gel as a SALVAGE DOSE (Salvage Day 8)

TREATMENTS FOR OCULAR SURFACE DISORDERS

RELATED APPLICATIONS

This application claims priority to U.S. Provisional Application No. 63/521,298, filed Jun. 15, 2023, and U.S. Provisional Application No. 63/450,597, filed Mar. 7, 2023, the contents of each of which is herein incorporated by reference in its entirety.

SEQUENCE LISTING

The instant application contains a Sequence Listing which has been submitted electronically in XML format and is hereby incorporated by reference in its entirety. Said XML copy, created on Jul. 11, 2023, is named H7475-00102_SL.xml and is 215,985 bytes in size.

FIELD

The inventions relate to connexin modulators and modulation and ocular surface defects or disorders.

INCORPORATION BY REFERENCE

All publications, patents, related applications, and other written or electronic materials mentioned, identified or referred to herein, including each and every United States patent, United States patent application publication, non-U.S. patent, non-U.S. and PCT published application, article and other document cited or noted herein, and all those listed as References Cited in any patent or patents that issue herefrom, are hereby incorporated by reference in their entirety. The information incorporated is as much a part of this application, and all patents issuing therefrom or claiming priority thereto, as if all of the text and other content was repeated in the application or patent, will be treated as part of the text and content of this application as filed and any patent issuing therefrom or claiming priority thereto, and any portion of any material incorporated by reference may be included herein by amendment if required. In the event of inconsistent usages between this document and any document incorporated by reference, the usage in the incorporated reference(s) should be considered supplementary to that of this document; for irreconcilable inconsistencies, including definitions appearing in patents or patent applications, the usage in this document controls.

TECHNICAL BACKGROUND

The following includes information that may be useful in understanding the present inventions. It is not an admission that any of the information, publications or documents specifically or implicitly referenced herein is prior art, or important, to the inventions described and claimed herein.

Gap junctions are specialized intercellular connections found between most animal cell-types. They are expressed in virtually all tissues of the body, except for mature skeletal muscle and mobile cell types such as sperm and erythrocytes and provide regulated physical communication between cells by directly linking the interiors of adjoining cells, allowing various molecules, ions and electrical impulses to directly pass through.

One gap junction channel is composed of two connexin hemichannels (connexons), which connect across the intercellular space between adjacent cells. Each hemichannel of a gap junction resides in the adjacent cell membrane, and each hemichannel is formed by the covalent oligomerization of six individual connexin (Cx) proteins. See, e.g., Yeager (1998) Structure of cardiac gap junction intercellular channels, *J Struct Biol* 121: 231-245. Hemichannels can comprise one or more different connexin proteins but are usually in the form of homohexamers.

The human connexin family of genes and proteins now numbers 21. They usually weigh between 25 and 60 kDa and have an average length of 380 amino acids. All connexins share a common structure as a 4-pass transmembrane (TM) protein that includes several domains, namely, a short intracellular N-terminus (NT), an intracellular loop (IL) and a C-terminus (CT) that is also localized in the cytoplasm, plus two extracellular loops (EL1 and EL2) located outside the cell. The cytoplasmic carboxy terminus can vary considerably in length. See, e.g., Unger, et al. (1999) Electron cryo-crystallography of a recombinant cardiac gap junction channel, *Novartis Found Symp* 219: 22-30 & discussion 31-43; Leith, E, et al., The connexin 43 C-terminus: A tail of many tales. *Biochimica et Biophysica Acta* Vol. 1860(1):48-64 (January 2018).

Connexin proteins are commonly named according to their molecular weights, e.g. Cx26 is the connexin protein of 26 kDa, Cx43 is 43 kDa, etc. The principal structural difference between connexin proteins is the length of the C-terminal cytoplasmic tail, with connexin 26 having almost no tail (16 amino acids), while connexins 43 and 32 have long and intermediate ones (73 and 156 amino acids, respectively).

Inherited or acquired alterations in the structure and function of connexin proteins have been linked with various diseases. See, e.g., Delmar, M, Laird, D W, et al. Connexins and Disease, *Cold Spring Harb Perspect Biol* 10:a029348 (2018); D W Laird and PD Lampe, Cellular mechanisms of connexin-based inherited diseases. *Trends in Cell Biology* Vol. 32, Issue 1, p 58-69 (January 2022).

Research has also associated connexins with assorted conditions and disorders. See, e.g., Willebrords, J, et al., Connexins and their channels in inflammation *Crit Rev Biochem Mol Biol.* 51(6): 413-439 (2016); Feng, J, Becker, D L, et al., Connexin 43 upregulation in burns promotes burn conversion through spread of apoptotic death signals, *Burns* 46(6):1389-1397 (September 2020); McDouall, A, Green, C R, et al., Connexins, Pannexins and Gap Junctions in Perinatal Brain Injury. *Biomedicines* 10:1445 (2022). Connexins have been proposed as therapeutics targets for a number of conditions, including spinal cord injury, perinatal brain injury, nervous system diseases (e.g. Alzheimer's disease, Parkinson's disease), cardiac disorders (e.g. myocardial infarction), ocular disorders (e.g. age-related macular degeneration, diabetic macular edema), acute and chronic wounds (e.g. venous leg ulcers, diabetic foot ulcers), ischemia-reperfusion injury, inflammation, burns and cancer. Reviewed in Laird and Lampe, Therapeutic strategies targeting connexins, *Nat Rev Drug Discov.* 17(12): 905-921 (December 2018); Lampe and Laird, Recent advances in connexin gap junction biology, Faculty Reviews 27:11-14 (May 2022). See Becker D L, et al., Translating connexin biology into therapeutics. *Semin. Cell Dev. Biol* 50, 49-58 (2016). See also the articles in the "Junctional Proteins" issue of *FEBS Letters Volume* 588, Issue 8, Pages: i, 1185-1490 (Apr. 17, 2014), including Zhang J, et al. Connexin hemichannel induced vascular leak suggests a new paradigm for cancer therapy (p. 1365-1371) and Martin P E, et al., *Connexins: Sensors of epidermal integrity that are therapeutic targets* (*p.* 1304-1314). See also, e.g., Van Campenhout R, et al., Mechanisms Underlying Connexin Hemichannel Activation in Disease. *Int J Mol Sci.* 22(7):3503 (April 2021) and U.S. Pat. Nos. 10,401,188 and 11,401,516, issued for "Channel Modulators."

Strategies for treating eye wounds are reviewed in Ziaei M, et al., Wound healing in the eye: Therapeutic prospects, *Advanced Drug Delivery Reviews* 126 (2018) 162-176. Ziaei et al. discusses, inter alia, "traditional" treatment strategies including (1) steroids and (2) contact lenses, for example, and a number of "modern" treatment strategies including (3) growth factors (epidermal growth factor, insulin-like growth factor, nerve growth factor and human growth hormone), (4) amniotic membrane-based products, (5) thymosin $4, (6) rebamipide, (7) stem cells and other blood derived products, etc., as well as (8) gap junction hemichannel modulation. See U.S. Pat. No. 8,034,789 issued Oct. 11, 2011, for "Antisense compounds targeted to connexins and methods of use thereof" and Ormonde, S., et al., Regulation of connexin43 gap junction protein triggers vascular recovery and healing in human ocular persistent epithelial defect wounds, *J. Membr. Biol.* 245 (2012) 381-388 (potential for Cx43 modulation discussed in regard to five compassionate use subjects, but without excluding "the possibility of vehicle effects"). More recently, the use of (9) topical insulin eye drops to treat persistent epithelial defects (PEDs) in the eye that are refractory to usual treatment in clinical practice has been proposed. Diaz-Valle, D, et al., Comparison of the efficacy of topical insulin with autologous serum eye drops in persistent epithelial defects of the cornea. *Acta Ophthalmol* 2022 June; 100(4):e912-e919. Others offer the use of (10) punctal plugs, (11) cyanoacrylate glue, (13) debridement, and (14) fibronectin tarsorrhaphy (partial or complete eyelid closure) as possible treatments. See also e.g. Katzman and Jeng, Management strategies for persistent epithelial defects of the cornea. *Saudi Journal of Ophthalmology* 28:168-172 (2014).

As noted in in Ziaei, et al., many current and emerging therapies proposed for ocular surface wound healing are still largely experimental or conceptual. For example, ocular use of gap junction regulators in humans has not been defined in the clinic, and there are no established doses, dose regimens or methods for the modulation of connexins, connexin gap junctions and/or connexin hemichannels for the treatment of non-healing or persistent ocular or corneal surface defects or disorders.

Such methods, doses and dose regimens are described and claimed herein and provide a long-needed means for treating subjects suffering with a non-healing or persistent ocular surface defect or disorder, and other ocular diseases, disorders and conditions described herein.

In contrast to the methods of treatment described and claimed herein, most current therapies to treat these ocular diseases, disorders and conditions do not treat their cause or causes, which often include uncontrolled inflammation, a have lead to limited success.

BRIEF SUMMARY

The inventions described and claimed herein have many attributes and embodiments including, but not limited to, those set forth or described or referenced in this Brief Summary. It is not intended to be all-inclusive and the inventions described and claimed herein are not limited to or by the features or embodiments identified in this introduction, which is included for purposes of illustration only and not restriction.

It is an object of the invention to provide methods, doses, dose regimens, compositions and kits for connexin modulation for the treatment of a subject for a non-healing or persistent ocular surface or corneal defect or disorder. In some embodiments, a compound or composition for modulation or inhibition of a connexin, a connexin gap junction and/or a connexin hemichannel is provided for treatment and dosed as described herein. In some embodiments, the non-healing ocular surface defect or disorder is a persistent epithelial defect (PED). In some embodiments, the non-healing ocular surface defect or disorder is a persistent corneal epithelial defect (PCED). In some embodiments, the subject is a human.

In some embodiments, the connexin modulator modulates or inhibits connexin expression. In some embodiments, the connexin modulator inhibits or modulates the expression of connexin 43.

In some embodiments, the connexin modulator is a connexin gap junction modulator. In some embodiments, the connexin gap junction modulator modulates connexin 43 gap junctions.

In some embodiments, the connexin modulator is a connexin hemichannel modulator. In some embodiments, the connexin hemichannel modulator modulates connexin 43 hemichannels. Modulation of a hemichannel may occur by any means. In some embodiments, for example, modulation may occur by inducing or promoting closure of a hemichannel; by preventing, blocking, inhibiting or decreasing hemichannel opening; by suppressing hemichannel permeability; by suppressing ATP release from hemichannels; and/or by triggering, inducing or promoting cellular internalization of a hemichannel and/or gap junction. Hemichannel modulators include blockers and other compounds that interfere with the passage of molecules through a connexin hemichannel. A hemichannel modulator can block or reduce the release of molecules through a hemichannel to an extracellular space, and/or block or reduce the entry of molecules through a hemichannel into an intracellular space. In some embodiments, hemichannel modulators fully or partially block hemichannel opening. In some embodiments, hemichannel modulators fully or partially block, slow or suppress the leak or the passage of molecules through a hemichannel to or from an extracellular space. In some embodiments, hemichannel modulators are compounds that decrease the open probability of a hemichannel.

In some embodiments of the present invention, modulation of gap junctions and hemichannels is accomplished by administration of a connexin expression modulator, a connexin peptidomimetic and/or a small molecule connexin modulator that modulates a corneal epithelial connexin, a corneal epithelial connexin gap junction, or a corneal epithelial connexin hemichannel in a dose regimen disclosed herein. In some embodiments of the present invention, modulation of gap junctions and hemichannels is accomplished by administration of a connexin expression modulator, a connexin peptidomimetic and/or a small molecule connexin modulator that modulates a corneal vascular connexin using a dose regimen disclosed herein. In some embodiments of the present invention, in a dose regimen disclosed herein, modulation of gap junctions and hemichannels is accomplished by administration of a connexin expression modulator, a connexin peptidomimetic and/or a small molecule connexin modulator that modulates (e.g., reduce, slows, inhibits or eliminates) inflammation.

In some embodiments, the connexin modulator, the connexin gap junction modulator and/or the connexin hemichannel modulators used in methods of the invention modulates one or more connexins in the human corneal epithelium, namely, connexin 26, connexin 30, connexin 30.3, connexin 31, connexin 31.1, connexin 32, connexin 43, connexin 45, connexin 50 and connexin 58.

In some embodiments, the connexin modulator comprises an antisense molecule. In some embodiments, the antisense molecule is a connexin43 antisense oligonucleotide. In some embodiments, the connexin modulator may be a connexin 43 antisense polynucleotide comprising, consisting essentially of, or consisting of a sequence according to SEQ ID NOS. 1-16 and/or modified versions thereof. In some embodiments, antisense oligonucleotide comprises, consists essentially of, or consists of 5'-GTA ATT GCG GCA AGA AGA ATT GTT TCT GTC-3' (SEQ ID NO:1; lufepirsen). In some embodiments, the antisense oligonucleotide may be chemically modified or may be an unmodified oligonucleotide, e.g. a modified or an unmodified DNA oligonucleotide.

In some embodiments, the connexin modulator comprises a connexin peptidomimetic. In some embodiments, the connexin peptidomimetic is a connexin43 peptidomimetic. In some embodiments, the connexin peptidomimetic comprises, consists essentially of, or consists of SRPTEKT (SEQ ID NO:101). In some embodiments, the connexin peptidomimetic comprises, consists essentially of, or consists of Gap19, XG19, Gap26 or Gap27. In some embodiments, the connexin peptidomimetic is a connexin26 peptidomimetic (e.g. Gap26 i.e., VCYDKSFPISHVR (SEQ ID NO:102), a connexin32 peptidomimetic (e.g. INCTLQPGCNSV (SEQ ID NO: 103) or $^{37,43}$Gap27, which is SRPTEKTIFII (SEQ ID NO: 104) or a connexin45 peptidomimetic, or a connexin50 peptidomimetic (e.g. TAT-Cx50L2, i.e., GGERAPLAADQGSVKKSSSSSKGTKK (SEQ ID NO: 105) or TAT-Cx50CT, i.e., SRARSDDLTV (SEQ ID NO: 106)).

In some embodiments, the connexin modulator comprises a small molecule connexin, connexin gap junction or connexin hemichannel modulator. In some embodiments, the small molecule connexin modulator inhibits or blocks connexin hemichannel opening. In some embodiments, the small molecule connexin modulator moderates ATP release from connexin hemichannels. In some embodiments, the small molecule connexin modulator inhibits or blocks Cx43 hemichannel opening and moderates ATP release from Cx43 hemichannels. In some embodiments, the small molecule connexin modulator is a compound according to Formula I (e.g. tonabersat). In some embodiments, the small molecule connexin modulator is a tonabersat prodrug compound according to Formula II.

In some embodiments, the invention relates to methods for the modulation of a connexins, gap junction channels and/or hemichannels using a therapeutically effective amount of a connexin modulator in a dose regimen described herein. In some embodiments, a therapeutically effective amount of a connexin antisense compound (e.g. lufepirsen) is administered. In some embodiments, a therapeutically effective amount of a connexin peptidomimetic compound (e.g. Peptide5, Gap19, XG19, CXT 1 to CXT 5, Antp/CXT 1 to Antp/CXT 5, etc.) is administered. In some embodiments, a therapeutically effective amount of a small molecule connexin hemichannel blocker compound (e.g. tonabersat or a tonabersat prodrug) is administered.

In some embodiments, the invention relates to methods for the modulation of a connexins, gap junction channels and/or hemichannels using new particular doses and newly discovered and clinically confirmed dose regimens of connexin modulators, gap junction modulators and/or hemichannel modulators for ocular surface recovery in a subject with a non-healing or persistent ocular surface or corneal defect or disorder, or both. Non-healing ocular surface or corneal defect or disorders treated using the doses, compositions, dose regimens and methods of the invention include persistent epithelial defects (PED) and persistent corneal epithelial defect (PCED). They include PEDs and PCEDs from any cause including chemical injury, thermal injury, disease and inflammation.

In some embodiments, the non-healing ocular surface defect or disorder results from a chemical and/or thermal injury. In some embodiments, the non-healing ocular surface defect or disorder results from a physical trauma or injury. In certain embodiments, the non-healing ocular surface defect or disorder is a PED or PCED resulting from a chemical and/or thermal injury. In some embodiments, the chemical and/or thermal injury resulting in a PED or PCED is a severe chemical and/or thermal injury. In some embodiments, severe ocular surface and/or corneal burns and injuries are those with greater than 50% conjunctival or >6 clock hours of limbal involvement. These include ocular surface and corneal burns and injuries ≥3 on the Dua Classification scale. In some embodiments, the non-healing ocular surface or corneal defect or disorder results from inflammation, or from an inflammatory disease. In some embodiments, the non-healing ocular surface or corneal defect or disorder results from inflammation of the eye. In some embodiments, the non-healing ocular surface or corneal defect or disorder results from an inflammatory disease of the eye, the ocular surface, or the cornea.

All PED and PCED etiologies, no matter the cause, may be treated using the methods and compositions of the invention as described herein. PED and PCED etiologies include not only inflammation and inflammatory disease, neurotrophic disease and neurotrophic keratitis, but chemical, mechanical, thermal causes, and epithelial/limbal stem cell deficiency. In some embodiments, methods, compositions and/or doses of the invention are used to treat PED and/or PCED caused by or resulting from chemical injury. In some embodiments, methods, compositions and/or doses of the invention are used to treat PED and/or PCED caused by or resulting from thermal injury. In some embodiments, methods and/or doses of the invention are used to treat PED and/or PCED caused by or resulting from mechanical injury. In some embodiments, methods and/or doses of the invention are used to treat PED and/or PCED caused by or resulting from inflammation or an inflammatory disease. In some embodiments, methods, compositions and/or doses of the invention are used to treat PED and/or PCED caused by or resulting from neurotrophic disease (e.g. neurotrophic keratitis).

In some embodiments, the non-healing ocular surface defect or disorder is an ocular surface ulcer. In some embodiments, the non-healing ocular surface defect or disorder is a corneal ulcer. In some embodiments, the ocular surface ulcer or the corneal ulcer is caused by a bacterium, a virus, a fungus or a parasite. In some embodiments, the ocular surface ulcer or the ocular surface ulcer or the corneal ulcer results from acanthamoeba keratitis, fungal keratitis or herpes simplex keratitis. In other embodiments, the ocular surface ulcer or the corneal ulcer is caused by a trauma such as an abrasion (e.g. scratch or cut) or a foreign body in the eye. In another embodiment, the ocular surface ulcer or the corneal ulcer is caused by allergic eye disease. In another embodiment, the ocular surface ulcer or the corneal ulcer is caused by dry eye. In some embodiments, the non-healing ocular surface ulcer or corneal ulcer is caused by or results from inflammation or an inflammatory disease, disorder, or condition. In some embodiments, the ocular surface ulcer or the corneal ulcer results from another cause (e.g. an injury or burn).

In some embodiments of the methods described and claimed herein, a connexin inhibitor or modulator is administered to subject having a non-healing surface defect or disorder on Day 1, Day 2 and on about Day 14. In some embodiments, a connexin inhibitor or modulator is administered to the subject again on about Day 28. In some embodiments, a connexin inhibitor or modulator may be administered to a subject having a non-healing surface defect or disorder again on about Day 35. In some embodiments, a connexin inhibitor or modulator may also be administered to a subject on Day 7 and/or Day 21. In some embodiments, the non-healing surface defect or disorder to be treated is a PED. In some embodiments, the non-healing surface defect or disorder to be treated is a PCED. In some embodiments, the PED or PCED results from a chemical and/or thermal injury, or from inflammation.

In some embodiments, a single dose of a connexin modulator is administered in a regimen for treating a non-healing surface defect or disorder as described and claimed herein (e.g., single doses administered on Days, 1, 2 and 14, and so on, including in other dose regimens described herein). In some embodiments, the daily dose of a connexin modulator for administration in a dose regimen of the present invention is administered in divided amounts (e.g. one-half dose, administered to the subject twice per day on Days, 1, 2 and 14, etc.). In some embodiments, a single dose or divided dose of a connexin modulator is administered on one or more or all of days in each of the dose regimens described herein.

In some embodiments of the present invention, the method for treating a subject for a non-healing ocular surface defect comprises administering to the subject a therapeutically effective amount of a connexin modulator, wherein the connexin modulator is administered at least once on Day 1, at least once on Day 2, and at least once at about Day 14. In some embodiments, the connexin modulator is a connexin 43 modulator. In some embodiments, the connexin 43 modulator modulates connexin 43 expression. In some embodiments, the connexin 43 expression modulator is an antisense molecule. In some embodiments, the connexin 43 antisense molecule is lufepirsen. In some embodiments, lufepirsen is administered in a composition comprising a nonionic polyoxyethylene-polyoxypropylene block copolymer carrier (e.g. Pluronic F-127). In some embodiments, lufepirsen is administered in a composition comprising a cellulose-based carrier, e.g., hydroxyethylcellulose, carboxymethylcellulose hydroxymethylcellulose, hydroxypropylmethylcellulose, etc., or other pharmaceutically acceptable carrier.

In some embodiments, from 3 to 4 doses of a connexin modulator, e.g. lufepirsen, are administered at Days 1, 2 and 14 (and, optionally, on or about Day 28). In other embodiments, 4 to 5 doses are administered, with a dose or doses of a connexin modulator, e.g. lufepirsen or another connexin antisense or modulator, also administered at about Day 35, in addition to Days 1, 2 and 14 (or in addition to Days 1, 2, 14 and, optionally, about Day 28). In some embodiments of these dose regimens, doses of a connexin modulator, e.g. lufepirsen, may also be administered at about Day 7 and/or Day 21 In some embodiments, connexin modulator doses, e.g. lufepirsen, are administered on Days, 1, 2, 14 and 28.

In some embodiments, connexin modulator doses, e.g. lufepirsen, are administered on Days 1, 2, 14 and 21.

In some embodiments, connexin modulator doses, e.g. lufepirsen, are administered on Days 1, 2, 7, 14 and 21.

In some embodiments, connexin modulator doses, e.g. lufepirsen, are administered on Days 1, 2, 7, 14, 21 and 28.

In some embodiments, connexin modulator doses, e.g. lufepirsen, are administered on Days 1, 2, 14, 28 and 35. In some embodiments, connexin modulator doses, e.g. lufepirsen, are administered on Days 1, 2, 7, 14, 28 and 35. In some embodiments, connexin modulator doses, e.g. lufepirsen, are administered on Days 1, 2, 7, 14, 21, 28 and 35. In some embodiments, connexin modulator doses, e.g. lufepirsen, are administered on Days, 1, 2, 7, 14, 21, 28, and 35. In some embodiments, a dose is also administered in any of these dosing regimens after Day 35. In some embodiments, administration is to a PED or PCED. In some embodiments, the connexin modulator comprises a connexin antisense molecule (e.g. lufepirsen). In some embodiments, the connexin modulator comprises a connexin peptidomimetic (e.g., Peptide5, Gap19, XG19, αCT1, etc.). In some embodiments, the connexin modulator comprises a small molecule connexin hemichannel blocker (e.g., tonabersat). In some embodiments, the connexin modulator is a connexin 43 modulator. In some embodiments, administration is to a PED or PCED. The connexin modulator may be administered in a single or divided dose on any dosing days.

In some embodiments, 3 doses of a connexin modulator (e.g. lufepirsen) are administered over 14 days to treat a non-healing or persistent ocular or corneal surface defect in a subject, including, for example, on Days 1 and 2. In some embodiments, 4 doses of a connexin modulator (e.g. lufepirsen) are administered over about 28 days. In some embodiments, 5 doses of a connexin modulator (e.g. lufepirsen) are administered over about 28 to about 35 days. In some embodiments, 6-7 doses of a connexin modulator (e.g. lufepirsen) are administered over about 35 days. For example, in one embodiment, a connexin modulator (e.g. lufepirsen) is administered 4 times over Days 1 and 2, on about Day 14 and 28. In another embodiment, a connexin modulator (e.g. lufepirsen) is administered 5 times over Days 1 and 2, on about Day 14, on about Day 28 and on about Day 35. In another embodiment, a connexin modulator (e.g. lufepirsen) is administered 5 times over Days 1 and 2, on about Day 7, on about Day 14 and on about Day 28. In another embodiment, a connexin modulator (e.g. lufepirsen) is administered 6 times over Days 1 and 2, on about Day 7, on about Day 14, on about Day 21 and on about Day 28. In another embodiment, a connexin modulator (e.g. lufepirsen) is administered 7 times over Days 1 and 2, on about Day 7, on about Day 14, on about Day 21 and on about Day 28. Reference to "administration" here refers, of course, to administration of a connexin modulator in a single dose or in divided doses. In some embodiments of the present invention, modulation of connexins, gap junctions and/or hemichannels is accomplished by administration of a connexin antisense oligonucleotide (e.g. lufepirsen) to the eye of a subject having a non-healing or persistent ocular surface or corneal defect or disorder (e.g. a PED or a PCED).

In some embodiments, the amount of connexin modulator administered to a subject with a non-healing ocular surface defect or disorder (e.g. a PED) or non-healing corneal surface defect or disorder (e.g. a PCED) in any of the dosing schedules described herein (e.g. Days 1, 2 and 14; Days 1, 2, 14 and, optionally, Day 28; Days 1, 2, 7, 14, 21, and, optionally, Day 28; and so on) is a therapeutically effective amount.

In some embodiments, the amount of connexin modulator administered to a subject with a non-healing ocular surface defect or disorder (e.g. a PED) or non-healing corneal surface defect or disorder (e.g. a PCED) in any of the dosing schedules described herein is one or more of the dose amounts described herein (e.g. milligram per milliliter (mg/mL) connexin modulator dosing), micromolar (M) connexin modulator concentration dosing, milligram (mg) connexin modulator dosing, etc.). The particular doses described herein may be administered to a subject with a non-healing ocular surface defect or disorder (e.g. a PED) or non-healing corneal surface defect or disorder (e.g. a PCED), for example, on Days 1, 2, 14 and, optionally, Day 28 and/or Day 35; on Days 1, 2, 14 and optionally on Days 7, 21 and/or 28; etc., or any other dose regimen described herein.

In some embodiments of the method of the present invention, the connexin modulator administered to the non-healing surface defect or disorder in a subject is 0.06 wt. % lufepirsen. In some embodiments, the connexin modulator administered to a subject with a non-healing surface defect or disorder is 0.006 wt. % lufepirsen. In some embodiments, the connexin modulator administered is at least about 0.06 wt. % lufepirsen. In some embodiments, the connexin modulator administered to a subject with a non-healing surface defect or disorder is at least about 0.006 wt. % lufepirsen. In some embodiments, administration is to a PED or PCED. In some embodiments, a composition comprising or consisting essentially of a pharmaceutically acceptable carrier and about 0.06 wt. % lufepirsen, about 0.006 wt. % lufepirsen, at least about 0.06 wt. % lufepirsen or least about 0.006 wt. % lufepirsen is administered to heal the non-healing surface defect or disorder in a subject.

In some embodiments of the present invention, the non-healing surface defect or disorder is treated with composition comprising 0.6 mg/mL lufepirsen. In some embodiments of the present invention, the non-healing surface defect or disorder is treated with composition comprising 0.06 mg/mL lufepirsen. In some embodiments, the composition comprises at least about 0.6 mg/mL lufepirsen. In some embodiments, the composition comprises at least about 0.06 mg/mL lufepirsen. In some embodiments, administration is to a PED or PCED.

In some embodiments of the present invention, the non-healing surface defect or disorder in a subject is treated with a composition comprising or consisting essentially of about 0.18 mg of lufepirsen in the regimens described herein. In some embodiments, each dose of lufepirsen applied to the non-healing surface defect or disorder in or on the subject comprises or consists essentially of at least about 0.18 mg of lufepirsen in the regimens described herein. In some embodiments of the present invention, the non-healing surface defect or disorder is treated with composition comprising or consisting essentially of about 0.018 mg of lufepirsen in the regimens described herein. In some embodiments, each dose of lufepirsen applied to the non-healing surface defect or disorder comprises or consists essentially of at least about 0.018 mg of lufepirsen in the regimens described herein. In some embodiments, administration is to a PED or PCED.

In some embodiments, about 0.18 mg of lufepirsen (or other connexin antisense or connexin modulator), about 0.018 mg of lufepirsen (or other connexin antisense or connexin modulator), or from about 0.1 mg, 0.2 mg, 0.3 mg, 0.4 mg or about 0.5 mg to about 1 mg of lufepirsen (or another connexin antisense, or other connexin modulator) is administered to the non-healing or persistent ocular surface or corneal defect or disorder in a single dose, or in two or more divided doses, e.g., for twice daily administration in up to 6 doses administered on Days 1, 2 and 14. In other embodiments, at least about 0.1 mg, 0.2 mg, 0.3 mg, 0.4 mg or 0.5 mg or at least about 1 mg of lufepirsen (or another connexin antisense, or other connexin modulator) is administered in a single dose, or in two or more divided doses to the non-healing surface defect or disorder, e.g., for twice daily administration in up to 6 to 10 doses administered on Days 1, 2 and 14, or using other dose regimen described herein that includes Day 28 and/or Day 35. In other embodiments, at least about 0.5 mg or at least about 1 mg of lufepirsen (or another connexin antisense, or other connexin modulator) is administered in single or divided doses, e.g., for twice daily administration, in up to 14 doses administered on Days 1, 2 and 14, and one or more of Day 7, Day 21, Day 28 and/or Day 35, for example. In some embodiments, administration is to a PED or PCED in a subject. In some embodiments, the connexin antisense administered to the subject in the amounts described herein comprises or consists essentially of an antisense compound having a sequence according to SEQ ID NOS:2-16. In some embodiments, the connexin antisense administered to the subject in the amounts described herein on the days described herein, comprises or consists essentially of another connexin 43 antisense compound.

In any of the embodiments of these doses and dosing regimens and methods, the lufepirsen doses may be administrated to a PED or PCED in a subject. In some embodiments of these doses and dosing regimens and methods, the connexin modulator dose administered comprises another connexin antisense or modulator, e.g., another Cx43 antisense or Cx43 modulator other than or in addition to lufepirsen, or a modulator of another ocular or corneal epithelial connexin other than or in addition to Cx43. In some embodiments, the connexin antisense administered to the subject in the amounts described herein on the days described herein, comprises or consists essentially of an antisense compound for modulating expression of one or more connexins selected from the group consisting of connexin 26, connexin 30, connexin 30.3, connexin 31, connexin 31.1, connexin 32, connexin 43, connexin 45, connexin 50 and connexin 58.

In some embodiments of the present invention, the volume of a composition comprising or consisting essentially of a connexin modulator administered a non-healing surface defect or disorder in a subject is about 300 μL. In other embodiments, the volume of the composition administered is from about 250 μL to about 1.0 mL. In some embodiments, the composition comprises about 0.01 mg, 0.018 mg, from about 0.18 mg to about 0.2 mg of lufepirsen, or from about 0.18 mg or 0.2 mg or 0.5 mg to about 1 mg of lufepirsen. In some embodiments, the composition comprises at least about 0.018 mg lufepirsen, at least about 0.18 mg of lufepirsen, at least about 0.5 mg of lufepirsen or at least about 1.0 mg of lufepirsen. In some embodiments, instead of or in addition to lufepirsen, the composition comprises about 0.01 mg, about 0.018 mg, from about 0.18 mg to about 0.2 mg, or from about 0.18 mg or 0.2 mg or 0.5 mg to about 1 mg of another connexin 43 antisense compound (or other connexin modulator, including, for example, other antisense, peptidomimetic, small molecule connexin modulators that modulate connexin 43 or another ocular or corneal epithelial connexin(s)). In some embodiments, instead of or in addition to lufepirsen, the composition comprises at least about 0.018 mg, at least about 0.18 mg of, at least about 0.5 mg or at least about 1.0 mg of another connexin antisense or other connexin modulator (e.g. other antisense, peptidomimetic and/or small molecule connexin modulators that modulate connexin 43 or other ocular or corneal epithelial connexin(s)).

In some embodiments, the composition for use in the methods of the invention comprises a reverse thermosetting gel. In some embodiments, the composition for use in the methods of the invention comprises a pluronic gel, also known as a poloxamer gel. In some embodiments, the composition for use in the methods of the invention comprises poloxamer F-127 (poloxamer 407 or Pluronic F-127). In some embodiments, the composition for use in the methods of the invention comprises about 20-30 mg/mL of a poloxamer F-127. In some embodiments, the composition for use in the methods of the invention comprises about 22-25 mg/mL of a poloxamer F-127. In some embodiments, the composition for use in the methods of the invention comprises about 22.6 mg/mL of a poloxamer F-127.

In some embodiments, the connexin modulator is lufepirsen in a composition comprising Pluronic F-127, a buffer or buffers and water for injection. Buffers incorporated in the lufepirsen composition may comprise sodium phosphate dibasic heptahydrate or potassium phosphate (monobasic) or both. In some embodiments, the composition comprises 0.06% or 0.006% lufepirsen, at least about 0.06% or at least about 0.006% lufepirsen. In some embodiments, the buffered composition comprises 0.6 mg/mL or 0.06 mg/mL lufepirsen, at least about 0.6 mg/mL or at least about 0.06 mg/mL lufepirsen. In some embodiments, about 300 mL of the lufepirsen composition is administered to a non-healing surface disorder on Day 1, Day 2 and on Day 14. If necessary or desired, in some embodiments, about 300 μL of a lufepirsen dose is administered to a subject having a non-healing surface disorder again on about Day 28. If necessary or desired, in some embodiments, about 300 μL of a lufepirsen dose is administered to a subject having a non-healing surface disorder again on about Day 35. In other embodiments, if deemed necessary or desired, about 300 μL of the lufepirsen composition is also administered to a subject having a non-healing surface disorder again on Day 7 and/or on about Day 21. In some embodiments, the non-healing surface disorder treated with the composition is a PED or PCED. In some embodiments, the PED or PCED results from a chemical and/or thermal injury or other trauma. In some embodiments, from about 300 μL to 1.0 mL of the lufepirsen composition is administered to the non-healing surface disorder. In some embodiments, the connexin modulator administered in this composition comprises another connexin 43 antisense compound. In some embodiments, the connexin modulator administered in this composition comprises an antisense compound against another ocular or corneal epithelial connexin. In some embodiments, the connexin modulator administered in this composition comprises another connexin 43 antisense compound, an antisense compound against another ocular or corneal epithelial connexin, and/or another connexin modulator (e.g. a peptidomimetic or small molecule connexin modulator).

In some embodiments of the present invention, modulation of gap junctions and hemichannels is accomplished by administration of a small molecule hemichannel blocker that blocks or modulates opening of a corneal epithelial connexin hemichannel. In some embodiments, treatment of a non-healing ocular surface defect by modulation of a corneal epithelial hemichannel is accomplished by topical, oral or systemic administration of a small molecule hemichannel blocker. In some embodiments, a therapeutically effective amount of the small molecule is administered in a dose regimen described herein. In some embodiments, the dose of the small molecule is administered in a dose regimen described herein is one or more of the doses set forth herein. In some embodiments, the small molecule hemichannel blocker is tonabersat.

In any embodiment of the invention, the administration of the connexin modulator may be topical. In some embodiments, a connexin antisense connexin modulator (e.g. lufepirsen) is administered topically. In some embodiments, a connexin peptidomimetic connexin modulator (e.g., XG19) is administered topically. In some embodiments, a small molecule connexin modulator (e.g. tonabersat) is administered topically. In some embodiments, a combination of one or more compounds selected from the group consisting of connexin antisense connexin modulators (e.g. lufepirsen), connexin peptidomimetic connexin modulators (e.g., XG19), and small molecule connexin modulators (e.g. tonabersat) is administered topically. In some embodiments, one or more compounds selected from the group consisting of a connexin antisense connexin modulators (e.g. lufepirsen), connexin peptidomimetic connexin modulators (e.g., XG19), and small molecule connexin modulators (e.g. tonabersat) and another therapeutic agent or agents is/are administered topically. In some embodiments, the other therapeutic agent or agents is selected from the group consisting of antibiotics, antivirals, anti-parasitics, antifungals, steroids, anti-inflammatories and immunosuppressants. In some embodiments, the other therapeutic agent or agents is selected from the group consisting of pannexin 1 (Panx1) inhibitors (e.g. probenecid, $^{10}$Panx1), inhibitors of its associated P2X receptors (and any of its isoforms), and inhibitors Panx1-P2X signalosomes. In some embodiments, one or more compounds selected selected from the group consisting of pannexin 1 (Panx1) inhibitors (e.g. probenecid), inhibitors of is associate P2X receptors (and any of it isoforms), and inhibitors of Panx1-P2X signalosomesis is administered (e.g. topically), alone or together with a connexin modulator or another therapeutic agent. Other useful pannexin inhibitors are described in U.S. Pat. No. 10,465,188 ("Channel Modulators").

In some embodiments, the subject has an amniotic membrane affixed to the surface of the eye to be treated. In some embodiments, the amniotic membrane is a permanent surgical graft. In some embodiments, the amniotic membrane is a dehydrated sutureless graft. In some embodiments, the amniotic membrane is a cryopreserved sutureless graft.

In some embodiments, a connexin modulator, gap junction modulator and/or hemichannel modulator is administered to the subject under an amniotic membrane. In some embodiments, an amniotic membrane is affixed to the eye of the subject after application of the modulator to the non-healing surface defect or disorder.

In some embodiments, a connexin modulator, a gap junction modulator and/or a hemichannel modulator is/are administered to the subject under a contact lens. In some embodiments, the contact lens is applied to the eye of the subject at about the same time as, immediately after or sometime following administration of the connexin modulator, a gap junction modulator and/or a hemichannel modulator. In some embodiments, the contact lens is a silicon hydrogel contact lens. In some embodiments, the lens is loaded with a connexin modulator, a gap junction modulator and/or a hemichannel modulator prior to application of the lens to the non-healing surface defect or disorder in or on the eye of the subject. In some embodiments, the modulator is lufepirsen.

In some embodiments, the contact lens is a therapeutic contact bandage lens. Therapeutic contact bandage lenses are also referred to as "bandage lenses" and "therapeutic bandage lenses." In some embodiments, the therapeutic bandage lens is, for example, a soft contact lens, a gas permeable (scleral) lens or a 3D-printed bio-gel. Some suitable FDA-approved soft bandage lenses include Acuvue Oasys with Hydraclear Plus (Johnson & Johnson Vision), Air Optix Night & Day Aqua (Alcon), PureVision (Bausch+ Lomb) and UCL 55% (United Contact Lens) and Kontur (Kontur Kontact Lens).

In some embodiments, the present invention relates to methods for the modulation of a connexin, a connexin gap junction channel and/or a connexin hemichannel using doses and dose regimens of connexin modulators (including e.g. gap junction modulators and/or hemichannel modulators) for ocular surface recovery and/or corneal epithelial recovery. In some embodiments, modulation of gap junctions and hemichannels is accomplished by administration of a connexin 43 antisense oligonucleotide, a connexin 43 peptidomimetic and/or a small molecule connexin 43 hemichannel blocker. In other embodiments, connexin 26, connexin 30, connexin 30.3, connexin 31, connexin 31.1, connexin 32, connexin 45, connexin 50 and/or connexin 58 modulators are used, alone or in combination with or in conjunction with a connexin 43 modulator.

In some embodiments, a gap junction modulator or hemichannel modulator (e.g. lufepirsen) is applied topically to the eye of a subject with a non-healing or persistent ocular surface and/or corneal epithelial disorder and another topically administered gap junction modulator (e.g. Peptide5, Ga19, XG19, or another peptidomimetic) or topically, orally or systemically dispensed hemichannel modulator (e.g. tonabersat, or another orally or systemically bioavailable gap junction and/or hemichannel modulator) is administered to the subject at the same time as, or before or after the topically applied gap junction modulator or hemichannel modulator.

In some embodiments, the method comprises co-administering a topical connexin modulator and/or a gap junction modulator and a systemically available connexin hemichannel modulator. The co-administration of the gap junction channel modulator can be simultaneously with, subsequent to, or before the administration of the connexin hemichannel modulator. In some embodiments, compounds of Formula I, for example tonabersat, compounds of Formula II and/or a peptidomimetic (e.g. Peptide5, XG19, etc.), may be co-administered with a connexin expression modulator, e.g., lufepirsen, or anti-connexin peptidomimetic.

In some embodiments, the invention provides the use of a connexin modulator in the manufacture of a medicament for treatment of a non-healing or persistent ocular surface and/or corneal defect or disorder modulation. In some embodiments, the medicament comprises or consists essentially of a connexin antisense molecule, e.g. lufepirsen, including in the amounts and/or concentrations described herein. In some embodiments, the medicament comprises or consists essentially of a connexin peptidomimetic, e.g. Peptide5, Gap19, XG19, an αCT1 peptide (e.g., CXT 1, CXT, CXT 3, CXT 4, CXT 5, or any other C-terminal connexin peptidomimetic, with or without a C-terminally or N-terminally attached cell-penetrating peptide), etc. In some embodiments, the medicament comprises or consists essentially of a small molecule connexin hemichannel blocker, e.g. a compound according to Formula I, including tonabersat, carabersat, and prodrugs thereof, including tonabersat prodrugs according to Formula II.

In some embodiments, connexin modulators and connexin43 modulators include means for down-regulating the connexin transcription or translation of a connexin, such as antisense molecules, for example. Means for connexin modulation also include ZO-1 binding peptides in the case of connexin 43 (e.g. αCT1, αCT1, CXT 1, CXT 2, CXT 3, CXT 4, CXT 5, etc.) for example. Preferred gap junction channel modulators are connexin43 expression modulators, connexin43 gap junction modulators and connexin 43 hemichannel modulators. Especially preferred connexin 43 modulators include lufepirsen, XG19 and tonabersat.

In some embodiments, the invention relates to pharmaceutical compositions and articles of manufacture, including kits with instructions for use, comprising a therapeutically effective amount of a connexin modulator, and dose regimens for treating non-healing ocular and corneal surface defects and disorders with one or more connexin modulators, including connexin expression modulators, gap junction modulators and/or hemichannel modulators. In some embodiments, the kit includes or is associated with instructions (e.g. online instructions) for dosing and treating PED and/or a PCED as described herein.

In some embodiments, the connexin modulators (e.g. connexin expression modulators, connexin gap junction modulators and connexin hemichannel modulators, including, for example, modulators of Cx26, Cx30, Cx30.3, Cx31.1, Cx32, Cx36, Cx37, Cx40, Cx43, Cx45, Cx50 or Cx58 connexins, gap junctions and/or hemichannels) are combined with a pharmaceutically acceptable carrier or diluent to produce a pharmaceutical composition. In some embodiments, suitable carriers and diluents include buffered, aqueous solutions, isotonic saline solutions, for example phosphate-buffered saline, isotonic water, and the like. In some embodiments, the carrier is a pluronic or poloxamer gel. In some embodiments, the gel is pluronic F-127. In some embodiments, the pharmaceutical composition comprises a buffer. In some embodiments, the buffer comprises or consists essentially of sodium phosphate dibasic heptahydrate or sodium phosphate monobasic or both.

In some embodiments, methods of the invention, the doses and the dose regimens, and the connexin modulators (e.g. connexin expression modulators, connexin gap junction modulators and connexin hemichannel modulators, including, for example, modulators of Cx26, Cx30, Cx30.3, Cx31.1, Cx32, Cx36, Cx37, Cx40, Cx43, Cx45, Cx50 or Cx58 connexins, gap junctions and/or hemichannels) described herein are used for the treatment of a subject for uveitis, which includes inflammation of the middle layer of the eye, the uvea, and surrounding tissue. In some embodiments, connexin 43 modulators are used to treat one or more forms of uveitis. In some embodiments, other connexin modulators are used, including, for example, connexin 26 modulators, connexin 45 modulators or others, alone or in combination. In some embodiments, anterior uveitis is treated. In some embodiments, intermediate uveitis is treated. In some embodiments, posterior uveitis is treated. In some embodiments, panuveitis is treated. In some embodiments, the uveits to be treated results from any cause, or is multifactorial. In each of these embodiments, one or more symptoms of uveitis are treated or are alleviated, in whole or in part, using methods of the invention, the doses and the dose regimens, and the connexin modulators as described herein.

In some embodiments, methods of the invention, any of the doses and the dose regimens, and any the connexin modulators (e.g. connexin expression modulators, connexin gap junction modulators and connexin hemichannel modulators, including, for example, modulators of Cx26, Cx30, Cx30.3, Cx31.1, Cx32, Cx36, Cx37, Cx40, Cx43, Cx45, Cx50 or Cx58 connexins, gap junctions and/or hemichannels) described herein are used for the treatment of a subject for blepharitis.

In some embodiments, methods of the invention, the doses and the dose regimens, and the connexin modulators (e.g. connexin expression modulators, connexin gap junction modulators and connexin hemichannel modulators, including, for example, modulators of Cx26, Cx30, Cx30.3, Cx31.1, Cx32, Cx36, Cx37, Cx40, Cx43, Cx45, Cx50 or Cx58 connexins, gap junctions and/or hemichannels) described or referenced herein are used for the treatment of a subject with any stage of dry eye disease (DED), also known as dry eye syndrome (DES), keratoconjunctivitis sicca (KCS), and keratitis sicca.

In other embodiments, methods of the invention, the doses and the dose regimens, and the connexin modulators described or referenced herein are used for the treatment of a subject for Sjögren's syndrome-associated KCS and one or more symptoms of Sjögren's syndrome-associated KCS are treated or are alleviated, in whole or in part.

In other embodiments, methods of the invention, the doses and the dose regimens, and the connexin modulators described or referenced herein are used for the treatment of a subject for Fuchs' dystrophy, and the treatment results in the alleviation of one or more symptoms of Fuchs' dystrophy, in whole or in part.

In some embodiments, in addition use of the present invention for ocular surface recovery and/or corneal epithelial recovery, the present invention relates to methods for the modulation of a connexin, a connexin gap junction channel and/or a connexin hemichannel using doses and dose regimens of connexin modulators (including e.g. gap junction modulators and/or hemichannel modulators) for uvea recovery, sclera recovery, recovery of tear glands and tear ducts, recovery of meibomian glands, eyelid recovery, etc. In some embodiments, modulation of gap junctions and hemichannels is accomplished by administration of a connexin 43 antisense oligonucleotide, a connexin 43 peptidomimetic and/or a small molecule connexin 43 hemichannel blocker. In other embodiments, connexin 26, connexin 30, connexin 30.3, connexin 31, connexin 31.1, connexin 32, connexin 45, connexin 50 and/or connexin 58 modulators are used, alone or in combination with or in conjunction with a connexin 43 modulator and/or another therapeutic agent.

In some embodiments, doses of the connexin modulators described or referenced herein are administered with, or co-formulated for administration to a subject with, effective amounts of one or more compounds selected from the group consisting of anti-microbial agents, antibiotics, antivirals, anti-fungals, anti-parasitics, dilating eye drops, steroidal anti-inflammatories, immunosuppressants, immunomodulatory agents, dry eye treatment agents (e.g. Tyrvaya, Rstasis, Cequa, Xiidra, Eysuvis), artificial tear compositions, and lubricating agents.

In some embodiments, one or more of the connexin modulators described or referenced herein are formulated with one more anti-microbial agents for use in the methods and regimens described herein.

In some embodiments, one or more of the connexin modulators described or referenced herein are formulated with one more anti-bacterial agents for use in the methods and regimens described herein.

In some embodiments, one or more of the connexin modulators described or referenced herein are formulated with one more anti-parasitic agents for use in the methods and regimens described herein.

In some embodiments, one or more of the connexin modulators described or referenced herein are formulated with one more anti-fungal agents for use in the methods and regimens described herein.

In some embodiments, one or more of the connexin modulators described or referenced herein are formulated with one more anti-viral agents for use in the methods and regimens described herein.

BRIEF DESCRIPTION OF THE FIGURES

FIG. 1 shows the dose regimen from a connexin modulator clinical trial for the treatment of ocular surface defects and disorders comprising a non-healing persistent corneal epithelial defect.

DETAILED DISCLOSURE

In some aspects, inventions described and claimed herein relate to modulators of connexins, connexin gap junctions, and connexin hemichannels, and their use in methods for the treatment of non-healing ocular defects and disorders, including non-healing corneal defects and disorders, and doses and dose regimens therefor.

In some embodiments, inventions described and claimed herein relate to modulators of connexins, connexin gap junctions, and connexin hemichannels, and their use in methods for the treatment of other ocular defects, diseases, disorders and conditions, including uveitis, blepharitis, Sjögren's syndrome-associated keratoconjunctivitis sicca, Fuchs' dystrophy, and all forms of dry eye disease.

In order to maintain a smooth optical surface, the corneal epithelium has to continuously renew itself so as to maintain its function as a barrier to fluctuating external surroundings and various environmental insults. After trauma, the cornea typically re-epithelializes promptly thereby minimizing the risk of infection, opacification, or perforation. A persistent epithelial defect or persistent corneal epithelial defect is usually referred to as an ocular or corneal epithelial lesion that does not heal after approximately two weeks of treatment with standard therapies. They can occur, for example, following exposure to toxic agents, chemicals, mechanical injury, thermal insult, and ocular surface infections and are associated with significant clinical morbidity in patients, resulting in discomfort or visual loss. The major risk factor for most non-healing ocular surface defect or disorder is vision loss.

In one aspect this invention relates to pharmaceutical compositions, articles of manufacture, kits and methods for treating a subject having (or at risk for having) a non-healing or persistent ocular surface or corneal defect or disorder, for example, an ocular persistent epithelial defect or a persistent corneal epithelial defect, by administering a therapeutically effective amount of at least one connexin modulator to the eye of said subject using new, clinically validated dosing regimens. Therapeutically effective doses may be used with these new dosing regimens. New, clinically validated doses may be used with these new dosing regimens. These doses used with these dosing regimens proved for durable closure of non-healing ocular surface or corneal defects or disorders, including, for example, ocular persistent epithelial defects and persistent corneal epithelial defects.

In one embodiment, a composition comprising a connexin modulator is applied topically to the eye of the subject. In one embodiment, the connexin modulator is administered topically to the eye of the subject followed by application of a bandage contact lens, and/or an amniotic membrane. In some embodiments, the connexin modulator is a connexin 43 modulator. In some embodiments, the connexin 43 modulator modulates connexin 43 expression. In some embodiments, the connexin modulator (e.g. a connexin 43 modulator) is placed into a bandage contact lens which is then placed on the eye of the subject.

In some embodiments of the methods of this invention, a non-healing ocular surface defect or disorder is treated by pulsed application of a connexin modulator in a dosing regimen as described herein (e.g. three to seven times over 14 to about 35 days). In some embodiments, a connexin modulator is administered. In some embodiments, a connexin gap junction modulator is administered. In some embodiments, a connexin hemichannel blocker or modulator is administered. In some embodiments, the connexin modulator blocks or modulates connexin protein expression (e.g. connexin 43 protein expression). In some embodiments, the connexin gap junction modulator and/or the connexin hemichannel blocker or modulator blocks or modulates connexin 43 gap junctions and/or connexin 43 hemichannels.

In some embodiments, the inventions relate to pharmaceutical compositions, articles of manufacture, and methods for treating non-healing ocular surface defects or disorders by administering a therapeutically effective amount of at least one connexin modulator to the eye of said subject, and/or orally or systemically, for example, in the case of non-topically administered connexin modulators. In some embodiments, more than one connexin modulator is administered to the eye of said subject, and/or orally or systemically.

In some embodiments the non-healing ocular surface defect or disorder is a persistent epithelial defect (PED). In some embodiments the non-healing ocular surface defect or disorder is a persistent corneal epithelial defect (PCED). In methods of the invention, administering dose described herein, or another therapeutically effective amount, of at least one connexin modulator in pulse-dose format, with administrations on Day 1 and Day 2, followed by administration on Day 14 and optionally on or on about Day 28 (and also optionally administration on or on about Day 35) is effective for healing a persistent or non-healing ocular surface or corneal epithelial defect or disorder. See Example 2, below. Connexin modulator doses may also be administered on Day 7 and/or Day 21. In some embodiments, the connexin modulator is a connexin 43 modulator (e.g. a connexin expression modulator, such as an antisense connexin expression modulator, including a Cx43 antisense). Other embodiments include other connexin 43 gap junction modulators and connexin 43 hemichannel blockers or modulators (e.g. peptidomimetics and small molecules).

In some embodiments, doses of a connexin modulator, e.g. lufepirsen, are administered at Days 1, 2 and 14. In some embodiments, connexin modulator doses, e.g. lufepirsen, are administered on Days 1, 2, 14 and 28 (e.g. if the surface defect does not heal following administrations on Days 1, 2 and 14). In some embodiments, connexin modulator doses, e.g. lufepirsen, are administered on Days 1, 2, 7, 14, and 21 (e.g. if the surface defect does not heal following administrations on Days 1, 2, 14 and 28). In some embodiments, connexin modulator doses, e.g. lufepirsen, are administered on Days 1, 2, 7, 14, 21, and 28. In some embodiments, connexin modulator doses, e.g. lufepirsen, are administered on Days, 1, 2, 7, 14, 21, 28 and 35. In some embodiments, a dose is administered after Day 35. In some embodiments, therapeutically effective dose of a connexin modulator (e.g. lufepirsen) are administered on Days 1, 2 and 14, and on one more of Days 7, 21, 28 and 35. In some embodiments, administration using the doses and dose regimens described is to a PED or PCED. In some embodiments, the connexin modulator comprises a connexin antisense molecule (e.g. lufepirsen). In some embodiments, the connexin modulator comprises a connexin peptidomimetic (e.g., Peptide5, Gap19, XG19, Gap26, Gap27, αCT1, etc.). In some embodiments, the connexin modulator comprises a small molecule connexin hemichannel blocker (e.g., tonabersat). In some embodiments, the connexin modulator is a connexin 43 modulator.

In some embodiments, connexin modulator doses, e.g. lufepirsen, are administered on Days 1, 2, 14 and 21.

In some embodiments, connexin modulator doses, e.g. lufepirsen, are administered on Days 1, 2, 7, 14 and 21.

In some embodiments, connexin modulator doses, e.g. lufepirsen, are administered on Days 1, 2, 7, 14, 21 and 28.

In some embodiments, 3 doses of a connexin modulator (e.g. lufepirsen) are administered over 14 days to treat a non-healing or persistent ocular or corneal surface defect in a subject, including, for example, on Days 1 and 2. In some embodiments, 4 doses of a connexin modulator (e.g. lufepirsen) are administered over about 28 days. In some embodiments, 5 doses of a connexin modulator (e.g. lufepirsen) are administered over about 28 to about 35 days. In some embodiments, 6-7 doses of a connexin modulator (e.g. lufepirsen) are administered over about 35 days. For example, in one embodiment, a connexin modulator (e.g. lufepirsen) is administered 4 times over Days 1 and 2, on about Day 14 and 28. In another embodiment, a connexin modulator (e.g. lufepirsen) is administered 5 times over Days 1 and 2, on about Day 14, on about Day 28 and on about Day 35. In another embodiment, a connexin modulator (e.g. lufepirsen) is administered 5 times over Days 1 and 2, on about Day 7, on about Day 14 and on about Day 28. In another embodiment, a connexin modulator (e.g. lufepirsen) is administered 6 times over Days 1 and 2, on about Day 7, on about Day 14, on about Day 21 and on about Day 28. In another embodiment, a connexin modulator (e.g. lufepirsen) is administered 7 times over Days 1 and 2, on about Day 7, on about Day 14, on about Day 21 and on about Day 28. Reference to "administration" here refers, of course, to administration of a connexin modulator in a single dose or in divided doses.

In some embodiments, the connexin modulator is a modulator of Cx26, Cx30, Cx31.1, Cx36, Cx37, Cx40, Cx43, Cx45, Cx50, Cx57 or any other connexin in the eye or blood vessels.

In some embodiments, the connexin modulator is a modulator of Cx26, Cx30, Cx30.3, Cx31, Cx31.1, Cx32, Cx43, Cx45, Cx50, and Cx58, or any other connexin in the corneal epithelium. Transcripts encoding these ten connexin isoforms have been detected by reverse transcriptase-polymerase chain reaction in both central and peripheral corneal epithelium. Six (Cx26, Cx31, Cx32, Cx43, Cx45, and Cx58) were confirmed by laser scanning confocal microscopy. Cx26 was detected throughout the central corneal epithelium and in the mid and superficial layers of the limbal epithelium. Cx43 and Cx45 were localized to the basal and suprabasal epithelial cells. Cx58 was expressed in the superficial epithelium throughout the cornea, and Cx31 and Cx32 were mainly expressed in the central corneal epithelium. See Yuan, X, et al., Expression Pattern of Connexins in the Corneal and Limbal Epithelium of a Primate. Cornea 28(2): 194-199 (February 2009); Zhai, J, et al., Connexin expression patterns in diseased human corneas. *Exp. Ther. Med.* 7, 791-798 (2014). In some embodiments, the connexin modulator is a Cx43 connexin modulator, for example, a Cx43 expression modulator (e.g., an anti-Cx43 antisense), a Cx43 gap junction modulator or a Cx43 hemichannel modulator (e.g. an anti-connexin 43 peptidomimetic or a small molecule). In some embodiments, the modulator is a modified or unmodified antisense polynucleotide or peptidomimetic, e.g. a modified or unmodified Cx43 antisense polynucleotide or C43 peptidomimetic, or other corneal epithelial, endothelial or vascular connexin. In some embodiments, the modulator can include or exclude any of the foregoing connexins.

In some embodiments, the amount of connexin modulator administered to a subject with a non-healing ocular surface defect or disorder (e.g. a PED) or non-healing corneal surface defect or disorder (e.g. a PCED) in any of the dosing schedules described herein is a therapeutically effective amount. In some embodiments, a therapeutically effective amount of a connexin modulators is administered to the subject, for example, (1) on Days 1, 2 and 14, or (2) on Days 1, 2, 14 and, optionally, Day 28, or (3) on Days 1, 2, 7, 14, and about Day 21 and, optionally, on about Day 28 and 35, or (4) on the Days set forth in any of the other dosing schedules recited herein in addition to these dosing regimens (1)-(3). In some embodiments, a therapeutically effective amount of lufepirsen is administered.

In some embodiments, the amount of a connexin modulator administered to a subject with a non-healing ocular surface defect or disorder (e.g. a PED) or non-healing corneal surface defect or disorder (e.g. a PCED) in any of the dosing schedules described herein (e.g. (1) Days 1, 2, 14 and, optionally, Day 28 and/or Day 35; (2) Days 1, 2, 14 and optionally on Days 7, 21 and/or 28; (3) Days 1, 2, 14 and optionally on Days 7, 21, 28 and/or 35; (4) Days 1, 2 and 14 and any more or more or all of Days 7, 21 and 28, and optionally Day 35; or (5) on the Days set forth in other dosing schedules recited herein, etc., is one or more of the particular dose amounts described herein, including, for example, milligram per milliliter (mg/mL) connexin modulator dosing (e.g., a composition comprising or consisting essentially of about or at least about 0.6 mg/mL of a connexin modulator), micromolar (M) connexin modulator dosing (e.g., a composition comprising or consisting essentially of a concentration of about or at least about 19 μM of a connexin modulator), milligram (mg) connexin modulator dosing (e.g., a composition comprising or consisting essentially of about or at least about 0.18 mg of a connexin modulator), and so on, etc.).

In some embodiments, the connexin modulator comprises an antisense molecule. See Examples 1 and 2, below. In some embodiments, the antisense molecule is a connexin43 antisense oligonucleotide. In some embodiments, the connexin modulator may be a connexin 43 antisense polynucleotide comprising, consisting essentially of, or consisting of a sequence according to SEQ ID NOS. 1-3, SEQ ID NOS: 4-16 and/or modified versions thereof. In some embodiments, the antisense oligonucleotide comprises, consists essentially of, or consists of 5'-GTA ATT GCG GCA AGA AGA ATT GTT TCT GTC-3' (SEQ ID NO:1; lufepirsen). In some embodiments, the antisense oligonucleotide may be chemically modified or may be an unmodified oligonucleotide, e.g. a modified or an unmodified DNA oligonucleotide. In some embodiments, oligonucleotides are modified by changing one or more of the phosphodiester linkages, the ribose backbone and/or the nucleobase. Other modifications are described herein. Other modifications are known in the art and described in various publication, including, for example, in Shen, X. and Corey, DR, Chemistry, mechanism and clinical status of antisense oligonucleotides and duplex RNAs, *Nucleic Acids Res.* 2018 Feb. 28; 46(4): 1584-1600. Methods of manufacture are also known in the art. See, e.g., Abramova T, Frontiers and Approaches to Chemical Synthesis of Oligodeoxyribonucleotides, *Molecules* 2013 January; 18(1): 1063-1075; Hao M, et al., Current and Emerging Methods for the Synthesis of Single-Stranded DNA *Genes* (*Basel*) 2020 Jan. 21; 11(2):116. See also Anwar, S., et al. Enhancing the Effectiveness of Oligonucleotide Therapeutics Using Cell-Penetrating Peptide Conjugation, Chemical Modification, and Carrier-Based Delivery Strate and Carrier-Based Delivery Strategies. *Pharmaceutics* 2023, 15, 1130.

In some methods of the invention, the connexin modulator administered to the non-healing surface defect or disorder in a subject is 0.06% lufepirsen. In some embodiments, the connexin modulator administered to a subject with a non-healing surface defect or disorder is 0.006% lufepirsen. In some embodiments, the connexin modulator administered is at least about 0.06% lufepirsen. In some embodiments, the connexin modulator administered to a subject with a non-healing surface defect or disorder is at least about 0.006% lufepirsen. In some embodiments, administration is to a PED or PCED. In some embodiments, a composition comprising or consisting essentially of a pharmaceutically acceptable carrier and about 0.06% lufepirsen, about 0.006% lufepirsen, at least about 0.06% lufepirsen or least about 0.006% lufepirsen is administered to heal the non-healing surface defect or disorder in a subject. Lufepirsen doses described herein and below may be prepared as described in Example 1. In some embodiments, the connexin modulator administered in the amounts described is a connexin antisense molecule other than (or in addition to) lufepirsen. In some embodiments, the connexin modulator administered in the amounts described is a connexin peptidomimetic (e.g. XG19). In some embodiments, the connexin modulator in the amounts described is a connexin hemichannel blocker (e.g. tonabersat).

In some embodiments, the non-healing surface defect or disorder is treated with composition comprising or consisting essentially of 0.6 mg/mL lufepirsen. In some embodiments of the present invention, the non-healing surface defect or disorder is treated with composition comprising or consisting essentially of 0.06 mg/mL lufepirsen. In some embodiments, the composition comprises or consists essentially of at least about 0.6 mg/mL lufepirsen. In some embodiments, the composition comprises or consists essentially of at least about 0.06 mg/mL lufepirsen. In some embodiments, administration is to a PED or PCED. In some embodiments, the connexin modulator administered in the amounts described is a connexin antisense molecule other than (or in addition to) lufepirsen. In some embodiments, the connexin modulator administered in the amounts described is a connexin peptidomimetic (e.g. XG19). In some embodiments, the connexin modulator in the amounts described is a connexin hemichannel blocker (e.g. tonabersat).

In some embodiments, the non-healing surface defect or disorder in a subject is treated with a composition comprising or consisting essentially of about 0.18 mg of lufepirsen in the regimens described herein. In some embodiments, each dose of lufepirsen applied to the non-healing surface defect or disorder in or on the subject comprises or consists essentially of at least about 0.18 mg of lufepirsen in the regimens described herein. In some embodiments of the present invention, the non-healing surface defect or disorder is treated with composition comprising or consisting essentially of about 0.018 mg of lufepirsen in the regimens described herein. In some embodiments, each dose of lufepirsen applied to the non-healing surface defect or disorder comprises or consists essentially of at least about 0.018 mg of lufepirsen in the regimens described herein. In some embodiments, administration is to a PED or PCED. In some embodiments, the connexin modulator administered in the amounts described is a connexin antisense molecule other than (or in addition to) lufepirsen. In some embodiments, the connexin modulator administered in the amounts described is a connexin peptidomimetic (e.g. XG19). In some embodiments, the connexin modulator in the amounts described is a connexin hemichannel blocker (e.g. tonabersat).

In some embodiments, the therapeutically effective amount of the modulator, e.g. connexin modulator, for example a connexin 43 modulator, connexin 43 gap junction modulator and/or connexin 43 hemichannel modulator, which is effective in methods of the invention, comprises a composition that is about, or at least about, 2 micromolar (2 μM), 5 micromolar (5 μM), 10 micromolar (10 μM), 15 micromolar (15 μM), or 20 micromolar (20 μM), including doses of about (or at least about) 1.9 micromolar (1.9 μM) or 1.9405 micromolar (1.9405 μM), and about (or at least about) 19 to 19.4 micromolar or 19.405 micromolar (19 to 19.4 μM or 19.405 μM), of a connexin modulator (e.g. lufepirsen), or any amount within or between any two of these recited dosages. Other effective doses that are effective in methods of the invention for the treatment of ocular surface defects or disorders (e.g. ocular PEDs and PCEDs) include about, or at least about, a composition comprising 30 micromolar (30 μM) or 40 micromolar (40 μM) of a connexin modulator, for example, a connexin 43 modulator, a connexin 43 gap junction modulator and/or a connexin 43 hemichannel modulator (e.g. lufepirsen). In some embodiments, the therapeutically effective amount of the connexin modulator administered as described is a connexin antisense molecule other than (or in addition to) lufepirsen. In some embodiments, the therapeutically effective amount of the connexin modulator administered as described is a connexin peptidomimetic (e.g. XG19). In some embodiments, the therapeutically effective amount of the connexin modulator as described is a connexin hemichannel blocker (e.g. tonabersat).

In some embodiments, about 0.18 mg (or other connexin antisense), about 0.018 mg of lufepirsen (or other connexin antisense or connexin modulator), or from about 0.1 mg, 0.2 mg, 0.3 mg, 0.4 mg or about 0.5 mg to about 1 mg of lufepirsen is administered to the non-healing surface defect or disorder in a single dose, or in two or more divided doses, e.g., for twice daily administration in up to 6 doses administered on Days 1, 2 and 14. In other embodiments, at least about 0.1 mg, 0.2 mg, 0.3 mg, 0.4 mg or 0.5 mg or at least about 1 mg of lufepirsen is administered in a single dose, or in two or more divided doses to the non-healing surface defect or disorder, e.g., for twice daily administration in up to 6 to 10 doses administered on Days 1, 2 and 14, or using other dose regimen described herein that includes Day 28 and/or Day 35. In other embodiments, at least about 0.5 mg or at least about 1 mg of lufepirsen is administered in single or divided doses, e.g., for twice daily administration, in up to 14 doses administered on Days 1, 2 and 14, and one or more of Day 7, Day 21, Day 28 and/or Day 35, for example. In some embodiments, administration is to a PED or PCED in a subject. In some embodiments, other connexin modulators—including e.g. other connexin 43 modulators (and/or modulators of other connexins), and other antisense compounds, peptidomimetics and/or small molecules)—are administered in these dose amounts on these days. In some embodiments, the connexin modulator administered in the amounts described is a connexin antisense molecule other than (or in addition to) lufepirsen. In some embodiments, the connexin modulator administered in the amounts described is a connexin peptidomimetic (e.g. XG19). In some embodiments, the connexin modulator in the amounts described is a connexin hemichannel blocker (e.g. tonabersat).

In any of the embodiments of these doses and dosing regimens and methods, the lufepirsen doses may be administrated to a PED or PCED in a subject. In some embodiments of these doses and dosing regimens and methods, the connexin modulator dose administered comprises another connexin antisense or modulator, e.g., another Cx43 antisense or Cx43 modulator other than or in addition to lufepirsen, or a modulator of another ocular or corneal epithelial connexin other than or in addition to Cx43.

In some embodiments of the present invention, the volume of a composition comprising or consisting essentially of a connexin modulator administered a non-healing surface defect or disorder in a subject is about 300 μL. In other embodiments, the volume of the composition administered is from about 250 μL to about 1.0 mL. In some embodiments, the composition comprises about 0.01 mg, 0.018 mg, 0.18 mg to about 0.2 mg of lufepirsen, or from about 0.18 mg or 0.20 mg or 0.50 mg to about 1 mg of lufepirsen. In some embodiments, the composition comprises at least about 0.018 mg lufepirsen, at least about 0.18 mg of lufepirsen, at least about 0.5 mg of lufepirsen or at least about 1.0 mg of lufepirsen. In some embodiments, other connexin modulators, including e.g. other connexin 43 modulators other than lufepirsen (and/or modulators of other connexins), and other antisense compounds, peptidomimetics and/or small molecules), are administered in these amounts.

In some embodiments, the modulator is a small molecule connexin antagonist. In some embodiments, the modulator is a small molecule connexin antagonist comprises a compound according to Formula I, which includes tonabersat. Tonabersat, a benzoylamino benzopyran, is a modulator of gap junction channel and hemichannel activity, including connexin 43. In particular, tonabersat can block or inhibit hemichannels comprising connexin 43.

In some embodiments, the modulator is a connexin peptidomimetic. Connexin modulators including Peptide5 inhibit Cx43 hemichannel activity and/or ATP release during and following injury. Other connexin modulator peptidomimetics include Gap19 and XG19, and analogues thereof.

The instant inventions provide, inter alia, (1) methods for treating a non-healing ocular surface or corneal defect or disorder in a subject (e.g. a PED or a PCED) by administration of a therapeutically effective amount of a connexin modulator (e.g., a connexin expression modulator), a connexin gap junction modulator and/or a connexin hemichannel modulator in a dose regimen described herein to close and heal the defect or disorder; (2) methods for treating a non-healing ocular surface or corneal defect or disorder in a subject (e.g. a PED or a PCED) by administration of the connexin modulator doses described herein (e.g. in any of the dosing regimens described herein; and (3) the use of such modulators, including, for example, antisense modulators, peptidomimetic modulators and small molecule modulators, in the manufacture of a medicament (e.g. a pharmaceutical composition), and kits containing said medicaments that include or are associated with instructions for use in a method of the invention. See, e.g., Example 2, which describes clinically confirmed pulse dosing regimens for treating and healing non-healing persistent ocular defects.

In some embodiments, instant inventions provide, inter alia, (1) methods for treating uveitis, blepharitis, Sjögren's syndrome-associated keratoconjunctivitis sicca, Fuchs' dystrophy, and all forms of dry eye disease (e.g., evaporative dry eye, aqueous-deficient dry eye, and decreased wettability dry eye) in a subject by administration of a therapeutically effective amount of a connexin modulator (e.g., a connexin expression modulator, a connexin gap junction modulator and/or a connexin hemichannel modulator in a dose regimen described herein to treat the disorder; (2) methods for treating uveitis, blepharitis, Sjögren's syndrome-associated keratoconjunctivitis sicca, Fuchs' dystrophy, and all forms of dry eye disease (e.g., evaporative dry eye, aqueous-deficient dry eye, and decreased wettability dry eye) in a subject by administration of the connexin modulator doses described herein (e.g. in any of the dosing regimens described herein; and (3) the use of such modulators, including, for example, antisense modulators, peptidomimetic modulators and small molecule modulators, in the manufacture of a medicament (e.g. a pharmaceutical composition), and kits containing said medicaments that include or are associated with instructions for use in a method of the invention for treating uveitis, blepharitis, Sjögren's syndrome-associated keratoconjunctivitis sicca, Fuchs' dystrophy, and dry eye disease (e.g., evaporative dry eye, aqueous-deficient dry eye, and decreased wettability dry eye).

All non-healing or persistent ocular surface or corneal (e.g. corneal epithelial) defect or disorder of any etiology may be treated using the compositions and methods of the invention, including the dose and dose regimens. In some embodiments, the non-healing ocular surface defect or disorder is a PED. In some embodiments, the non-healing ocular surface defect or disorder is a PCED. In some embodiments, the non-healing ocular surface defect or disorder is a corneal ulcer. In some embodiments, the non-healing ocular surface or corneal defect or disorder results from a chemical and/or thermal injury. Non-healing ocular surface or corneal defects or disorders can occur following exposure to toxic agents, chemicals, mechanical injury, thermal insult, and ocular surface or corneal infections. In some embodiments, the non-healing ocular surface or corneal defect or disorder results from inflammation, or from an inflammatory disease. In some embodiments, the non-healing ocular surface or corneal defect or disorder results from inflammation of the eye. In some embodiments, the non-healing ocular surface or corneal defect or disorder results from an inflammatory disease of the eye, the ocular surface or the cornea. In some embodiments, the non-healing ocular surface defect or disorder results from a physical trauma or injury, including mechanical injury. In certain embodiments, the non-healing ocular surface defect or disorder is a PED or PCED resulting from a chemical and/or thermal injury. In some embodiments, the chemical and/or thermal injury resulting in a PCED is a severe chemical and/or thermal injury. In some embodiments, an ocular surface and/or corneal burn or injury to be treated in a method of the invention has greater than 50% conjunctival or >6 clock hours of limbal involvement. In some embodiments, the ocular surface and corneal burns and injuries to be treated by a method of the invention is ≥3 on the Dua Classification scale. In some embodiments of the invention, severe ocular and corneal burns and injuries are particularly responsive to treatments with connexin 43 modulators (e.g. lufepirsen) and/or modulators of other connexins using the methods described herein All PED and PCED etiologies, no matter the cause, may be treated using the methods of the invention as described herein. PED and PCED etiologies include not only inflammation and inflammatory disease, but chemical, mechanical, thermal causes, neurotrophic keratitis and limbal stem cell deficiency. In some embodiments, methods and/or doses of the invention are used to treat PED and/or PCED caused by or resulting from chemical injury. In some embodiments, methods and/or doses of the invention are used to treat PED and/or PCED caused by or resulting from thermal injury. In some embodiments, methods and/or doses of the invention are used to treat PED and/or PCED caused by or resulting from mechanical injury. In some embodiments, methods and/or doses of the invention are used to treat PED and/or PCED caused by or resulting from inflammation. In some embodiments, methods and/or doses of the invention are used to treat PED and/or PCED caused by or resulting from neurotrophic keratitis.

In some embodiments, the non-healing ocular surface defect or disorder is a corneal ulcer. In some embodiments, the corneal ulcer is caused by a bacterium, a virus, a fungus or a parasite. In some embodiments, the corneal ulcer results from acanthamoeba keratitis, fungal keratitis or herpes simplex keratitis. In other embodiments, the non-healing ocular surface defect or disorder, e.g. a corneal ulcer, is caused by a trauma such as an abrasion (e.g. scratch or cut) or a foreign body in the eye. In another embodiment, the non-healing ocular surface defect or disorder, e.g. a corneal ulcer, is caused by an allergy or an allergic eye disease. In another embodiment, the non-healing ocular surface defect or disorder, e.g. a corneal ulcer, is caused by dry eye. In some embodiments, the non-healing ocular surface defect or disorder, is a burn. In some embodiments, the non-healing ocular surface defect or disorder is a corneal burn or an ocular or corneal burn ulcer.

In some embodiments, methods of the invention, the doses and the dose regimens, and the connexin modulators (e.g. connexin expression modulators, connexin gap junction modulators and connexin hemichannel modulators, including, for example, modulators of Cx26, Cx30, Cx30.3, Cx31.1, Cx32, Cx36, Cx37, Cx40, Cx43, Cx45, Cx50 or Cx58 connexins, gap junctions and/or hemichannels) described herein are used for the treatment of uveitis, i.e. inflammation of middle layer of the eye, the uvea, and surrounding tissue. In some embodiments, connexin 43 modulators are used to treat one or more forms of uveitis. In some embodiments, other connexin modulators are used, including, for example, connexin 26 modulators, connexin 45 modulators or others, alone or in combination.

In some embodiments the uveitis to be treated as described herein is anterior uveitis (which affects, e.g., the iris at the front of the eye).

In some embodiments the uveitis to be treated as described herein is intermediate uveitis (which affects, e.g., the ciliary body and the vitreous).

In some embodiments the uveitis to be treated as described herein is posterior uveitis (which affects, e.g., the retina and the choroid at the back of the eye).

In some embodiments the uveitis to be treated as described herein is panuveitis (which affects, e.g., all parts of the uvea, from the front to the back of the eye).

In some embodiments, the uveitis to be treated as described herein is caused, in whole in or part, by one or more of ocular trauma, ocular injury, ocular surgery, infection (including, for example, cytomegalovirus (CMV) retinitis, histoplamosis, reactive arthritis, shingles, syphilis, toxoplamosis, cat-scratch disease, herpes zoster, tuberculosis, etc.), inflammation, inflammatory disease and an autoimmune disorder (including, for example, AIDS, Behcet's disease, lupus, multiple sclerosis, psoriasis, rheumatoid arthritis, ulcerative colitis, Vogt-Koyanagi-Harada (VKH) disease, etc.). In some embodiments, the uveitis to be treated as described herein is caused, in whole in or part, by an autoimmune or inflammatory disorder that affects other parts of the body, such as sarcoidosis, systemic lupus erythematosus or Crohn's disease. In some embodiments, the uveitis to be treated as described herein is caused, in whole in or part, by ankylosing spondylitis. In some embodiments, the uveitis to be treated as described herein occurs for no known reason.

In these uveitis treatment embodiments, one or more symptoms of uveitis are alleviated, in whole or in part, using methods of the invention, the doses and the dose regimens, and the connexin modulators as described herein, which may be administered alone or together with (or co-formulated with) other agents for the treatment of uveitis (e.g. antibiotics, antivirals or antifungals; dilating eye drops; steroidal anti-inflammatories; immunosuppressants. Symptoms of uveitis alleviated when treated as described herein include eye pain, eye redness, light sensitivity, blurred vision, dark/floating spots in the field of vision (floaters) and decreased vision.

In some embodiments, methods of the invention, the doses and the dose regimens, and the connexin modulators (e.g. connexin expression modulators, connexin gap junction modulators and connexin hemichannel modulators, including, for example, modulators of Cx26, Cx30, Cx30.3, Cx31.1, Cx32, Cx36, Cx37, Cx40, Cx43, Cx45, Cx50 or Cx58 connexins, gap junctions and/or hemichannels) described herein are used for the treatment of blepharitis. In some embodiments, the subject is treated for anterior blepharitis. In some embodiments, the subject is treated for posterior blepharitis. In some embodiments, one or more of the connexin modulators described or referenced herein administered with, or are formulated for administration or co-administration to the subject with, one more anti-microbial agents (e.g. erythromycin, bacitracin) and/or one or more immunomodulatory agents (e.g. a cyclosporine) and/or other blepharitis treatment agents for use in the methods and regimens described herein to treat blepharitis. In some embodiments, one or more of the connexin modulators described or referenced herein are administered with, or co-formulated with, one more anti-inflammatory agents (e.g. a steroid) for use in the methods and regimens described herein to treat blepharitis. In these blepharitis treatment embodiments, one or more symptoms of blepharitis are alleviated, in whole or in part, using methods of the invention and connexin modulators as described herein, including the doses and dose regimens. Symptoms of blepharitis alleviated when treated as described herein include feeling like there's something in the eye, burning or stinging eyes, watery eyes, itchy eyes, sensitivity to light, red and swollen eyes or eyelids, dry eye, crusty eyelids or eyelashes on waking, and blurry vision.

Dry eye is an ocular surface disease. In some embodiments, methods of the invention, the doses and the dose regimens, and the connexin modulators (e.g. connexin expression modulators, connexin gap junction modulators and connexin hemichannel modulators, including, for example, modulators of Cx26, Cx30, Cx30.3, Cx31.1, Cx32, Cx36, Cx37, Cx40, Cx43, Cx45, Cx50 or Cx58 connexins, gap junctions and/or hemichannels) described or referenced herein are used for the treatment of a subject with any stage of dry eye disease (DED), also known as dry eye syndrome (DES), keratoconjunctivitis sicca (KCS), and keratitis sicca. All stages of DED may be treated using the methods, doses, dose regimens, compositions and kits described herein, including DED stage 1, DED stage 2, DED stage 3 and DED stage 4. In some embodiments, the methods of the invention, the doses and the dose regimens, and compositions of the invention may be used alone or in conjunction with artificial tears and/or systemic or topical anti-inflammatories for the treatment of DED. In some embodiments, the connexin modulator doses for use as described herein are formulated with or within an artificial tear composition or with an anti-inflammatory and may be used for the treatment of DED. In some embodiments, the connexin modulator doses for use as described herein are formulated with anti-inflammatory compounds or compositions for topical administration in the treatment of DED, using known effective doses of at least one inflammatory. In some embodiments, the connexin modulator doses for use as described herein are administered alone or in conjunction with one or more DED treatments (e.g. Tyrvaya, Rstasis, Cequa, Xiidra, Eysuvis). In some embodiments, the connexin modulator doses for use as described herein are formulated with one or more DED treatments for administration together (e.g. one more connexin modulators with one more other dry eye treatments, such as for example, Tyrvaya, Rstasis, Cequa, Xiidra. Eysuvis). In some embodiments, the connexin modulator doses for use as described herein are formulated with at least one corticosteroid for co-administration. In these dry eye treatment embodiments, one or more symptoms of dry are alleviated, in whole or in part, using methods of the invention and connexin modulators as described herein, including the doses and dose regimens. Symptoms of dry eye alleviated when treated as described herein include dry, gritty, stinging or burning sensations in the eyes, redness, watery or teary eyes, and mucus that make the eyes feel "glued shut" after sleeping. Many people with dry eye also report the feeling of something in the eye or eyestrain, blurry vision or eye fatigue. Itching and light sensitivity are other symptoms of dry eye.

In other embodiments, methods of the invention, the doses and the dose regimens, and the connexin modulators described or referenced herein are used for the treatment of a subject for Sjögren's syndrome-associated KCS and one or more symptoms of Sjögren's syndrome-associated KCS are treated or are alleviated, in whole or in part. Symptoms of Sjögren's syndrome-associated KCS alleviated when treated as described herein include include itching, burning, a gritty, pulling, or foreign body sensation and/o or photosensitivity. A sharp stabbing pain, eye strain or fatigue, and blurred vision may also occur. Some patients note a flood of tears after severe irritation.

In other embodiments, methods of the invention, the doses and the dose regimens, and the connexin modulators described or referenced herein are used for the treatment of a subject for Fuchs' dystrophy, and the treatment results in the alleviation of one or more symptoms of Fuchs' dystrophy, in whole or in part. One of the first signs and symptoms of Fuchs' dystrophy is blurred vision, caused by fluid buildup in the cornea. In early stages of the disease, the excess fluid builds up overnight during sleep, causing blurry vision and/or discomfort when waking in the morning that can last for hours. In later stages of Fuchs' dystrophy, the periods of swelling, impaired vision and discomfort last longer, even up to the entire day. Other symptoms of Fuchs' dystrophy include rough or gritty feelings in the eye, occasionally accompanied by sharp eye pains, discomfort in bright light, fluctuating eyesight throughout the day or day to day, halos and/or glares from bright lights, and blurry vision combined with poor contrast in colors.

In some embodiments, one or more of the connexin modulators described or referenced herein are formulated with one more anti-microbial agents for use in the methods and regimens described herein.

In some embodiments, one or more of the connexin modulators described or referenced herein are formulated with one more anti-bacterial agents for use in the methods and regimens described herein.

In some embodiments, one or more of the connexin modulators described or referenced herein are formulated with one more anti-parasitic agents for use in the methods and regimens described herein.

In some embodiments, one or more of the connexin modulators described or referenced herein are formulated with one more anti-fungal agents for use in the methods and regimens described herein.

In some embodiments, one or more of the connexin modulators described or referenced herein are formulated with one more anti-viral agents for use in the methods and regimens described herein.

In some embodiments, one or more of the connexin modulators described or referenced herein are formulated with one more compounds selected from the group consisting of anti-microbial agents, anti-bacterial agents, anti-parasitic agents, anti-viral agents, anti-fungal agents and lubricating agents.

Definitions

It is understood that for various reasons, including the ability of patients to travel to a clinic or to an office or site for administration of a drug, patients' schedules, the availability of drug, etc., the day of administration of a connexin modulator pursuant to a dose regimen as described herein may need to be (and can be) adjusted. The term "about" when used with respect to the administration Day for a connexin modulator pursuant to an administration regimen described herein means, generally, that Day plus or minus one day. Thus, administration on "about Day 28" means administration on Day 28, but also includes administration on Day 27 or Day 29, for example.

As used herein, the term "connexin modulator" (also sometimes referred to as a connexin "inhibitor" or "antagonist") is a compound that prevents, inhibits, and/or reduces the function or activity of a connexin, a connexin gap junction channel or a connexin hemichannel, alone, together or separately, including, for example, prevention, inhibition and/or reduction in the function and/or activity and/or the formation of connexin hemichannels and/or connexin gap junctions, including the expression of a connexin protein, its trafficking and/or assembly. Such functions and activities may include, for example, docking of hemichannels on adjacent cells and opening to form a gap junction channel. They may also include intercellular communication between cells, and the flow of molecules between cells through a gap junction channel. Modulation of a hemichannel is the modulation of one or more functions and/or activities of a hemichannel, for example, the flow of molecules through a hemichannel. Such functions and activities may include, for example, the flow of molecules from the extracellular space or environment through a hemichannel into a cell, and/or the flow of molecules (e.g. adenosine triphosphate (ATP)) through a hemichannel from the intracellular space or environment of a cell into the extracellular space or environment. Prevention, inhibition and/or reduction of function or activity may be direct or indirect (for example, but not limited to, directly blocking a channel, inducing a conformational change, or modifying a connexin phosphorylation state or opening probability). Modulation of a hemichannel also includes suppressing the permeability of a hemichannel (e.g. lessening the flow of permeants through a hemichannel). In some embodiments, the permeant is adenosine triphosphate (ATP). The connexin modulator may be of any chemical nature. However, by way of example, the connexin modulator may be a nucleic acid (including antisense molecules, RNAi molecules, morpholinos, and other nucleic acids as described herein), a peptide or peptidomimetic, or a small molecule or other chemical. In certain embodiments, a connexin modulator is a compound that targets one or more components of a gap junction, including connexins, hemichannels, to inhibit or block its activity, expression, trafficking and/or assembly. "Inhibits" or "blocks" or "antagonizes" or "modulates" should not be taken to imply that the function, activity, expression, trafficking and/or assembly of a connexin, a connexin hemichannel (e.g. a connexin 43 hemichannel) or gap junction is completely inhibited or blocked or wholly antagonized or modulated, although this may be preferred, but should be taken to include any reduction in the function, activity, expression, trafficking and/or assembly of a connexin (including its transcription, translation and/or expression), a connexin hemichannel (including its permeability or its opening, or release of ATP, to the extracellular environment) or gap junction (including its opening to an adjacent cell, or creation from hemichannels in adjacent cells). Connexin modulators as used herein include connexin expression modulators, connexin gap junction modulators and connexin hemichannel modulators.

In some embodiments, in addition to Cx43 modulators, the connexin modulator is a modulator of any other connexin in the corneal epithelium, including Cx26, Cx30, Cx30.3, Cx31, Cx31.1, Cx32, Cx45, Cx50, and Cx58. In some embodiments, the connexin modulator may be a modulator of a connexin present in blood vessels, for example, a Cx37 modulator, a Cx40 modulator, a Cx43 modulator and/or a Cx45 modulator. Thus, as used herein, the term "connexin modulator" refers generally to connexin modulators, but also specifically to connexin 43 modulators and modulators of other connexins referenced herein (including connexin 43 and other gap junction and hemichannel modulators), and modulators of other blood vessel, endothelial and epithelial (e.g. ocular and corneal epithelial) connexins, gap junctions and hemichannels, unless otherwise provided. In some embodiments, the connexin modulator is a connexin43 modulator, e.g., a modulator of a connexin 43 expression, a connexin 43 hemichannel modulator that inhibits or blocks hemichannel opening or a connexin 43 peptidomimetic. In some embodiments, the gap junction modulator is or includes modulators of other connexins found on the ocular surface, including the cornea and corneal epithelium, and their hemichannels and gap junctions. In other embodiments, the connexin modulator is a modulator of any other connexin in the eye or blood vessels, including Cx36 and Cx57 in addition to Cx37, Cx40, Cx43 and Cx45 as well as previously noted Cx26, Cx30, Cx31.1 and Cx50, which are also found in the corneal epithelium. In some embodiments, the modulating agent can include or exclude any of the noted connexins, connexin gap junction and/or connexin hemichannels described herein. In some embodiments, an ocular surface defect or disorder, for example, a PED, a PCED and/or an ocular ulcer (including, e.g., an inflammatory ocular surface ulcer, or an ocular surface ulcer, disorder or defect characterized at least in part by inflammation) is treated with a connexin modulator (e.g. a connexin expression modulator, a connexin gap junction modulator and/or a connexin hemichannel modulator) to inhibit activation of one or more inflammasomes. In some embodiments, connexin modulators inhibit activation of an inflammatory cascade by an inflammasome. In some embodiments, activation and/or activity of the NLRP3 inflammasome is modulated (e.g. blocked or downregulated) by a connexin modulator. In some embodiments, activation of an inflammatory cascade by the NLRP3 inflammasome is modulated (e.g. blocked or downregulated) by a connexin modulator. Inflammasome modulation assists in closing a non-healing ocular surface or corneal defect or disorder, including those described herein, and in the treatment of other diseases, conditions and disorders described herein. In some embodiments, an ocular surface defect or disorder, for example, a PED, a PCED and/or an ocular ulcer is treated with an inflammasome modulator (e.g. a modulator of the NLRP3 inflammasome) that may not be a connexin modulator (e.g. a connexin 43 hemichannel modulator). Inflammasome modulators include those described, for example, in Leung and Lowery, The patent landscape of inflammasome modulators. *Nature Reviews Drug Discovery* 19, 158 (2020). See also Chauhan, D., et al., Therapeutic modulation of inflammasome pathways. *Immunol Rev.* 297(1): 123-138 (September 2020). Inflammasome modulators include selective G-protein coupled receptor 40 (GPR40) agonists (e.g. fasiglifam, which inhibits inflammasome activation by blocking formation of apoptosis-associated speck-like protein (ASC) containing a caspase recruitment domain (CARD), an inflammasome component), and ethyl pyruvate, which significantly suppresses activation of the NLRP3 inflammasome. Other inflammasome modulators unrelated to connexins and connexin hemichannels are known in the art. Modulation of the function of a hemichannel and/or a gap junction channel may occur by any means. However, by way of example only, modulation may occur by one or more of: preventing, blocking, inhibiting or decreasing the formation of a gap junction through hemichannel docking; inducing or promoting closure of a hemichannel; preventing, blocking, inhibiting or decreasing hemichannel opening; preventing, blocking, inhibiting or decreasing hemichannel permeability; inducing or promoting loss of coupling between hemichannels; triggering, inducing or promoting cellular internalization of a hemichannel and/or gap junction. Just as use of the words such as "blocking", "inhibiting", "preventing", "decreasing" and "antagonizing", and the like, should not be taken to imply complete blocking, inhibition, prevention, or antagonism, "inducing" or "promoting" should not be taken to imply complete prevention, block, inhibition or decrease in the formation of a gap junction through hemichannel docking; inducing or promoting the comlete closure of a hemichannel; completely preventing, blocking, inhibiting or decreasing hemichannel opening; completely preventing, blocking, inhibiting or decreasing hemichannel permeability; completely inducing or promoting loss of coupling between hemichannels; or triggering, inducing or promoting the complete loss of coupling or the complete internalization of a connexin hemichannel and/or gap junction (or group of hemichannels and/or gap junctions) and should be taken to include the partial induction or promotion of these things. Connexins, hemichannels and gap junctions may be present in cells of any type. Accordingly, reference to a "connexin," "hemichannel" or "gap junction" should be taken to include reference to a connexin, a hemichannel or gap junction present in any cell type, unless the context requires otherwise. In one embodiment, the hemichannel is an epithelial cell connexin, hemichannel or gap junction (e.g., an ocular or corneal epithelial cell connexin, hemichannel or gap junction). In one embodiment, the connexin, hemichannel or gap junction is a vascular connexin, hemichannel or gap junction. In one embodiment, the connexin, hemichannel or gap junction is a connexin, hemichannel or gap junction found in vascular endothelial cells and/or vascular smooth muscle cells. A "hemichannel blocker" is a compound that interferes with the passage of molecules through a connexin hemichannel. A hemichannel blocker can block or decrease hemichannel opening, block, decrease or suppress hemichannel opening, block or reduce the release of molecules through a hemichannel to an extracellular space, and/or block or reduce the entry of molecules through a hemichannel into an intracellular space. Hemichannel blockers include compounds that fully or partially block hemichannel leak or the passage of molecules through a hemichannel (e.g. to or from an extracellular space). Hemichannel blockers also include compounds that decrease the open probability of a hemichannel. Open probability is a measure of the percentage of time a channel remains open versus being closed (reviewed in Goldberg G S, et al., Selective permeability of gap junction channels *Biochimica et Biophysica Acta* 1662 (2004) 96-101). Examples of hemichannel blockers include peptides, small molecules, antibodies and antibody fragments. Hemichannel blockers include hemichannel modulators. Hemichannel blockers may interfere directly, or directly, with the passage of molecules through a connexin hemichannel, or with the permeability of a hemichannel.

In some embodiments, the connexin modulator may be a modulator of a connexin hemichannel present in blood vessels, for example, a connexin 43 hemichannel modulator and/or connexin 37 hemichannel modulator, a connexin 40 hemichannel modulator, a connexin 45 hemichannel modulator or another blood vessel connexin hemichannel. In some embodiments, the connexin modulator may be a modulator of a connexin hemichannel present in the ocular epithelium, e.g., the corneal epithelium. In some embodiments, the connexin modulator is a modulator of a Cx26, Cx30, Cx30.3, Cx31, Cx31.1, Cx32, Cx43, Cx45, Cx50, and/or Cx58 hemichannel, or any other connexin hemichannel in the corneal epithelium. In other embodiments, the connexin modulator is a modulator of any other connexin hemichannel in the eye or blood vessels, including Cx36 and Cx57 hemichannels in addition to Cx37, Cx40, Cx43 and Cx45 hemichannels as well as previously noted Cx26, Cx30, Cx31.1 and Cx50 hemichannels, which are also found in the corneal epithelium.

A "bandage contact lens" is any contact lens that can be used to protect the ocular surface. Bandage contact lenses are also referred to as "therapeutic contact lenses" and "therapeutic bandage contact lenses." They also help relieve pain and can assist in healing. The bandage contact lens will allow mechanical protection of the ocular surface, e.g. the cornea, from eyelid movement, and will also protect the surface of the eye, e.g., the corneal surface, from atmospheric exposure and further ocular insult and will limit dehydration. Bandage lenses include hydrogel lenses and silicon hydrogel lenses, and are well known in art. See Lim and Lim, Therapeutic Contact Lenses in the Treatment of Corneal and Ocular Surface Diseases—A Review *Asia-Pacific Journal of Ophthalmology* 9(6): 524-532 (November-December 2020); Jacobs et al., CLEAR Medical use of contact lenses, *Cont Lens Anterior Eye* 2021 April; 44(2): 289-329. In some embodiments, the therapeutic bandage lens is, for example, a soft contact lens, a gas permeable (scleral) lens or a 3D-printed bio-gel. Suitable FDA-approved soft bandage lenses include Acuvue Oasys with Hydraclear Plus (Johnson & Johnson Vision), Air Optix Night & Day Aqua (Alcon), PureVision (Bausch+Lomb) and UCL 55% (United Contact Lens) and Kontur (Kontur Kontact Lens).

A "small molecule" is defined herein to include compounds with a molecular weight below about 600 daltons and is generally an organic compound. Small molecule connexin modulators include the compounds of Formula I. A small molecule can be an active agent of a prodrug. Small molecules prodrugs include the compounds of Formula II, which are prodrugs of the small molecule hemichannel and connexin modulator, tonabersat.

As used herein, "treatment" (and grammatical variations thereof such as "treat" or "treating") refers to clinical intervention in an attempt to alter the course of the individual, tissue or cell being treated, and can be performed either for prophylaxis or during the course of clinical pathology. Desirable effects of treatment include, but are not limited to, closing a non-healing ocular defect or disorder (e.g. a PED or PCED) and preventing occurrence or recurrence of a non-healing ocular surface or corneal defect or disorder, alleviation of signs or symptoms, diminishment of any direct or indirect pathological consequences of the a non-healing ocular surface or corneal defect or disorder, decreasing the rate of progression of a non-healing ocular surface or corneal defect or disorder, amelioration or palliation of the a non-healing ocular defect or disorder, and remission or improved prognosis. The term does not necessarily imply that a subject is treated until total recovery, but this is generally the case with the pulse-dose delivery methods of the invention for treatment of a non-healing ocular surface or corneal defect or disorder. Accordingly, "treatment" may also include maintaining or promoting a complete or partial state of remission of a non-healing ocular defect or disorder. Durable wound closure may be defined as 100% skin re-epithelialization without drainage or dressing requirements at two consecutive evaluations at least 2 weeks, but no greater than 5 months, apart following closure after the last administration of a connexin modulator as described herein (e.g. on about Day 14, on about Day 28, or on about Day 35). In some embodiments, durable wound closure refers to wound closure for one month (e.g. 4 weeks, or 28 days). In some embodiments, "treatment" refers to treatment and clinical interventions as described above and herein or treating uveitis, blepharitis, Sjögren's syndrome-associated keratoconjunctivitis sicca, Fuchs' dystrophy, and dry eye disease (including evaporative dry eye, aqueous-deficient dry eye, and decreased wettability dry eye).

The term "preventing" means preventing in whole or in part, or ameliorating or controlling.

As used herein, "effective amount" or "therapeutically effective amount" refers to an amount effective, at dosages and for periods of time as described in the dose regimens herein, to achieve a desired result in treatment of a non-healing ocular or corneal defect or disorder (e.g. PED, PCED, ocular ulcer, corneal ulcer, etc). For example, and not by way of limitation, a "therapeutically effective amount" can refer to an amount of a connexin modulator compound or composition, including but not limited to those disclosed herein, that is able to close a non-healing ocular defect or disorder when administered in a dose regimen of the invention. In other embodiments, the result of treatment with an "effective amount" is durable and the non-healing ocular defect or disorder will remain closed following treatment. The doses disclosed herein are therapeutically effective amounts; however, the methods are not limited to those doses or dose amounts and include the use of other therapeutically effective amounts. In some embodiments, "effective amount" or "therapeutically effective amount" refers to an amount effective, at dosages and for periods of time as described in the dose regimens herein, to achieve a desired result in treatment of uveitis, blepharitis, Sjögren's syndrome-associated keratoconjunctivitis sicca, Fuchs' dystrophy, and dry eye disease (including evaporative dry eye, aqueous-deficient dry eye, and decreased wettability dry eye).

As used herein, "prophylactically effective amount" refers to an amount effective, for example, at administration on about Day 28 (and/or optionally on about Day 35), to achieve or assure a desired result or a desired prophylactic result, e.g. durable wound closure with nonrecurrence of the non-healing ocular defect or disorder. In some embodiments, a prophylactically effective amount of connexin modulator is administered to a subject with a closed ocular surface disorder (e.g. a close PED or PCED). In some embodiments, an effective amount of a connexin modulator is administered prophylactically to a subject with a closed ocular surface disorder (e.g. a PED or PCED). In some embodiments, "prophylactically effective amount" refers to an amount effective to achieve a desired prophylactic result in treatment of uveitis, blepharitis, Sjögren's syndrome-associated keratoconjunctivitis sicca, Fuchs' dystrophy, and dry eye disease (including evaporative dry eye, aqueous-deficient dry eye, and decreased wettability dry eye), including during or after the treatment of uveitis, blepharitis, Sjögren's syndrome-associated keratoconjunctivitis sicca, Fuchs' dystrophy, and any form of dry eye disease using the methods described herein.

The terms "peptide," "peptidomimetic" and "mimetic" include synthetic or genetically manufactured chemical compounds that may have the same or substantially the same structural and functional characteristics of protein regions which they mimic. By way of example, these may mimic the extracellular loops of opposing connexins involved in connexon-connexon docking and cell-cell channel formation, and/or the extracellular loops of hemichannel connexins, as well as the intracellular C-terminus of, for example, connexin 43 and others. As used herein, "peptidomimetics" (also known as peptide mimetics) which include peptide and peptide-based compounds, also include such non-peptide-based compounds such as peptide analogs. Peptidomimetics that are structurally similar to therapeutically useful peptides can be used to produce an equivalent or enhanced therapeutic or prophylactic effect. For example, the first extracellular loops of Cx37, Cx40 as well Cx43 are mimicked by peptides under the Gap26 code. Gap27 and Peptide5, on the other hand, mimic regions of the second extracellular loop. Gap27 targets Cx32, Cx40 and Cx43, while Peptide5 is used for Cx43 inhibition. Other peptidomimetics include JM2 (VFFK-GVKDRVKCRSD; SEQ ID NO:134), ΔSH3, CT9 (RPRDDLEI; SEQ ID NO:135) and CT9-TAT, CT10 (SR-PRDDLEI; SEQ ID NO:136), αCT (RQP-KIWFPNRRKPWKK-RPRPDDLEI (SEQ ID NO:137) in which the inhibitor peptide includes the Cx43 C-terminal amino acids 374-382 (RPRPDDLEI; SEQ ID NO:141) that encompass the ZO-1-binding sequence, which is in turn attached at its N-terminus to a 16-amino acid antennapedia internalization vector) mimic the C-terminal tail of Cx43 and Gap24 (GHGDPLHLEEVKC; SEQ ID NO:138) reproduces a sequence of the cytoplasmic loop of Cx32 while TAT-Gap24 (YGRKKRRQRRRGHGDPLHLEEVKC; SEQ ID NO: 139) also mimics a portion of the intracellular loop of Cx43. Both L2 and Gap19 also mimic the cytoplasmic loop but of Cx43. Peptides useful in the compositions and methods of the invention are described and referenced herein and include connexin mimetic peptides directed to connexin extracellular loops and connexin intracellular regions, and peptides that mimic regions of a connexin C-terminal tail (e.g. a connexin 43 C-terminus). Peptides and peptidomimetics useful in the compositions and methods of the invention include those set forth in Tables II and III.

In some embodiments, peptides and peptidomimetics are modified. In some embodiments, peptides and peptidomimetics are unmodified. Peptidomimetics are molecules able to mimic natural peptides and proteins. Generally, peptidomimetics are structural or functional mimics (e.g., identical or similar) to a paradigm polypeptide (i.e., a polypeptide that has a biological or pharmacological function or activity), but peptidomimetics can also be modified, e.g. have one or more peptide linkages optionally replaced by a linkage selected from the group consisting of, for example, $—CH_2NH—$, $—CH_2S—$, $—CH_2—CH_2—$, $—CH{=}CH—$ (cis and trans), $—COCH_2—$, $—CH(OH)CH_2—$, and $—CH_2SO—$. Peptidomimetics can also have been chemically modified to include unnatural amino acid substitutions, backbone amide bond modifications, rigid scaffolds, the addition of hydrophobic residues, and by other methods know in the art. The mimetic can be either entirely composed of natural amino acids, synthetic chemical compounds, non-natural analogues of amino acids, or, is a chimeric molecule of partly natural peptide amino acids and partly non-natural analogs of amino acids. The mimetic can also comprise any amount of natural amino acid conservative substitutions as long as such substitutions also do not substantially alter mimetic activity. In the case of connexins, these can mimic, for example, the extracellular loops of opposing connexins involved in connexon-connexon docking and cell-cell channel formation. For example, a mimetic composition can be useful as a gap junction modulating agent if it is capable of down-regulating biological actions or activities of hemichannels, such as, for example, preventing the docking of hemichannels to form gap-junction-mediated cell-cell communications, or preventing the opening of hemichannels to expose the cell cytoplasm to the extracellular millieu, etc. Peptidomimetics encompass those described herein, as well as those as may be known in the art, whether now known or later developed. Peptides and peptidomimetic connexin modulators may also be modified to increase stability, improve bioavailability and/or to increase cell membrane permeability.

The term “pharmaceutical formulation” refers to a preparation which is in such form as to permit the biological activity of an active ingredient contained therein to be effective, and which does not contain additional components that are unacceptably toxic to a subject to which the formulation would be administered. A “pharmaceutical composition” refers to a mixture of substances suitable for administering to a subject that includes an active ingredient or pharmaceutical agent. For example, a pharmaceutical composition may comprise a modified or unmodified antisense oligonucleotide and a sterile aqueous solution or a poloxamer or pluronic carrier.

A “pharmaceutically acceptable carrier,” as used herein, refers to an ingredient in a pharmaceutical formulation, other than an active ingredient, which can be safely administered to a subject. A pharmaceutically acceptable carrier includes, but is not limited to, a buffer, excipient, stabilizer, or preservative. Pharmaceutically acceptable carriers include poloxamers, e.g. Pluronic F-127. Pharmaceutically acceptable carriers for ocular administration will be ophthalmologically acceptable carriers suitable for application to (e.g. in or on) the eye.

As used herein, the term “subject” or the like, including “individual,” and “patient”, all of which may be used interchangeably herein, refers to any mammal, including humans, domestic and farm animals, and zoo, wild animal park, sports, or pet animals, such as dogs, horses, cats, sheep, pigs, cows, etc. The preferred mammal herein is a human, including adults, children, and the elderly. Preferred sports animals are horses and dogs. Preferred pet animals are dogs and cats. The subject may be, for example, an aquatic park animal, such as a dolphin, whale, seal or walrus. In certain embodiments, the subject, individual or patient is a human. Subjects are not meant to include animals used in scientific experiments (e.g. mice and rats).

As used herein, a “gap junction,” a “connexin gap junction” and a “connexin gap junction channel” refer to two hemichannels that connect across an intercellular space between adjacent cells and allow certain molecules to flow between those cells. They refer to the intercellular channels or clusters of intercellular channels that allow direct diffusion of ions and small molecules between adjacent cells. Gap junctions have been studies for decades and are well known in the art.

As used herein, the term “hemichannel” is a part of a gap junction (two hemichannels or connexons that connect across an intercellular space between adjacent cells to form a gap junction) and is comprised of a number of connexin proteins, typically homo- or hetero-meric hexamers of connexin proteins that form the pore for a gap junction between the cytoplasm of two adjacent cells. The hemichannel is supplied by a cell on one side of the junction, and by a cell on the other side, with two hemichannels from opposing cells normally coming together to form the complete intercellular gap junction channel. However, in some cells, and in cells under some circumstances, the hemichannel itself is active as a conduit between the cytoplasm and the extracellular space allowing the transference of ions and small molecules (e.g. ATP). Like their gap junction counterparts, connexin hemichannels have been long-studied and are also well known in the art.

Hemichannels and gap junction channels may be present in cells of any type. Reference to a “hemichannel” or a “gap junction channel” should be taken to include reference to a hemichannel or gap junction channel present in any ocular cell type, and in any ocular surface cell type, including cells of the cornea and/or corneal epithelium. In one embodiment of the invention, the hemichannel or gap junction channel is present in a cell in the eye. In one embodiment of the invention, the hemichannel or gap junction channel is present in a cell in the front of the eye, i.e., the anterior segment. In some embodiments of the invention, the hemichannel or gap junction channel is present in a cell in the cornea. In some embodiments of the invention, the hemichannel or gap junction channel is present in a cell in the corneal epithelium. In some embodiments of the invention, the hemichannel or gap junction channel is present in a cell in the microvasculature of the eye, including the corneal microvasculature. In some embodiments of the invention, the hemichannel or gap junction channel is present in a cell in the uvea. In some embodiments of the invention, the hemichannel or gap junction channel is present in a cell relating to dry eye disease, blepharitis (including e.g. cells of or relating to the eyelid margin), Sjögren’s syndrome-associated keratoconjunctivitis sicca (including e.g. cells of or relating to the conjunctiva), Fuchs' dystrophy (including e.g. corneal endothelial cells).

A "non-healing ocular surface defect or disorder" means a ocular surface defect or disorder that does not completely heal or close within about ten days to two weeks of standard clinical care. Non-healing ocular surface defect or disorder include ocular ulcers, corneal ulcers, ocular persistent epithelial defects (PEDs) and persistent corneal epithelial defects (PCEDs). Ocular ulcers include corneal ulcers, and include those described herein, including infectious ulcers, chemical ulcers, burn ulcers, traumatic or trauma-induced ulcers, inflammatory ulcers, and mixed-cause ulcers. A "non-healing" or "persistent" ocular surface or corneal defect or disorder (including for example PEDs and PCEDs) results from the failure of re-epithelialization and closure within 10-14 days, even with standard supportive treatment.

The phrase "consisting essentially of" refers to the specified materials and those that do not materially affect the basic and novel characteristics of the medicament (or steps, in the case of a method). The basic and novel characteristics of the inventions are described throughout the specification, and include the ability of connexin modulators, connexin modulator compositions and methods of the invention to block or modulate connexins, connexin gap junctions and/or connexin hemichannels and to attenuate, block or inhibit, for example the production, function or activity of a connexin, a connexin gap junction and/or a connexin hemichannel, or inflammasome activity (e.g. hemichannel-mediated inflammasome activity, such as a connexin hemichannel-mediated inflammasome activity or pannexin hemichannel-mediated inflammasome activity). Material changes in the basic and novel characteristics of the inventions, including the medicaments and methods described herein, include an unwanted or clinically undesirable, detrimental, disadvantageous or adverse activity to healing a disease, disorder or condition described or referred to hearing, a slowing in healing, a diminution of connexin, connexin gap junction and/or connexin hemichannel modulation and/or attenuation, or an unwanted diminution of connexin, connexin gap junction and/or connexin hemichannel activity or function. In one embodiment, a composition or medicament of the invention will comprise, consist essentially of, or consist of a connexin 43 hemichannel blocker, for example, a connexin 43 antisense molecule, a connexin 43 peptidomimetic or small molecule connexin 43 hemichannel blocker or prodrug thereof.

Antisense Modulators

A gap junction and/or connexin polynucleotide or oligonucleotide may be selected, for example, from modified or unmodified connexin polynucleotides or oligonucleotides, such as modified or unmodified connexin 43 antisense polynucleotides or oligonucleotides. In some embodiments, the modified connexin antisense polynucleotides, or oligonucleotides or polynucleotides comprise mixtures of modified and unmodified nucleotides. In some embodiments, the connexin 43 antisense compound used in the methods herein is an antisense oligonucleotide comprising naturally occurring nucleobases and an unmodified internucleoside linkage.

In some embodiments, the connexin 43 antisense compound is targeted to at least about 8 nucleobases of a nucleic acid molecule encoding a connexin having a nucleobase sequence selected from SEQ ID NO:17. The polynucleotides and oligonucleotides, for example, connexin 43 antisense compounds, may have from about 8 to about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, or about 80 nucleotides of SEQ ID NO:17, or a sequence complementary thereto, and/or the antisense polynucleotide or oligonucleotide may contain any range of lengths between any two of the recited lengths. The polynucleotides of this invention include synthesized polynucleotides having a length of less than 80 nucleotides, e.g., from 12-18 to about 50-80 nucleotides, preferably about 30 nucleotides or less, e.g., from 12 to about 30 nucleotides, and more preferably from about 15 to about 30 nucleotides. In one example, the polynucleotide has 30 nucleotides. The methods of this invention features, in some embodiments, the use of connexin 43 antisense compounds up to 40 nucleotides in length, for example, 15 to 40 nucleotides in length, comprising or consisting essentially of a nucleotide sequence selected from SEQ ID NO:1-17. The methods of this invention features, in some embodiments, the use of connexin 43 antisense compounds up to 40 nucleotides in length, for example, 15 to 40 nucleotides in length, comprising a nucleotide sequence selected from SEQ ID NO:4-17.

```
Human Cx 43, α1 (SEQ ID NO:  17)
LOCUS NM_000165 3088 bp mRNA linear PRI 26-OCT-2004

DEFINITION     Homo sapiens gap junction protein, alpha 1, 43 kDa (connexin 43)
               (GJA1), mRNA.
     1  acaaaaaagc ttttacgagg tatcagcact tttctttcat taggggaag gcgtgaggaa
    61  agtaccaaac agcagcggag ttttaaactt taaatagaca ggtctgagtg cctgaacttg
   121  ccttttcatt ttacttcatc ctccaaggag ttcaatcact tggcgtgact tcactacttt
   181  taagcaaaag agtggtgccc aggcaacatg ggtgactgga gcgccttagg caaactcctt
   241  gacaaggttc aagcctactc aactgctgga gggaaggtgt ggctgtcagt acttttcatt
   301  ttccgaatcc tgctgctggg gacagcggtt gagtcagcct ggggagatga gcagtctgcc
   361  tttcgttgta acactcagca acctggttgt gaaaatgtct gctatgacaa gtctttccca
   421  atctctcatg tgcgcttctg ggtcctgcag atcatatttg tgtctgtacc cacactcttg
   481  tacctggctc atgtgttcta tgtgatgcga aaggaagaga aactgaacaa gaaagaggaa
   541  gaactcaagg ttgcccaaac tgatggtgtc aatgtggaca tgcacttgaa gcagattgag
   601  ataaagaagt tcaagtacgg tattgaagag catggtaagg tgaaaatgcg aggggggttg
   661  ctgcgaacct acatcatcag tatcctcttc aagtctatct ttgaggtggc cttcttgctg
   721  atccagtggt acatctatgg attcagcttg agtgctgttt acacttgcaa aagagatccc
   781  tgcccacatc aggtggactg tttcctctct cgccccacgg agaaaaccat cttcatcatc
   841  ttcatgctgg tggtgtcctt ggtgtccctg gccttgaata tcattgaact cttctatgtt
   901  ttcttcaagg gcgttaagga tcgggttaag ggaaagagcg acccttacca tgcgaccagt
   961  ggtgcgctga gccctgccaa agactgtggg tctcaaaaat atgcttattt caatggctgc
  1021  tcctcaccaa ccgctcccct ctcgcctatg tctcctcctg ggtacaagct ggttactggc
  1081  gacagaaaca attcttcttg ccgcaattac aacaagcaag caagtgagca aaactgggct
  1141  aattacagtg cagaacaaaa tcgaatgggg caggcgggaa gcaccatctc taactcccat
  1201  gcacagcctt ttgatttccc cgatgataac cagaattcta aaaaactagc tgctggacat
```

-continued

```
1261  gaattacagc cactagccat tgtggaccag cgaccttcaa gcagagccag cagtcgtgcc
1321  agcagcagac ctcggcctga tgacctggag atctagatac aggcttgaaa gcatcaagat
1381  tccactcaat tgtggagaag aaaaaaggtg ctgtagaaag tgcaccaggt gttaattttg
1441  atccggtgga ggtggtactc aacagcctta ttcatgaggc ttagaaaaca caaagacatt
1501  agaataccta ggttcactgg gggtgtatgg ggtagatggg tggagaggga ggggataaga
1561  gaggtgcatg ttggtattta aagtagtgga ttcaaagaac ttagattata aataagagtt
1621  ccattaggtg atacatagat aagggctttt tctccccgca aacaccccta agaatggttc
1681  tgtgtatgtg aatgagcggg tggtaattgt ggctaaatat ttttgtttta ccaagaaact
1741  gaaataattc tggccaggaa taaatacttc ctgaacatct taggtctttt caacaagaaa
1801  aagacagagg attgtcctta agtccctgct aaaacattcc attgttaaaa tttgcacttt
1861  gaaggtaagc tttctaggcc tgaccctcca ggtgtcaatg gacttgtgct actatatttt
1921  tttattcttg gtatcagttt aaaattcaga caaggcccac agaataagat tttccatgca
1981  tttgcaaata cgtatattct ttttccatcc acttgcacaa tatcattacc atcacttttt
2041  catcattcct cagctactac tcacattcat ttaatggttt ctgtaaacat ttttaagaca
2101  gttgggatgt cacttaacat tttttttttt tgagctaaag tcagggaatc aagccatgct
2161  taatatttaa caatcactta tatgtgtgtc gaagagtttg ttttgtttgt catgtattgg
2221  tacaagcaga tacagtataa actcacaaac acagatttga aaataatgca catatggtgt
2281  tcaaatttga acctttctca tggattttg tggtgtgggc caatatggtg tttacattat
2341  ataattcctg ctgtggcaag taaagcacac tttttttttc tcctaaaatg tttttccctg
2401  tgtatcctat tatggatact ggttttgtta attatgattc tttattttct ctcctttttt
2461  taggatatag cagtaatgct attactgaaa tgaatttcct ttttctgaaa tgtaatcatt
2521  gatgcttgaa tgatagaatt ttagtactgt aaacaggctt tagtcattaa tgtgagagac
2581  ttagaaaaaa tgcttagagt ggactattaa atgtgcctaa atgaattttg cagtaactgg
2641  tattcttggg ttttcctact taatacacag taattcagaa cttgtattct attatgagtt
2701  tagcagtctt ttggagtgac cagcaacttt gatgtttgca ctaagatttt atttggaatg
2761  caagagaggt tgaaagagga ttcagtagta cacatacaac taatttattt gaactatatg
2821  ttgaagacat ctaccagttt ctccaaatgc ctttttttaaa actcatcaca gaagattggt
2881  gaaaatgctg agtatgacac ttttcttctt gcatgcatgt cagctacata aacagttttg
2941  tacaatgaaa attactaatt tgtttgacat tccatgttaa actacggtca tgttcagctt
3001  cattgcatgt aatgtagacc tagtccatca gatcatgtgt tctggagagt gttctttatt
3061  taaagtt ttaatttagt ataaacat
```

Modified oligonucleotide may comprise, for example, one or more of the following selected components: a modified internucleoside linkage, for example, a phosphorothioate linkage, and a modified sugar moiety, for example, a conformationally-strained sugar, for example, a Linked Nucleic Acid (LNA) or Bridged Nucleic Acid (BNA).

The chemical modification of the antisense polynucleotides disclosed or referenced herein may enhance their resistance to nucleases and may enhance their ability to enter cells. For example, phosphorothioate oligonucleotides may be used. Other deoxynucleotide analogs include methylphosphonates, phosphoramidates, phosphorodithioates, N3'P5'-phosphoramidates and oligoribonucleotide phosphorothioates and their 2'-O-alkyl analogs and 2'-O-methylribonucleotide methylphosphonates. Alternatively mixed backbone oligonucleotides ("MBOs") may be used. MBOs contain segments of phosphothioate oligodeoxynucleotides and appropriately placed segments of modified oligodeoxy- or oligoribonucleotides. MBOs have segments of phosphorothioate linkages and other segments of other modified oligonucleotides, such as methylphosphonate, which is non-ionic, and very resistant to nucleases or 2'-O-alkyloligoribonucleotides. Methods of preparing modified backbone and mixed backbone oligonucleotides are known in the art.

In some embodiments, an antisense polynucleotide disclosed or referenced herein may include an oligonucleotide sugar moiety that is a modified sugar moiety. In some embodiments, the modified sugar moiety can be a thiol-containing sugar moiety or a sugar moiety which is a conformationally-strained sugar. In some embodiments, the conformationally-strained sugar can be a locked nucleotide (locked nucleic acid, or LNA). In some embodiments, the locked nucleotide can be selected from one of the following types: 2'-O—$CH_2$-4' (oxy-LNA), 2'-$CH_2$—$CH_2$-4' (methylene-LNA), 2'-NH—$CH_2$-4' (amino-LNA), 2'-N($CH_3$)—$CH_2$-4' (methylamino-LNA), 2'-S—$CH_2$-4' (thio-LNA), and 2'-Se—$CH_2$-4' (seleno-LNA). In some embodiments, the conformationally-strained sugar can be a bridged nucleic acid (BNA). Some conformationally-strained sugar can be a locked nucleic acid are shown in Formula III and Formula IV in U.S. Pat. No. 10,465,188.

Also featured herein for use in methods of the invention are modified or unmodified epithelial, endothelial, corneal epithelial and/or vascular endothelial connexin antisense polynucleotides comprising from 8 to about 80 nucleotides of an connexin extracellular loop, intracellular region, C-terminus or other region for modulating expression of one or more connexins selected from the group consisting of connexin 26, connexin 30, connexin 30.3, connexin 31, connexin 31.1, connexin 32, connexin 43, connexin 45, connexin 50 and connexin 58. The polynucleotides include synthesized polynucleotides having a length of less than 80 nucleotides, e.g., from 12-18 to about 50-80 nucleotides, preferably about 30 nucleotides or less, e.g., from 12 to about 30 nucleotides, and more preferably from about 15 to about 30 nucleotides. In one example, the polynucleotide has 30 nucleotides.

In some embodiments of this invention, the connexin 43 or other antisense oligonucleotide or polynucleotide has at least about 80%, 85%, 90%, 95%, 97%, 98% or 99% homology to a polynucleotide having a sequence selected from SEQ ID NOs: 1 to 17. Connexin modulators that are oligonucleotides or polynucleotides may have at least about 80%, 85%, 90%, 95%, 97%, 98%, or 99% homology to an 8 to 80 nucleotide portion of their respective sequences.

TABLE I

List of some connexin 43 antisense oligonucleotide embodiments

| ASN code name | SEQ ID NO. for ASN sequence | ASN sequence | ASN target site from 5' end |
|---|---|---|---|
| | SEQ ID NO: 1 | GTAATTGCGGCAAGAAGAAT TGTTTCTGTC | |
| | SEQ ID NO: 2 | GTAATTGCGGCAGGAGGAAT TGTTTCTGTC | |
| | SEQ ID NO: 3 | GGCAAGAGACACCAAAGAC ACTACCAGCAT | |
| 24501 | SEQ ID NO: 5 | ACCCATGTTGCCTGGGCACC | 237-256 |
| 30004 | SEQ ID NO: 6 | GTAGGCTTGAACCTTGTCAA | 281-300 |
| 37503 | SEQ ID NO: 7 | TCTCCCCAGGCTGACTCAAC | 372-389 |
| LP2/ 37501 | SEQ ID NO: 4 | CCAGGCTGACTCAACCGCTG | 368-385 |
| 47001 | SEQ ID NO: 8 | CAGAAGCGCACATGAGAGAT | 464-483 |
| 47002 | SEQ ID NO: 9 | GAAGCGCACATGAGAGATTG | 462-481 |
| 50501 | SEQ ID NO: 10 | AGTGTGGGTACAGACACAAA | 500-519 |
| LP3 | SEQ ID NO: 11 | CAGACACAAATATGATCTGC | 490-509 |
| 50506 | SEQ ID NO: 12 | ATATGATCTGCAGGACCCAG | 481-500 |
| 112304 | SEQ ID NO: 13 | GTAATTGCGGCAAGAAGAAT | 1134-1153 |
| 1233 | SEQ ID NO: 14 | AGGCTGTGCATGGGAGTTAG | 1233-1252 |
| 133704 | SEQ ID NO: 15 | CGCTGGTCCACAATGGCTAG | 1316-1335 |
| 133705 | SEQ ID NO: 16 | GCTGGCTCTGCTTGAAGGTC | 1335-1354 |

Table I lists the polynucleotide sequences of several embodiments of connexin 43 polynucleotide modulators useful in the methods of the invention. When sequences such as SEQ ID NO:1-16 are noted, they and other Cx43 and other connexin antisense compounds represent both modified and unmodified oligonucleotides or polynucleotides. In some embodiments, the linkages between the nucleotides, and the structure of the sugar moiety of the nucleotides may be modified. In some embodiments, the internucleoside linkage between any two nucleotides can be a standard phosphodiester linkage. In some embodiments, the internucleoside linkage between any two nucleotides can be a phosphorothioate linkage. For example, SEQ ID NO:1 can be one of the following selected structures: $G_sT_sA_sAS$-TTGCGGCAAGAAGAATTGTTTC$_s$T$_s$G$_s$T$_s$C (SEQ ID NO: 356), wherein "$_s$" denotes a phosphorothioate linkage between the two nucleotides. As another non-limiting example, SEQ ID NO:1 can be (G)(T)(A)(A) TTGCGGCAAGAAGAATTGTTTC(T)(G)(T)(C) (SEQ ID NO: 357), wherein the parenthetical nucleotides have modified sugar moieties, as described below. In some embodiments the Cx43 antisense compounds may be modified by substituting one or more uridine nucleotides residues for one or more thymine nucleotides in SEQ ID NOs:1-17 or in the sequence of another connexin (e.g., Cx26, C32, Cx45, etc.).

Certain connexin modulators, including for example connexin 43 modulators, provide downregulation of connexin expression (for example, by downregulation of mRNA transcription or translation) or otherwise decrease or inhibit the activity of the connexin protein, connexin hemichannels or gap junctions. In the case of downregulation, this will have the effect of reducing direct cell-cell communication by gap junctions, or exposure of cell cytoplasm to the extracellular space by hemichannels, at the site at which connexin expression is downregulated.

In certain embodiments, an anti-connexin antisense prevents, decreases or alters the activity or function of a hemichannel or a gap junction. As described herein, modulation of the gap junction activity or function by anti-connexin antisense compounds can lead to the closing of gap junctions, closing of hemichannels, and/or passage of molecules or ions through gap junctions and/or hemichannels.

Connexin modulators may also comprise one or polynucleotides selected, for example, from the group consisting of morpholino oligonucleotides, RNAi molecules, siRNA molecules, PNA molecules, DNAzymes, and 5'-end-mutated U1 small nuclear RNAs, and analogs of the preceding. These and other compounds may be used alone or in combination with one more connexi modulators.

Synthesis of antisense polynucleotides and other anti-connexin polynucleotides such as RNAi, siRNA, and ribozyme polynucleotides as well as polynucleotides having modified and mixed backbones can be performed. See e.g. Stein C. A. and Krieg A. M. (eds), Applied Antisense Oligonucleotide Technology, 1998 (Wiley-Liss).

The antisense polynucleotide may inhibit transcription and/or translation of a connexin protein (e.g. connexin 43). The antisense polynucleotide is generally antisense to connexin protein mRNA, for example, connexin 43. Such a polynucleotide may be capable of hybridizing to connexin protein mRNA and may thus inhibit the expression of connexin by interfering with one or more embodiments of connexin protein mRNA metabolism including transcription, mRNA processing, mRNA transport from the nucleus, translation or mRNA degradation. The antisense polynucleotide typically hybridizes to the connexin mRNA to form a duplex which can cause direct inhibition of translation and/or destabilization of the mRNA. Such a duplex may be susceptible to degradation by nucleases. Preferably the polynucleotide is a specific inhibitor of transcription and/or translation from the connexin 43 gene or mRNA, and does not inhibit transcription and/or translation from other genes or mRNAs.

The connexin modulator product may bind to the connexin 43 gene or mRNA either (i) 5' to the coding sequence, and/or (ii) to the coding sequence, and/or (iii) 3' to the coding sequence. The antisense polynucleotide may hybridize to part of the connexin protein mRNA, such as connexin 43 mRNA. Typically, the antisense polynucleotide hybridizes to the ribosome binding region or the coding region of the connexin protein mRNA. The polynucleotide may be complementary to a region of the connexin mRNA. For example, the polynucleotide may be the exact complement of a part of connexin mRNA. However, absolute complementarity is not required and polynucleotides which have sufficient complementarity to form a duplex having a melting temperature of greater than about 20° C., 30° C. or 40° C. under physiological conditions are particularly suitable for use in the present invention. Thus, the polynucleotide is typically a homologue of a sequence complementary to the mRNA. The polynucleotide may be a polynucleotide which hybridizes to the connexin protein mRNA under conditions of medium to high stringency such as 0.03M sodium chloride and 0.03M sodium citrate at from about 50° C. to about 60° C.

Antisense polynucleotides may be part of compositions which may comprise polynucleotides to more than one connexin protein. Preferably, one connexin protein to which polynucleotides are directed is connexin 43. Others include connexins found in the ocular and/or corneal epithelium. Some embodiments of the invention are described with reference to oligodeoxynucleotides. However, other suitable polynucleotides (such as RNA polynucleotides) may be used.

Peptidomimetic Modulators

In some embodiments, connexin modulators, including connexin, connexin gap junction and connexin hemichannel modulators, useful in methods of the invention include not only connexin oligonucleotides or polynucleotides, such as connexin 43 antisense oligonucleotides or polynucleotides, and others, but also connexin peptides or peptidomimetics, such as connexin 43 peptides or peptidomimetics, sometimes referred to anti-connexin peptides or peptidomimetics, e.g., anti-connexin hemichannel blocking peptides or peptidomimetics, which may be used in methods of the invention and dosed according to the one or more of the schedules described herein. They include, for example, peptides or peptidomimetic connexin modulators comprising or consisting essentially of sequences corresponding to portions of connexin extracellular domains, connexin transmembrane regions, and connexin carboxy-terminus regions. In some embodiments, connexin, connexin gap junction and connexin hemichannel modulators useful in methods of the invention include connexin 43 peptides or peptidomimetics with sequences according to a portion of the amino acid sequence of SEQ ID NO:100 (connexin 43 protein).

In some embodiments, the connexin modulators useful in methods of the invention for treating non-healing ocular defects or disorders (e.g. PED) in a subject, including non-healing corneal defects or disorders (e.g., PCED) are anti-connexin 43 peptides or peptidomimetics. In some embodiments, anti-connexin 43 peptides or peptidomimetic that may be used in methods of the invention and dosed according to the one or more of the schedules described herein is a peptide comprising or consisting essentially of a portion of an extracellular domain of a connexin (e.g. connexin 43) and/or a peptide comprising or consisting essentially of a portion of a carboxy-terminal portion of a connexin (e.g. connexin 43), including those described and/or referenced herein.

The protein sequence of connexin 43 is shown below.

```
Connexin 43
                                              (SEQ ID NO:  100)
Met Gly Asp Trp Ser Ala Leu Gly Lys Leu Leu Asp Lys Val Gln Ala
1               5                   10                  15

Tyr Ser Thr Ala Gly Gly Lys Val Trp Leu Ser Val Leu Phe Ile Phe
            20                  25                  30

Arg Ile Leu Leu Leu Gly Thr Ala Val Glu Ser Ala Trp Gly Asp Glu
        35                  40                  45

Gln Ser Ala Phe Arg Cys Asn Thr Gln Gln Pro Gly Cys Glu Asn Val
    50                  55                  60

Cys Tyr Asp Lys Ser Phe Pro Ile Ser His Val Arg Phe Trp Val Leu
65                  70                  75                  80

Gln Ile Ile Phe Val Ser Val Pro Thr Leu Leu Tyr Leu Ala His Val
                85                  90                  95

Phe Tyr Val Met Arg Lys Glu Glu Lys Leu Asn Lys Lys Glu Glu Glu
            100                 105                 110

Leu Lys Val Ala Gln Thr Asp Gly Val Asn Val Asp Met His Leu Lys
        115                 120                 125

Gln Ile Glu Ile Lys Lys Phe Lys Tyr Gly Ile Glu Glu His Gly Lys
    130                 135                 140
```

-continued

```
Val Lys Met Arg Gly Gly Leu Leu Arg Thr Tyr Ile Ile Ser Ile Leu
145                 150                 155                 160

Phe Lys Ser Ile Phe Glu Val Ala Phe Leu Leu Ile Gln Trp Tyr Ile
                165                 170                 175

Tyr Gly Phe Ser Leu Ser Ala Val Tyr Thr Cys Lys Arg Asp Pro Cys
            180                 185                 190

Pro His Gln Val Asp Cys Phe Leu Ser Arg Pro Thr Glu Lys Thr Ile
        195                 200                 205

Phe Ile Ile Phe Met Leu Val Val Ser Leu Val Ser Leu Ala Leu Asn
    210                 215                 220

Ile Ile Glu Leu Phe Tyr Val Phe Phe Lys Gly Val Lys Asp Arg Val
225                 230                 235                 240

Lys Gly Lys Ser Asp Pro Tyr His Ala Thr Ser Gly Ala Leu Ser Pro
                245                 250                 255

Ala Lys Asp Cys Gly Ser Gln Lys Tyr Ala Tyr Phe Asn Gly Cys Ser
            260                 265                 270

Ser Pro Thr Ala Pro Leu Ser Pro Met Ser Pro Pro Gly Tyr Lys Leu
        275                 280                 285

Val Thr Gly Asp Arg Asn Asn Ser Ser Cys Arg Asn Tyr Asn Lys Gln
    290                 295                 300

Ala Ser Glu Gln Asn Trp Ala Asn Tyr Ser Ala Glu Gln Asn Arg Met
305                 310                 315                 320

Gly Gln Ala Gly Ser Thr Ile Ser Asn Ser His Ala Gln Pro Phe Asp
                325                 330                 335

Phe Pro Asp Asp Asn Gln Asn Ser Lys Lys Leu Ala Ala Gly His Glu
            340                 345                 350

Leu Gln Pro Leu Ala Ile Val Asp Gln Arg Pro Ser Ser Arg Ala Ser
        355                 360                 365

Ser Arg Ala Ser Ser Arg Pro Arg Pro Asp Asp Leu Glu Ile
    370                 375                 380
```

In some embodiments, connexin 43 (Cx43) and other connexin peptide modulators useful in carrying out methods of the invention and dosed according to the one or more of the schedules described herein include peptides such as Peptide5, i.e., VDCFLSRPTEKT (SEQ ID NO:107), as Gap19, i.e., KQIEIKKFK (SEQ ID NO:108), Gap26, i.e., VCYDKSFPISHVR (SEQ ID NO:102), Gap27, a peptide called alpha connexin carboxyl terminus 1 (αCT1), and more, each targeting different binding sites with varying specificity and size. The connexin mimetic peptide Gap27, targeted to the SRPTEKTIFII sequence (SEQ ID NO: 104) (amino acids 204-214) on the second extracellular loop of Cx43 ("LLIQWYIYGFSLSAVYTCK-RDPCPHQVDCFLSRPTEKTIFII", disclosed as SEQ ID NO:109), is a versatile inhibitor of connexin-mediated communication. In some embodiments the connexin 43 modulator may comprise or consist essentially of, for example, a peptide or peptidomimetic comprising or consisting essentially of SRPTEKTIF (SEQ ID NO:110).

In addition to Peptide5, Gap19, Gap 26, and Gap 27, another peptidomimetic particularly useful in the compositions, doses and dosing methods and schedules, kits and articles of manufacture disclosed herein is the fusion peptide designated XG19, i.e., lclrpvGGKQIEIKKFK, wherein lower case denotes the D-isomer [SEQ ID NO:111]). The XG19 peptidomimetic and its connexin modulation actions are described in U.S. Pat. No. 11,466,069, incorporated in its entirety herein by reference, as noted above.

In some embodiments, the invention provides compositions for use in the methods of the invention for treating a disease or disorder of the eye comprising a construct comprising (a) a targeting carrier peptide derived from the X-protein of the Hepatitis B virus and (b) a peptide capable of interacting with an intracellular domain of a connexin. In some embodiments, the targeting carrier peptide derived from the X-protein of the Hepatitis B virus comprises an amino acid sequence selected from the group consisting of all targeting carrier peptide described in U.S. Pat. No. 11,466,069. In some embodiments, the peptide capable of interacting with an intracellular domain interacts with the intracellular domain of one or more of connexin Cx26, Cx30, Cx30.3, Cx31.1, Cx32, Cx36, Cx37, Cx40, Cx43, Cx45, Cx50 and Cx58, including those described herein. In some embodiments, the peptide capable of interacting with an intracellular domain interacts with the intracellular domain of connexin 43. In some embodiments, the peptide capable of interacting with the intracellular domain of connexin 43 includes any of the connexin 43 intracellular interacting peptides described in U.S. Pat. No. 11,466,069, as well as those peptides described herein that interact with the intracellular domain of connexin 43.

In some embodiments, the connexin 43 modulators which may be used in methods of the invention and dosed according to the one or more of the schedules described herein can comprise peptides having a sequence comprising or consisting essentially of, for example, one or more of the following sequences: "Peptide 1" ADCFLSRPTEKT (SEQ ID NO: 112), "Peptide 2" VACFLSRPTEKT (SEQ ID NO: 113), "Peptide 11" VDCFLSRPTAKT (SEQ ID NO: 114), "Peptide 12" VDCFLSRPTEAT (SEQ ID NO: 115), "Peptide 5" VDCFLSRPTEKT (SEQ ID NO: 107), "Mod1" CFLSRPT-EKT (SEQ ID NO: 116) and "Mod2" LSRPTEKT (SEQ ID NO: 117). In some embodiments, the carboxy-terminus of an anti-connexin peptide or peptidomimetic modulator can be modified. In some embodiments, the carboxy-terminus modification can comprise n-alkyl chains which can optionally be further linked to hydrogen or other moieties. In some embodiments, the connexin 43 peptides can include or exclude any of the peptides listed above or disclosed herein.

In some embodiments, the peptide or peptidomimetic comprises or consists essentially of from 7 to 40 amino acids of a connexin including, e.g., SEQ ID NO: 101 (SRPTEKT), SEQ ID NO: 107 (VDCFLSRPTEKT) and does not comprise a connexin C-terminal peptide.

Anti-connexin agents include peptides having an amino acid sequence that comprises about 5 to 20 contiguous amino acids of a connexin protein such as connexin 43 (SEQ ID NO:100), peptides having an amino acid sequence that comprises about 8 to 15 contiguous amino acids of connexin 43, or peptides having an amino acid sequence that comprises about 11 to 13 contiguous amino acids of connexin 43. Other anti-connexin agents include a peptide having an amino acid sequence that comprises at least about 5, at least about 6, at least about 7, at least about 8, at least about 9, at least about 10, at least about 11, at least about 12, at least about 13, at least about 14, at least about 15, at least about 20, at least about 25, or at least about 30 contiguous amino acids of connexin 43. Other anti-connexin 43 modulators comprise the extracellular domains of connexin 43, for example, peptide or peptidomimetic comprising or consisting essentially of SRPTEKT (SEQ ID NO: 101) or VDCFLSRPTEKT (SEQ ID NO: 107).

In other anti-connexin compounds, mimetic peptides are based on the extracellular domains of connexin 43 corresponding to the amino acids at positions 37-76 and 178-208 of connexin 43 protein sequence. Thus, certain anti-connexin peptides useful in methods of the invention have an amino acid sequence comprising or consisting essentially of about 7 to about 40 of the amino acids corresponding to the regions at positions 37-76 and 178-208 of the connexin 43 protein sequence. The peptides need not have an amino acid sequence identical to those portions of the connexin 43 protein sequence, and conservative amino acid changes may be made such that the peptides retain binding activity or functional activity in the assays described herein and otherwise known in the art. In other embodiments, mimetic peptides are based on peptide target regions within the connexin protein other than the extracellular domains (e.g. portions of the connexin 43 protein sequence not corresponding to positions 37-76 and 178-208).

In addition to therapeutically effective modified or unmodified peptide or peptidomimetics comprising or consisting essentially of a portion of an extracellular or transmembrane domain or C-terminal domain of a connexin 43, for example, other embodiments include modified or unmodified peptides or peptidomimetics comprising or consisting essentially of a portion of, for example, an extracellular or transmembrane domain of one or more other connexins found in the ocular and/or corneal epithelium may be used in methods of the invention and dosed according to the one or more of the schedules described herein. Other embodiments include modified or unmodified peptides or peptidomimetics comprising or consisting essentially of, for example, a portion of an extracellular or transmembrane domain of one or more other connexins found in blood vessels (e.g. endothelium, etc.), including ocular and/or corneal blood vessels.

In some embodiments, the anti-connexin peptidomimetic useful in a method of the invention and which may be dosed according to the one or more of the schedules described herein is a connexin 45 peptidomimetic modulator comprising portions of the connexin 45 protein that antagonize or inhibit or block connexin-connexin interactions. In some embodiments the connexin 45 modulator may comprise, for example, a peptide or peptidomimetic comprising or consisting essentially of a portion of the E2 or C terminal domain of connexin 45, for example, comprising SRPTEKT (SEQ ID NO: 101). The peptide or peptidomimetic may also comprise, for example DCFISRPTEKT (SEQ ID NO: 118). Exemplary peptide sequences for connexin 45 peptides and peptidomimetic modulators useful in methods of the invention are also provided in Table 63 of U.S. Pat. No. 10,465,188.

In some embodiments, a connexin modulator comprises a peptide comprising an amino acid sequence corresponding to a portion of a transmembrane region of connexin 45 or a C-terminal region of connexin 45. In particular non-limiting embodiments, for example, the anti-connexin compound is a peptide having an amino acid sequence that comprises about 3 to about 30 contiguous amino acids of the known connexin 45 sequence, a peptide having an amino acid sequence that comprises about 5 to about 20 contiguous amino acids of the known connexin 45 sequence, a peptide having an amino acid sequence that comprises about 8 to about 15 contiguous amino acids of the known connexin 45 sequence, or a peptide having an amino acid sequence that comprises about 11, 12, or 13 contiguous amino acids of the known connexin 45 sequence. Other non-limiting embodiments include an anti-connexin compound that is a peptide having an amino acid sequence that comprises at least about 3, 4, 5, 6, 7, 8, 9, 10, 11, 12, 13, 14, 15, 20, 25, or 30 contiguous amino acids of the known connexin 45 sequence. In certain anti-connexin compounds provided herein, mimetic peptides are based on the extracellular domains of connexin 45 corresponding to the amino acids at positions 46-75 and 199-228 of the known connexin 45 sequence. Thus, certain peptide described herein have an amino acid sequence corresponding to the regions at positions 46-75 and 199-228 of the known connexin 45 sequence. The peptides need not have an amino acid sequence identical to those portions of the known connexin 45 sequence. and conservative amino acid changes may be made such that the peptides retain binding activity or functional activity in the assays described herein and otherwise known in the art. In other embodiments, mimetic peptides are based on peptide target regions within the connexin protein other than the extracellular domains (e.g. portions of the known connexin 45 sequence not corresponding to positions 46-75 and 199-228). See WO2006/134494, disclosing various connexin sequences.

Some peptidomimetic connexin modulators useful in methods of the invention include VDCFLSRPTEKT (SEQ ID NO: 107) and SRPTEKTIFII (SEQ ID NO: 104), which bind, for example, to the Cx43 extracellular domain.

In some embodiments, the connexin 26 peptidomimetic connexin modulator useful in a method of the invention and dosed according to the one or more of the schedules described herein is Gap26. In other embodiments, the anti-connexin peptidomimetic for use in a method of the invention is a connexin32 peptidomimetic (e.g. INCTLQPGCNSV (SEQ ID NO: 103) or $^{32}$Gap27, i.e., SRPTEKTIFII (SEQ ID NO:104) or a connexin50 peptidomimetic (e.g. TAT-Cx50L2, i.e., GGERAPLAADQGSVKKSSSSSKGTKK (SEQ ID NO:105) or TAT-Cx50CT, i.e., SRARSDDLTV (SEQ ID NO:106)).

In some embodiments, peptides and peptidomimetics include peptides and peptidomimetics useful for the inhibition of gap junction channels and hemichannels corresponding to specific sequences within extracellular loops E1 and E2 involving the conserved QPG and SHVR (SEQ ID NO: 359) motifs of E1 (Gap26 peptide) and the SRPTEK motif (SEQ ID NO: 360) in E2 (Gap27 peptide) as well as the cytoplasmic loop (Gap19 peptide). Useful peptidomimetic connexin modulators are described in U.S. Pat. No. 9,248, 141 ("Methods of treatment by administering anti-connexin peptides and mimetics"). Other useful peptide connexin modulators are described in U.S. Pat. No. 11,466,069 ("Methods of treatment and novel constructs"), including XG19 and other constructs comprising a targeting carrier peptide derived from the X-protein of the Hepatitis B virus and a peptide capable of interacting with an intracellular domain of a connexin (e.g. connexin 43).

Other connexin peptide modulators useful in methods of the invention are provided in Table 64 of U.S. Pat. No. 10,465,188. Useful peptide modulators of connexin 43 (Cx43) and other connexins that may be dosed in embodiments of the invention are also referenced in Caufirez et al., and in King, D R, et al., Mechanisms of Connexin Regulating Peptides *Int. J. Mol. Sci.* 22:10186 (September 2021) and FIG. 1 ("Schematic of the Cx43 protein in the plasma membrane with colored lines indicating the positions of described peptides targeting EL, IL and CT regions") and Table 1 ("Connexin Peptides").

In some embodiments the peptides may also be used as promoieties. See, e.g. Vig, B S, et al., Amino acids as promoieties in drug design and Development. *Advanced Drug Delivery Reviews* 65(10): p 1370-1385 (2013); Dhokchawle, B, et al., Promoieties Used In Prodrug Design: A Review. *Indian Journal of Pharmaceutical Education* 48(2):35-40 (2013).

The gap junction modulators or anti-connexin hemichannel blocking peptides or peptidomimetics may be unmodified, or modified as desired (e.g. to increase stability, to further stabilize peptide conformation, increase bioactivity, increase cell permeability, etc.). See e.g. DeGruyter, J N, et al., Residue-Specific Peptide Modification: A Chemist's Guide. *Biochemistry* 56, 30, 3863-3873 (2017); Boto, A, et al. Site-selective modification of peptide backbones. *Org. Chem. Front.* 8:6720-6759 (2021) (review article). Thus, for example, peptidomimetics used in methods of the invention may contain one or more modified amino acids, amino acid analogs, or may be otherwise modified to improve bioavailability or to increase penetration across the cell membrane.

Other peptide sequences known to inhibit the inter-connexin binding that can regulate connexin activity are the cytoplasmic loop of connexin 43 (amino acids 119-144) L2 peptide and subparts of the L2 peptide of connexin 43. In some embodiments, these peptides may include or exclude, for example, the nine amino acid sequence of Gap19, KQIEIKKFK (SEQ ID NO: 108); the native Gap19 sequence, DGVNVEMHLKQIEIKKFKYGIEEHGK (SEQ ID NO: 119); the His144→Glu L2 derivative of Gap19, as reported by Shibayama (Shibayama, J. et al., *Biophys. J.* 91, 405404063, 2006), DGVNVEMHLKQIEIKKFKYGIEEQGK (SEQ ID NO: 120); the TAT-Gap19 sequence, YGRKKRRQRRRKQIEIKKFK (SEQ ID NO: 121); the SH3 binding domain, CSSPTAPLSPMSPPGYK (SEQ ID NO: 122), or subpart thereof PTAPLSPMSPP (SEQ ID NO: 123); the C-terminal sequence of the CT9 or CT10 peptide, with or without a TAT leader sequence to increase cell penetration, for example, RPRDDEI (CT9; SEQ ID NO: 124), SRPRDDLEI (CT10; SEQ ID NO: 125), YGRKKRRQRRRSRPRDDEI (TAT-CT9; SEQ ID NO: 126), or YGRKKRRQRRRRPRDDEI (TAT-CT10; SEQ ID NO: 127). Other peptidomimetic sequences that can be included or excluded in the compositions, methods, kits or articles of manufacture disclosed herein are those reported by Dhein (Dhein, S., Naunyn-Schmiedeberg's *Arch. Pharm.,* 350: 174-184, 1994); the AAP10 peptide, H2N-Gly-Ala-Gly-4Hyp-Pro-Tyr-CONH2 (SEQ ID NO: 128), and the ZP123 peptide (rotigapeptide), Ac-D-Tyr-Pro-D-4Hyp-Gly-D-Ala-Gly-$NH_2$ (SEQ ID NO: 129), (Dhein, S., et al. *Cell Commun. Adhes.* 10, 371-378, 2013). Rotigapeptide is comprised of the D-form of the peptides for enhanced efficacy over the native L-form of the peptide.

In some embodiments, the therapeutically effective modified or unmodified peptide or peptidomimetic comprises a portion of the E1 extracellular domain of a connexin, such as the connexin 43 E1 (ESAWGDEQSAFRCNTQQPGCENVCYDKSFPISHVR; SEQ ID NO:130) or the connexin 45 E1 (GESIYYDEQSKFVCNTEQPGCENVCYDAFAPLSHVR; SEQ ID NO:131). In some embodiments, the therapeutically effective modified or unmodified peptide or peptidomimetic comprises a portion of the E2 extracellular domain of a connexin, such as the connexin 43 E2 (LLIQWYIYGFSLSAVYTCKRDPCPHQVDCFLSRPTEKT; SEQ ID NO:132) or the connexin 45 E2 (LIGQYFLYGFQVHPFYVCSRLPCHPKIDCFISRPTEKT; SEQ ID NO:133).

In certain embodiments, the connexin 43 modulator peptides of the present invention can be linked at the amino or carboxy terminus to a cellular internalization transporter. The cellular internalization transporter linked to connexin 43 modulator peptides of the present invention may be any internalization sequence known or newly discovered in the art, or conservative variants thereof. Non-limiting examples of cellular internalization transporters and sequences include antennapedia sequences, TAT, HIV-Tat, Penetratin, Antp-3A (Antp mutant), Buforin II, Transportan, MAP (model amphipathic peptide), K-FGF, Ku70, Prion, pVEC, Pep-1, SynB1, Pep-7, HN-1, BGSC (Bis-Guanidinium-Spermidine-Cholesterol, and BGTC (BisGuanidinium-Tren-Cholesterol). Cellular internalization transporters are useful for peptidomimetics such as Gap19 and the αCT peptides. The sequences of exemplary cellular internalization peptides are known in the art. See, e.g., Table 65 in U.S. Pat. Nos. 10,465,188; 11,466,069.

In one embodiment, the peptide sequence CFLSRPTEKT (SEQ ID NO:116) or VDCFLSRPTEKT (SEQ ID NO:107) can be conjugated to two dodecyl groups to create a modified peptide which can modulate connexin 43, "C12-C12-Cxn43 MP" (SEQ ID NO: 358). See SEQ ID NO: 237 in U.S. Pat. No. 10,465,188. The resulting structure "C12-C12-Cxn43MP" (SEQ ID NO: 358) is shown below.

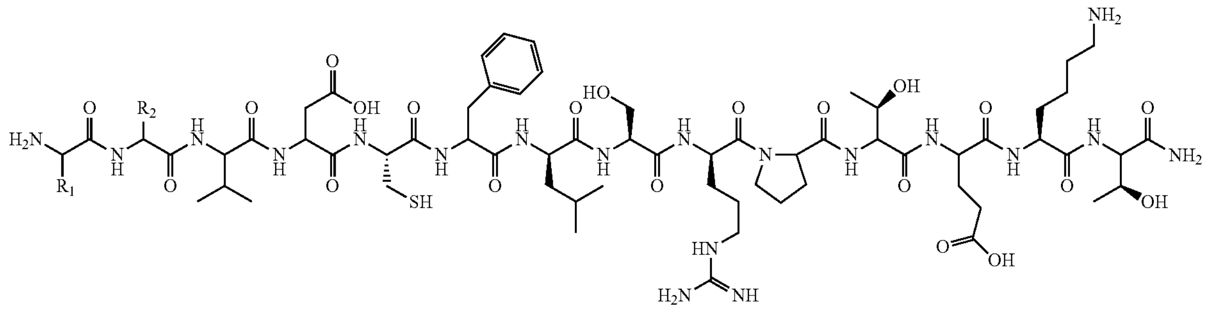

In the structure of C12-C12-Cxn43 MP (SEQ ID NO: 358), R1 and R2 can be hydrogen or alkyl groups. In some aspects, R1=R2=n-dodecyl chains.

In some embodiments, the therapeutically effective modified or unmodified peptide or peptidomimetic comprises a portion of the C-terminal domain of a connexin, such as connexin 43 or connexin 45, preferably connexin 43. Some embodiments of anti-connexin 43 modulators useful in methods of the invention comprise the C-terminus region of connexin 43, or modified versions thereof. See e.g. O'Quinn, M P, et al., A Peptide Mimetic of the Connexin43 Carboxyl-Terminus Reduces Gap Junction Remodeling and Induced Arrhythmia Following Ventricular Injury. *Circ Res.* 108(6): 704-715 (March 2011). C-terminus connexin peptidomimetic modulators, including αCT1 (alpha connexin carboxy terminus 1) peptides (also referred to as αCT1 or ACT1 peptides in publications), are described, for example, in Montgomery et al., Connexin 43-Based Therapeutics for Dermal Wound Healing *Int. J. Mol. Sci.* 2018, 19, 1778, and U.S. Pat. No. 8,815,556 ("Compositions and methods for tissue engineering, tissue regeneration and wound healing"). See also WO2006/069181. Preferred connexin carboxy-terminal polypeptides are connexin 43 carboxy-terminal polypeptides. Such compounds are described in US Patent Publication No. 20070042964 ("Compositions and methods for modulating connexin hemichannels"). If a connexin peptide or peptidomimetic modulator comprises a portion of an intracellular domain of a connexin (e.g. an αCT peptide, such as CT9, CT10, αCT1, etc.), the peptide may be conjugated to a cell internalization transporter including those noted or referenced herein. In some embodiments, a connexin peptidomimetic modulator useful in methods of then invention may block zona occludens (ZO-1) binding to connexin 43 and modulate connexin gap junctions and hemichannels to advantage. See FIG. 2 in Caufriez, A, et al. Peptide-based targeting of connexins and pannexins for therapeutic purposes. *Expert Opinion on Drug Discovery* 15(10):1213-1222 (2020).

In some embodiments, the connexin modulator may be a gap junction closing compound and/or hemichannel closing compound. In some embodiments, the gap junction closing compounds and hemichannel closing compounds are connexin 43 gap junction closing compounds and connexin 43 hemichannel closing compounds (e.g. a Cx43 C-terminus peptidomimetic).

Various useful peptidomimetic peptides mimic sequences of connexin extracellular regions. The first extracellular loops of Cx37, Cx40 as well Cx43 are mimicked by peptides under the Gap26 code. Gap27 and Peptide5 mimic regions of the second extracellular loop. Gap27 targets Cx32, Cx40 and Cx43, while Peptide5 is used for Cx43 inhibition. JM2, ΔSH3, CT9, CT10, αCT mimic the C-terminal tail of Cx43 and Gap24 reproduces a sequence of the cytoplasmic loop of Cx32. Both L2 and Gap19 also mimic the cytoplasmic loop but of Cx43.

The extracellular loops of connexin hemichannels are also good targets for peptidomimetic connexin inhibitors useful in the invention due to their accessibility in contrast to their full channel counterparts. Nevertheless, peptides containing the conserved motives QPG and SHVR (SEQ ID NO: 359) of the first extracellular loop and the SRPTEK motif (SEQ ID NO: 360) of the second extracellular loop interfere with the formation of gap junctions. This led to the development of peptide mimetics $^{43}$Gap26, $^{37,40}$Gap26, $^{32}$Gap27, $^{40}$Gap27, $^{43}$Gap27 and $^{43}$Peptide5 (note that the superscript in the nomenclature of these peptide analogues refers to Cx subtypes they can target).

The conserved SHVR motif (SEQ ID NO: 359) of the first extracellular loop is incorporated in the sequence of useful Gap26 peptide mimetics. The two slightly different sequences are both categorized under the Gap26 code, one targeting Cx37 and Cx40, and the other targeting only Cx43. Cells treated with either of these Gap26 peptides showed Cx hemichannel inhibition within minutes.

There are three Gap27 peptides, each targeting different Cx types, namely Cx32, Cx40 and Cx43 that are useful in compositions and methods of the invention. These peptides mimic the conserved SRPTEK motif (SEQ ID NO: 360) of the second extracellular loop, but have the same time-dependent effect on gap junction activity as Gap26. Like Gap27, Peptide5 contains the SRPTEK motif (SEQ ID NO: 360). However, the mimicked sequence of Peptide5 is shifted in the direction of the N-terminal tail in comparison to that of Gap27. Peptide5 can inhibit Cx43 hemichannels at a concentration of 5-10 μM, but incubation at higher concentration (100 μM or higher) can also leads to inhibition of gap junctions in some circumstances.

Other peptides useful in compositions and methods of the invention mimic sequences of connexin intracellular regions. The interaction between the cytoplasmic loop and C-terminal tail mediates the gating mechanism of Cx hemichannels and gap junctions. Gap junctions are in an open state when there is no interaction between the C-terminal tail and cytoplasmic loop, while such interaction is critical for Cx hemichannel opening. The CT10 peptidomimetic reproduces the last 10 amino acids of the C-terminal tail of Cx43. Inhibition of Cx43-mediated ATP release by a peptide mimetic, called TAT-L2, pinpointed its mimicked L2 region (amino acid 119 to 144) as an essential sequence of the cytoplasmic loop in the interaction with the Cx43 C-terminal tail. To date, 2 peptides mimicking the L2 region are available, namely $^{43}$Gap19 and $^{32}$Gap24. $^{43}$Gap19 inhibits Cx43 hemichannel currents by binding to the C-terminal tail, thereby inhibiting the cytoplasmic loop/C-terminal tail interaction. $^{43}$Gap19 has the advantage of being a selective inhibitor, as it does not affect gap junction or Panx1 channel activity. $^{32}$Gap24 is a peptide that mimics a 13 amino acid long stretch of the L2 region of Cx32 and can also be used in methods of the invention. Cx32 is one of the ten human corneal epithelial connexin that can be usefully targeted as described herein. In vitro studies showed that Cx32 hemichannel-mediated ATP release is inhibited by $^{32}$Gap24 at concentrations of 17 μM without affecting gap junctions.

Peptides targeting intracellular regions of Cx proteins need to access the intracellular environment. Cell-penetrating peptides for this purpose are described herein (e.g. the TAT-peptide, an oligoarginine tag and the Xentry peptide), and can be anchored to Cx-derived peptide sequences in order to enhance the uptake into the cell via endocytosis. $^{43}$Gap19 can enter the cell on its own due to the KKFK cell-translocation motif (SEQ ID NO: 361) of the L2 region. Nonetheless, comparison of the IC50 (half maximal inhibitory concentration) of $^{43}$Gap19 itself (47 μM) and TAT-$^{43}$Gap19 (7 μM) for the inhibition of ATP release in glioma cells showed that the entry of $^{43}$Gap19 into the cell can be improved by linking to a TAT-tag. All 5 available peptides mimicking the C-terminal tail are derived from Cx43.

αCT1 mimics the last 9 amino acids of Cx43 and is linked to an antennapedia sequence that facilitates cellular internalization of the peptide mimetic. The interaction between Cx43 and the PDZ-domain of ZO-1, a region that is suggested to be involved in the regulation of Cx trafficking and gap junction assembly, is disrupted by αCT1. This interference reportedly leads to increased gap junction plaque formation and decreased Cx hemichannel activity.

If a peptide or peptidomimetic modulator comprises a portion of an intracellular domain of a connexin, the peptide may, in some embodiments, be conjugated to a cell internalization transporter and may, in some instances, block zona occludens (ZO-1) binding to connexin 43.

In some embodiments of this invention, the connexin modulator is a peptide or peptidomimetic shown in Table II below (E2 and T2 refer to the location of a peptide in, for example, the second extracellular domain or the second transmembrane domain).

TABLE II

| SEQ ID NO: | Identifier | Sequence |
|---|---|---|
| SEQ ID NO: 140 | CXT 2 | PSSRASSRASSRPRPDDLEI |
| SEQ ID NO: 141 | CXT 1 | RPRPDDLEI |
| SEQ ID NO: 142 | CXT 3 | RPRPDDLEV |
| SEQ ID NO: 143 | CXT 4 | RPRPDDVPV |
| SEQ ID NO: 144 | CXT 5 | KARSDDLSV |
| SEQ ID NO: 145 | hCx40 | QKPEVPNGVSPGHRLPHGYHSDKRRLSKASSKARSD DLSV |
| SEQ ID NO: 146 | Antp/CXT 2 | RQPKIWFPNRRKPWKKPSSRASSRASSRPRPDDLEI |
| SEQ ID NO: 147 | Antp/CXT 2 | RQPKIWFPNRRKPWKKPSSRASSRASSRPRPDDLEI |
| SEQ ID NO: 148 | Antp/CXT 1 | RQPKIWFPNRRKPWKKRPRPDDLEI |
| SEQ ID NO: 149 | Antp/CXT 3 | RQPKIWFPNRRKPWKKRPRPDDLEV |
| SEQ ID NO: 150 | Antp/CXT 4 | RQPKIWFPNRRKPWKKRPRPDDVPV |
| SEQ ID NO: 151 | Antp/CXT 5 | RQPKIWFPNRRKPWKKKARSDDLSV |
| SEQ ID NO: 152 | conservative Cx43 variant | RPKPDDLDI |
| SEQ ID NO: 153 | HIV-Tat/CXT 1 | GRKKRRQRPPQRPRPDDLEI |
| SEQ ID NO: 154 | Penetratin/CXT 1 | RQIKIWFQNRRMKWKKRPRPDDLEI |
| SEQ ID NO: 155 | Antp-3A/CXT 1 | RQIAIWFQNRRMKWAARPRPDDLEI |
| SEQ ID NO: 156 | Tat/CXT 1 | RKKRRQRRRRPRPDDLEI |
| SEQ ID NO: 157 | Buforin II/Vnrs 1 | TRSSRAGLQFPVGRVHRLLRKRPRPDDLEI |
| SEQ ID NO: 158 | Transportan/ CXT 1 | GWTLNSAGYLLGKINKALAALAKKILRPRPDDLEI |
| SEQ ID NO: 169 | MAP/CXT 1 | KLALKLALKALKAALKLARPRPDDLEI |
| SEQ ID NO: 160 | K-FGF/CXT 1 | AAVALLPAVLLALLAPRPRPDDLEI |
| SEQ ID NO: 161 | Ku70/CXT 1 | VPMLKPMLKERPRPDDLEI |
| SEQ ID NO: 162 | Prion/CXT 1 | MANLGYWLLALFVTMWTDVGLCKKRPKPRPRPDDL EI |
| SEQ ID NO: 163 | pVEC/CXT 1 | LLIILRRRIRKQAHAHSKRPRPDDLEI |
| SEQ ID NO: 164 | Pep-1/CXT 1 | KETWWETWWTEWSQPKKKRKVRPRPDDLEI |
| SEQ ID NO: 165 | SynB1/CXT 1 | RGGRLSYSRRRFSTSTGRRPRPDDLEI |
| SEQ ID NO: 166 | Pep-7/CXT 1 | SDLWEMMMVSLACQYRPRPDDLEI |
| SEQ ID NO: 167 | HN-1/CXT 1 | TSPLNIHNGQKLRPRPDDLEI |
| SEQ ID NO: 174 | SEQ-Mod4 | VDCFLSRPTE |
| SEQ ID NO: 175 | SEQ-Mod5 | VDCFLSRP |
| SEQ ID NO: 176 | SEQ-Mod6 | VDCFLS |
| SEQ ID NO: 177 | HIV-Tat/SEQ- | GRKKRRQRPPQVDCFLSRPTEKT |

TABLE II-continued

| SEQ ID NO: | Identifier | Sequence |
|---|---|---|
| | pept5 | |
| SEQ ID NO: 178 | Penetratin/ SEQ-pept5 | RQIKIWFQNRRMKWKKVDCFLSRPTEKT |
| SEQ ID NO: 179 | Antp-3A/SEQ-pept5 | RQIAIWFQNRRMKWAAVDCFLSRPTEKT |
| SEQ ID NO: 180 | Tat/SEQ-pept5 | RKKRRQRRRVDCFLSRPTEKT |
| SEQ ID NO: 181 | Buforin II/ SEQ-pept5 | TRSSRAGLQFPVGRVHRLLRKVDCFLSRPTEKT |
| SEQ ID NO: 182 | Transportan/ SEQ-pept5 | GWTLNSAGYLLGKINKALAALAKKILVDCFLSRPTEK T |
| SEQ ID NO: 183 | MAP/SEQ-pept5 | KLALKLALKALKAALKLAVDCFLSRPTEKT |
| SEQ ID NO: 184 | K-FGF/SEQ-pept5 | AAVALLPAVLLALLAPVDCFLSRPTEKT |
| SEQ ID NO: 185 | Ku70/SEQ-pept5 | VPMLKPMLKEVDCFLSRPTEKT |
| SEQ ID NO: 186 | Prion/SEQ-pept5 | MANLGYWLLALFVTMWTDVGLCKKRPKPVDCFLSR PTEKT |
| SEQ ID NO: 187 | pVEC/SEQ-pept5 | LLIILRRRIRKQAHAHSKVDCFLSRPTEKT |
| SEQ ID NO: 188 | Pep-1/SEQ-pept5 | KETWWETWWTEWSQPKKKRKVVDCFLSRPTEKT |
| SEQ ID NO: 189 | SynB1/SEQ-pept5 | RGGRLSYSRRRFSTSTGRVDCFLSRPTEKT |
| SEQ ID NO: 190 | Pep-7/SEQ-pept5 | SDLWEMMMVSLACQYVDCFLSRPTEKT |
| SEQ ID NO: 191 | HN-1/SEQ-pept5 | TSPLNIHNGQKLVDCFLSRPTEKT |
| SEQ ID NO: 192 | SEQ M3E2 | FEVAFLLIQWI |
| SEQ ID NO: 193 | SEQ E2a | LLIQWYIGFSL |
| SEQ ID NO: 194 | SEQ E2b | SLSAVYTCKRDPCPHQ |
| SEQ ID NO: 196 | SEQ M1E1 | LGTAVESAWGDEQ |
| SEQ ID NO: 197 | SEQ E1a | QSAFRCNTQQPG |
| SEQ ID NO: 198 | SEQ E1b | QQPGCENVCYDK |
| SEQ ID NO: 200 | SEQ E2d | KRDPCHQVDCFLSRPTEK |
| SEQ ID NO: 291 | Peptide 1 | ADCFLSRPTEKT |
| SEQ ID NO: 292 | Peptide 2 | VACFLSRPTEKT |
| SEQ ID NO: 293 | Peptide 11 | VDCFLSRPTAKT |
| SEQ ID NO: 294 | Peptide 12 | VDCFLSRPTEAT |
| SEQ ID NO: 108 | Gap 19-subpart | KQIEIKKFK |
| SEQ ID NO: 300 | Gap 19-full | DGVNVEMHLKQIEIKKFKYGIEEHGK |
| SEQ ID NO: 301 | Gap 19-deriv | DGVNVEMHLKQIEIKKFKYGIEEQGK |
| SEQ ID NO: 302 | TAT-Gap19 | YGRKKRRQRRRKQIEIKKFK |
| SEQ ID NO: 303 | SH3-full | CSSPTAPLSPMSPPGYK |
| SEQ ID NO: 304 | SH3-subpart | PTAPLSPMSPP |
| SEQ ID NO: 309 | AAP10 | $H_2N$-Gly-Ala-Gly-4Hyp-Pro Tyr-$CONH_2$ |

TABLE II-continued

| SEQ ID NO: | Identifier | Sequence |
|---|---|---|
| SEQ ID NO: 310 | ZP123 | Ac-D-Tyr-Pro-D-4Hyp-Gly-D-Ala-Gly-$NH_2$ |
| SEQ ID NO: 311 | plsl/SEQ-pept5 | RVIRVWFQNKRCKDKKVDCFLSRPTEKT |
| SEQ ID NO: 312 | MGB Peptide P-beta/SEQ-pept5 | GALFLGFLGAAGSTMGAWSQPKKKRKVVDCFLSRPTEKT |
| SEQ ID NO: 313 | MGB Peptide P-alpha/SEQ-pept5 | GALFLAFLAAALSLMGLWSQPKKKRRVVDCFLSRPTEKT |
| SEQ ID NO: 343 | huCx26 | MYVFYVMYDGFSMQRLVKCNAWPCPNTVDCFVSRPTEKT |
| SEQ ID NO: 344 | huCx30 | MYVFYFLYNGYHLPWVLKCGIDPCPNLVDCFISRPTEKT |
| SEQ ID NO: 345 | huCx30.3 | LYIFHRLYKDYDMPRVVACSVEPCPHTVDCYISRPTEKK |
| SEQ ID NO: 346 | huCx31 | LYLLHTLWHGFNMPRLVQCANVAPCPNIVDCYIARPTEKK |
| SEQ ID NO: 347 | huCx31.1 | LYVFHSFYPKYILPPVVKCHADPCPNIVDCFISKPSEKN |
| SEQ ID NO: 348 | huCx32 | MYVFYLLYPGYAMVRLVKCDVYPCPNTVDCFVSRPTEKT |
| SEQ ID NO: 349 | huCx36 | LYGWTMEPVFVCQRAPCPYLVDCFVSRPTEKT |
| SEQ ID NO: 350 | huCx37 | LYGWTMEPVFVCQRAPCPYLVDCFVSRPTEKT |
| SEQ ID NO: 351 | huCx40.1 | GALHYFLFGFLAPKKFPCTRPPCTGVVDCYVSRPTEKS |
| SEQ ID NO: 353 | huCx46 | IAGQYFLYGFELKPLYRCDRWPCPNTVDCFISRPTEKT |
| SEQ ID NO: 354 | huCx46.6 | LVGQYLLYGFEVRPFFPCSRQPCPHVVDCFVSRPTEKT |
| SEQ ID NO: 355 | huCx40 | IVGQYFIYGIFLTTLHVCRRSPCPHPVNCYVSRPTEKN |

In some embodiments the connexin 43 modulator may comprise, for example, a peptide or peptidomimetic comprising, for example SEQ ID NO: 101 (SRPTEKT). The peptide or peptidomimetic may also comprise, for example SEQ ID NO: 168 (VDCFLSRPTEKT). The peptide may contain one or more modified amino acids, amino acid analogs, or may be otherwise modified to improve bioavailability or to increase penetration across the cell membrane. For example, SEQ ID NO: 107 may be modified to obtain SEQ ID NOS: 177-191 and 311-313. In some embodiments, the peptide or peptidomimetic comprising, for example SEQ ID NO: 101 (SRPTEKT) or SEQ ID NO: 107 (VDCFLSRPTEKT) comprises from 7 to 40 amino acids or amino acid analogues and does not comprise a C-terminal peptide. In some embodiments the peptides may also be used as promoieties.

In some embodiments, the Connexin 45 modulators can be peptide or peptidomimetics comprising portions of the Connexin 45 protein that antagonize or inhibit or block connexin-connexin interactions. Exemplary peptide sequences for Connexin 45 peptides and peptidomimetic modulators are provided in Table III.

TABLE III

Sequences of Connexin 45 modulator peptides or peptidomimetics

| SEQ ID NO. | Sequence |
|---|---|
| SEQ ID NO: 237 | LTAVGGESIYYDEQSKFVCNTEQPGCENVCYDAFAPLSHVRFWVFQ |
| SEQ ID NO: 238 | LTAVGGESIYYDEQS |
| SEQ ID NO: 239 | DEQSKFVCNTEQP |
| SEQ ID NO: 241 | TEQPGCENVCYDA |
| SEQ ID NO: 242 | VCYDAFAPLSHVR |
| SEQ ID NO: 243 | APLSHVRFWVFQ |
| SEQ ID NO: 245 | FEVGFLIGQYF |

TABLE III-continued

| Sequences of Connexin 45 modulator peptides or peptidomimetics | |
|---|---|
| SEQ ID NO. | Sequence |
| SEQ ID NO: 246 | LIGQYFLYGFQV |
| SEQ ID NO: 247 | GFQVHPFYVCSRLP |
| SEQ ID NO: 248 | SRLPCHPKIDCF |
| SEQ ID NO: 249 | IDCFISRPTEKT |
| SEQ ID NO: 250 | SRPTEKTIFLL |
| SEQ ID NO: 252 | YVCSRLPCHP |
| SEQ ID NO: 253 | QVHPFYVCSRL |
| SEQ ID NO: 254 | FEVGFLIGQYFLY |
| SEQ ID NO: 255 | GQYFLYGFQVHP |
| SEQ ID NO: 256 | GFQVHPFYVCSR |
| SEQ ID NO: 257 | AVGGESIYYDEQ |
| SEQ ID NO: 258 | YDEQSKFVCNTE |
| SEQ ID NO: 259 | NTEQPGCENVCY |
| SEQ ID NO: 260 | CYDAFAPLSHVR |
| SEQ ID NO: 261 | FAPLSHVRFWVF |
| SEQ ID NO: 262 | LIGQY |
| SEQ ID NO: 263 | QVHPF |
| SEQ ID NO: 264 | YVCSR |
| SEQ ID NO: 265 | SRLPC |
| SEQ ID NO: 266 | LPCHP |
| SEQ ID NO: 267 | GESIY |
| SEQ ID NO: 268 | YDEQSK |
| SEQ ID NO: 269 | SKFVCN |
| SEQ ID NO: 270 | TEQPGCEN |
| SEQ ID NO: 271 | VCYDAFAP |

TABLE III-continued

| Sequences of Connexin 45 modulator peptides or peptidomimetics | |
|---|---|
| SEQ ID NO. | Sequence |
| SEQ ID NO: 272 | LSHVRFWVFQ |
| SEQ ID NO: 273 | LIQYFLYGFQVHPF |
| SEQ ID NO: 274 | VHPFYCSRLPCHP |
| SEQ ID NO: 275 | VGGESIYYDEQSKFVCNTEQPG |
| SEQ ID NO: 276 | TEQPGCENVCYDAFAPLSHVRF |
| SEQ ID NO: 277 | AFAPLSHVRFWVFQ |
| SEQ ID NO: 278 | IDCFISRPTEKTIFLL |
| SEQ ID NO: 279 | DCFISRPTEKT |
| SEQ ID NO: 101 | SRPTEKT |

In some embodiments the connexin 45 modulator may comprise, for example, a peptide or peptidomimetic comprising, a portion of the E2 or C terminal domain of connexin 45, for example, comprising SEQ ID NO: 101 (SRPTEKT). The peptide or peptidomimetic may also comprise, for example SEQ ID NO: 279 (DCFISRPTEKT). In some embodiments the peptides may only be 3 amino acids in length, including SRL, PCH, LCP, CHP, IYY, SKF, QPC, VCY, APL, HVR, or longer.

When specific proteins are referred to herein, derivatives, variants, and fragments are contemplated and included. Protein derivatives and variants are well understood to those of skill in the art and can involve insertional, substitutional or deletional amino acid sequence variants known in the art.

The gap junction modulators and anti-connexin hemichannel blocking peptides or peptidomimetics are made chemically, synthetically, or otherwise manufactured.

Connexin Hemichannel Modulators

Any modulator that is capable of eliciting a desired inhibition of the passage (e.g., transport) of molecules through a connexin gap junction and/or connexin hemichannel in ocular or corneal blood vessels, and well as connexin gap junctions and/or connexin hemichannel in the ocular or corneal epithelium, may be used in embodiments of the invention and dosed according to the one or more of the schedules described herein. Any connexin agents that modulates the passage of molecules through a gap junction or connexin hemichannel are also provided in particular embodiments (e.g., those that modulate, block or lessen the passage of molecules from the cytoplasm of a cell into an extracellular space or adjoining cell cytoplasm, including ATP). Such anti-connexin modulators may modulate the passage of molecules through a gap junction or connexin hemichannel with or without gap junction uncoupling (blocking the transport of molecules through gap junctions). Such compounds include, for example, binding proteins (e.g. scFvs, antibodies, etc.), polypeptides (e.g. peptidomimetics), and organic compounds (e.g. tonabersat and compounds of Formula I and/or Formula II) that can, for example, block the function or activity of a gap junction or a hemichannel in whole or in part (e.g. by modulating release of ATP from connexin hemichannels).

In some embodiments, the modulator used in methods of the invention is a gap junction closing or blocking compound or hemichannel closing or blocking compound (e.g. tonabersat). In some embodiments, the modulator can be a small molecule, which may also be referred to herein as an anti-connexin or a connexin or connexin gap junction or connexin hemichannel modulator. In some embodiments, methods of the invention feature the use of compounds of Formula I, for example tonabersat and/or carabersat, to directly and immediately block Cx43 hemichannels and to cause a concentration and time-dependent reduction in GJ coupling and/or hemichannel inhibition (e.g., blocking hemichannel opening and/or modulating or blocking ATP release from connexin hemichannels). Carabersat is N-[(3R, 4S)-6-acetyl-3-hydroxy-2,2-dimethyl-3,4-dihydrochromen-4-yl]-4-fluorobenzamide) and is also referred to as trans-(+)-6-acetyl-4-(S)-(4-fluorobenzoylamino)-3,4-dihydro-2, 2-dimethyl-2H-1-benzo[b]pyran-3R-ol,hemihydrate. Tonabersat is also known by the IUPAC name N-[(3S,4S)-6-acetyl-3-hydroxy-2,2-dimethyl-3,4-dihydrochromen-4-yl]-3-chloro-4-fluorobenzamide or (3S-cis)-N-(6-acetyl-3,4-dihydro-3-hydroxy-2,2-(dimethyl-d6)-2H-1-benzopyran-4-yl)-3-chloro-4-fluorobenzamide).

In some embodiments, the anti-connexin or connexin or connexin gap junction or connexin hemichannel modulator is a compound according to Formula I:

(I)

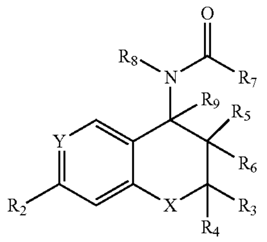

wherein Y is C—$R_1$;

$R_1$ is acetyl;

$R_2$ is hydrogen, $C_3$_cycloalkyl, $C_{1-6}$ alkyl optionally interrupted by oxygen or substituted by hydroxy, $C_{1-6}$ alkoxy or substituted aminocarbonyl, $C_{1-6}$ alkylcarbonyl, $C_{1-6}$ alkoxycarbonyl, $C_{1-6}$ alkylcarbonyloxy, $C_{1-6}$ alkoxy, nitro, cyano, halo, trifluoromethyl, or $CF_3$—S—; or a group $CF_3$-A-, where A is —$CF_2$—, —CO—, —$CH_2$—, CH(OH), $SO_2$, SO, $CH_2$—O, or CONH; or a group $CF_2$H-A'- where A' is oxygen, sulphur, SO, $SO_2$, $CF_2$ or CFH; trifluoromethoxy, $C_{1-6}$ alkylsulphinyl, perfluoro $C_{2-6}$ alkylsulphonyl, $C_{1-6}$ alkylsulphonyl, $C_{1-6}$ alkoxysulphinyl, $C_{1-6}$ alkoxysulphonyl, aryl, heteroaryl, arylcarbonyl, heteroarylcarbonyl, phosphono, arylcarbonyloxy, heteroarylcarbonyloxy, arylsulphinyl, heteroarylsulphinyl, arylsulphonyl, or heteroarylsulphonyl in which any aromatic moiety is optionally substituted, $C_{1-6}$ alkylcarbonylamino, $C_{1-6}$ alkoxycarbonylamino, $C_{1-6}$ alkyl-thiocarbonyl, $C_{1-6}$ alkoxy-thiocarbonyl, $C_{1-6}$ alkyl-thiocarbonyloxy, 1-mercapto $C_{2-7}$ alkyl, formyl, or aminosulphinyl, aminosulphonyl or aminocarbonyl, in which any amino moiety is optionally substituted by one or two $C_{1-6}$ alkyl groups, or $C_{1-6}$ alkylsulphinylamino, $C_{1-6}$ alkylsulphonylamino, $C_{1-6}$ alkoxysulphinylamino or $C_{1-6}$ alkoxysulphonylamino, or ethylenyl terminally substituted by $C_{1-6}$ alkylcarbonyl, nitro or cyano, or —C($C_{1-6}$ alkyl)NOH or —C($C_{1-6}$ alkyl)$NNH_2$; or amino optionally substituted by one or two $C_{1-6}$alkyl or by $C_{2-7}$ alkanoyl;

one of $R_3$ and $R_4$ is hydrogen or $C_{1-4}$ alkyl and the other is $C_{1-4}$ alkyl, $CF_3$, or $CH_2X^a$, where $X^a$ is fluoro, chloro, bromo, iodo, $C_{1-4}$ alkoxy, hydroxy, $C_{1-4}$ alkylcarbonyloxy, —S—$C_{1-4}$ alkyl, nitro, amino optionally substituted by one or two $C_{1-4}$ alkyl groups, cyano or $C_{1-4}$ alkoxycarbonyl; or $R_3$ and $R_4$ together are $C_{2-5}$ polymethylene optionally substituted by $C_{1-4}$ alkyl;

$R_5$ is $C_{1-6}$ alkylcarbonyloxy, benzoyloxy, $ONO_2$, benzyloxy, phenyloxy or $C_{1-6}$ alkoxy and $R_6$ and $R_9$ are hydrogen or $R_5$ is hydroxy and $R_6$ is hydrogen or $C_{1-2}$ alkyl and $R_9$ is hydrogen;

$R_7$ is heteroaryl or phenyl, both of which are optionally substituted one or more times independently with a group or atom selected from chloro, fluoro, bromo, iodo, nitro, amino optionally substituted once or twice by $C_{1-4}$ alkyl, cyano, azido, $C_{1-4}$ alkoxy, trifluoromethoxy and trifluoromethyl;

$R_8$ is hydrogen, $C_{1-6}$ alkyl, $OR_{11}$ or $NHCOR_{10}$ wherein $R_{11}$ is hydrogen, $C_{1-6}$ alkyl, formyl, $C_{1-6}$ alkanoyl, aroyl or aryl-$C_{1-6}$ alkyl and $R_{10}$ is hydrogen, $C_{1-6}$ alkyl, $C_{1-6}$ alkoxy, mono or di $C_{1-6}$ alkyl amino, amino, amino-$C_{1-6}$ alkyl, hydroxy-$C_{1-6}$ alkyl, halo-$C_{1-6}$ alkyl, $C_{1-6}$ acyloxy-$C_{1-6}$ alkyl, $C_{1-6}$ alkoxycarbonyl-$C_{1-6}$ alkyl, aryl or heteroaryl; the $R_8$—N—CO—$R_7$ group being cis to the $R_5$ group;

and X is oxygen or $NR_{12}$ where $R_{12}$ is hydrogen or $C_{1-6}$alkyl.

For any of the Markush groups set forth above, in some embodiments, each group can include or exclude any of the species listed for that group.

In some embodiments, the small molecule connexin modulator can be Tonabersat, carabersat, or SB-204269. SB-204269 is also known as (trans-(+)-6-acetyl-4S-(4-fluorobenzoylamino)-3,4-dihydro-2,2-dimethyl-2H-benzo[b] pyran-3R-ol). Carabersat is also known as N-[(3R,4S)-6-Acetyl-3-hydroxy-2,2-dimethyl-3,4-dihydro-2H-chromen-4-yl]-4-fluorobenzamide. Tonabersat is also known as N-(6-Acetyl-3-hydroxy-2,2-dimethyl-3,4-dihydro-2H-chromen-4-yl)-3-chloro-4-fluorobenzamide.

For any of the Markush groups set forth above, that group can include or exclude any of the species listed for that group.

In some embodiments, the modulator may be a pro-drug of any the compounds for use in this invention. In one aspect the connexin modulator pro-drug of this invention may be a compound of Formula II:

(II)

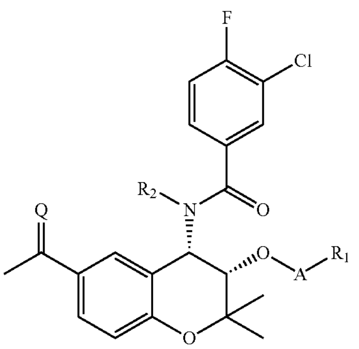

wherein

Q is O or an oxime, $R_2$ is H,

A is a direct bond, —C(O)O*—, —$C(R_3)(R_4)O$*—, —C(O)O—$C(R_3)(R_4)O$*—, or —$C(R_3)(R_4)OC(O)$O*— wherein the atom marked * is directly connected to $R_1$, $R_3$ and $R_4$ are selected independently from H, fluoro, $C_{1-4}$ alkyl, and $C_{1-4}$ fluoroalkyl, or $R_3$ and $R_4$ together with the atom to which they are attached form a cyclopropyl group, $R_1$ is selected from groups [1], [2], [2A], [3], [4], [5] and [6] wherein the atom marked ** is directly connected to A:

[1]

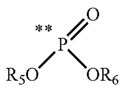

[2]

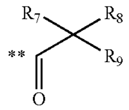

[2a]

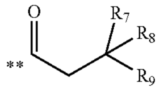

[3]

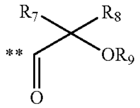

[4]

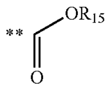

[5]

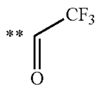

[6]

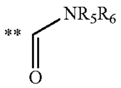

wherein $R_5$ and $R_6$ are each independently selected from H, $C_{1-4}$ alkyl, $C_{1-4}$ fluoroalkyl, and benzyl;

$R_7$ is independently selected from H, $C_{1-4}$ alkyl, and $C_{1-4}$ fluoroalkyl;

$R_8$ is selected from:

(i) H, $C_{1-4}$ alkyl, or $C_{1-4}$ fluoroalkyl, (ii) the side chain of a natural or unnatural alpha-amino acid, or a peptide as described herein, and (iii) biotin or chemically linked to biotin;

$R_9$ is selected from H, —$N(R_{11})(R_{12})$, —$N^+(R_{11})(R_{12})(R_{13})X^-$, and —$N(R_{11})C(O)R_{14}$;

wherein $R_1$, $R_{12}$, and $R_{13}$ are independently selected from H, $C_{1-4}$ alkyl, and $C_{1-4}$ fluoroalkyl, $R_{14}$ is H, $C_{1-4}$ alkyl, or $C_{1-4}$ fluoroalkyl, $R_{15}$ is selected from $C_{1-4}$ alkyl and $C_{1-4}$ fluoroalkyl, and $X^-$ is a pharmaceutically acceptable anion.

In some embodiments, $R_2$ is B—$R_{21}$ wherein,

B is a direct bond, —C(O)O*—, —$C(R_{23})(R_{24})O$*, C(O)O$C(R_{23})(R_{24})$*, or —$C(R_{23})(R_{24})OC(O)O$* wherein the atom marked * is directly connected to $R_{21}$, $R_{23}$ and $R_{24}$ are selected independently from H, fluoro, $C_{1-4}$ alkyl, and $C_{1-4}$ fluoroalkyl, $R_{21}$ is selected from groups [21], [22], [22A], [23], [24], [25] and [26] wherein the atom marked ** is directly connected to B:

[21]

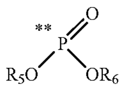

[22]

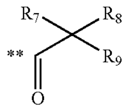

[22a]

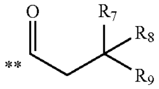

[23]

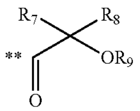

[24]

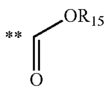

[25]

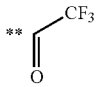

[26]

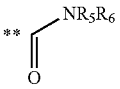

wherein $R_5$, $R_6$, $R_7$, $R_8$, $R_9$, and $R_{15}$ are as defined herein.

For any of the Formula II Markush groups set forth above, that group can include or exclude any of the species listed for that group.

In some embodiments, the peptide as described herein can be a connexin modulator, calmodulin modulator, or pannexin modulator.

In some embodiments,

Q is an oxime of formula =$NOR_{43}$, wherein $R_{43}$ is (i) selected from H, $C_{1-4}$ fluoroalkyl or optionally substituted $C_{1-4}$ alkyl, and (ii) -$A_{300}$-$R_{300}$ wherein $A_{300}$ is a direct bond, —C(O)O*—, —$C(R_3)(R_4)O$*—, —C(O)O—$C(R_3)(R_4)O$*—, or —$C(R_3)(R_4)OC(O)$O*— wherein the atom marked * is directly connected to R300, $R_3$ and $R_4$ are selected independently from H, fluoro, $C_{1-4}$ alkyl, and $C_{1-4}$ fluoroalkyl, or $R_3$ and $R_4$ together with the atom to which they are attached form a cyclopropyl group, $R_{300}$ is selected from groups [1], [2], [2A], [3], [4], [5] and [6] wherein the atom marked ** is directly connected to $A_{300}$:

[1]

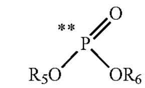

[2]

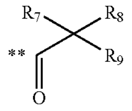

[2a]

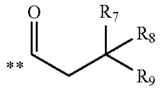

[3]

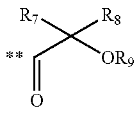

[4]

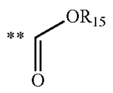

[5]

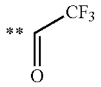

[6]

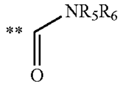

wherein $R_5$ and $R_6$ are each independently selected from H, $C_{1-4}$ alkyl, $C_{1-4}$ fluoroalkyl, and benzyl;

$R_7$ is independently selected from H, $C_{1-4}$ alkyl, and $C_{1-4}$ fluoroalkyl;

$R_8$ is selected from:

(iii) H, $C_{1-4}$ alkyl, or $C_{1-4}$ fluoroalkyl, (iv) the side chain of a natural alpha-amino acid, and (v) biotin or chemically linked to biotin;

$R_9$ is selected from H, —$N(R_{11})(R_{12})$, —$N^+(R_{11})(R_{12})(R_{13})X^-$, and —$N(R_{11})C(O)R_{14}$;

wherein $R_{11}$, $R_{12}$, and $R_{13}$ are independently selected from H, $C_{1-4}$ alkyl, and $C_{1-4}$ fluoroalkyl, $R_{14}$ is H, $C_{1-4}$ alkyl, or $C_{1-4}$ fluoroalkyl, $R_{15}$ is selected from $C_{1-4}$ alkyl and $C_{1-4}$ fluoroalkyl, and $X^-$ is a pharmaceutically acceptable anion.

In one embodiment of Formula II $R_{43}$, is $C_{1-4}$ alkyl optionally substituted with a phosphate group ($P(O)OR_{61}R_{62}$). In an example of such an embodiment $OR_{43}$ is —$OCH_2P(O)OR_{61}OR_{62}$, wherein $R_{61}$ and $R_{62}$ are independently H or $C_{1-4}$ alkyl.

In another embodiment of Formula II $R_{43}$ is an amino acid derivative having the structure $C(O)CH(R_{100})NH_2$ wherein the group $R_{100}$ is the side chain of a natural or unnatural amino acid or a peptide as described herein.

In some embodiments, the natural amino acid is selected from one of the 22 canonical amino acids. In some embodiments, the unnatural amino acid is selected from any amino acid which is not one of the 22 canonical amino acids. In some embodiments, the unnatural amino acid is selected from: (cis)-3-Aminobicyclo[2.2.1]heptane-2-carboxylic acid hydrochloride, exo-cis-3-Aminobicyclo[2.2.1]hept-5-ene-2-carboxylic acid hydrochloride, cis-2-Amino-2-methylcyclohexanecarboxylic acid hydrochloride, (R)-2-(Boc-amino)octanedioic acid, Boc-4-(Fmoc-amino)-L-phenylalanine, Boc-(2-indanyl)-Gly-OH, (R)-4-Boc-3-morpholineacetic acid, (S)-4-Boc-3-morpholineacetic acid, Boc-pentafluoro-D-phenylalanine, Boc-pentafluoro-L-phenylalanine, Boc-Phe(2-Br)—OH, Boc-Phe(4-Br)—OH, Boc-D-Phe(4-Br)—OH, Boc-D-Phe(3-Cl)—OH, Boc-Phe (4-NH2)-OH, Boc-Phe(3,5-F2)-OH, 2-(4-Boc-piperazino)-2-(2-fluorophenyl)acetic acid, 2-(4-Boc-piperazino)-2-(4-fluorophenyl)acetic acid, 2-(4-Boc-piperazino)-2-phenylacetic acid, 2-(4-Boc-piperazino)-2-(3-pyridyl)acetic acid, penicillamine, thialysine. quisqualic acid, canavanine. azetidine-2-carboxylic acid, Carboxyglutamic acid, Hydroxyproline, Hypusine, and Pyroglutamic acid.

In one embodiment of Formula II $OR_{43}$ is —$OC(O)CH(CH(CH_3)_2)NH_2$.

For any of the Formula II Markush groups set forth above, in some embodiments, each group can include or exclude any of the species listed for that group.

In some embodiments "promoiety" refers to a species acting as a protecting group which masks a functional group within an active agent, thereby converting the active agent into a pro-drug. The active agent may be any of the modulators or ocular therapeutics disclosed herein. Typically, the promoiety will be attached to the drug via bond(s) that are cleaved by enzymatic or non-enzymatic means in vivo, thereby converting the pro-drug into its active form. In some embodiments the promoiety may also be an active agent. In some embodiments the promoiety may be bound to a connexin modulator, a connexin gap junction modulator, or a connexin hemichannel modulator. In some embodiments the promoiety may be bound to any of the polynucleotides, peptides or peptidomimetics, small molecule antagonists and/or other treatments disclosed herein. In some embodiments the promoeity may be bound to a compound of Formula I. In some embodiments the pro-drug may be a compound of Formula II.

In some embodiments the promoiety may be any peptidomimetic or peptide antagonist of this disclosure. In some embodiments, the promoeity is a single amino acid which is optionally protected on its functional groups. In some embodiments, the promoeity is a targeting species. In some embodiments, the promoeity is a substrate for an influx or efflux transporters on the cell membrane, for example those described in Gaudana, R. et al. *The AAPS Journal,* 12:3, 348-360 (2012). The promoeity can be, for example, chemically-linked biotin. The promoeity can be, for example, chemically-linked D-serine.

In some embodiments, compounds of Formula I or Formula II, e.g., tonabersat, carabersat or analogues thereof, are nonionic, are in the form of a free base, a free acid, or a pharmaceutically acceptable salt. By way of example, a pharmaceutically acceptable salt includes a hydrochloride salt and salts derived from acid including, but not limited to, hydrobromic acid, hydrochloric acid, phosphoric acid, acetic acid, fumaric acid, maleic acid, salicylic acid, citric acid, oxalic acid, lactic acid, malic acid, succinic acid, methanesulphonic acid and p-toluene sulphonic acid, a salt of itself. In one embodiment, the salt is a hydrochloride salt. In one embodiment, the salt is a succinate salt.

In other embodiments, one or more polymorph, one or more isomer, and/or one or more solvate of a compound of Formula I or Formula II, e.g., tonabersat, carabersat or analogues thereof, may be used.

Other Connexin 43 Modulators

In addition to connexin antisense (e.g. lufepirsen), connexin peptidomimetics (e.g., Peptide5, XG19, etc.) and connexin hemichannel antagonists (e.g. tonabersat), connexin binding proteins, including antibodies, antigen-binding antibody fragments, and the like, are also suitable connexin modulators for use in methods of the invention and dosed with a therapeutically effective amount according to the one or more of the dosing schedules described herein. Binding proteins include, for example, monoclonal antibodies, polyclonal antibodies, antibody fragments (including, for example, Fab, $F(ab')_2$ and Fv fragments; single chain antibodies; single chain Fvs; and single chain binding molecules such as those comprising, for example, a binding domain, hinge, CH2 and CH3 domains, recombinant antibodies, and antibody fragments which are capable of binding an antigenic determinant (i.e., that portion of a molecule, generally referred to as an epitope) that makes contact with a particular antibody or other binding molecule. These binding proteins, including antibodies, anti-binding antibody fragments, and so on, may be chimeric or humanized or otherwise made to be less immunogenic in the subject to whom they are to be administered, and may be synthesized, produced recombinantly, or produced in expression libraries. Any binding molecule known in the art or later discovered is envisioned, such as those referenced herein and/or described in greater detail in the art. For example, binding proteins include not only antibodies, and the like, but also ligands, receptors, peptidomimetics, or other binding fragments or molecules (for example, produced by phage display) that bind to a target (e.g., a connexin protein or connexin hemichannel epitope). Methods of synthesizing antibodies and binding fragments as well as peptides and polypeptides, including peptidomimetics and peptide analogs can also be performed using suitable methods. See e.g. Lihu Yang et al., Proc. Natl. Acad. Sci. U.S.A., 1; 95(18): 10836-10841 (Sep. 1, 1998); Harlow and Lane (1988) "Antibodies: A Laboratory Manuel" Cold Spring Harbor Publications, New York; Harlow and Lane (1999) "Using Antibodies" A Laboratory Manual, Cold Spring Harbor Publications, New York.

Connexin modulators also include antibodies and binding fragments (e.g. scFvs, human $V_H$ or $V_L$ domains, humanized camelid $V_{HH}$ domains, $Ig_{NAR}$ single domains, etc.) thereof that bind connexin protein, and connexin peptides and polypeptides, including peptidomimetics and peptide analogs of connexin that modulate hemichannel or gap junction activity or function, and other gap junction blocking agents and gap junction protein phosphorylating agents. Connexin protein peptides and polypeptides may, for example, bind to connexin protein to inhibit its function, or may inhibit connexin function by mimicking regions of connexin protein to inhibit or disrupt its binding to other gap junction proteins. Strategies known in the art may be used to improve the naturally short half-life of antibody fragments, including PEGylation, the use of repeating peptide sequences, polysialylation, albumin or IgG binding or fusions, and other approaches.

Binding molecules will generally have a desired specificity, including but not limited to binding specificity, and desired affinity. Affinity, for example, may be a $K_a$ of greater than or equal to about $10^4\ M^{-1}$, greater than or equal to about $10^6\ M^{-1}$, greater than or equal to about $10^7\ M^{-1}$, greater than or equal to about $10^8\ M^{-1}$. Affinities of even greater than about $10^8\ M^{-1}$ are suitable, such as affinities equal to or greater than about $10^9\ M^{-1}$, about $10^{10}\ M^{-1}$, about $10^{11}\ M^{-1}$, and about $10^{12}\ M^{-1}$. Affinities of binding proteins useful to treat subjects according to the present invention can be readily determined using conventional techniques, for example those described by Scatchard, et al., 1949 *Ann. N.Y. Acad. Sci.* 51: 660.

Other compounds used for modulating, blocking or closing gap junctions (e.g. phosphorylating connexin 43 tyrosine and/or serine residue) have been reported in U.S. Pat. Nos. 7,153,822 and 7,250,397.

Connexin Modulator Combinations and Combined Administration

Methods, uses and compositions of the invention may comprise the use of a combination of two or more connexin modulators, for example, connexin antisense modulators (e.g. lufepirsen), connexin peptidomimetics (e.g. Peptide5, Gap19, XG19), and small molecule (e.g. compounds of Formula I, such as tonabersat and/or prodrugs thereof, including compounds of Formula II). Two or more connexin modulators may be administered alone or together. In some embodiments, two or more separate pharmaceutical compositions that each contain one or more connexin modulators are provided for administration. Pharmaceutical compositions are also provided for co-administration in the form of a combined preparation, for example, as an admixture of two or more modulators, e.g. gap junction, connexin and/or hemichannel modulators which may be modified or unmodified, for example one or more gap junction, connexin and/or hemichannel modulator polynucleotides and one or more gap junction, connexin and/or hemichannel modulator peptides or peptidomimetics, and optionally one or more small molecule hemichannel blockers or inhibitors that can reduce hemichannel opening and function.

Treatment of a subject for the ocular conditions described herein with one or more pharmaceutical compositions of the invention, e.g., an anti-connexin antisense and a gap junction modulator such as a connexin hemichannel blocking agent, e.g., a peptide or peptidomimetic, or a first anti-connexin agent and a second anti-connexin agent, may comprise their simultaneous, separate, sequential or sustained administration.

The term "a combined preparation" includes a "kit of parts" or "article of manufacture" in the sense that the combination partners as defined above can be dosed independently or by use of different fixed combinations with distinguished amounts of the combination partners (a) and (b), i.e. simultaneously, separately or sequentially, whether in pharmaceutical form (e.g. topical or oral) or dressing/matrix form (e.g. connexin modulator-impregnated bandage contact lens) or both in accordance with the methods, doses and Day-dosing schedules of the invention. The parts of the kit can then, for example, be administered simultaneously or chronologically staggered, that is at different time points and with equal or different time intervals for any part of the kit of parts.

In one embodiment a combined preparation is administered, wherein two or more separate connexin modulator compositions are administered to a subject in accordance with the methods, doses and dosing schedules of the invention, wherein the first composition comprises a therapeutically effective amount of modulator, such as a gap junction, connexin modulator, e.g., an anti-connexin 43 polynucleotide, peptide, or peptidomimetic, or a hemichannel closing compound, and the second composition comprises a therapeutically effective amount of a second modulator, such as a gap junction, hemichannel and/or connexin modulator, e.g., an anti-connexin 43 polynucleotide, peptide, or peptidomimetic, a hemichannel closing compound and/or an ocular treatment agent. In another embodiment a third composition is administered comprising one or more anti-connexin polynucleotides, peptides, or peptidomimetics, a hemichannel closing compound and/or an ocular treatment agent.

The modulators, including connexin, connexin hemichannel and connexin gap junction modulators, can be dosed, administered, or formulated in methods of the invention as described herein.

Doses and Dose Regimens

Examples of effective doses that may be used for the treatment of non-healing ocular surface defects or disorders (e.g. ocular PEDs), non-healing corneal defects or disorders (e.g. PCEDs), and other ocular diseases, disorders and conditions (e.g. uveitis, blepharitis, Sjögren's syndrome-associated keratoconjunctivitis sicca, Fuchs' dystrophy, and all forms of dry eye disease (e.g., evaporative dry eye, aqueous-deficient dry eye, and decreased wettability dry eye) and like or similar or related diseases, disorders and conditions, are described and claimed herein. In some embodiments, the therapeutically effective amount of the modulator, e.g. connexin modulator, for example a connexin 43 modulator, connexin 43 gap junction modulator and/or connexin 43 hemichannel modulator, which is effective in methods of the invention, comprises a composition having about, or at least about, 0.1 mg, 0.2 mg or 0.3 mg of a connexin modulator (e.g. lufepirsen), including doses of about (or at least about) 0.18 mg and about (or at least about) 0.018 mg of a connexin modulator (e.g. lufepirsen), or any amount within or between any two of these recited dosages. Other effective doses that are effective in methods of the invention for the treatment of ocular surface defects or disorders (e.g. ocular PEDs and PCEDs) include about, or at least about, 1.0 mg of a connexin modulator, for example, a connexin 43 modulator, a connexin 43 gap junction modulator and/or a connexin 43 hemichannel modulator (e.g. lufepirsen).

In some embodiments, the therapeutically effective amount of the modulator, e.g. connexin modulator, for example a connexin 43 modulator, connexin 43 gap junction modulator and/or connexin 43 hemichannel modulator, which is effective in methods of the invention, comprises a composition that is about, or at least about, 2 micromolar (2 μM), 5 micromolar (5 μM), 10 micromolar (10 μM), 15 micromolar (15 μM), or 20 micromolar (20 μM), including doses of about (or at least about) 1.9 micromolar (1.9 μM) or 1.9405 micromolar (1.9405 μM), and about (or at least about) 19 to 19.4 micromolar or 19.405 micromolar (19 to 19.4 μM or 19.405 μM), of a connexin modulator (e.g. lufepirsen), or any amount within or between any two of these recited dosages. Other effective doses that are effective in methods of the invention for the treatment of ocular surface defects or disorders (e.g. ocular PEDs and PCEDs) include about, or at least about, a composition comprising 30 micromolar (30 μM) or 40 micromolar (40 μM) of a connexin modulator, for example, a connexin 43 modulator, a connexin 43 gap junction modulator and/or a connexin 43 hemichannel modulator (e.g. lufepirsen).

In some methods of the invention, the connexin modulator administered to the non-healing surface defect or disorder in a subject is 0.06% lufepirsen. In some embodiments, the connexin modulator administered to a subject with a non-healing surface defect or disorder is 0.006% lufepirsen. In some embodiments, the connexin modulator administered is at least about 0.06% lufepirsen. In some embodiments, the connexin modulator administered to a subject with a non-healing surface defect or disorder is at least about 0.006% lufepirsen. In some embodiments, administration is to a PED or PCED. In some embodiments, a composition comprising or consisting essentially of a pharmaceutically acceptable carrier and about 0.06% lufepirsen, about 0.006% lufepirsen, at least about 0.06% lufepirsen or least about 0.006% lufepirsen is administered to heal the non-healing surface defect or disorder in a subject. Lufepirsen doses described herein and below may be prepared as described in Example 1.

In some embodiments, the non-healing surface defect or disorder is treated with composition comprising or consisting essentially of 0.6 mg/mL lufepirsen. In some embodiments of the present invention, the non-healing surface defect or disorder is treated with composition comprising or consisting essentially of 0.06 mg/mL lufepirsen. In some embodiments, the composition comprises or consists essentially of at least about 0.6 mg/mL lufepirsen. In some embodiments, the composition comprises or consists essentially of at least about 0.06 mg/mL lufepirsen. In some embodiments, administration is to a PED or PCED.

In some embodiments, the non-healing surface defect or disorder in a subject is treated with a composition comprising or consisting essentially of about 0.018 to about 0.18 mg of lufepirsen in the regimens described herein. In some embodiments, each dose of lufepirsen applied to the non-healing surface defect or disorder in or on the subject comprises or consists essentially of at least about 0.18 mg of lufepirsen or at least about 0.18 mg of lufepirsen in the regimens described herein. In some embodiments of the present invention, the non-healing surface defect or disorder is treated with composition comprising or consisting essentially of from about or at least about 0.01 mg, about or at least about 0.018 mg, about or at least about 0.18 mg to about or at least about 0.2 mg of lufepirsen, or from about or at least about 0.18 mg or 0.20 mg or 0.50 mg to about or at least about 1 mg of lufepirsen of lufepirsen in the regimens described herein. In some embodiments, each dose of lufepirsen applied to the non-healing surface defect or disorder comprises or consists essentially of at least about 0.15 mg, at least about 0.2 mg, at least about 0.25 mg, at least about 0.3 mg, at least about 0.35 mg, at least about 0.4 mg, at least about 0.45 mg or at least about 0.5 mg of lufepirsen in the regimens described herein. In some embodiments, administration is to a PED or PCED.

These doses are also useful for the treatment of uveitis, blepharitis, Sjögren's syndrome-associated keratoconjunctivitis sicca, Fuchs' dystrophy, and all forms of dry eye disease (e.g., evaporative dry eye, aqueous-deficient dry eye, and decreased wettability dry eye) and like or similar or related diseases, disorders and conditions.

In some embodiments, the above noted doses are administered topically to the eye of a subject with a non-healing or persistent ocular or corneal surface defect or disorder. In some embodiments, the doses referenced herein are administered intraocularly, including by injection (e.g., intravitreal, intracameral, etc.). Connexin modulators administered by routes other than topical (e.g. oral or parenteral) will be adjusted as needed to approximate these topical doses.

In some embodiments, a dose of lufepirsen (or other connexin antisense or connexin modulator) is/are administered to the non-healing surface defect or disorder in a single dose, or in two or more divided doses, e.g., for twice daily administration in up to 6 doses administered on Days 1, 2 and 14, for twice daily administration to the non-healing surface defect or disorder in up to 8 doses administered on Days 1, 2, 14 and 28, etc. In other embodiments, about or at least about 0.1 to 0.5 mg or at least about 1 mg of lufepirsen is administered in single or divided doses, e.g., for twice daily administration, in up to 14 doses administered on Days 1, 2 and 14, and one or more of Day 7, Day 21, Day 28 and/or Day 35, for example. In some embodiments, administration is to a PED or PCED in a subject.

In some embodiments, connexin modulator doses, e.g. lufepirsen, are administered on Days 1, 2, 14 and 21.

In some embodiments, connexin modulator doses, e.g. lufepirsen, are administered on Days 1, 2, 7, 14 and 21.

In some embodiments, connexin modulator doses, e.g. lufepirsen, are administered on Days 1, 2, 7, 14, 21 and 28.

In some embodiments, 3 doses of a connexin modulator (e.g. lufepirsen) are administered over 14 days to treat a non-healing or persistent ocular or corneal surface defect in a subject, including, for example, on Days 1 and 2. In some embodiments, 4 doses of a connexin modulator (e.g. lufepirsen) are administered over about 28 days. In some embodiments, 5 doses of a connexin modulator (e.g. lufepirsen) are administered over about 28 to about 35 days. In some embodiments, 6-7 doses of a connexin modulator (e.g. lufepirsen) are administered over about 35 days. For example, in one embodiment, a connexin modulator (e.g. lufepirsen) is administered 4 times over Days 1 and 2, on about Day 14 and 28. In another embodiment, a connexin modulator (e.g. lufepirsen) is administered 5 times over Days 1 and 2, on about Day 14, on about Day 28 and on about Day 35. In another embodiment, a connexin modulator (e.g. lufepirsen) is administered 5 times over Days 1 and 2, on about Day 7, on about Day 14 and on about Day 28. In another embodiment, a connexin modulator (e.g. lufepirsen) is administered 6 times over Days 1 and 2, on about Day 7, on about Day 14, on about Day 21 and on about Day 28. In another embodiment, a connexin modulator (e.g. lufepirsen) is administered 7 times over Days 1 and 2, on about Day 7, on about Day 14, on about Day 21 and on about Day 28. Reference to "administration" here refers, of course, to administration of a connexin modulator in a single dose or in divided doses.

Wherever a dose of a connexin modulator is not specified in a dose regimen or method of the invention for the treatment of a non-healing ocular or corneal surface defect or disorder (e.g. a dose of lufepirsen or another connexin expression modulator, a connexin peptidomimetic and/or a hemichannel blocker), dosing with a therapeutically effective amount of a connexin modulator(s) is intended.

In some embodiments, one or more connexin modulators is/are administered using one or more of the dose regimens described herein to a subject having an ocular diseases, disorders and condition selected from the group consisting of uveitis, blepharitis, Sjögren's syndrome-associated keratoconjunctivitis sicca, Fuchs' dystrophy, and all forms of dry eye disease (e.g., evaporative dry eye, aqueous-deficient dry eye, and decreased wettability dry eye).

Wherever a dose of a connexin modulator is specified for Day 7, 14, 21, 28 or 35 in a dose regimen or method of the invention for the treatment of a non-healing ocular or corneal surface defect or disorder (e.g. a dose of lufepirsen or another connexin expression modulator, a connexin peptidomimetic and/or a hemichannel blocker), or other disease, disorder or condition, dosing on about that day with a therapeutically effective amount of a connexin modulator(s) is intended.

Administration of connexin modulators (e.g. lufepirsen, etc.) and pharmaceutical compositions comprising or consisting essentially of a connexin modulator(s) is provided for in certain dose regimens. In one embodiment, a composition comprising one or more gap junction, hemichannel and/or connexin modulator polynucleotides (and/or other connexin modulator(s), e.g., a peptidomimetic or small molecule connexin modulator) is administered on treatment Day 1 and treatment Day 2, followed by administration at Day 14. In another embodiment, the composition is administered on treatment Day 1 and treatment Day 2, followed by administration at Day 14 and Day 28. In another embodiment, the composition is administered on Day 1 and Day 2, followed by administration at Day 14, Day 28 and Day 35. In other embodiments of these dosing regimens, the composition is also optionally administered on Day 7 and/or Day 21.

In some embodiments the disease, disorder or condition to be treated is a non-healing ocular surface defect or disorder is a persistent epithelial defect (PED). In some embodiments the non-healing ocular surface defect or disorder is a persistent corneal epithelial defect (PCED). In some embodiments the non-healing ocular surface defect or disorder is a corneal ulcer. In some embodiments the disease, disorder or condition to be treated is selected from the group consisting of uveitis, blepharitis, Sjögren's syndrome-associated keratoconjunctivitis sicca, Fuchs' dystrophy, and all forms of dry eye disease (e.g., evaporative dry eye, aqueous-deficient dry eye, and decreased wettability dry eye). In methods of the invention, administering a therapeutically effective amount of at least one connexin modulator in pulse-dose format, with administrations on Day 1 and Day 2, followed by Day 14 and optionally on or on about Day 28 (and also optionally administration on or on about Day 35) is effective for healing the non-healing ocular surface defect or disorder, or other disease, disorder or condition. See Example 2, below. Connexin modulator doses may also be administered on Day 7 and/or Day 21. In some embodiments, the connexin modulator is a connexin 43 modulator (e.g. a connexin expression modulator, such as an antisense connexin expression modulator, including a Cx43 antisense). Other embodiments include other connexin 43 gap junction modulators and connexin 43 hemichannel blockers or modulators (e.g. peptidomimetics and small molecules).

In some embodiments, doses of a connexin modulator (e.g. lufepirsen or another modulator) are administered at Days 1, 2 and 14. In some embodiments, connexin modulator doses, e.g. lufepirsen, are administered on Days, 1, 2, 14 and 28. In some embodiments, connexin modulator doses, e.g. lufepirsen, are administered on Days, 1, 2, 14, 28 and 35. In some embodiments, connexin modulator doses, e.g. lufepirsen, are administered on Days, 1, 2, 7, 14, and 21. In some embodiments, connexin modulator doses, e.g. lufepirsen, are administered on Days, 1, 2, 7, 14, 21, and 28. In some embodiments, connexin modulator doses, e.g. lufepirsen, are administered on Days, 1, 2, 7, 14, 21, 28, and 35. In some embodiments, a dose is administered after Day 35. In some embodiments, administration using the doses and dose regimens described is to a PED or PCED. In some embodiments, the connexin modulator comprises a connexin antisense molecule (e.g. lufepirsen). In some embodiments, the connexin modulator comprises a connexin peptidomimetic (e.g., Peptide5, Gap19, XG19, Gap26, Gap27, αCT1, etc.). In some embodiments, the connexin modulator comprises a small molecule connexin hemichannel blocker (e.g., tonabersat). In some embodiments, the connexin modulator is a connexin 43 modulator.

All descriptions with respect to dosing, unless otherwise expressly stated, apply to the modulators of the invention, including connexin modulators, connexin gap junction modulators and connexin hemichannel modulators. All descriptions with respect to dosing, unless otherwise expressly stated, also apply to all indications described or referenced herein for treatment, including ocular surface defects and corneal surface defects. All descriptions with respect to dosing, unless otherwise expressly stated, apply to the treatment of uveitis, blepharitis, Sjögren's syndrome-associated keratoconjunctivitis sicca, Fuchs' dystrophy, and all forms of dry eye disease (e.g., evaporative dry eye, aqueous-deficient dry eye, and decreased wettability dry eye).

Formulations

The pharmaceutical compositions of this invention include various delivery forms and formulations, as desired or appropriate, including formulations for topical administration, as well as forms and formulations for drug administration that are appropriate for systemic administration (e.g., oral and enteral, etc.), parenteral administration (e.g., injection, infusion, implantation, etc.), intraocular administration, and so on.

Such delivery forms and formulations include those for the treatment of a subject as disclosed herein. The pharmaceutical formulations of this invention may further comprise one or more pharmaceutically acceptable excipients. The pharmaceutically acceptable excipients for ocular administration may be ophthalmologically acceptable excipients. In some embodiments, the formulations may provide for sustained delivery of the connexin modulator and/or ocular treatment agent to a selected segment or compartment of the eye. The formulations may, in some embodiments, provide high ocular (including via topical or oral administration, for example) drug bioavailability, be safe and non-toxic, and/or have little systemic side effects or complications at the site of administration. Exemplary polynucleotide formulations for use in the methods of this invention have the ease of localized delivery and ease of administration.

Such delivery forms and formulations include those for the treatment of a subject as disclosed herein. The pharmaceutical formulations of this invention may further comprise one or more pharmaceutically acceptable excipients. The pharmaceutically acceptable excipients for ocular administration may be ophthalmologically acceptable excipients. In some embodiments, the formulations may provide for sustained delivery of the connexin modulator and/or ocular treatment agent to a selected segment or compartment of the eye. The formulations may, in some embodiments, provide high ocular (including via topical or oral administration, for example) drug bioavailability, be safe and non-toxic, and/or have little systemic side effects or complications at the site of administration. Exemplary polynucleotide formulations for use in the methods of this invention have the ease of localized delivery, ease of administration and a “no side effect” profile.

In some embodiments the pharmaceutical formulations of this invention may comprise any of the modulators, e.g. gap junction, hemichannel and/or connexin modulators described herein, for example, a modified or unmodified connexin 43 antisense oligonucleotide or polynucleotide or a modified or unmodified connexin 43 peptide or peptidomimetic. Connexin 43 antisense oligonucleotide that are included in the formulation may be, in some embodiments, an unmodified connexin 43 antisense oligodeoxynucleotide or a modified connexin 43 antisense oligodeoxynucleotide. In some embodiments, the pharmaceutical compositions can include or exclude any of the foregoing.

The modulators, including connexin, connexin hemichannel and connexin gap junction modulators may be present in the formulation in a substantially isolated form. It will be understood that the product may be mixed with carriers or diluents that will not interfere with the intended purpose of the product and still be regarded as substantially isolated. A product of the invention may also be in a substantially purified form, in which case it will generally comprise about 80%, 85%, or 90%, e.g. at least about 88%, at least about 90, 95 or 98%, or at least about 99% of a polynucleotide, for example (or other connexin modulator such as a connexin 43 modulator) or dry mass of the preparation. As described in Example 1, the lufepirsen compositions used in the clinical trial to treat non-healing ocular defects described in Example 2 included 94.2% pure lufepirsen (with an assay of 106%) and had a final drug product purity of 94.9% (with an assay of 97%).

The pharmaceutical formulations for use in the dosing, dose regimens and methods of the invention may comprise one or more pharmaceutically acceptable excipients suitable for delivering the modulators (e.g. lufepirsen), including connexin, connexin hemichannel and connexin gap junction modulators to the eye.

The modulators, including gap junction, hemichannel and/or connexin modulators, of the present invention can also be formulated into microparticle (microspheres, Mps) or nanoparticle (nanospheres, Nps) formulations, or both. In some embodiments of the invention, a nanoparticle or microparticle is used. Such as a particle comprise poly (lactic-co-glycolic acid) (“PLGA”) loaded with the gap junction, connexin, and/or hemichannel modulators, for example, connexin 43 modulators. The modulators can be loaded into the particle volume, onto the particle exterior surface, or both. Particle formulations may be administered, for example, topically to the eye or subconjunctivally. In some embodiments, the particle formulations of any of the gap junction, hemichannel and/or connexin modulators of this disclosure (e.g. connexin 43 modulators) may also comprise liposomes.

A modulator, e.g., a connexin, connexin hemichannel and connexin gap junction modulator, may be administered alone or in combination with one or more additional ingredients and may be formulated into pharmaceutical compositions including one or more pharmaceutically acceptable excipients, diluents and/or carriers. Pharmaceutically acceptable diluents, carriers and/or excipients includes substances useful in preparing a pharmaceutical composition, and are generally safe, non-toxic and neither biologically nor otherwise undesirable. Pharmaceutically acceptable diluents, carriers and/or excipients include those suitable for veterinary use as well as human pharmaceutical use. By way of example, diluents, carriers and/or excipients include solutions, solvents, dispersion media, delay agents, polymeric and lipidic agents, emulsions and the like. By way of further example, suitable liquid carriers, especially for injectable solutions, include water, aqueous saline solution, aqueous dextrose solution, and the like, and vehicles such as liposomes being also especially suitable for administration of agents.

Suitable carriers and diluents include buffered, aqueous solutions, saline, dextrose, glycerol, isotonic saline solutions, for example phosphate-buffered saline, isotonic water, and the like and combinations thereof. In some embodiments, carriers may include propylene glycol, dimethyl isosorbide, and water, and even more particularly, phosphate buffered saline, isotonic water, deionized water, monofunctional alcohols and symmetrical alcohols. In some embodiments pharmaceutically acceptable carrier or diluent may be or contain a thermosetting poloxamer (which may be a liquid or gel, depending on the temperature), a carboxycellulose (e.g. carboxymethylcellulose), a collagen (e.g., a Type I collagen), a collagenous material comprising tropocollagen, a hyaluronan or derived-hyaluronic acid, and/or an oil (e.g., Emu oil). Suitable carriers can be large, slowly metabolized macromolecules such as proteins, polysaccharides, polylactic acids, polyglycolic acids, polymeric amino acids, and amino acid copolymers. The pharmaceutical compositions of this invention do not comprise a connexin modulator in sterile water as the only vehicle. In some embodiments, the formulations will comprise connexin modulators, for example, connexin 43 modulators, for example, 43 antisense oligonucleotide that are included in the formulation may be, in some embodiments, an unmodified or modified connexin 43 antisense oligodeoxynucleotide.

Compositions may take the form of any standard known dosage form including tablets, pills, capsules, semisolids, powders, sustained release formulation, solutions, suspensions, elixirs, aerosols, liquids for injection, gels, creams, transdermal delivery devices (for example, a transdermal patch), inserts such as ocular inserts, or any other appropriate compositions. Persons of ordinary skill in the art to which the invention relates will readily appreciate the most appropriate dosage form having regard to the nature of the condition to be treated and the active agent to be used (e.g., antisense, peptidomimetic, small molecule, etc.) without any undue experimentation.

Preferably the modulator, e.g. connexin modulators of the invention are combined with a pharmaceutically acceptable carrier or diluent to produce a pharmaceutical composition. Connexin modulators may be formulated as compositions for any desired route of administration, including topical, oral, systemic, transdermal, nasal, sublingual, buccal, etc. including formulations for injection (e.g. intracameral injection, subcutaneous injection, intramuscular injection, intravenous injection, etc.).

Pharmaceutically acceptable salts can also be present, e.g., mineral acid salts such as hydrochlorides, hydrobromides, phosphates, sulfates, and the like; and the salts of organic acids such as citrates, acetates, propionates, malonates, benzoates, and the like.

In one aspect the reverse-thermosetting gel may be a liquid at low temperatures, for example at 2-8° C., and which undergoes a reversible liquid to gel transition at temperatures greater than approximately 15° C. Thus, in some embodiments the carrier may be a liquid at temperatures below approximately 15° C., but may form a gel at temperatures above approximately 15° C., such as room temperature or at body temperature. In some instances, the gel is a nonionic polyoxyethylene-polyoxypropylene copolymer gel. In some embodiments the gel is a pluronic gel. The pluronic gel may be, for example, poloxamer 407, also sometimes referred to as Pluronic F-127 (BASF). In some embodiments, the formulations of this invention may comprise from about 15 to about 30% (w/v) gel. In some embodiments, the formulations of this invention may comprise from about 20 to about 25% (w/v) gel. In some embodiments, the formulations of this invention may comprise about 22.6% (w/v) poloxamer 407 gel. In some embodiments, the composition or formation comprises 226.0 mg/mL of a poloxamer (e.g. poloxamer 407). See Example 1.

Other suitable formulations include pluronic gel-based formulations, hydroxymethylcellulose formulations, hydroxyethylcellulose formulations, carboxymethylcellulose (CMC)-based formulations, and hydroxypropylmethylcellulose (HPMC)-based formulations. The composition may be formulated for any desired form of delivery, including topical, instillation, parenteral, intramuscular, subcutaneous, or transdermal administration. Other useful formulations include slow or delayed release preparations.

In addition, if desired substances such as wetting or emulsifying agents, stabilizing or pH buffering agents, or preservatives may also be present. In some embodiments, the pharmaceutical compositions of this invention will comprise suitable ophthalmically acceptable buffers, such as acetate buffers, citrate buffers, phosphate buffers, borate buffers and mixtures thereof. In some embodiments, the buffers useful in the present invention include boric acid, sodium borate, sodium phosphates, including mono, di- and tri-basic phosphates, such as sodium phosphate monobasic monohydrate and sodium phosphate dibasic heptahydrate, and mixtures thereof. In some embodiments, the preservative may be stabilized chlorine dioxide, cationic polymers or quaternary ammonium compounds. In some embodiments the pharmaceutical compositions may also comprise wetting agents, nutrients, viscosity builders, antioxidants, and the like, for example, disodium ethylene diamine tetraacetate, alkali metal hexametaphosphate, citric acid, sodium citrate, sodium metabisulfite, sodium thiosulfate, N-acetylcysteine, butylated hydroxyanisole, butylated hydroxytoluene, polyvinyl alcohol, polyoxamers, polyvinyl pyrrollidone, hydroxypropyl methyl cellulose, hydroxyethylmethyl cellulose, and mixtures thereof and mixtures thereof. In some embodiments, the pharmaceutical formulations of this invention will not include a preservative. In some embodiments, the connexin modulator composition or formulation comprises sodium phosphate dibasic heptahydrate or potassium phosphate, monobasic or both. See Example 1.

Where the modulator, e.g. gap junction, connexin, and/or hemichannel modulator is a nucleic acid, such as a polynucleotide, uptake of nucleic acids by mammalian cells may be enhanced by the of known transfection techniques including the use of transfection agents. Such techniques may be used with certain anti-connexin agents, including polynucleotides. The formulation that is administered may contain such transfection agents. Examples of useful transfection agents include cationic agents (for example calcium phosphate and DEAE-dextran) and lipofectants (for example Lipofectam™ and Transfectam™), and surfactants.

The connexin, gap junction, and/or hemichannel modulators, for example, connexin 43 modulators may also be formulated to provide controlled release to the eye. In some embodiments of this invention, the formulations may be immediate, or extended or sustained release dosage forms, e.g., for release within several hours, within one day or, for example, within 1-2 days.

The compositions may be formulated in accordance with standard techniques known in the art, including those as may be found in such standard references as Gennaro A R: Remington: The Science and Practice of Pharmacy, $20^{th}$ ed., Lippincott, Williams & Wilkins, 2000, for example.

Any container suitable for storing and/or administering a pharmaceutical composition may be used in a combination product of the invention. Suitable containers will be appreciated by persons skilled in the art. By way of example, such containers include vials and syringes. The containers may be suitably sterilized and hermetically sealed.

In some embodiments, administering a connexin modulator (for example, a connexin 43 modulator or connexin 45 modulator, preferably a connexin 43 modulator, e.g. lufepirsen), to the eye of a subject provides a therapeutically effective amount of the connexin modulator to the eye or specific compartment or portion of the eye by means of administration as desired and appropriate depending on the nature of the connexin modulator, including but not limited to topical administration.

Therapeutically effective amounts include but are not limited to the doses described herein. Described doses and other therapeutically effective amounts are administered in one or more of the therapeutically effective dose regimens described herein.

Administration

Administration of a modulator, e.g. a connexin modulator, a gap junction channel modulator and/or a hemichannel modulator compounds and compositions may be administered by one of the following routes: oral, topical, systemic (including intravenous, intra-arterial, intraperitoneal, transdermal, intranasal, or by suppository), parenteral (including intramuscular, subcutaneous, or intravenous or intra-arterial injection), and the like. In some embodiments, the connexin modulator, gap junction channel modulator and/or hemichannel modulator compounds and compositions are administered topically. In some embodiments, the connexin modulator, gap junction channel modulator and/or hemichannel modulator compounds and compositions are administered systemically. In some embodiments, the connexin modulator, gap junction channel modulator and/or hemichannel modulator compounds and compositions are administered orally. In some embodiments, the connexin modulator, gap junction channel modulator and/or hemichannel modulator compounds and compositions are administered by intracameral injection formulation and route of administration, as this may be a preferred route of administration (or if topical is less effective) for treatment, e.g. of uveitis and Fuchs' dystrophy.

In some embodiments of the methods of this invention, the connexin modulator, connexin gap junction modulator and/or connexin hemichannel modulator, may be administered locally by topical administration to the eye of the subject. In some embodiments, the connexin modulator is administered by topical, corneal and/or subconjunctival administration, or by local injection. Topical formulations of the gap junction, hemichannel and/or connexin modulators can comprise ointments, gels, which may be, for example, thermosetting gels, drops, sprays, liquids and powders, or a sustained or non-sustained release dosage form. Bioavailable systemically administered connexin modulators, connexin gap junction modulators and/or connexin hemichannel modulators may be administered, with or without concomitant local administration to the eye, for example, by oral administration, intravenous administration, enterally through the gastrointestinal system (e.g. oral, rectal, sublingual, buccal), parenterally (e.g. intravenously, intramuscularly, subcutaneously, transdermally), intranasally, by nasal inhalation, and by mouth inhalation. In some embodiments, non-topical administration, including intraperitoneal administration or orally or by parenteral administration, may be employed provided that a therapeutically effective dose contacts the eye or portion thereof (e.g. cornea) to be healed. In some embodiments, in addition to administration of a connexin modulator by topical administration, orally available connexin modulators (e.g., tonabersat) administration may also be administered by intraperitoneal, oral or parenteral administration, provided that a therapeutically effective dose contacts the eye.

In some embodiments, administering a connexin modulator, for example, a connexin expression modulator, a peptidomimetic or small molecule gap junction modulator and/or a hemichannel modulator (for example, a connexin 43 modulator or a modulator or any other connexin in the eye, the cornea, the corneal epithelium or in blood vessels), to the eye of a subject provides a therapeutically effective amount of the connexin modulator(s) to the eye. In some embodiments, a bandage contact lens is applied to the eye following administration of s connexin modulator(s), whether topically or by another route of administration. In some embodiments, the connexin modulator is placed in a bandage contact lens which is the applied to the eye of the subject with a non-healing ocular defect or disorder (e.g. a PED or PCED) or other disease, disorder or condition described or referenced herein. In some embodiments, the connexin modulator is administered under an amniotic membrane. In some embodiments, an amniotic membrane is applied to the eye following administration of the connexin modulator. The modulator may be a connexin 43 modulator. In some embodiments, the connexin modulator is embedded in a matrix comprising a bandage contact lens or other implantable device. In some embodiments, the connexin modulator matrix (e.g. bandage contact lens connexin modulator matrix) provides for slow or sustained release of the connexin modulator contact lens. As used herein, "matrix" includes for example, matrices such as polymeric matrices, biodegradable or non-biodegradable matrices, and other carriers useful for making implants or applied structures for delivering the non-healing ocular and/or or corneal surface disorder or neuropathic treatment connexin modulators. Compositions and methods for the preparation of drug-containing contact lenses have been developed and are known in the art. See e.g. Wang Z, et al., Novel Contact Lenses Embedded with Drug-Loaded Zwitterionic Nanogels for Extended Ophthalmic Drug Delivery. Nanomaterials 11:2328 (2021).

In some embodiments of the present invention, the subject with a non-healing surface defect or disorder, e.g., a PCED, has an amniotic membrane graft. In some embodiments, the gap junction modulator or the hemichannel modulator, e.g. lufepirsen, is administered under an amniotic membrane graft. In some embodiments, an amniotic membrane graft is applied to the non-healing surface disorder, e.g. a PCED, after application of the gap junction modulator or the hemichannel modulator, e.g. lufepirsen.

Articles of Manufacture/Kits

In another embodiment of the invention, an article of manufacture, or "kit", containing materials useful for treating a non-healing ocular surface or corneal defect and disorder (e.g. a PED or PCED) is provided. In another embodiment of the invention, an article of manufacture, or "kit", is provide that contains materials useful for treating uveitis, blepharitis, Sjögren's syndrome-associated keratoconjunctivitis sicca, Fuchs' dystrophy, and/or dry eye disease (e.g., evaporative dry eye, aqueous-deficient dry eye, and decreased wettability dry eye).

The kit comprises a container with a composition comprising one or more modulators, e.g. a connexin modulator such as a connexin antisense, a connexin peptidomimetic and/or a small molecule hemichannel blocker, for example. The kit may further comprise a label or package insert, on or associated with the container, which includes instructions for dosing as described herein. The term "package insert" refers to instructions customarily included in commercial packages of therapeutic products that contain information about the indications, usage, dosage, administration, contraindications and/or warnings concerning the use of the modulator, which may be provided physically or via an online link, for example. Suitable containers include, e.g., bottles, vials, etc. The container may be formed from a variety of materials such as glass or plastic. In some embodiments, the label or package insert indicates that the composition is used for treating a non-healing ocular surface or corneal surface defect and disorder (e.g. a PED or PCED). In some embodiments, the label or package insert indicates that the composition is used for treating uveitis, blepharitis, Sjögren's syndrome-associated keratoconjunctivitis sicca, Fuchs' dystrophy, and all forms of dry eye disease (e.g., evaporative dry eye, aqueous-deficient dry eye, and decreased wettability dry eye).

A kit may comprise one or more pharmaceutical compositions, in separate vessels, or a partitioned vessel, together with packaging and instructions for use. The kit may also comprise a pharmaceutically acceptable carrier. In some embodiments the kit may also include components for administering the pharmaceutical compositions, for example, a syringe, needle, microneedle, etc. In some embodiments, the kit comprises a bandage contact lens for application to the subject following administration of a connexin modulator or for using in applying the connexon modulator. The connexin modulator will be dosed on separate days and may include packaging and/or instructions for chronologically staggered administration in accordance with methods of the invention.

Manufacture

The polynucleotides of this invention can be manufactured using solid-phase chemistries for synthesizing oligonucleotides, chemistries known in the art for synthesizing and preparing peptides and peptidomimetics, and chemistries know in the art for synthesizing organic compounds (e.g. tonabersat, and other compounds of Formula I and Formula II). In one aspect, the formulations of this invention will comprise a salt of the polynucleotides of this invention, such as the sodium salt of the polynucleotides of this invention. The kit may also comprise a pharmaceutically acceptable carrier. In one embodiment the formulation may comprise the sodium salt of a polynucleotide having any one of SEQ. ID. NO:1-16 or a portion of SEQ ID NO:17, for example. In some embodiments, the polynucleotide having any one of SEQ. ID. NO:1-16 may be a modified oligodeoxynucleotide having any one of SEQ. ID. NO:1-16, or a portion of SEQ ID NO:17.

In some embodiments, the formulations of this invention are substantially pure. By substantially pure is meant that the formulations comprise less than about 10%, 5%, or 1%, and preferably less than about 0.1%, of any nucleotide or non-nucleotide impurity. In some embodiments the total impurities, including metabolites of the connexin 43 modulating agent, will be not more than 15%. In some embodiments the total impurities, including metabolites of the connexin 43 modulating agent, will be not more than 12%. In some embodiments the total impurities, including metabolites of the connexin 43 modulating agent, will be not more than 11%. In other embodiments the total impurities, including metabolites of the connexin 43 modulating agent, will be not more than 10%. See e.g. Example 1, which describes the preparation of lufepirsen compositions with a final drug product purity of 94.9%.

Sterile compositions comprising the connexin 43 modulating agents of this invention prepared using aseptic processing by dissolving the anti-connexin modulating agent in the formulation vehicle. In one embodiment, the formulation may also be sterilized by filtration. Excipients used in the manufacture of the formulations of this invention are widely used in pharmaceutical products and released to pharmacopeial standards.

EXAMPLES

The below work was undertaken to evaluate whether connexin modulation could be used in patients for the treatment of non-healing ocular defects and disorders, including ocular persistent epithelial defects and persistent corneal epithelial defects.

This work described in the Examples was carried out over several years in multiple countries in an effort to work to discover and identify previously unknown but clinically useful therapeutic doses and dosing regimens in a randomized, double-blind placebo-controlled human clinical trial.

The successful results of this work and these efforts are described.

Example 1

Preparation of Lufepirsen® (Lufepirsen) Compositions for Topical Application in Subjects with Persistent Corneal Epithelial Defects Compositions comprising the connexin 43 modulator, lufepirsen (5'-GTA ATT GCG GCA AGA AGA ATT GTT TCT GTC-3' [SEQ ID NO:1]) for topical ocular administration were prepared using by dissolving the anti-connexin modulating agent in the formulation vehicle and buffers added, as shown in the table below.

| Ingredient | Reference to Standards | Concentration | Function |
|---|---|---|---|
| Lufepirsen | API-SPC-C06A | 0.6 or 0.06 mg/mL | Active |
| Poloxamer 407 | USP NF | 226.0 mg/mL | Thermosetting excipient |
| Sodium phosphate dibasic heptahydrate | USP NF | 0.99 mg/mL | Buffer |
| Potassium phosphate, Monobasic | USP NF | 0.25 mg/mL | Buffer |
| Water for Injection | USP | QS (dose dependent) | Diluent |

USP = United States Pharmacopeia;
NF = National Formulary

Compositions comprising 0.6 mg/ml or 0.06% of the lufepirsen connexin 43 modulator were prepared to a final volume of 300 μL for administration using by dissolving 0.18 mg lufepirsen or 19.40491591203 micromolar (μM) [005 API (lot $C_{06}$A14001)] in the poloxamer pharmaceutical formulation vehicle with buffers.

Compositions comprising 0.06 mg/ml or 0.006% of the lufepirsen connexin 43 modulator were prepared to a final volume of 300 μL for administration using by dissolving 0.018 mg lufepirsen or 1.940491591203 micromolar (μM) [005 API (lot C06A14001)] in the in the poloxamer pharmaceutical formulation vehicle with buffers.

Lufepirsen purities were 94.2% with an assay of 106% and drug product purities were 94.9% with an assay of 100%. The lufepirsen compositions were used in the clinical trial as described in Example 2.

Example 2

A Phase 2, Randomized, Prospective, Double-Masked, Vehicle-Controlled Study to Assess the Efficacy and Safety of Lufepirsen® (Lufepirsen) Applied Topically in Subjects with Persistent Epithelial Defects (PED) Resulting from Ocular Chemical and/or Thermal Injuries.

This Example describes the use of an exemplary connexin modulator (lufepirsen) in a randomized, prospective, vehicle-controlled, double-masked, human clinical trial to treat non-healing ocular surface defects. Lufepirsen is a connexin 43 antisense oligonucleotide according to SEQ ID NO:1. The vehicle comparator in the trial was Pluronic F-127.

Study Subjects: A total of 35 subjects were enrolled in this clinical trial. All eligible subjects presented with a non-infected, persistent epithelial defect (PED) of the cornea as a result of a chemical and/or thermal ocular injury, that was refractory to current standard of care for at least 14 days. Of the 35 subjects, 24 subjects received topical ocular dose administrations of LUFEPIRSEN and 11 subjects received Vehicle. There were 12 subjects who did not re-epithelialize, or did not remain re-epithelized for 28 days that received either one (Salvage Day 1) or two administrations (Salvage Day 8) of LUFEPIRSEN 0.06% in an open-label fashion. The results are described below.

Study Objective: The objective of this clinical protocol was to assess the efficacy and safety of two topical ocular dose concentrations of LUFEPIRSEN in a novel protocol for treatment of non-healing corneal PEDs resulting from severe chemical and/or thermal ocular injuries.

Study Endpoints: The primary, secondary and other endpoints evaluated in this human clinical are set forth below:

Primary Endpoint:

Corneal epithelial recovery, defined as a cornea that re-epithelializes by Day 28 of treatment and remains re-epithelialized for at least 28 days after initial re-epithelialization was first recorded, as assessed by the Investigator.

Secondary Endpoints:

The time to epithelialization defined as the time from randomization to the time of initial re-epithelialization.

Improvement of visual acuity from baseline over the course of the study period.

Number of LUFEPIRSEN treatment doses required for recovery of the corneal epithelium.

Exploratory Endpoints:

Change from baseline in PED area defined as the largest diameter times the largest one perpendicular to it, within the confines of the epithelial defect.

Corneal re-epithelialization, defined as a cornea that has re-epithelialized by Day 28 of treatment.

Change from baseline in ocular symptoms.

Primary, secondary, and exploratory endpoints were also assessed (as applicable) for the open-label section of the study.

Descriptive comparison of intrasubject corneal re-epithelization to fellow eye in subjects with bilateral injuries Safety:

Incidence of Treatment Emergent Adverse Events.

Treatment Dosing: The study comprised of a 28-day Treatment Period, followed by a Post-treatment Follow-up Period of at least 28 days to evaluate both safety and re-epithelization status (durability), both of which were double-masked (i.e., double-blinded). Once determined to be eligible, subjects were randomized to receive either LUFEPIRSEN 0.06% or LUFEPIRSEN 0.006% or Vehicle in a 1:1:1 ratio respectively. Investigational product was applied under a bandage contact lens (BCL) and to the fornices of the study eye at the following time points during the Treatment Period:

Day 1

Day 2

Day 14 (if the cornea has not re-epithelialized)

Salvage Dosing: However, if by Day 28 of the Treatment Period a subject's cornea had not fully re-epithelialized, irrespective of the investigational product assignment at randomization, that subject was entered into the open-label period of the study and received up to two salvage dose applications of LUFEPIRSEN 0.06% applied under a BCL and to both fornices of the eye, with LUFEPIRSEN 0.06% applied on Salvage Day 1 and, if re-epithelialization was still not achieved, on Salvage Day 8 of the open-label section of the study. Twelve subjects receiving salvage therapy were followed up to 14 days from first salvage dose application to determine if re-epithelialization occurred (Day 41) and then returned >28 days, to confirm that re-epithelialization was maintained (durability).

For each subject, the 28-day masked Treatment Period ended when EITHER, corneal re-epithelialization was first recorded following up to a maximum of three masked applications of investigational product OR subjects enters the open-label section of the study as a result of an unhealed PED at Day 28.

Those subjects who achieved re-epithelialization immediately began the 28-day Post-Healing Follow-up Period (with no further investigational product applied). The aim of the post epithelialization follow-up period was to assess the durability of the epithelium.

For those subjects that achieve re-epithelialization but epithelialization was NOT sustained during the 28-day Post-treatment Follow-up Period, the subject was eligible to receive the salvage dose(s) of LUFEPIRSEN 0.06% and enter the open-label section of the study (Salvage Day 1). If re-epithelialization was not achieved by Salvage Day 8 of the open-label section of the study, a second dose of LUFEPIRSEN 0.06% was applied. If re-epithelialization occurs within 14-days of the first salvage dose, a final assessment of the epithelium durability was performed 28 days later.

Subjects also exited the study if epithelialization was not achieved within 14 days of receiving salvage dose applications of LUFEPIRSEN 0.06% in the open-label section of the study. There were 12 subjects who received Salvage (high dose open label LUFEPIRSEN) in the NEX-PED-005 study. Eleven subjects received 1 dose at Day 28, with one subject receiving 2 doses (Day 28 and Day 35).

The maximum duration for study participation for a subject was 98 days (+2 days). this assumes re-epithelialization on day 28 of the masked treatment period, enabling the post-healing follow-up period to start. in cases where durability was not sustained 28 days later, the subject then became eligible for the 0.06% LUFEPIRSEN salvage dose (s), enabling that subject to potentially participate in the open-label section of the study for up to a further 41 days (14 days+28 days (+2 days)). Table 1 shows the schedule of assessments for details of the visit schedule and the procedures to be conducted at each study visit.

Investigational Product Administration for Randomized Subjects: Each investigational product dose application comprised a volume to fill the BCL (100 μL) and cover the inner surfaces of the superior and inferior fornices (100 μL instilled per fornix). The eye was then covered with a double eye pad and taped shut for approximately 8 hours.

No topical ocular standard of care treatment was permitted 2 hours before or 8 hours following investigational product administration. Outside of this period, subjects continued to receive the standard of care regimen prescribed to them by the Investigator.

Three treatment arms were evaluated in the study. Randomization was in a 1:1:1 ratio:

GROUP A—LUFEPIRSEN 0.06%

GROUP B—LUFEPIRSEN 0.006%

GROUP C—Vehicle

There was a single application of investigational product on Day 1 and Day 2. A potential additional application of investigational product was scheduled at Day 14 if re-epithelialization has not occurred.

If re-epithelialization of the study eye had not occurred at the end of the 28-day masked Treatment Period, or following initial re-epithelialization durability was not maintained, subjects received up to two salvage dose applications of LUFEPIRSEN 0.06% in the open-label section of the study.

Study Description: Potentially eligible subjects presented with a clinically non-infected PED as a result of a severe chemical and/or thermal injury refractory to standard of care. Clinical signs of the ocular injury include de-epithelialization, conjunctival inflammation (hyperemia), limbal ischemia and corneal edema.

Before the entry of a subject was considered, the PED must have been present for at least 14 days, with the day of injury being counted as the first day, and in the opinion of the Investigator, the defect must not have shown a clinically meaningful improvement in healing despite conventional standard of care over a period of at least 14 days. Conventional standard of care included: antibiotics, steroid drops, cycloplegic agents, ascorbic acid, amniotic membrane placement, debridement of the necrotic epithelium, etc.

Subject consent to participate in the study was obtained by the Principal Investigator or suitably qualified designee before any protocol-specific procedures were undertaken. Eligibility assessments and baseline evaluations were performed prior to Day 1 of the Treatment Period, with final eligibility checks such as confirmation of a negative urine pregnancy test for women of childbearing potential and pre-treatment measures of the PED dimensions performed before subjects are randomized to treatment. The eligibility assessment and Day 1 visits may be combined at the Investigator's discretion, when subject's documented medical history confirmed the epithelial defect had been present for over 14 days and was non-responsive to SOC. The visits may also be combined assuming the medical history has been confirmed and the subject was experiencing logistical challenges such as, subject needs to travel long distances to the site or due to transport difficulties and restrictions as a result of the COVID-19 pandemic, PROVIDING all assessments required prior to randomization have been undertaken, documented, and subject eligibility was confirmed.

The first investigational product application occurred following randomization on Day 1 of the Treatment Period, with the second application administered on Day 2. For each single application, a BCL filled with 100 μL investigational product was applied immediately on the study eye followed by an application of 100 μL into each of the superior and inferior fornices. The eye was then covered with a double eye pad and taped shut for approximately 8 hours. Importantly, subjects continued to receive SOC prescribed to them over the duration of the treatment period EXCEPT 2 hours before IP application and 8 hours after.

Each subject then attended twice-weekly assessment visits until corneal re-epithelialization occurs.

If re-epithelialization of the defect had NOT occurred by Day 14, another single application of masked investigational product was administered.

If corneal re-epithelialization has NOT occurred by Day 28 of the masked Treatment Period, subjects received up to two salvage dose applications of LUFEPIRSEN 0.06% in the open-label section of the study. If re-epithelialization has not occurred within 14 days of the first salvage dose application(s) of LUFEPIRSEN 0.06%, the subject exited the open-label section of the study.

Once re-epithelialization has occurred, regardless of time frame within the masked Treatment Period, the subject entered the Post-healing Follow-up Period and continue to wear the BCL for 2 weeks to allow the new epithelium to become anchored to the basement membrane and avoid premature traumatic detachment of the cell layer. Subjects were assessed again 28 days following initial re-epithelialization to confirm durability of the epithelium. The subject then exited the study having completed all visits.

If, after initial epithelialization, the epithelium breaks down within the 28-day Post-treatment Follow-up period, the subject received up to two salvage dose applications of LUFEPIRSEN 0.06%, given 7 days apart, in the open-label section of the study.

If a re-epithelialized cornea develops within 14 days of the first open-label salvage dose application, these subjects will also be followed for 28 days to assess durability of re-epithelization but was analyzed outside of the masked study population. See FIG. 1. At each study visit following randomization until the end of the Treatment Period, the subject will undergo assessments as detailed in a Schedule of Assessments. Assessments included slit lamp examination to assess the condition of the anterior segment of the eye (including the eyelids, sclera, conjunctiva, cornea, anterior chamber, and lens), photography, measurement of the epithelial defect, visual acuity, intraocular pressure and the ocular symptom questionnaire. The occurrence of any Treatment Emergent Adverse Events will also be assessed at each study visit, and up to 30 days following the final application of investigational product.

Standard of Care during the Treatment Period and the Open-label section of the study: From the start of Day 1 through to the END of the Treatment Period EXCEPT for 2 hours before and the 8-hour period after investigational product administration, the subjects continued to receive the standard of care regimen prescribed to them by the Investigator at the study site. Details of the medications administered, doses, and dosing regimens were recorded in the source documentation and case report form.

Bandage contact lenses (BCL) for IP administration was provided by the Sponsor and were to be worn during the Treatment Period, replaced only when a new BCL was used for IP administration on dosing days, or if indicated, e.g., discomfort or BCL falling out.

Systemic standard of care was not defined by the protocol but by the Investigator's or study site routine practice. However, systemic medications and regimen for the treatment of the PED were to remain unchanged for the duration of the study, until re-epithelialization or study exit.

Use of topical anesthetic drops was only permitted for ophthalmic assessments conducted at each study visit.

Inclusion Criteria: A subject was eligible for inclusion in the study only if ALL of the following criteria applied.

1. Male and female of any age.
2. Clinically non-infected, corneal persistent epithelial defect (PED) as a result of a severe chemical and/or thermal ocular injury in one or both eyes.
3. Documentation of the PED being non-responsive to current standard of care for at least 14 days with day 1 being the day of injury.
4. An epithelial defect measuring at least 2 mm along the largest diameter at Day 1 of the Treatment Period.
5. Providing written informed consent and ability to comply with the visit and dosing schedule.

The blind was broken, and an analysis was conducted when 35 randomized subjects (LUFEPIRSEN 0.06% (n=12), LUFEPIRSEN 0.006% (n=12)) had completed study. Utilizing the full data set, 66.7% (8 of 12) of LUFEPIRSEN 0.06% subjects and 66.7% (8 of 12) of LUFEPIRSEN 0.006% subjects achieved corneal epithelial recovery. In contrast, Vehicle subjects achieved only 27.3% (3 of 11) recovery, and each of these 3 subjects who recovered did so after receiving only 2 doses of Vehicle on Days 1 and 2, while 3 subjects who did not recover also received 2 doses with the remaining non-recovering Vehicle cohort subjects receiving 3 doses of Vehicle.

Thus, subjects with a non-healing ocular surface defect receiving the connexin modulator LUFEPIRSEN (n=24) were almost two and half times (2.44 times) more likely to heal on application of a connexin modulator and exhibited a 39.4% comparative improvement in corneal epithelial recovery over the VEH group (n=11). These findings are clinically meaningful and, despite the small sample population, clearly approached statistical significance (Fisher's exact test: p=0.065). In general, treatment was well tolerated, with TEAEs across all 3 treatment groups being similarly characterized as mild to moderate in severity and unlikely/unrelated to study drug. A SAE deemed not related to study drug was reported.

These data from a randomized, prospective, vehicle-controlled, double-masked, human clinical trial to treat non-healing ocular surface defects corroborate the use of a connexin modulator (e.g., LUFEPIRSEN) in the dose regimens described herein using the doses described herein, or in a dose regimen as described herein using a different, therapeutically effective dose, to durably heal a non-healing or persistent ocular surface defect, including persistent corneal epithelial defects. The data establish both safety and clinical proof of concept for the unique connexin modulators doses and dose regimens described and claimed herein, and confirm their utility in the therapeutic management of patients with a non-healing ocular surface or corneal defect or disorder.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents. Reference to any applications, patents and publications in this specification is not, and should not be taken as, an acknowledgment or any form of suggestion that they constitute valid prior art or form part of the common general knowledge in any country in the world.

The specific methods and compositions described herein are representative of preferred embodiments and are exemplary and not intended as limitations on the scope of the invention. Other objects, aspects, and embodiments will occur to those skilled in the art upon consideration of this specification and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, any of the terms "comprising", "consisting essentially of", and "consisting of" may be replaced with either of the other two terms in the specification. Also, the terms "comprising", "including", containing", etc. are to be read expansively and without limitation. The methods and processes illustratively described herein suitably may be practiced in differing orders of steps, and that they are not necessarily restricted to the orders of steps indicated herein or in the claims. It is also that as used herein and in the appended claims, the singular forms "a," "an," and "the" include plural reference unless the context clearly dictates otherwise. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants. Furthermore, titles, headings, or the like are provided to enhance the reader's comprehension of this document and should not be read as limiting the scope of the present invention. Any examples of aspects, embodiments or components of the invention referred to herein are to be considered non-limiting.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or embodiments of the invention are described in terms of Markush groups, those skilled in the art will recognize that the invention is also thereby described in terms of any individual member or subgroup of members of the Markush group.

SEQUENCE LISTING

```
Sequence total quantity: 361
SEQ ID NO: 1            moltype = DNA  length = 30
FEATURE                 Location/Qualifiers
```

-continued

```
source                  1..30
                        mol_type = other DNA
                        organism = synthetic construct
SEQUENCE: 1
gtaattgcgg caagaagaat tgtttctgtc                                   30

SEQ ID NO: 2            moltype = DNA  length = 30
FEATURE                 Location/Qualifiers
source                  1..30
                        mol_type = other DNA
                        organism = synthetic construct
SEQUENCE: 2
gtaattgcgg caggaggaat tgtttctgtc                                   30

SEQ ID NO: 3            moltype = DNA  length = 30
FEATURE                 Location/Qualifiers
source                  1..30
                        mol_type = other DNA
                        organism = synthetic construct
SEQUENCE: 3
ggcaagagac accaaagaca ctaccagcat                                   30

SEQ ID NO: 4            moltype = DNA  length = 20
FEATURE                 Location/Qualifiers
source                  1..20
                        mol_type = other DNA
                        organism = synthetic construct
SEQUENCE: 4
ccaggctgac tcaaccgctg                                              20

SEQ ID NO: 5            moltype = DNA  length = 20
FEATURE                 Location/Qualifiers
source                  1..20
                        mol_type = other DNA
                        organism = synthetic construct
SEQUENCE: 5
acccatgttg cctgggcacc                                              20

SEQ ID NO: 6            moltype = DNA  length = 20
FEATURE                 Location/Qualifiers
source                  1..20
                        mol_type = other DNA
                        organism = synthetic construct
SEQUENCE: 6
gtaggcttga accttgtcaa                                              20

SEQ ID NO: 7            moltype = DNA  length = 20
FEATURE                 Location/Qualifiers
source                  1..20
                        mol_type = other DNA
                        organism = synthetic construct
SEQUENCE: 7
tctccccagg ctgactcaac                                              20

SEQ ID NO: 8            moltype = DNA  length = 20
FEATURE                 Location/Qualifiers
source                  1..20
                        mol_type = other DNA
                        organism = synthetic construct
SEQUENCE: 8
cagaagcgca catgagagat                                              20

SEQ ID NO: 9            moltype = DNA  length = 20
FEATURE                 Location/Qualifiers
source                  1..20
                        mol_type = other DNA
                        organism = synthetic construct
SEQUENCE: 9
gaagcgcaca tgagagattg                                              20

SEQ ID NO: 10           moltype = DNA  length = 20
FEATURE                 Location/Qualifiers
source                  1..20
                        mol_type = other DNA
                        organism = synthetic construct
SEQUENCE: 10
agtgtgggta cagacacaaa                                              20

SEQ ID NO: 11           moltype = DNA  length = 20
```

-continued

```
FEATURE                Location/Qualifiers
source                 1..20
                       mol_type = other DNA
                       organism = synthetic construct
SEQUENCE: 11
cagacacaaa tatgatctgc                                              20

SEQ ID NO: 12          moltype = DNA  length = 20
FEATURE                Location/Qualifiers
source                 1..20
                       mol_type = other DNA
                       organism = synthetic construct
SEQUENCE: 12
atatgatctg caggacccag                                              20

SEQ ID NO: 13          moltype = DNA  length = 20
FEATURE                Location/Qualifiers
source                 1..20
                       mol_type = other DNA
                       organism = synthetic construct
SEQUENCE: 13
gtaattgcgg caagaagaat                                              20

SEQ ID NO: 14          moltype = DNA  length = 20
FEATURE                Location/Qualifiers
source                 1..20
                       mol_type = other DNA
                       organism = synthetic construct
SEQUENCE: 14
aggctgtgca tgggagttag                                              20

SEQ ID NO: 15          moltype = DNA  length = 20
FEATURE                Location/Qualifiers
source                 1..20
                       mol_type = other DNA
                       organism = synthetic construct
SEQUENCE: 15
cgctggtcca caatggctag                                              20

SEQ ID NO: 16          moltype = DNA  length = 20
FEATURE                Location/Qualifiers
source                 1..20
                       mol_type = other DNA
                       organism = synthetic construct
SEQUENCE: 16
gctggctctg cttgaaggtc                                              20

SEQ ID NO: 17          moltype = DNA  length = 3085
FEATURE                Location/Qualifiers
source                 1..3085
                       mol_type = genomic DNA
                       organism = Homo sapiens
SEQUENCE: 17
acaaaaaagc ttttacgagg tatcagcact tttctttcat tagggggaag gcgtgaggaa  60
agtaccaaac agcagcggag ttttaaactt taaatagaca ggtctgagtg cctgaacttg  120
ccttttcatt ttacttcatc ctccaaggag ttcaatcact tggcgtgact tcactacttt  180
taagcaaaag agtggtgccc aggcaacatg ggtgactgga gcgccttagg caaactcctt  240
gacaaggttc aagcctactc aactgctgga gggaaggtgt ggctgtcagt acttttcatt  300
ttccgaatcc tgctgctggg gacagcggtt gagtcagcct ggggagatga gcagtctgcc  360
tttcgttgta acactcagca acctggttgt gaaaatgtct gctatgacaa gtctttccca  420
atctctcatg tgcgcttctg ggtcctgcag atcatatttg tgtctgtacc cacactcttg  480
tacctggctc atgtgttcta tgtgatgcga aaggaagaga aactgaacaa gaaagaggaa  540
gaactcaagg ttgcccaaac tgatggtgtc aatgtggaca tgcacttgaa gcagattgag  600
ataaagaagt tcaagtacgg tattgaagag catggtaagg tgaaaatgcg aggggggttg  660
ctgcgaacct acatcatcag tatcctcttc aagtctatct ttgaggtggc cttcttgctg  720
atccagtggt acatctatgg attcagcttg agtgctgttt acacttgcaa aagagatccc  780
tgcccacatc aggtggactg tttcctctct cgccccacgg agaaaaccat cttcatcatc  840
ttcatgctgg tggtgtcctt ggtgtccctg gccttgaata tcattgaact cttctatgtt  900
ttcttcaagg gcgttaagga tcgggttaag ggaaagagcg acccttacca tgcgaccagt  960
ggtgcgctga gccctgccaa agactgtggg tctcaaaaat atgcttattt caatggctgc  1020
tcctcaccaa ccgctcccct ctcgcctatg tctcctcctg ggtacaagct ggttactggc  1080
gacagaaaca attcttcttg ccgcaattac aacaagcaag caagtgagca aaactgggct  1140
aattacagtg cagaacaaaa tcgaatgggg caggcgggaa gcaccatctc taactcccat  1200
gcacagcctt ttgatttccc cgatgataac cagaattcta aaaaactagc tgctggacat  1260
gaattacagc cactagccat tgtggaccag cgaccttcaa gcagagccag cagtcgtgcc  1320
agcagcagac ctcggcctga tgacctggag atctagatac aggcttgaaa gcatcaagat  1380
tccactcaat tgtggagaag aaaaaaggtg ctgtagaaag tgcaccaggt gttaattttg  1440
atccggtgga ggtggtactc aacagcctta ttcatgaggc ttagaaaaca caaagacatt  1500
agaataccta ggttcactgg gggtgtatgg ggtagatggg tggagaggga ggggataaga  1560
```

-continued

```
gaggtgcatg ttggtattta aagtagtgga ttcaaagaac ttagattata aataagagtt  1620
ccattaggtg atacatagat aagggctttt tctccccgca aacaccccta agaatggttc  1680
tgtgtatgtg aatgagcggg tggtaattgt ggctaaatat ttttgtttta ccaagaaact  1740
gaaataattc tggccaggaa taaatacttc ctgaacatct taggtctttt caacaagaaa  1800
aagacagagg attgtcctta agtccctgct aaaacattcc attgttaaaa tttgcacttt  1860
gaaggtaagc tttctaggcc tgaccctcca ggtgtcaatg gacttgtgct actatatttt  1920
tttattcttg gtatcagttt aaaattcaga caaggcccac agaataagat tttccatgca  1980
tttgcaaata cgtatattct ttttccatcc acttgcacaa tatcattacc atcacttttt  2040
catcattcct cagctactac tcacattcat ttaatggttt ctgtaaacat ttttaagaca  2100
gttgggatgt cacttaacat tttttttttt tgagctaaag tcagggaatc aagccatgct  2160
taatatttaa caatcactta tatgtgtgtc gaagagtttg ttttgtttgt catgtattgg  2220
tacaagcaga tacagtataa actcacaaac acagatttga aaataatgca catatggtgt  2280
tcaaatttga acctttctca tggatttttg tggtgtgggc caatatggtg tttacattat  2340
ataattcctg ctgtggcaag taaagcacac ttttttttttc tcctaaaatg tttttccctg  2400
tgtatcctat tatggatact ggttttgtta attatgattc tttattttct ctcctttttt  2460
taggatatag cagtaatgct attactgaaa tgaatttcct ttttctgaaa tgtaatcatt  2520
gatgcttgaa tgatagaatt ttagtactgt aaacaggctt tagtcattaa tgtgagagac  2580
ttagaaaaaa tgcttagagt ggactattaa atgtgcctaa atgaattttg cagtaactgg  2640
tattcttggg ttttcctact taatacacag taattcagaa cttgtattct attatgagtt  2700
tagcagtctt ttggagtgac cagcaacttt gatgtttgca ctaagatttt atttggaatg  2760
caagagaggt tgaaagagga ttcagtagta cacatacaac taatttattt gaactatatg  2820
ttgaagacat ctaccagttt ctccaaatgc cttttttaaa actcatcaca gaagattggt  2880
gaaaatgctg agtatgacac ttttcttctt gcatgcatgt cagctacata aacagttttg  2940
tacaatgaaa attactaatt tgtttgacat tccatgttaa actacggtca tgttcagctt  3000
cattgcatgt aatgtagacc tagtccatca gatcatgtgt tctggagagt gttctttatt  3060
taaagtttta atttagtata aacat                                        3085
```

SEQ ID NO: 18 moltype = length =
SEQUENCE: 18
000

SEQ ID NO: 19 moltype = length =
SEQUENCE: 19
000

SEQ ID NO: 20 moltype = length =
SEQUENCE: 20
000

SEQ ID NO: 21 moltype = length =
SEQUENCE: 21
000

SEQ ID NO: 22 moltype = length =
SEQUENCE: 22
000

SEQ ID NO: 23 moltype = length =
SEQUENCE: 23
000

SEQ ID NO: 24 moltype = length =
SEQUENCE: 24
000

SEQ ID NO: 25 moltype = length =
SEQUENCE: 25
000

SEQ ID NO: 26 moltype = length =
SEQUENCE: 26
000

SEQ ID NO: 27 moltype = length =
SEQUENCE: 27
000

SEQ ID NO: 28 moltype = length =
SEQUENCE: 28
000

SEQ ID NO: 29 moltype = length =
SEQUENCE: 29
000

SEQ ID NO: 30 moltype = length =
SEQUENCE: 30
000

-continued

```
SEQ ID NO: 31          moltype =   length =
SEQUENCE: 31
000

SEQ ID NO: 32          moltype =   length =
SEQUENCE: 32
000

SEQ ID NO: 33          moltype =   length =
SEQUENCE: 33
000

SEQ ID NO: 34          moltype =   length =
SEQUENCE: 34
000

SEQ ID NO: 35          moltype =   length =
SEQUENCE: 35
000

SEQ ID NO: 36          moltype =   length =
SEQUENCE: 36
000

SEQ ID NO: 37          moltype =   length =
SEQUENCE: 37
000

SEQ ID NO: 38          moltype =   length =
SEQUENCE: 38
000

SEQ ID NO: 39          moltype =   length =
SEQUENCE: 39
000

SEQ ID NO: 40          moltype =   length =
SEQUENCE: 40
000

SEQ ID NO: 41          moltype =   length =
SEQUENCE: 41
000

SEQ ID NO: 42          moltype =   length =
SEQUENCE: 42
000

SEQ ID NO: 43          moltype =   length =
SEQUENCE: 43
000

SEQ ID NO: 44          moltype =   length =
SEQUENCE: 44
000

SEQ ID NO: 45          moltype =   length =
SEQUENCE: 45
000

SEQ ID NO: 46          moltype =   length =
SEQUENCE: 46
000

SEQ ID NO: 47          moltype =   length =
SEQUENCE: 47
000

SEQ ID NO: 48          moltype =   length =
SEQUENCE: 48
000

SEQ ID NO: 49          moltype =   length =
SEQUENCE: 49
000

SEQ ID NO: 50          moltype =   length =
SEQUENCE: 50
000
```

-continued

```
SEQ ID NO: 51          moltype =   length =
SEQUENCE: 51
000

SEQ ID NO: 52          moltype =   length =
SEQUENCE: 52
000

SEQ ID NO: 53          moltype =   length =
SEQUENCE: 53
000

SEQ ID NO: 54          moltype =   length =
SEQUENCE: 54
000

SEQ ID NO: 55          moltype =   length =
SEQUENCE: 55
000

SEQ ID NO: 56          moltype =   length =
SEQUENCE: 56
000

SEQ ID NO: 57          moltype =   length =
SEQUENCE: 57
000

SEQ ID NO: 58          moltype =   length =
SEQUENCE: 58
000

SEQ ID NO: 59          moltype =   length =
SEQUENCE: 59
000

SEQ ID NO: 60          moltype =   length =
SEQUENCE: 60
000

SEQ ID NO: 61          moltype =   length =
SEQUENCE: 61
000

SEQ ID NO: 62          moltype =   length =
SEQUENCE: 62
000

SEQ ID NO: 63          moltype =   length =
SEQUENCE: 63
000

SEQ ID NO: 64          moltype =   length =
SEQUENCE: 64
000

SEQ ID NO: 65          moltype =   length =
SEQUENCE: 65
000

SEQ ID NO: 66          moltype =   length =
SEQUENCE: 66
000

SEQ ID NO: 67          moltype =   length =
SEQUENCE: 67
000

SEQ ID NO: 68          moltype =   length =
SEQUENCE: 68
000

SEQ ID NO: 69          moltype =   length =
SEQUENCE: 69
000

SEQ ID NO: 70          moltype =   length =
SEQUENCE: 70
```

```
000

SEQ ID NO: 71           moltype =   length =
SEQUENCE: 71
000

SEQ ID NO: 72           moltype =   length =
SEQUENCE: 72
000

SEQ ID NO: 73           moltype =   length =
SEQUENCE: 73
000

SEQ ID NO: 74           moltype =   length =
SEQUENCE: 74
000

SEQ ID NO: 75           moltype =   length =
SEQUENCE: 75
000

SEQ ID NO: 76           moltype =   length =
SEQUENCE: 76
000

SEQ ID NO: 77           moltype =   length =
SEQUENCE: 77
000

SEQ ID NO: 78           moltype =   length =
SEQUENCE: 78
000

SEQ ID NO: 79           moltype =   length =
SEQUENCE: 79
000

SEQ ID NO: 80           moltype =   length =
SEQUENCE: 80
000

SEQ ID NO: 81           moltype =   length =
SEQUENCE: 81
000

SEQ ID NO: 82           moltype =   length =
SEQUENCE: 82
000

SEQ ID NO: 83           moltype =   length =
SEQUENCE: 83
000

SEQ ID NO: 84           moltype =   length =
SEQUENCE: 84
000

SEQ ID NO: 85           moltype =   length =
SEQUENCE: 85
000

SEQ ID NO: 86           moltype =   length =
SEQUENCE: 86
000

SEQ ID NO: 87           moltype =   length =
SEQUENCE: 87
000

SEQ ID NO: 88           moltype =   length =
SEQUENCE: 88
000

SEQ ID NO: 89           moltype =   length =
SEQUENCE: 89
000

SEQ ID NO: 90           moltype =   length =
```

-continued

```
SEQUENCE: 90
000

SEQ ID NO: 91          moltype =   length =
SEQUENCE: 91
000

SEQ ID NO: 92          moltype =   length =
SEQUENCE: 92
000

SEQ ID NO: 93          moltype =   length =
SEQUENCE: 93
000

SEQ ID NO: 94          moltype =   length =
SEQUENCE: 94
000

SEQ ID NO: 95          moltype =   length =
SEQUENCE: 95
000

SEQ ID NO: 96          moltype =   length =
SEQUENCE: 96
000

SEQ ID NO: 97          moltype =   length =
SEQUENCE: 97
000

SEQ ID NO: 98          moltype =   length =
SEQUENCE: 98
000

SEQ ID NO: 99          moltype =   length =
SEQUENCE: 99
000

SEQ ID NO: 100         moltype = AA  length = 382
FEATURE                Location/Qualifiers
source                 1..382
                       mol_type = protein
                       organism = unidentified
SEQUENCE: 100
MGDWSALGKL LDKVQAYSTA GGKVWLSVLF IFRILLLGTA VESAWGDEQS AFRCNTQQPG  60
CENVCYDKSF PISHVRFWVL QIIFVSVPTL LYLAHVFYVM RKEEKLNKKE EELKVAQTDG  120
VNVDMHLKQI EIKKFKYGIE EHGKVKMRGG LLRTYIISIL FKSIFEVAFL LIQWYIYGFS  180
LSAVYTCKRD PCPHQVDCFL SRPTEKTIFI IFMLVVSLVS LALNIIELFY VFFKGVKDRV  240
KGKSDPYHAT SGALSPAKDC GSQKYAYFNG CSSPTAPLSP MSPPGYKLVT GDRNNSSCRN  300
YNKQASEQNW ANYSAEQNRM GQAGSTISNS HAQPFDFPDD NQNSKKLAAG HELQPLAIVD  360
QRPSSRASSR ASSRPRPDDL EI                                           382

SEQ ID NO: 101         moltype = AA  length = 7
FEATURE                Location/Qualifiers
source                 1..7
                       mol_type = protein
                       organism = synthetic construct
SEQUENCE: 101
SRPTEKT                                                            7

SEQ ID NO: 102         moltype = AA  length = 13
FEATURE                Location/Qualifiers
source                 1..13
                       mol_type = protein
                       organism = synthetic construct
SEQUENCE: 102
VCYDKSFPIS HVR                                                     13

SEQ ID NO: 103         moltype = AA  length = 12
FEATURE                Location/Qualifiers
source                 1..12
                       mol_type = protein
                       organism = synthetic construct
SEQUENCE: 103
INCTLQPGCN SV                                                      12

SEQ ID NO: 104         moltype = AA  length = 11
FEATURE                Location/Qualifiers
```

-continued

```
source                  1..11
                        mol_type = protein
                        organism = synthetic construct
SEQUENCE: 104
SRPTEKTIFI I                                                    11

SEQ ID NO: 105          moltype = AA  length = 26
FEATURE                 Location/Qualifiers
source                  1..26
                        mol_type = protein
                        organism = synthetic construct
SEQUENCE: 105
GGERAPLAAD QGSVKKSSSS SKGTKK                                    26

SEQ ID NO: 106          moltype = AA  length = 10
FEATURE                 Location/Qualifiers
source                  1..10
                        mol_type = protein
                        organism = synthetic construct
SEQUENCE: 106
SRARSDDLTV                                                      10

SEQ ID NO: 107          moltype = AA  length = 12
FEATURE                 Location/Qualifiers
source                  1..12
                        mol_type = protein
                        organism = synthetic construct
SEQUENCE: 107
VDCFLSRPTE KT                                                   12

SEQ ID NO: 108          moltype = AA  length = 9
FEATURE                 Location/Qualifiers
source                  1..9
                        mol_type = protein
                        organism = synthetic construct
SEQUENCE: 108
KQIEIKKFK                                                       9

SEQ ID NO: 109          moltype = AA  length = 42
FEATURE                 Location/Qualifiers
source                  1..42
                        mol_type = protein
                        organism = synthetic construct
SEQUENCE: 109
LLIQWYIYGF SLSAVYTCKR DPCPHQVDCF LSRPTEKTIF II                  42

SEQ ID NO: 110          moltype = AA  length = 9
FEATURE                 Location/Qualifiers
source                  1..9
                        mol_type = protein
                        organism = synthetic construct
SEQUENCE: 110
SRPTEKTIF                                                       9

SEQ ID NO: 111          moltype = AA  length = 17
FEATURE                 Location/Qualifiers
source                  1..17
                        mol_type = protein
                        organism = synthetic construct
SITE                    1
                        note = D-amino acid
SITE                    2
                        note = D-amino acid
SITE                    3
                        note = D-amino acid
SITE                    4
                        note = D-amino acid
SITE                    5
                        note = D-amino acid
SITE                    6
                        note = D-amino acid
SEQUENCE: 111
LCLRPVGGKQ IEIKKFK                                              17

SEQ ID NO: 112          moltype = AA  length = 12
FEATURE                 Location/Qualifiers
source                  1..12
                        mol_type = protein
                        organism = synthetic construct
```

```
SEQUENCE: 112
ADCFLSRPTE KT                                                   12

SEQ ID NO: 113          moltype = AA  length = 12
FEATURE                 Location/Qualifiers
source                  1..12
                        mol_type = protein
                        organism = synthetic construct
SEQUENCE: 113
VACFLSRPTE KT                                                   12

SEQ ID NO: 114          moltype = AA  length = 12
FEATURE                 Location/Qualifiers
source                  1..12
                        mol_type = protein
                        organism = synthetic construct
SEQUENCE: 114
VDCFLSRPTA KT                                                   12

SEQ ID NO: 115          moltype = AA  length = 12
FEATURE                 Location/Qualifiers
source                  1..12
                        mol_type = protein
                        organism = synthetic construct
SEQUENCE: 115
VDCFLSRPTE AT                                                   12

SEQ ID NO: 116          moltype = AA  length = 10
FEATURE                 Location/Qualifiers
source                  1..10
                        mol_type = protein
                        organism = synthetic construct
SEQUENCE: 116
CFLSRPTEKT                                                      10

SEQ ID NO: 117          moltype = AA  length = 8
FEATURE                 Location/Qualifiers
source                  1..8
                        mol_type = protein
                        organism = synthetic construct
SEQUENCE: 117
LSRPTEKT                                                        8

SEQ ID NO: 118          moltype = AA  length = 11
FEATURE                 Location/Qualifiers
source                  1..11
                        mol_type = protein
                        organism = synthetic construct
SEQUENCE: 118
DCFISRPTEK T                                                    11

SEQ ID NO: 119          moltype = AA  length = 26
FEATURE                 Location/Qualifiers
source                  1..26
                        mol_type = protein
                        organism = unidentified
SEQUENCE: 119
DGVNVEMHLK QIEIKKFKYG IEEHGK                                    26

SEQ ID NO: 120          moltype = AA  length = 26
FEATURE                 Location/Qualifiers
source                  1..26
                        mol_type = protein
                        organism = synthetic construct
SEQUENCE: 120
DGVNVEMHLK QIEIKKFKYG IEEQGK                                    26

SEQ ID NO: 121          moltype = AA  length = 20
FEATURE                 Location/Qualifiers
source                  1..20
                        mol_type = protein
                        organism = unidentified
SEQUENCE: 121
YGRKKRRQRR RKQIEIKKFK                                           20

SEQ ID NO: 122          moltype = AA  length = 17
FEATURE                 Location/Qualifiers
source                  1..17
                        mol_type = protein
```

```
                        organism = unidentified
SEQUENCE: 122
CSSPTAPLSP MSPPGYK                                                  17

SEQ ID NO: 123          moltype = AA  length = 11
FEATURE                 Location/Qualifiers
source                  1..11
                        mol_type = protein
                        organism = unidentified
SEQUENCE: 123
PTAPLSPMSP P                                                        11

SEQ ID NO: 124          moltype = AA  length = 7
FEATURE                 Location/Qualifiers
source                  1..7
                        mol_type = protein
                        organism = synthetic construct
SEQUENCE: 124
RPRDDEI                                                             7

SEQ ID NO: 125          moltype = AA  length = 9
FEATURE                 Location/Qualifiers
source                  1..9
                        mol_type = protein
                        organism = synthetic construct
SEQUENCE: 125
SRPRDDLEI                                                           9

SEQ ID NO: 126          moltype = AA  length = 19
FEATURE                 Location/Qualifiers
source                  1..19
                        mol_type = protein
                        organism = synthetic construct
SEQUENCE: 126
YGRKKRRQRR RSRPRDDEI                                                19

SEQ ID NO: 127          moltype = AA  length = 18
FEATURE                 Location/Qualifiers
source                  1..18
                        mol_type = protein
                        organism = synthetic construct
SEQUENCE: 127
YGRKKRRQRR RRPRDDEI                                                 18

SEQ ID NO: 128          moltype = AA  length = 6
FEATURE                 Location/Qualifiers
source                  1..6
                        mol_type = protein
                        organism = synthetic construct
SITE                    1
                        note = Aminated residue
SITE                    4
                        note = 4-hydroxyproline
SITE                    6
                        note = Amidated residue
SEQUENCE: 128
GAGPPY                                                              6

SEQ ID NO: 129          moltype = AA  length = 6
FEATURE                 Location/Qualifiers
source                  1..6
                        mol_type = protein
                        organism = synthetic construct
SITE                    1
                        note = Acetylated D-amino acid
SITE                    3
                        note = D-4-hydroxyproline
SITE                    5
                        note = D-amino acid
SITE                    6
                        note = Aminated residue
SEQUENCE: 129
YPPGAG                                                              6

SEQ ID NO: 130          moltype = AA  length = 35
FEATURE                 Location/Qualifiers
source                  1..35
                        mol_type = protein
                        organism = unidentified
```

-continued

```
SEQUENCE: 130
ESAWGDEQSA FRCNTQQPGC ENVCYDKSFP ISHVR                          35

SEQ ID NO: 131          moltype = AA  length = 36
FEATURE                 Location/Qualifiers
source                  1..36
                        mol_type = protein
                        organism = unidentified
SEQUENCE: 131
GESIYYDEQS KFVCNTEQPG CENVCYDAFA PLSHVR                         36

SEQ ID NO: 132          moltype = AA  length = 38
FEATURE                 Location/Qualifiers
source                  1..38
                        mol_type = protein
                        organism = unidentified
SEQUENCE: 132
LLIQWYIYGF SLSAVYTCKR DPCPHQVDCF LSRPTEKT                       38

SEQ ID NO: 133          moltype = AA  length = 38
FEATURE                 Location/Qualifiers
source                  1..38
                        mol_type = protein
                        organism = unidentified
SEQUENCE: 133
LIGQYFLYGF QVHPFYVCSR LPCHPKIDCF ISRPTEKT                       38

SEQ ID NO: 134          moltype = AA  length = 15
FEATURE                 Location/Qualifiers
source                  1..15
                        mol_type = protein
                        organism = synthetic construct
SEQUENCE: 134
VFFKGVKDRV KGRSD                                                15

SEQ ID NO: 135          moltype = AA  length = 8
FEATURE                 Location/Qualifiers
source                  1..8
                        mol_type = protein
                        organism = synthetic construct
SEQUENCE: 135
RPRDDLEI                                                        8

SEQ ID NO: 136          moltype = AA  length = 9
FEATURE                 Location/Qualifiers
source                  1..9
                        mol_type = protein
                        organism = synthetic construct
SEQUENCE: 136
SRPRDDLEI                                                       9

SEQ ID NO: 137          moltype = AA  length = 25
FEATURE                 Location/Qualifiers
source                  1..25
                        mol_type = protein
                        organism = synthetic construct
SEQUENCE: 137
RQPKIWFPNR RKPWKKRPRP DDLEI                                     25

SEQ ID NO: 138          moltype = AA  length = 13
FEATURE                 Location/Qualifiers
source                  1..13
                        mol_type = protein
                        organism = synthetic construct
SEQUENCE: 138
GHGDPLHLEE VKC                                                  13

SEQ ID NO: 139          moltype = AA  length = 24
FEATURE                 Location/Qualifiers
source                  1..24
                        mol_type = protein
                        organism = synthetic construct
SEQUENCE: 139
YGRKKRRQRR RGHGDPLHLE EVKC                                      24

SEQ ID NO: 140          moltype = AA  length = 20
FEATURE                 Location/Qualifiers
source                  1..20
                        mol_type = protein
```

-continued

```
                        organism = synthetic construct
SEQUENCE: 140
PSSRASSRAS SRPRPDDLEI                                                20

SEQ ID NO: 141          moltype = AA  length = 9
FEATURE                 Location/Qualifiers
source                  1..9
                        mol_type = protein
                        organism = synthetic construct
SEQUENCE: 141
RPRPDDLEI                                                            9

SEQ ID NO: 142          moltype = AA  length = 9
FEATURE                 Location/Qualifiers
source                  1..9
                        mol_type = protein
                        organism = synthetic construct
SEQUENCE: 142
RPRPDDLEV                                                            9

SEQ ID NO: 143          moltype = AA  length = 9
FEATURE                 Location/Qualifiers
source                  1..9
                        mol_type = protein
                        organism = synthetic construct
SEQUENCE: 143
RPRPDDVPV                                                            9

SEQ ID NO: 144          moltype = AA  length = 9
FEATURE                 Location/Qualifiers
source                  1..9
                        mol_type = protein
                        organism = synthetic construct
SEQUENCE: 144
KARSDDLSV                                                            9

SEQ ID NO: 145          moltype = AA  length = 40
FEATURE                 Location/Qualifiers
source                  1..40
                        mol_type = protein
                        organism = synthetic construct
SEQUENCE: 145
QKPEVPNGVS PGHRLPHGYH SDKRRLSKAS SKARSDDLSV                          40

SEQ ID NO: 146          moltype = AA  length = 36
FEATURE                 Location/Qualifiers
source                  1..36
                        mol_type = protein
                        organism = synthetic construct
SEQUENCE: 146
RQPKIWFPNR RKPWKKPSSR ASSRASSRPR PDDLEI                              36

SEQ ID NO: 147          moltype = AA  length = 36
FEATURE                 Location/Qualifiers
source                  1..36
                        mol_type = protein
                        organism = synthetic construct
SEQUENCE: 147
RQPKIWFPNR RKPWKKPSSR ASSRASSRPR PDDLEI                              36

SEQ ID NO: 148          moltype = AA  length = 25
FEATURE                 Location/Qualifiers
source                  1..25
                        mol_type = protein
                        organism = synthetic construct
SEQUENCE: 148
RQPKIWFPNR RKPWKKRPRP DDLEI                                          25

SEQ ID NO: 149          moltype = AA  length = 25
FEATURE                 Location/Qualifiers
source                  1..25
                        mol_type = protein
                        organism = synthetic construct
SEQUENCE: 149
RQPKIWFPNR RKPWKKRPRP DDLEV                                          25

SEQ ID NO: 150          moltype = AA  length = 25
FEATURE                 Location/Qualifiers
source                  1..25
```

```
                         mol_type = protein
                         organism = synthetic construct
SEQUENCE: 150
RQPKIWFPNR RKPWKKRPRP DDVPV                                             25

SEQ ID NO: 151           moltype = AA  length = 25
FEATURE                  Location/Qualifiers
source                   1..25
                         mol_type = protein
                         organism = synthetic construct
SEQUENCE: 151
RQPKIWFPNR RKPWKKKARS DDLSV                                             25

SEQ ID NO: 152           moltype = AA  length = 9
FEATURE                  Location/Qualifiers
source                   1..9
                         mol_type = protein
                         organism = synthetic construct
SEQUENCE: 152
RPKPDDLDI                                                               9

SEQ ID NO: 153           moltype = AA  length = 20
FEATURE                  Location/Qualifiers
source                   1..20
                         mol_type = protein
                         organism = synthetic construct
SEQUENCE: 153
GRKKRRQRPP QRPRPDDLEI                                                   20

SEQ ID NO: 154           moltype = AA  length = 25
FEATURE                  Location/Qualifiers
source                   1..25
                         mol_type = protein
                         organism = synthetic construct
SEQUENCE: 154
RQIKIWFQNR RMKWKKRPRP DDLEI                                             25

SEQ ID NO: 155           moltype = AA  length = 25
FEATURE                  Location/Qualifiers
source                   1..25
                         mol_type = protein
                         organism = synthetic construct
SEQUENCE: 155
RQIAIWFQNR RMKWAARPRP DDLEI                                             25

SEQ ID NO: 156           moltype = AA  length = 18
FEATURE                  Location/Qualifiers
source                   1..18
                         mol_type = protein
                         organism = synthetic construct
SEQUENCE: 156
RKKRRQRRRR PRPDDLEI                                                     18

SEQ ID NO: 157           moltype = AA  length = 30
FEATURE                  Location/Qualifiers
source                   1..30
                         mol_type = protein
                         organism = synthetic construct
SEQUENCE: 157
TRSSRAGLQF PVGRVHRLLR KRPRPDDLEI                                        30

SEQ ID NO: 158           moltype = AA  length = 35
FEATURE                  Location/Qualifiers
source                   1..35
                         mol_type = protein
                         organism = synthetic construct
SEQUENCE: 158
GWTLNSAGYL LGKINKALAA LAKKILRPRP DDLEI                                  35

SEQ ID NO: 159           moltype =   length =
SEQUENCE: 159
000

SEQ ID NO: 160           moltype = AA  length = 25
FEATURE                  Location/Qualifiers
source                   1..25
                         mol_type = protein
                         organism = synthetic construct
SEQUENCE: 160
```

```
AAVALLPAVL LALLAPRPRP DDLEI                                        25

SEQ ID NO: 161         moltype = AA  length = 19
FEATURE                Location/Qualifiers
source                 1..19
                       mol_type = protein
                       organism = synthetic construct
SEQUENCE: 161
VPMLKPMLKE RPRPDDLEI                                               19

SEQ ID NO: 162         moltype = AA  length = 37
FEATURE                Location/Qualifiers
source                 1..37
                       mol_type = protein
                       organism = synthetic construct
SEQUENCE: 162
MANLGYWLLA LFVTMWTDVG LCKKRPKPRP RPDDLEI                           37

SEQ ID NO: 163         moltype = AA  length = 27
FEATURE                Location/Qualifiers
source                 1..27
                       mol_type = protein
                       organism = synthetic construct
SEQUENCE: 163
LLIILRRRIR KQAHAHSKRP RPDDLEI                                      27

SEQ ID NO: 164         moltype = AA  length = 30
FEATURE                Location/Qualifiers
source                 1..30
                       mol_type = protein
                       organism = synthetic construct
SEQUENCE: 164
KETWWETWWT EWSQPKKKRK VRPRPDDLEI                                   30

SEQ ID NO: 165         moltype = AA  length = 27
FEATURE                Location/Qualifiers
source                 1..27
                       mol_type = protein
                       organism = synthetic construct
SEQUENCE: 165
RGGRLSYSRR RFSTSTGRRP RPDDLEI                                      27

SEQ ID NO: 166         moltype = AA  length = 24
FEATURE                Location/Qualifiers
source                 1..24
                       mol_type = protein
                       organism = synthetic construct
SEQUENCE: 166
SDLWEMMMVS LACQYRPRPD DLEI                                         24

SEQ ID NO: 167         moltype = AA  length = 21
FEATURE                Location/Qualifiers
source                 1..21
                       mol_type = protein
                       organism = synthetic construct
SEQUENCE: 167
TSPLNIHNGQ KLRPRPDDLE I                                            21

SEQ ID NO: 168         moltype = AA  length = 12
FEATURE                Location/Qualifiers
source                 1..12
                       mol_type = protein
                       organism = synthetic construct
SEQUENCE: 168
VDCFLSRPTE KT                                                      12

SEQ ID NO: 169         moltype = AA  length = 27
FEATURE                Location/Qualifiers
source                 1..27
                       mol_type = protein
                       organism = synthetic construct
SEQUENCE: 169
KLALKLALKA LKAALKLARP RPDDLEI                                      27

SEQ ID NO: 170         moltype =   length =
SEQUENCE: 170
000

SEQ ID NO: 171         moltype =   length =
```

```
SEQUENCE: 171
000

SEQ ID NO: 172          moltype =   length =
SEQUENCE: 172
000

SEQ ID NO: 173          moltype =   length =
SEQUENCE: 173
000

SEQ ID NO: 174          moltype = AA  length = 10
FEATURE                 Location/Qualifiers
source                  1..10
                        mol_type = protein
                        organism = synthetic construct
SEQUENCE: 174
VDCFLSRPTE                                                  10

SEQ ID NO: 175          moltype = AA  length = 8
FEATURE                 Location/Qualifiers
source                  1..8
                        mol_type = protein
                        organism = synthetic construct
SEQUENCE: 175
VDCFLSRP                                                    8

SEQ ID NO: 176          moltype = AA  length = 6
FEATURE                 Location/Qualifiers
source                  1..6
                        mol_type = protein
                        organism = synthetic construct
SEQUENCE: 176
VDCFLS                                                      6

SEQ ID NO: 177          moltype = AA  length = 23
FEATURE                 Location/Qualifiers
source                  1..23
                        mol_type = protein
                        organism = synthetic construct
SEQUENCE: 177
GRKKRRQRPP QVDCFLSRPT EKT                                   23

SEQ ID NO: 178          moltype = AA  length = 28
FEATURE                 Location/Qualifiers
source                  1..28
                        mol_type = protein
                        organism = synthetic construct
SEQUENCE: 178
RQIKIWFQNR RMKWKKVDCF LSRPTEKT                              28

SEQ ID NO: 179          moltype = AA  length = 28
FEATURE                 Location/Qualifiers
source                  1..28
                        mol_type = protein
                        organism = synthetic construct
SEQUENCE: 179
RQIAIWFQNR RMKWAAVDCF LSRPTEKT                              28

SEQ ID NO: 180          moltype = AA  length = 21
FEATURE                 Location/Qualifiers
source                  1..21
                        mol_type = protein
                        organism = synthetic construct
SEQUENCE: 180
RKKRRQRRRV DCFLSRPTEK T                                     21

SEQ ID NO: 181          moltype = AA  length = 33
FEATURE                 Location/Qualifiers
source                  1..33
                        mol_type = protein
                        organism = synthetic construct
SEQUENCE: 181
TRSSRAGLQF PVGRVHRLLR KVDCFLSRPT EKT                        33

SEQ ID NO: 182          moltype = AA  length = 38
FEATURE                 Location/Qualifiers
source                  1..38
                        mol_type = protein
```

```
                       organism = synthetic construct
SEQUENCE: 182
GWTLNSAGYL LGKINKALAA LAKKILVDCF LSRPTEKT                    38

SEQ ID NO: 183         moltype = AA  length = 30
FEATURE                Location/Qualifiers
source                 1..30
                       mol_type = protein
                       organism = synthetic construct
SEQUENCE: 183
KLALKLALKA LKAALKLAVD CFLSRPTEKT                             30

SEQ ID NO: 184         moltype = AA  length = 28
FEATURE                Location/Qualifiers
source                 1..28
                       mol_type = protein
                       organism = synthetic construct
SEQUENCE: 184
AAVALLPAVL LALLAPVDCF LSRPTEKT                               28

SEQ ID NO: 185         moltype = AA  length = 22
FEATURE                Location/Qualifiers
source                 1..22
                       mol_type = protein
                       organism = synthetic construct
SEQUENCE: 185
VPMLKPMLKE VDCFLSRPTE KT                                     22

SEQ ID NO: 186         moltype = AA  length = 40
FEATURE                Location/Qualifiers
source                 1..40
                       mol_type = protein
                       organism = synthetic construct
SEQUENCE: 186
MANLGYWLLA LFVTMWTDVG LCKKRPKPVD CFLSRPTEKT                  40

SEQ ID NO: 187         moltype = AA  length = 30
FEATURE                Location/Qualifiers
source                 1..30
                       mol_type = protein
                       organism = synthetic construct
SEQUENCE: 187
LLIILRRRIR KQAHAHSKVD CFLSRPTEKT                             30

SEQ ID NO: 188         moltype = AA  length = 33
FEATURE                Location/Qualifiers
source                 1..33
                       mol_type = protein
                       organism = synthetic construct
SEQUENCE: 188
KETWWETWWT EWSQPKKKRK VVDCFLSRPT EKT                         33

SEQ ID NO: 189         moltype = AA  length = 30
FEATURE                Location/Qualifiers
source                 1..30
                       mol_type = protein
                       organism = synthetic construct
SEQUENCE: 189
RGGRLSYSRR RFSTSTGRVD CFLSRPTEKT                             30

SEQ ID NO: 190         moltype = AA  length = 27
FEATURE                Location/Qualifiers
source                 1..27
                       mol_type = protein
                       organism = synthetic construct
SEQUENCE: 190
SDLWEMMMVS LACQYVDCFL SRPTEKT                                27

SEQ ID NO: 191         moltype = AA  length = 24
FEATURE                Location/Qualifiers
source                 1..24
                       mol_type = protein
                       organism = synthetic construct
SEQUENCE: 191
TSPLNIHNGQ KLVDCFLSRP TEKT                                   24

SEQ ID NO: 192         moltype = AA  length = 11
FEATURE                Location/Qualifiers
source                 1..11
```

```
                        mol_type = protein
                        organism = synthetic construct
SEQUENCE: 192
FEVAFLLIQW I                                                    11

SEQ ID NO: 193          moltype = AA  length = 11
FEATURE                 Location/Qualifiers
source                  1..11
                        mol_type = protein
                        organism = synthetic construct
SEQUENCE: 193
LLIQWYIGFS L                                                    11

SEQ ID NO: 194          moltype = AA  length = 16
FEATURE                 Location/Qualifiers
source                  1..16
                        mol_type = protein
                        organism = synthetic construct
SEQUENCE: 194
SLSAVYTCKR DPCPHQ                                               16

SEQ ID NO: 195          moltype =   length =
SEQUENCE: 195
000

SEQ ID NO: 196          moltype = AA  length = 13
FEATURE                 Location/Qualifiers
source                  1..13
                        mol_type = protein
                        organism = synthetic construct
SEQUENCE: 196
LGTAVESAWG DEQ                                                  13

SEQ ID NO: 197          moltype = AA  length = 12
FEATURE                 Location/Qualifiers
source                  1..12
                        mol_type = protein
                        organism = synthetic construct
SEQUENCE: 197
QSAFRCNTQQ PG                                                   12

SEQ ID NO: 198          moltype = AA  length = 12
FEATURE                 Location/Qualifiers
source                  1..12
                        mol_type = protein
                        organism = synthetic construct
SEQUENCE: 198
QQPGCENVCY DK                                                   12

SEQ ID NO: 199          moltype =   length =
SEQUENCE: 199
000

SEQ ID NO: 200          moltype = AA  length = 18
FEATURE                 Location/Qualifiers
source                  1..18
                        mol_type = protein
                        organism = synthetic construct
SEQUENCE: 200
KRDPCHQVDC FLSRPTEK                                             18

SEQ ID NO: 201          moltype =   length =
SEQUENCE: 201
000

SEQ ID NO: 202          moltype =   length =
SEQUENCE: 202
000

SEQ ID NO: 203          moltype =   length =
SEQUENCE: 203
000

SEQ ID NO: 204          moltype =   length =
SEQUENCE: 204
000

SEQ ID NO: 205          moltype =   length =
SEQUENCE: 205
```

-continued

000

SEQ ID NO: 206 moltype = length =
SEQUENCE: 206
000

SEQ ID NO: 207 moltype = length =
SEQUENCE: 207
000

SEQ ID NO: 208 moltype = length =
SEQUENCE: 208
000

SEQ ID NO: 209 moltype = length =
SEQUENCE: 209
000

SEQ ID NO: 210 moltype = length =
SEQUENCE: 210
000

SEQ ID NO: 211 moltype = length =
SEQUENCE: 211
000

SEQ ID NO: 212 moltype = length =
SEQUENCE: 212
000

SEQ ID NO: 213 moltype = length =
SEQUENCE: 213
000

SEQ ID NO: 214 moltype = length =
SEQUENCE: 214
000

SEQ ID NO: 215 moltype = length =
SEQUENCE: 215
000

SEQ ID NO: 216 moltype = length =
SEQUENCE: 216
000

SEQ ID NO: 217 moltype = length =
SEQUENCE: 217
000

SEQ ID NO: 218 moltype = length =
SEQUENCE: 218
000

SEQ ID NO: 219 moltype = length =
SEQUENCE: 219
000

SEQ ID NO: 220 moltype = length =
SEQUENCE: 220
000

SEQ ID NO: 221 moltype = length =
SEQUENCE: 221
000

SEQ ID NO: 222 moltype = length =
SEQUENCE: 222
000

SEQ ID NO: 223 moltype = length =
SEQUENCE: 223
000

SEQ ID NO: 224 moltype = length =
SEQUENCE: 224
000

SEQ ID NO: 225 moltype = length =

```
SEQUENCE: 225
000

SEQ ID NO: 226          moltype =   length =
SEQUENCE: 226
000

SEQ ID NO: 227          moltype =   length =
SEQUENCE: 227
000

SEQ ID NO: 228          moltype =   length =
SEQUENCE: 228
000

SEQ ID NO: 229          moltype =   length =
SEQUENCE: 229
000

SEQ ID NO: 230          moltype =   length =
SEQUENCE: 230
000

SEQ ID NO: 231          moltype =   length =
SEQUENCE: 231
000

SEQ ID NO: 232          moltype =   length =
SEQUENCE: 232
000

SEQ ID NO: 233          moltype =   length =
SEQUENCE: 233
000

SEQ ID NO: 234          moltype =   length =
SEQUENCE: 234
000

SEQ ID NO: 235          moltype =   length =
SEQUENCE: 235
000

SEQ ID NO: 236          moltype =   length =
SEQUENCE: 236
000

SEQ ID NO: 237          moltype = AA  length = 46
FEATURE                 Location/Qualifiers
source                  1..46
                        mol_type = protein
                        organism = synthetic construct
SEQUENCE: 237
LTAVGGESIY YDEQSKFVCN TEQPGCENVC YDAFAPLSHV RFWVFQ                  46

SEQ ID NO: 238          moltype = AA  length = 15
FEATURE                 Location/Qualifiers
source                  1..15
                        mol_type = protein
                        organism = synthetic construct
SEQUENCE: 238
LTAVGGESIY YDEQS                                                    15

SEQ ID NO: 239          moltype = AA  length = 13
FEATURE                 Location/Qualifiers
source                  1..13
                        mol_type = protein
                        organism = synthetic construct
SEQUENCE: 239
DEQSKFVCNT EQP                                                      13

SEQ ID NO: 240          moltype =   length =
SEQUENCE: 240
000

SEQ ID NO: 241          moltype = AA  length = 13
FEATURE                 Location/Qualifiers
source                  1..13
                        mol_type = protein
```

-continued

```
                          organism = synthetic construct
SEQUENCE: 241
TEQPGCENVC YDA                                                      13

SEQ ID NO: 242            moltype = AA  length = 13
FEATURE                   Location/Qualifiers
source                    1..13
                          mol_type = protein
                          organism = synthetic construct
SEQUENCE: 242
VCYDAFAPLS HVR                                                      13

SEQ ID NO: 243            moltype = AA  length = 12
FEATURE                   Location/Qualifiers
source                    1..12
                          mol_type = protein
                          organism = synthetic construct
SEQUENCE: 243
APLSHVRFWV FQ                                                       12

SEQ ID NO: 244            moltype =   length =
SEQUENCE: 244
000

SEQ ID NO: 245            moltype = AA  length = 11
FEATURE                   Location/Qualifiers
source                    1..11
                          mol_type = protein
                          organism = synthetic construct
SEQUENCE: 245
FEVGFLIGQY F                                                        11

SEQ ID NO: 246            moltype = AA  length = 12
FEATURE                   Location/Qualifiers
source                    1..12
                          mol_type = protein
                          organism = synthetic construct
SEQUENCE: 246
LIGQYFLYGF QV                                                       12

SEQ ID NO: 247            moltype = AA  length = 14
FEATURE                   Location/Qualifiers
source                    1..14
                          mol_type = protein
                          organism = synthetic construct
SEQUENCE: 247
GFQVHPFYVC SRLP                                                     14

SEQ ID NO: 248            moltype = AA  length = 12
FEATURE                   Location/Qualifiers
source                    1..12
                          mol_type = protein
                          organism = synthetic construct
SEQUENCE: 248
SRLPCHPKID CF                                                       12

SEQ ID NO: 249            moltype = AA  length = 12
FEATURE                   Location/Qualifiers
source                    1..12
                          mol_type = protein
                          organism = synthetic construct
SEQUENCE: 249
IDCFISRPTE KT                                                       12

SEQ ID NO: 250            moltype = AA  length = 11
FEATURE                   Location/Qualifiers
source                    1..11
                          mol_type = protein
                          organism = synthetic construct
SEQUENCE: 250
SRPTEKTIFL L                                                        11

SEQ ID NO: 251            moltype =   length =
SEQUENCE: 251
000

SEQ ID NO: 252            moltype = AA  length = 10
FEATURE                   Location/Qualifiers
source                    1..10
```

```
                        mol_type = protein
                        organism = synthetic construct
SEQUENCE: 252
YVCSRLPCHP                                                    10

SEQ ID NO: 253          moltype = AA  length = 11
FEATURE                 Location/Qualifiers
source                  1..11
                        mol_type = protein
                        organism = synthetic construct
SEQUENCE: 253
QVHPFYVCSR L                                                  11

SEQ ID NO: 254          moltype = AA  length = 13
FEATURE                 Location/Qualifiers
source                  1..13
                        mol_type = protein
                        organism = synthetic construct
SEQUENCE: 254
FEVGFLIGQY FLY                                                13

SEQ ID NO: 255          moltype = AA  length = 12
FEATURE                 Location/Qualifiers
source                  1..12
                        mol_type = protein
                        organism = synthetic construct
SEQUENCE: 255
GQYFLYGFQV HP                                                 12

SEQ ID NO: 256          moltype = AA  length = 12
FEATURE                 Location/Qualifiers
source                  1..12
                        mol_type = protein
                        organism = synthetic construct
SEQUENCE: 256
GFQVHPFYVC SR                                                 12

SEQ ID NO: 257          moltype = AA  length = 12
FEATURE                 Location/Qualifiers
source                  1..12
                        mol_type = protein
                        organism = synthetic construct
SEQUENCE: 257
AVGGESIYYD EQ                                                 12

SEQ ID NO: 258          moltype = AA  length = 12
FEATURE                 Location/Qualifiers
source                  1..12
                        mol_type = protein
                        organism = synthetic construct
SEQUENCE: 258
YDEQSKFVCN TE                                                 12

SEQ ID NO: 259          moltype = AA  length = 12
FEATURE                 Location/Qualifiers
source                  1..12
                        mol_type = protein
                        organism = synthetic construct
SEQUENCE: 259
NTEQPGCENV CY                                                 12

SEQ ID NO: 260          moltype = AA  length = 12
FEATURE                 Location/Qualifiers
source                  1..12
                        mol_type = protein
                        organism = synthetic construct
SEQUENCE: 260
CYDAFAPLSH VR                                                 12

SEQ ID NO: 261          moltype = AA  length = 12
FEATURE                 Location/Qualifiers
source                  1..12
                        mol_type = protein
                        organism = synthetic construct
SEQUENCE: 261
FAPLSHVRFW VF                                                 12

SEQ ID NO: 262          moltype = AA  length = 5
FEATURE                 Location/Qualifiers
```

-continued

```
source                 1..5
                       mol_type = protein
                       organism = synthetic construct
SEQUENCE: 262
LIGQY                                                              5

SEQ ID NO: 263         moltype = AA  length = 5
FEATURE                Location/Qualifiers
source                 1..5
                       mol_type = protein
                       organism = synthetic construct
SEQUENCE: 263
QVHPF                                                              5

SEQ ID NO: 264         moltype = AA  length = 5
FEATURE                Location/Qualifiers
source                 1..5
                       mol_type = protein
                       organism = synthetic construct
SEQUENCE: 264
YVCSR                                                              5

SEQ ID NO: 265         moltype = AA  length = 5
FEATURE                Location/Qualifiers
source                 1..5
                       mol_type = protein
                       organism = synthetic construct
SEQUENCE: 265
SRLPC                                                              5

SEQ ID NO: 266         moltype = AA  length = 5
FEATURE                Location/Qualifiers
source                 1..5
                       mol_type = protein
                       organism = synthetic construct
SEQUENCE: 266
LPCHP                                                              5

SEQ ID NO: 267         moltype = AA  length = 5
FEATURE                Location/Qualifiers
source                 1..5
                       mol_type = protein
                       organism = synthetic construct
SEQUENCE: 267
GESIY                                                              5

SEQ ID NO: 268         moltype = AA  length = 6
FEATURE                Location/Qualifiers
source                 1..6
                       mol_type = protein
                       organism = synthetic construct
SEQUENCE: 268
YDEQSK                                                             6

SEQ ID NO: 269         moltype = AA  length = 6
FEATURE                Location/Qualifiers
source                 1..6
                       mol_type = protein
                       organism = synthetic construct
SEQUENCE: 269
SKFVCN                                                             6

SEQ ID NO: 270         moltype = AA  length = 8
FEATURE                Location/Qualifiers
source                 1..8
                       mol_type = protein
                       organism = synthetic construct
SEQUENCE: 270
TEQPGCEN                                                           8

SEQ ID NO: 271         moltype = AA  length = 8
FEATURE                Location/Qualifiers
source                 1..8
                       mol_type = protein
                       organism = synthetic construct
SEQUENCE: 271
VCYDAFAP                                                           8

SEQ ID NO: 272         moltype = AA  length = 10
```

```
FEATURE                Location/Qualifiers
source                 1..10
                       mol_type = protein
                       organism = synthetic construct
SEQUENCE: 272
LSHVRFWVFQ                                                         10

SEQ ID NO: 273         moltype = AA  length = 14
FEATURE                Location/Qualifiers
source                 1..14
                       mol_type = protein
                       organism = synthetic construct
SEQUENCE: 273
LIQYFLYGFQ VHPF                                                    14

SEQ ID NO: 274         moltype = AA  length = 13
FEATURE                Location/Qualifiers
source                 1..13
                       mol_type = protein
                       organism = synthetic construct
SEQUENCE: 274
VHPFYCSRLP CHP                                                     13

SEQ ID NO: 275         moltype = AA  length = 22
FEATURE                Location/Qualifiers
source                 1..22
                       mol_type = protein
                       organism = synthetic construct
SEQUENCE: 275
VGGESIYYDE QSKFVCNTEQ PG                                           22

SEQ ID NO: 276         moltype = AA  length = 22
FEATURE                Location/Qualifiers
source                 1..22
                       mol_type = protein
                       organism = synthetic construct
SEQUENCE: 276
TEQPGCENVC YDAFAPLSHV RF                                           22

SEQ ID NO: 277         moltype = AA  length = 14
FEATURE                Location/Qualifiers
source                 1..14
                       mol_type = protein
                       organism = synthetic construct
SEQUENCE: 277
AFAPLSHVRF WVFQ                                                    14

SEQ ID NO: 278         moltype = AA  length = 16
FEATURE                Location/Qualifiers
source                 1..16
                       mol_type = protein
                       organism = synthetic construct
SEQUENCE: 278
IDCFISRPTE KTIFLL                                                  16

SEQ ID NO: 279         moltype = AA  length = 11
FEATURE                Location/Qualifiers
source                 1..11
                       mol_type = protein
                       organism = synthetic construct
SEQUENCE: 279
DCFISRPTEK T                                                       11

SEQ ID NO: 280         moltype =   length =
SEQUENCE: 280
000

SEQ ID NO: 281         moltype =   length =
SEQUENCE: 281
000

SEQ ID NO: 282         moltype =   length =
SEQUENCE: 282
000

SEQ ID NO: 283         moltype =   length =
SEQUENCE: 283
000
```

-continued

```
SEQ ID NO: 284          moltype =   length =
SEQUENCE: 284
000

SEQ ID NO: 285          moltype =   length =
SEQUENCE: 285
000

SEQ ID NO: 286          moltype =   length =
SEQUENCE: 286
000

SEQ ID NO: 287          moltype =   length =
SEQUENCE: 287
000

SEQ ID NO: 288          moltype =   length =
SEQUENCE: 288
000

SEQ ID NO: 289          moltype =   length =
SEQUENCE: 289
000

SEQ ID NO: 290          moltype =   length =
SEQUENCE: 290
000

SEQ ID NO: 291          moltype = AA  length = 12
FEATURE                 Location/Qualifiers
source                  1..12
                        mol_type = protein
                        organism = synthetic construct
SEQUENCE: 291
ADCFLSRPTE KT                                                12

SEQ ID NO: 292          moltype = AA  length = 12
FEATURE                 Location/Qualifiers
source                  1..12
                        mol_type = protein
                        organism = synthetic construct
SEQUENCE: 292
VACFLSRPTE KT                                                12

SEQ ID NO: 293          moltype = AA  length = 12
FEATURE                 Location/Qualifiers
source                  1..12
                        mol_type = protein
                        organism = synthetic construct
SEQUENCE: 293
VDCFLSRPTA KT                                                12

SEQ ID NO: 294          moltype = AA  length = 12
FEATURE                 Location/Qualifiers
source                  1..12
                        mol_type = protein
                        organism = synthetic construct
SEQUENCE: 294
VDCFLSRPTE AT                                                12

SEQ ID NO: 295          moltype =   length =
SEQUENCE: 295
000

SEQ ID NO: 296          moltype =   length =
SEQUENCE: 296
000

SEQ ID NO: 297          moltype =   length =
SEQUENCE: 297
000

SEQ ID NO: 298          moltype =   length =
SEQUENCE: 298
000

SEQ ID NO: 299          moltype =   length =
SEQUENCE: 299
000
```

```
SEQ ID NO: 300          moltype = AA  length = 26
FEATURE                 Location/Qualifiers
source                  1..26
                        mol_type = protein
                        organism = synthetic construct
SEQUENCE: 300
DGVNVEMHLK QIEIKKFKYG IEEHGK                                       26

SEQ ID NO: 301          moltype = AA  length = 26
FEATURE                 Location/Qualifiers
source                  1..26
                        mol_type = protein
                        organism = synthetic construct
SEQUENCE: 301
DGVNVEMHLK QIEIKKFKYG IEEQGK                                       26

SEQ ID NO: 302          moltype = AA  length = 20
FEATURE                 Location/Qualifiers
source                  1..20
                        mol_type = protein
                        organism = synthetic construct
SEQUENCE: 302
YGRKKRRQRR RKQIEIKKFK                                              20

SEQ ID NO: 303          moltype = AA  length = 17
FEATURE                 Location/Qualifiers
source                  1..17
                        mol_type = protein
                        organism = synthetic construct
SEQUENCE: 303
CSSPTAPLSP MSPPGYK                                                 17

SEQ ID NO: 304          moltype = AA  length = 11
FEATURE                 Location/Qualifiers
source                  1..11
                        mol_type = protein
                        organism = synthetic construct
SEQUENCE: 304
PTAPLSPMSP P                                                       11

SEQ ID NO: 305          moltype =   length =
SEQUENCE: 305
000

SEQ ID NO: 306          moltype =   length =
SEQUENCE: 306
000

SEQ ID NO: 307          moltype =   length =
SEQUENCE: 307
000

SEQ ID NO: 308          moltype =   length =
SEQUENCE: 308
000

SEQ ID NO: 309          moltype = AA  length = 6
FEATURE                 Location/Qualifiers
source                  1..6
                        mol_type = protein
                        organism = synthetic construct
SITE                    1
                        note = Aminated residue
SITE                    4
                        note = 4-hydroxyproline
SITE                    6
                        note = Amidated residue
SEQUENCE: 309
GAGPPY                                                             6

SEQ ID NO: 310          moltype = AA  length = 6
FEATURE                 Location/Qualifiers
source                  1..6
                        mol_type = protein
                        organism = synthetic construct
SITE                    1
                        note = Acetylated D-amino acid
SITE                    3
```

```
                        note = D-4-hydroxyproline
SITE                    5
                        note = D-amino acid
SITE                    6
                        note = Aminated residue
SEQUENCE: 310
YPPGAG                                                                       6

SEQ ID NO: 311          moltype = AA  length = 28
FEATURE                 Location/Qualifiers
source                  1..28
                        mol_type = protein
                        organism = synthetic construct
SEQUENCE: 311
RVIRVWFQNK RCKDKKVDCF LSRPTEKT                                               28

SEQ ID NO: 312          moltype = AA  length = 39
FEATURE                 Location/Qualifiers
source                  1..39
                        mol_type = protein
                        organism = synthetic construct
SEQUENCE: 312
GALFLGFLGA AGSTMGAWSQ PKKKRKVVDC FLSRPTEKT                                   39

SEQ ID NO: 313          moltype = AA  length = 39
FEATURE                 Location/Qualifiers
source                  1..39
                        mol_type = protein
                        organism = synthetic construct
SEQUENCE: 313
GALFLAFLAA ALSLMGLWSQ PKKKRRVVDC FLSRPTEKT                                   39

SEQ ID NO: 314          moltype =   length =
SEQUENCE: 314
000

SEQ ID NO: 315          moltype =   length =
SEQUENCE: 315
000

SEQ ID NO: 316          moltype =   length =
SEQUENCE: 316
000

SEQ ID NO: 317          moltype =   length =
SEQUENCE: 317
000

SEQ ID NO: 318          moltype =   length =
SEQUENCE: 318
000

SEQ ID NO: 319          moltype =   length =
SEQUENCE: 319
000

SEQ ID NO: 320          moltype =   length =
SEQUENCE: 320
000

SEQ ID NO: 321          moltype =   length =
SEQUENCE: 321
000

SEQ ID NO: 322          moltype =   length =
SEQUENCE: 322
000

SEQ ID NO: 323          moltype =   length =
SEQUENCE: 323
000

SEQ ID NO: 324          moltype =   length =
SEQUENCE: 324
000

SEQ ID NO: 325          moltype =   length =
SEQUENCE: 325
000
```

-continued

```
SEQ ID NO: 326         moltype =   length =
SEQUENCE: 326
000

SEQ ID NO: 327         moltype =   length =
SEQUENCE: 327
000

SEQ ID NO: 328         moltype =   length =
SEQUENCE: 328
000

SEQ ID NO: 329         moltype =   length =
SEQUENCE: 329
000

SEQ ID NO: 330         moltype =   length =
SEQUENCE: 330
000

SEQ ID NO: 331         moltype =   length =
SEQUENCE: 331
000

SEQ ID NO: 332         moltype =   length =
SEQUENCE: 332
000

SEQ ID NO: 333         moltype =   length =
SEQUENCE: 333
000

SEQ ID NO: 334         moltype =   length =
SEQUENCE: 334
000

SEQ ID NO: 335         moltype =   length =
SEQUENCE: 335
000

SEQ ID NO: 336         moltype =   length =
SEQUENCE: 336
000

SEQ ID NO: 337         moltype =   length =
SEQUENCE: 337
000

SEQ ID NO: 338         moltype =   length =
SEQUENCE: 338
000

SEQ ID NO: 339         moltype =   length =
SEQUENCE: 339
000

SEQ ID NO: 340         moltype =   length =
SEQUENCE: 340
000

SEQ ID NO: 341         moltype =   length =
SEQUENCE: 341
000

SEQ ID NO: 342         moltype =   length =
SEQUENCE: 342
000

SEQ ID NO: 343         moltype = AA  length = 39
FEATURE                Location/Qualifiers
source                 1..39
                       mol_type = protein
                       organism = synthetic construct
SEQUENCE: 343
MYVFYVMYDG FSMQRLVKCN AWPCPNTVDC FVSRPTEKT                         39

SEQ ID NO: 344         moltype = AA  length = 39
FEATURE                Location/Qualifiers
```

```
source                 1..39
                       mol_type = protein
                       organism = synthetic construct
SEQUENCE: 344
MYVFYFLYNG YHLPWVLKCG IDPCPNLVDC FISRPTEKT                          39

SEQ ID NO: 345         moltype = AA  length = 39
FEATURE                Location/Qualifiers
source                 1..39
                       mol_type = protein
                       organism = synthetic construct
SEQUENCE: 345
LYIFHRLYKD YDMPRVVACS VEPCPHTVDC YISRPTEKK                          39

SEQ ID NO: 346         moltype = AA  length = 40
FEATURE                Location/Qualifiers
source                 1..40
                       mol_type = protein
                       organism = synthetic construct
SEQUENCE: 346
LYLLHTLWHG FNMPRLVQCA NVAPCPNIVD CYIARPTEKK                         40

SEQ ID NO: 347         moltype = AA  length = 39
FEATURE                Location/Qualifiers
source                 1..39
                       mol_type = protein
                       organism = synthetic construct
SEQUENCE: 347
LYVFHSFYPK YILPPVVKCH ADPCPNIVDC FISKPSEKN                          39

SEQ ID NO: 348         moltype = AA  length = 39
FEATURE                Location/Qualifiers
source                 1..39
                       mol_type = protein
                       organism = synthetic construct
SEQUENCE: 348
MYVFYLLYPG YAMVRLVKCD VYPCPNTVDC FVSRPTEKT                          39

SEQ ID NO: 349         moltype = AA  length = 32
FEATURE                Location/Qualifiers
source                 1..32
                       mol_type = protein
                       organism = synthetic construct
SEQUENCE: 349
LYGWTMEPVF VCQRAPCPYL VDCFVSRPTE KT                                 32

SEQ ID NO: 350         moltype = AA  length = 32
FEATURE                Location/Qualifiers
source                 1..32
                       mol_type = protein
                       organism = synthetic construct
SEQUENCE: 350
LYGWTMEPVF VCQRAPCPYL VDCFVSRPTE KT                                 32

SEQ ID NO: 351         moltype = AA  length = 38
FEATURE                Location/Qualifiers
source                 1..38
                       mol_type = protein
                       organism = synthetic construct
SEQUENCE: 351
GALHYFLFGF LAPKKFPCTR PPCTGVVDCY VSRPTEKS                           38

SEQ ID NO: 352         moltype =   length =
SEQUENCE: 352
000

SEQ ID NO: 353         moltype = AA  length = 38
FEATURE                Location/Qualifiers
source                 1..38
                       mol_type = protein
                       organism = synthetic construct
SEQUENCE: 353
IAGQYFLYGF ELKPLYRCDR WPCPNTVDCF ISRPTEKT                           38

SEQ ID NO: 354         moltype = AA  length = 38
FEATURE                Location/Qualifiers
source                 1..38
                       mol_type = protein
                       organism = synthetic construct
```

```
SEQUENCE: 354
LVGQYLLYGF EVRPFFPCSR QPCPHVVDCF VSRPTEKT                          38

SEQ ID NO: 355          moltype = AA  length = 38
FEATURE                 Location/Qualifiers
source                  1..38
                        mol_type = protein
                        organism = synthetic construct
SEQUENCE: 355
IVGQYFIYGI FLTTLHVCRR SPCPHPVNCY VSRPTEKN                          38

SEQ ID NO: 356          moltype = DNA  length = 30
FEATURE                 Location/Qualifiers
source                  1..30
                        mol_type = other DNA
                        organism = synthetic construct
modified_base           1
                        mod_base = OTHER
                        note = Nucleotide with phosphorothioate linkage
modified_base           2
                        mod_base = OTHER
                        note = Nucleotide with phosphorothioate linkage
modified_base           3
                        mod_base = OTHER
                        note = Nucleotide with phosphorothioate linkage
modified_base           4
                        mod_base = OTHER
                        note = Nucleotide with phosphorothioate linkage
modified_base           26
                        mod_base = OTHER
                        note = Nucleotide with phosphorothioate linkage
modified_base           27
                        mod_base = OTHER
                        note = Nucleotide with phosphorothioate linkage
modified_base           28
                        mod_base = OTHER
                        note = Nucleotide with phosphorothioate linkage
modified_base           29
                        mod_base = OTHER
                        note = Nucleotide with phosphorothioate linkage
SEQUENCE: 356
gtaattgcgg caagaagaat tgtttctgtc                                   30

SEQ ID NO: 357          moltype = DNA  length = 30
FEATURE                 Location/Qualifiers
source                  1..30
                        mol_type = other DNA
                        organism = synthetic construct
misc_difference         1
                        note = Nucleotide with any modified sugar moiety
misc_difference         2
                        note = Nucleotide with any modified sugar moiety
misc_difference         3
                        note = Nucleotide with any modified sugar moiety
misc_difference         4
                        note = Nucleotide with any modified sugar moiety
misc_difference         27
                        note = Nucleotide with any modified sugar moiety
misc_difference         28
                        note = Nucleotide with any modified sugar moiety
misc_difference         29
                        note = Nucleotide with any modified sugar moiety
misc_difference         30
                        note = Nucleotide with any modified sugar moiety
SEQUENCE: 357
gtaattgcgg caagaagaat tgtttctgtc                                   30

SEQ ID NO: 358          moltype = AA  length = 14
FEATURE                 Location/Qualifiers
source                  1..14
                        mol_type = protein
                        organism = synthetic construct
VARIANT                 1
                        note = Any amino acid, wherein the side chain can be
                         hydrogen or n-dodecyl
VARIANT                 2
                        note = Any amino acid, wherein the side chain can be
                         hydrogen or n-dodecyl
SEQUENCE: 358
```

-continued

```
XXLDCFLSRP TEKT                                                    14

SEQ ID NO: 359         moltype = AA  length = 4
FEATURE                Location/Qualifiers
source                 1..4
                       mol_type = protein
                       organism = synthetic construct
SEQUENCE: 359
SHVR                                                               4

SEQ ID NO: 360         moltype = AA  length = 6
FEATURE                Location/Qualifiers
source                 1..6
                       mol_type = protein
                       organism = synthetic construct
SEQUENCE: 360
SRPTEK                                                             6

SEQ ID NO: 361         moltype = AA  length = 4
FEATURE                Location/Qualifiers
source                 1..4
                       mol_type = protein
                       organism = synthetic construct
SEQUENCE: 361
KKFK                                                               4
```

We claim:

1. A method for treating a subject for a non-healing ocular surface defect, comprising administering to the eye of the subject a therapeutically effective amount of a composition comprising a connexin 43 modulator, wherein the connexin 43 modulator is lufepirsen (SEQ ID NO: 1) and the composition is administered at a dose of about 0.006 wt. % lufepirsen or 0.06 wt. % lufepirsen at least once on day 1, at least once on day 2, and at least once on about day 14.

2. The method of claim 1, wherein the non-healing ocular surface defect is a persistent corneal epithelial defect or a persistent epithelial defect.

3. The method of claim 1, wherein the non-healing ocular surface defect results from a chemical injury, a thermal injury, or inflammation.

4. The method of claim 1, wherein the subject has an amniotic membrane graft.

5. The method of claim 2, wherein the non-healing ocular surface defect is the persistent epithelial defect.

6. The method of claim 2, wherein the non-healing ocular surface defect is the persistent corneal epithelial defect.

7. The method of claim 1, wherein the connexin 43 modulator modulates connexin 43 in the cornea.

8. The method of claim 1, wherein said connexin 43 modulator is administered by topical administration.

9. The method of claim 1, further comprising the step of placing a bandage contact lens over the non-healing ocular surface defect.

10. The method of claim 6, wherein the connexin 43 modulator is formulated with a pluronic gel.

11. A method for treating a subject for a persistent corneal epithelial defect, comprising administering to the eye of the subject a composition comprising about 0.06% or about 0.006% lufepirsen on day 1, on day 2, and on about day 14.

12. The method according to claim 11, further comprising administering to the subject the composition comprising about 0.06% or about 0.006% lufepirsen on about day 7 and/or on about day 21.

13. The method according to claim 11, further comprising administering to the subject the composition comprising about 0.06% or about 0.006% lufepirsen on about day 28 and/or on about day 35.

14. The method according to claim 12, further comprising administering to the subject the composition comprising about 0.06% or about 0.006% lufepirsen on about day 28 and/or on about day 35.

15. A pharmaceutical composition comprising about 0.6 or 0.06 mg/mL lufepirsen, about 226.9 mg/mL poloxamer 407, about 0.99 mg/mL sodium phosphate dibasic heptahydrate and about 0.25 mg/mL potassium phosphate, monobasic.

16. The pharmaceutical composition according to claim 15 having a final volume of about 300 μL.

17. A method for treating a subject for a non-healing ocular surface defect, comprising administering to the eye of the subject the pharmaceutical composition according to claim 16 at least once on day 1, at least once on day 2, and at least once on about day 14.

18. The method according to claim 17, further comprising administering said pharmaceutical composition to the eye of the subject on about day 7 and on about day 21.

19. The method according to claim 18, further comprising administering said pharmaceutical composition to the eye of the subject on about day 28.

20. The method according to claim 18, further comprising administering said pharmaceutical composition to the eye of the subject on about day 35.

* * * * *